US007863041B2

(12) United States Patent
Rupprecht et al.

(10) Patent No.: US 7,863,041 B2
(45) Date of Patent: Jan. 4, 2011

(54) RABIES VIRUS VECTOR SYSTEMS AND COMPOSITIONS AND METHODS THEREOF

(75) Inventors: Charles E. Rupprecht, Lawrenceville, GA (US); Xianfu Wu, Atlanta, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 243 days.

(21) Appl. No.: 12/090,083

(22) PCT Filed: Oct. 13, 2006

(86) PCT No.: PCT/US2006/040134

§ 371 (c)(1),
(2), (4) Date: Apr. 11, 2008

(87) PCT Pub. No.: WO2007/047459

PCT Pub. Date: Apr. 26, 2007

(65) Prior Publication Data

US 2008/0274130 A1    Nov. 6, 2008

Related U.S. Application Data

(60) Provisional application No. 60/727,038, filed on Oct. 14, 2005.

(51) Int. Cl.
C12N 15/00    (2006.01)
A61K 39/205    (2006.01)
(52) U.S. Cl. .................................. 435/320.1; 424/224.1
(58) Field of Classification Search ........................ None
See application file for complete search history.

(56) References Cited

U.S. PATENT DOCUMENTS

| | | | |
|---|---|---|---|
| 4,040,904 A | 8/1977 | Slater | |
| 4,393,201 A | 7/1983 | Curtis et al. | |
| 5,695,757 A | 12/1997 | Rupprecht et al. | |
| 5,789,229 A | 8/1998 | Wert et al. | |
| 6,719,981 B1 | 4/2004 | Mabatsion et al. | |
| 2002/0131981 A1 | 9/2002 | Dietzschold et al. | |
| 2003/0113346 A1 | 6/2003 | Dietzchold et al. | |
| 2003/0224017 A1 | 12/2003 | Samal et al. | |
| 2004/0208900 A1 | 10/2004 | Fu | |

FOREIGN PATENT DOCUMENTS

| | | |
|---|---|---|
| EP | 0 702 085 A1 | 3/1996 |
| EP | 0 780 475 A1 | 6/1997 |
| EP | 1 253 197 A1 | 10/2002 |
| EP | 1 394 259 A2 | 3/2004 |
| WO | WO 95/09249 | 4/1995 |
| WO | WO 00/32755 | 6/2000 |

OTHER PUBLICATIONS

Wu et al., Glycoprotein gene relocation in rabies virus, Virus Research, 2008, 131:95-99.*
Anilionis et al., "Structure of the glycoprotein gene in rabis virus," *Nature*, 294:275-278 (1981).
Bridgen et al., "Rescue of a segmented negative-strand RNA virus entirely from cloned complementary DNAs," *Proc. Natl. Acad. Sci. USA*, 93:15400-15404 (1996).
Conzelmann et al., "Molecular Cloning and Complete Nucleotide Sequence of the Attenuated Rabies Virus SAD B19," *Virology*, 175:485-499 (1990).
Dietzschold et al., "Characterization of an antigenic determinant of the glycoprotein that correlates with pathogenicity of rabies virus," *Proc. Natl. Acad. Sci., USA* 80:60-74 (1983).
Dietzschold et al., "New Approaches to the Development of Live Attenuated Rabies Vaccines," *Hybridoma and Hybridomics*, 21(2):129-134 (2002).
Dietzschold et al., "New approaches to the prevention and eradication of rabies," *Expert Rev. Vaccines*, 2(3):399-406 (2003).
Faber, et al., "Overexpression of the Rabies Virus Glycoprotein Results in Enhancement of Apoptosis and Antiviral Immune Response," *Journal of Virology*, 76(7):3374-3381 (2002).
Fodor et al., "Nucleotide and deduced amino acid sequences of the glycoprotein gene of rabies virus vaccine strain Vnukove-32," *Arch. Virol.*, 135:451-459 (1994).
Gaudin, Yves, "Rabies Virus-induced Membrane Fusion Pathway," *The Journal of Cell Biology*, 150(3):601-611 (2000).
Hiramatsu et al., "Comparative Sequence Analysis of the M Gene Among Rabies Virus Strains and its Expression by Recombinant Vaccinia Virus," *Virus Genes*, 7(1):83-88 (1993).
Inoue et al., "An improved method for recovering rabies virus from cloned cDNA," *J. Virol. Method.*, 107, 229-236 (2003).
Ito et al., "A unique mutation of glycoprotein gene of the attenuated RC-HL strain of rabies virus, a seed virus used for production of animal vaccine in Japan," *Microl. Immunol.*, 38:479-482 (1994).

(Continued)

*Primary Examiner*—Stacy B Chen
(74) *Attorney, Agent, or Firm*—Klarquist Sparkman, LLP

(57) ABSTRACT

Rabies Virus compositions and methods are provided. The full-length sequence of Rabies Virus strain Evelyn-Rokitnicki-Abelseth (ERA) is disclosed. A reverse genetics system for producing recombinant ERA virus and derivatives thereof is provided, along with compositions including ERA and/or ERA derivative strain viruses, nucleic acids and/or proteins. In some instances, the compositions are immunogenic compositions useful for the pre- or post-exposure treatment of Rabies Virus.

19 Claims, 9 Drawing Sheets

OTHER PUBLICATIONS

Ito et al., "Improved Recovery of Rabies Virus from Cloned cDNA Using a Vaccinia Virus-Free Reverse Genetics System," *Microbiol. Immunol.*, 47(8):613-617 (2003).

Lawson et al., "The ERA Strain of Rabies Vaccine," *Can. J. Comp. Med*, 36:339-344 (1972).

Martins et al., "Pathogenesis of rabies virus by ERA and PV strains administered orally in hamsters (*M. auratus*)," *Brazilian Journal of Veterinary Research and Animal Science*, 40:79-84 (2003).

McKenna et al., "Recombinant Rhabdoviruses as Potential Vaccines for HIV-1 and Other Diseases," *Current HIV Research*, 1:229-237 (2003).

Morimoto et al., "Structure and transcription of the glycoprotein gene of attenuated HEP-Flury strain of rabies virus," *Virol.*, 173:465-477 (1989).

Rupprecht et al., "The ascension of wildlife rabies: a cause for public health concern or intervention?" *Emerg. Infect. Dis.*, 1(4):107-114 (1995).

Schnell et al., "Polymerase activity of in vitro mutated rabies virus L protein," *Virol.*, 214:522-530 (1995).

Schnell et al., "The application of reverse genetics technology in the studies of rabies virus (RV) pathogenesis and for the development of novel RV vaccines," *Journal of NeuroVirology*, 11:76-81 (2005).

Tordo et al., "Completion of the Rabies Virus Genome Sequence Determination: Highly Conserved Domains among the L (polymerase) Proteins of Unsegmented Negative-Strand RNA Viruses," Virology, 165:565-576 (1988).

Tuffereau et al., "Arginine or lysine in position 333 of ERA and CVS glycoprotein is necessary for rabies virulence in adult mice," *Virology* 172:206-212 (1989).

Wandeler et al., "Oral immunization of wildlife against rabies: concept and first field experiments," *Rev. Infect. Dis.*, 10 suppl.4:649-653 (1988).

Wojczyk et al., "The role of site-specific N-glycosylation in secretion of soluble forms of rabies virus glycoprotein," *Glycobiology*, 8(2) 121-130 (1998).

Wu et al., "Both Viral Transcription and Replication Are Reduced when the Rabies Virus Nucleoprotein is Not Phosphorylated," *Journal of Virology*, 76(9):4153-4161 (2002).

Yamada et al., "Multigenic Relation to the Attenuation of Rabies Virus," *Microbiol. Immunol.*, 50(1):25-32 (2006).

Fu et al., "Inhibition of Rabies Virus Infection by an Oligodeoxynucleotide Complementary to Rabies Virus Genomic RNA," *Antisense & Nucleic Acid Drug Development*, 6:87-93 (1996).

Hemachudha et al., "Human rabies: a disease of complex neuropathogenetic mechanisms and diagnostic challenges," *Lancet Neurology*, 1:101-109 (2002).

Ito et al., "Rescue of Rabies Virus from Cloned cDNA and Identification of the Pathogenicity-related gene: Glycoprotein Gene is Associated with Virulence for Adult Mice," *Journal of Virology*, 75:9121-9128 (2001).

Rupprecht et al., "Oral vaccination of dogs with recombinant rabies virus vaccines," *Virus Research*, 111:101-105 (2005).

Rupprecht et al., "Rabies re-examined," *Lancet Infectious Diseases*, 2:327-343 (2002).

Schnell et al., "Infectious rabies virus from cloned cDNA," *The EMBO Journal*, 13:4195-4203 (1994).

* cited by examiner

Fig. 1A

Hammerhead RZ · antigenomic ERA genome · +HDV RZ

5' — P M G L — 3'

Construction of transcription plasmid for ERA +cDNA

Fig. 1B

N P M G psi L — Full length ERA cDNA

F1 fragment pSKF1 construct

Blp1   F2 fragment

Kpn1 ............................ Pst1

Nhe1                                                Not1 pSKFIF2 construct pSKF construct

HdRz                                                HDVRz pTMF construct for virus recovery

Fig. 3

| N | P | M | G | Ψ | L | | rERA |

| N | P | M | G | L | | ERA- |

| N | P | M | G | GFP | L | | ERAgreen1 |

| N | P | GFP | M | G | L | | ERAgreen2 |

| N | P | M | G | G | L | | ERA2g |

| N | P | M | G* | Ψ | L | | ERAg3 |

| N | P | M | G* | G* | L | | ERA2g3 |

| N | P | M | L | | ERA-G |

| N | P | G | M | L | | ERAgm |

| N | P | G | M | G | Ψ | L | | ERAgmg |

FIG. 9A

Survival rates of hamster against Alabama Bat Rabies Virus infection treated with PEP and live attenuated ERA-R333 mutant

FIG. 9B

Survival rates of hamster against Thai Street Dog Rabies Virus infection treated with PEP and live attenuated ERA-R333 mutant

FIG. 9C

Survival rates of hamster against Texas Coyote Dog Rabies Virus infection treated with PEP and live attenuated ERA-R333 mutant

SEQUENCE LISTING

<160> NUMBER OF SEQ ID NOS: 65

<210> SEQ ID NO 1
<211> LENGTH: 11931
<212> TYPE: DNA
<213> ORGANISM: rabies virus
<220> FEATURE:
<221> NAME/KEY: misc_feature
<222> LOCATION: (1)..(58)
<223> OTHER INFORMATION: Leader Region
<220> FEATURE:
<221> NAME/KEY: CDS
<222> LOCATION: (71)..(1420)
<223> OTHER INFORMATION: N gene
<220> FEATURE:
<221> NAME/KEY: CDS
<222> LOCATION: (1514)..(2404)
<223> OTHER INFORMATION: P gene
<220> FEATURE:
<221> NAME/KEY: CDS
<222> LOCATION: (2496)..(3101)
<223> OTHER INFORMATION: M gene
<220> FEATURE:
<221> NAME/KEY: CDS
<222> LOCATION: (3317)..(4888)
<223> OTHER INFORMATION: G gene
<220> FEATURE:
<221> NAME/KEY: misc_feature
<222> LOCATION: (4964)..(5362)
<223> OTHER INFORMATION: Psi region
<220> FEATURE:
<221> NAME/KEY: CDS
<222> LOCATION: (5417)..(11797)
<223> OTHER INFORMATION: L gene
<220> FEATURE:
<221> NAME/KEY: misc_feature
<222> LOCATION: (11862)..(11931)
<223> OTHER INFORMATION: Trailer region

<400> SEQUENCE: 1

```
acgcttaaca accagatcaa agaaaaaaca gacattgtca attgcaaagc aaaaatgtaa        60
cacccctaca atg gat gcc gac aag att gta ttc aaa gtc aat aat cag         109
         Met Asp Ala Asp Lys Ile Val Phe Lys Val Asn Asn Gln
           1               5                  10 gtg gtc tct ttg aag cct gag att atc gtg gat caa cat gag tac aag        157
Val Val Ser Leu Lys Pro Glu Ile Ile Val Asp Gln His Glu Tyr Lys
         15                  20                  25 tac cct gcc atc aaa gat ttg aaa aag ccc tgt ata acc cta gga aag        205
Tyr Pro Ala Ile Lys Asp Leu Lys Lys Pro Cys Ile Thr Leu Gly Lys
 30                  35                  40                  45 gct ccc gat tta aat aaa gca tac aag tca gtt ttg tca ggc atg agc        253
Ala Pro Asp Leu Asn Lys Ala Tyr Lys Ser Val Leu Ser Gly Met Ser
                 50                  55                  60 gcc gcc aaa ctt gat cct gac gat gta tgt tcc tat ttg gca gcg gca        301
Ala Ala Lys Leu Asp Pro Asp Asp Val Cys Ser Tyr Leu Ala Ala Ala
             65                  70                  75 atg cag ttt ttt gag ggg aca tgt ccg gaa gac tgg acc agc tat gga        349
Met Gln Phe Phe Glu Gly Thr Cys Pro Glu Asp Trp Thr Ser Tyr Gly
         80                  85                  90 atc gtg att gca cga aaa gga gat aag atc acc cca ggt tct ctg gtg        397
Ile Val Ile Ala Arg Lys Gly Asp Lys Ile Thr Pro Gly Ser Leu Val
     95                 100                 105 gag ata aaa cgt act gat gta gaa ggg aat tgg gct ctg aca gga ggc        445
Glu Ile Lys Arg Thr Asp Val Glu Gly Asn Trp Ala Leu Thr Gly Gly
110                 115                 120                 125 atg gaa ctg aca aga gac ccc act gtc cct gag cat gcg tcc tta gtc        493
```

```
                Met Glu Leu Thr Arg Asp Pro Thr Val Pro Glu His Ala Ser Leu Val
                                130                 135                 140 ggt ctt ctc ttg agt ctg tat agg ttg agc aaa ata tcc ggg caa aac        541
Gly Leu Leu Leu Ser Leu Tyr Arg Leu Ser Lys Ile Ser Gly Gln Asn
                145                 150                 155 act ggt aac tat aag aca aac att gca gac agg ata gag cag att ttt        589
Thr Gly Asn Tyr Lys Thr Asn Ile Ala Asp Arg Ile Glu Gln Ile Phe
            160                 165                 170 gag aca gcc cct ttt gtt aaa atc gtg gaa cac cat act cta atg aca        637
Glu Thr Ala Pro Phe Val Lys Ile Val Glu His His Thr Leu Met Thr
        175                 180                 185 act cac aaa atg tgt gct aat tgg agt act ata cca aac ttc aga ttt        685
Thr His Lys Met Cys Ala Asn Trp Ser Thr Ile Pro Asn Phe Arg Phe
190                 195                 200                 205 ttg gcc gga acc tat gac atg ttt ttc tcc cgg att gag cat cta tat        733
Leu Ala Gly Thr Tyr Asp Met Phe Phe Ser Arg Ile Glu His Leu Tyr
                210                 215                 220 tca gca atc aga gtg ggc aca gtt gtc act gct tat gaa gac tgt tca        781
Ser Ala Ile Arg Val Gly Thr Val Val Thr Ala Tyr Glu Asp Cys Ser
                225                 230                 235 gga ctg gta tca ttt act ggg ttc ata aaa caa atc aat ctc acc gct        829
Gly Leu Val Ser Phe Thr Gly Phe Ile Lys Gln Ile Asn Leu Thr Ala
            240                 245                 250 aga gag gca ata cta tat ttc ttc cac aag aac ttt gag gaa gag ata        877
Arg Glu Ala Ile Leu Tyr Phe Phe His Lys Asn Phe Glu Glu Glu Ile
        255                 260                 265 aga aga atg ttt gag cca ggg cag gag aca gct gtt cct cac tct tat        925
Arg Arg Met Phe Glu Pro Gly Gln Glu Thr Ala Val Pro His Ser Tyr
270                 275                 280                 285 ttc atc cac ttc cgt tca cta ggc ttg agt ggg aaa tct cct tat tca        973
Phe Ile His Phe Arg Ser Leu Gly Leu Ser Gly Lys Ser Pro Tyr Ser
                290                 295                 300 tca aat gct gtt ggt cac gtg ttc aat ctc att cac ttt gta gga tgc       1021
Ser Asn Ala Val Gly His Val Phe Asn Leu Ile His Phe Val Gly Cys
                305                 310                 315 tat atg ggt caa gtc aga tcc cta aat gca acg gtt att gct gca tgt       1069
Tyr Met Gly Gln Val Arg Ser Leu Asn Ala Thr Val Ile Ala Ala Cys
            320                 325                 330 gct cct cat gaa atg tct gtt cta ggg ggc tat ctg gga gag gaa ttc       1117
Ala Pro His Glu Met Ser Val Leu Gly Gly Tyr Leu Gly Glu Glu Phe
        335                 340                 345 ttc ggg aaa ggg aca ttt gaa aga aga ttc ttc aga gat gag aaa gaa       1165
Phe Gly Lys Gly Thr Phe Glu Arg Arg Phe Phe Arg Asp Glu Lys Glu
350                 355                 360                 365 ctt caa gaa tac gag gcg gct gaa ctg aca aag act gac gta gca ctg       1213
Leu Gln Glu Tyr Glu Ala Ala Glu Leu Thr Lys Thr Asp Val Ala Leu
                370                 375                 380 gca gat gat gga act gtc aac tct gac gac gag gac tac ttc tca ggt       1261
Ala Asp Asp Gly Thr Val Asn Ser Asp Asp Glu Asp Tyr Phe Ser Gly
                385                 390                 395 gaa acc aga agt ccg gag gct gtt tat act cga atc atg atg aat gga       1309
Glu Thr Arg Ser Pro Glu Ala Val Tyr Thr Arg Ile Met Met Asn Gly
            400                 405                 410 ggt cga cta aag aga tct cac ata cgg aga tat gtc tca gtc agt tcc       1357
Gly Arg Leu Lys Arg Ser His Ile Arg Arg Tyr Val Ser Val Ser Ser
        415                 420                 425 aat cat caa gcc cgt cca aac tca ttc gcc gag ttt cta aac aag aca       1405
Asn His Gln Ala Arg Pro Asn Ser Phe Ala Glu Phe Leu Asn Lys Thr
430                 435                 440                 445
```

-continued

| | |
|---|---|
| tat tcg agt gac tca taagaagttg aacaacaaaa tgccggaaat ctacggattg<br>Tyr Ser Ser Asp Ser<br>450 | 1460 |
| tgtatatcca tcatgaaaaa aactaacacc cctcctttcg aaccatccca aac atg<br>                                                                    Met | 1516 |
| agc aag atc ttt gtc aat cct agt gct att aga gcc ggt ctg gcc gat<br>Ser Lys Ile Phe Val Asn Pro Ser Ala Ile Arg Ala Gly Leu Ala Asp<br>               455                   460                 465 | 1564 |
| ctt gag atg gct gaa gaa act gtt gat ctg atc aat aga aat atc gaa<br>Leu Glu Met Ala Glu Glu Thr Val Asp Leu Ile Asn Arg Asn Ile Glu<br>       470                 475                 480 | 1612 |
| gac aat cag gct cat ctc caa ggg gaa ccc ata gaa gtg gac aat ctc<br>Asp Asn Gln Ala His Leu Gln Gly Glu Pro Ile Glu Val Asp Asn Leu<br>485                 490                 495 | 1660 |
| cct gag gat atg ggg cga ctt cac ctg gat gat gga aaa tcg ccc aac<br>Pro Glu Asp Met Gly Arg Leu His Leu Asp Asp Gly Lys Ser Pro Asn<br>500                 505                 510               515 | 1708 |
| cct ggt gag atg gcc aag gtg gga gaa ggc aag tat cga gag gac ttt<br>Pro Gly Glu Met Ala Lys Val Gly Glu Gly Lys Tyr Arg Glu Asp Phe<br>               520                   525                 530 | 1756 |
| cag atg gat gaa gga gag gat ctt agc ttc ctg ttc cag tca tac ctg<br>Gln Met Asp Glu Gly Glu Asp Leu Ser Phe Leu Phe Gln Ser Tyr Leu<br>       535                 540                 545 | 1804 |
| gaa aat gtt gga gtc caa ata gtc aga caa atg agg tca gga gag aga<br>Glu Asn Val Gly Val Gln Ile Val Arg Gln Met Arg Ser Gly Glu Arg<br>550                 555                 560 | 1852 |
| ttt ctc aag ata tgg tca cag acc gta gaa gag att ata tcc tat gtc<br>Phe Leu Lys Ile Trp Ser Gln Thr Val Glu Glu Ile Ile Ser Tyr Val<br>565                 570                 575 | 1900 |
| gcg gtc aac ttt ccc aac cct cca gga aag tct tca gag gat aaa tca<br>Ala Val Asn Phe Pro Asn Pro Pro Gly Lys Ser Ser Glu Asp Lys Ser<br>580                 585                 590               595 | 1948 |
| acc cag act act ggc cga gag ctc aag aag gag aca aca ccc act cct<br>Thr Gln Thr Thr Gly Arg Glu Leu Lys Lys Glu Thr Thr Pro Thr Pro<br>               600                   605                 610 | 1996 |
| tct cag aga gaa agc caa tca tcg aaa gcc agg atg gcg gct caa att<br>Ser Gln Arg Glu Ser Gln Ser Ser Lys Ala Arg Met Ala Ala Gln Ile<br>       615                 620                 625 | 2044 |
| gct tct ggc cct cca gcc ctt gaa tgg tcg gcc acc aat gaa gag gat<br>Ala Ser Gly Pro Pro Ala Leu Glu Trp Ser Ala Thr Asn Glu Glu Asp<br>630                 635                 640 | 2092 |
| gat cta tca gtg gag gct gag atc gct cac cag att gca gaa agt ttc<br>Asp Leu Ser Val Glu Ala Glu Ile Ala His Gln Ile Ala Glu Ser Phe<br>645                 650                 655 | 2140 |
| tcc aaa aaa tat aag ttt ccc tct cga tcc tca ggg ata ctc ttg tat<br>Ser Lys Lys Tyr Lys Phe Pro Ser Arg Ser Ser Gly Ile Leu Leu Tyr<br>660                 665                 670               675 | 2188 |
| aat ttt gag caa ttg aaa atg aac ctt gat gat ata gtt aaa gag gca<br>Asn Phe Glu Gln Leu Lys Met Asn Leu Asp Asp Ile Val Lys Glu Ala<br>               680                   685                 690 | 2236 |
| aaa aat gta cca ggt gtg acc cgt tta gcc cat gac ggg tcc aaa ctc<br>Lys Asn Val Pro Gly Val Thr Arg Leu Ala His Asp Gly Ser Lys Leu<br>       695                 700                 705 | 2284 |
| ccc cta aga tgt gta ctg gga tgg gtc gct ttg gcc aac cct aag aaa<br>Pro Leu Arg Cys Val Leu Gly Trp Val Ala Leu Ala Asn Pro Lys Lys<br>710                 715                 720 | 2332 |
| ttc cag ttg tta gtc gaa tcc gac aag ctg agt aaa atc atg caa gat<br>Phe Gln Leu Leu Val Glu Ser Asp Lys Leu Ser Lys Ile Met Gln Asp<br>725                 730                 735 | 2380 |

```
gac ttg aat cgc tat aca tct tgc taaccgaacc tctccactca gtccctctag      2434
Asp Leu Asn Arg Tyr Thr Ser Cys
740                 745 acaataaagt ccgagatgtc ctaaagtcaa catgaaaaaa acaggcaaca ccactgataa      2494 a atg aac ttt cta cgt aag ata gtg aaa aat tgc agg gac gag gac act      2543
  Met Asn Phe Leu Arg Lys Ile Val Lys Asn Cys Arg Asp Glu Asp Thr
              750                 755                 760 caa aaa ccc tct ccc gtg tca gcc cct ctg gat gac gat gac ttg tgg      2591
Gln Lys Pro Ser Pro Val Ser Ala Pro Leu Asp Asp Asp Asp Leu Trp
765                 770                 775 ctt cca ccc cct gaa tac gtc ccg ctg aaa gaa ctt aca agc aag aag      2639
Leu Pro Pro Pro Glu Tyr Val Pro Leu Lys Glu Leu Thr Ser Lys Lys
780                 785                 790                 795 aac atg agg aac ttt tgt atc aac gga ggg gtt aaa gtg tgt agc ccg      2687
Asn Met Arg Asn Phe Cys Ile Asn Gly Gly Val Lys Val Cys Ser Pro
                800                 805                 810 aat ggt tac tcg ttc agg atc ctg cgg cac att ctg aaa tca ttc gac      2735
Asn Gly Tyr Ser Phe Arg Ile Leu Arg His Ile Leu Lys Ser Phe Asp
            815                 820                 825 gag ata tat tct ggg aat cat agg atg atc ggg tta gcc aaa gta gtt      2783
Glu Ile Tyr Ser Gly Asn His Arg Met Ile Gly Leu Ala Lys Val Val
        830                 835                 840 att gga ctg gct ttg tca gga tct cca gtc cct gag ggc atg aac tgg      2831
Ile Gly Leu Ala Leu Ser Gly Ser Pro Val Pro Glu Gly Met Asn Trp
    845                 850                 855 gta tac aaa ttg agg aga acc ttt atc ttc cag tgg gct gat tcc agg      2879
Val Tyr Lys Leu Arg Arg Thr Phe Ile Phe Gln Trp Ala Asp Ser Arg
860                 865                 870                 875 ggc cct ctt gaa ggg gag gag ttg gaa tac tct cag gag atc act tgg      2927
Gly Pro Leu Glu Gly Glu Glu Leu Glu Tyr Ser Gln Glu Ile Thr Trp
                880                 885                 890 gat gat gat act gag ttc gtc gga ttg caa ata aga gtg att gca aaa      2975
Asp Asp Asp Thr Glu Phe Val Gly Leu Gln Ile Arg Val Ile Ala Lys
            895                 900                 905 cag tgt cat atc cag ggc aga atc tgg tgt atc aac atg aac ccg aga      3023
Gln Cys His Ile Gln Gly Arg Ile Trp Cys Ile Asn Met Asn Pro Arg
        910                 915                 920 gca tgt caa cta tgg tct gac atg tct ctt cag aca caa agg tcc gaa      3071
Ala Cys Gln Leu Trp Ser Asp Met Ser Leu Gln Thr Gln Arg Ser Glu
    925                 930                 935 gag gac aaa gat tcc tct ctg ctt cta gaa taatcagatt atatcccgca        3121
Glu Asp Lys Asp Ser Ser Leu Leu Leu Glu
940                 945 aatttatcac ttgtttacct ctggaggaga gaacatatgg gctcaactcc aacccttggg    3181
agcaatataa caaaaaacat gttatggtgc cattaaaccg ctgcatttca tcaaagtcaa    3241
gttgattacc tttacatttt gatcctcttg gatgtgaaaa aaactattaa catccctcaa    3301
aagactcaag gaaag atg gtt cct cag gct ctc ctg ttt gta ccc ctt ctg    3352
              Met Val Pro Gln Ala Leu Leu Phe Val Pro Leu Leu
                            950                 955                 960 gtt ttt cca ttg tgt ttt ggg aaa ttc cct att tac acg ata cca gac      3400
Val Phe Pro Leu Cys Phe Gly Lys Phe Pro Ile Tyr Thr Ile Pro Asp
            965                 970                 975 aag ctt ggt ccc tgg agc ccg att gac ata cat cac ctc agc tgc cca      3448
Lys Leu Gly Pro Trp Ser Pro Ile Asp Ile His His Leu Ser Cys Pro
        980                 985                 990 aac aat ttg gta gtg gag gac  gaa gga tgc acc aac  ctg tca ggg ttc    3496
Asn Asn Leu Val Val Glu Asp  Glu Gly Cys Thr Asn  Leu Ser Gly Phe
    995                 1000                 1005
```

```
                                              -continued tcc tac atg gaa ctt aaa gtt gga tac atc tta gcc ata aaa atg   3541
Ser Tyr Met Glu Leu Lys Val Gly Tyr Ile Leu Ala Ile Lys Met
1010            1015                1020 aac ggg ttc act tgc aca ggc gtt gtg acg gag gct gaa acc tat   3586
Asn Gly Phe Thr Cys Thr Gly Val Val Thr Glu Ala Glu Thr Tyr
1025            1030                1035 act aac ttc gtt ggt tat gtc aca acc acg ttc aaa aga aag cat   3631
Thr Asn Phe Val Gly Tyr Val Thr Thr Thr Phe Lys Arg Lys His
1040            1045                1050 ttc cgc cca aca cca gat gca tgt aga gcc gcg tac aac tgg aag   3676
Phe Arg Pro Thr Pro Asp Ala Cys Arg Ala Ala Tyr Asn Trp Lys
1055            1060                1065 atg gcc ggt gac ccc aga tat gaa gag tct cta cac aat ccg tac   3721
Met Ala Gly Asp Pro Arg Tyr Glu Glu Ser Leu His Asn Pro Tyr
1070            1075                1080 cct gac tac cac tgg ctt cga act gta aaa acc acc aag gag tct   3766
Pro Asp Tyr His Trp Leu Arg Thr Val Lys Thr Thr Lys Glu Ser
1085            1090                1095 ctc gtt atc ata tct cca agt gtg gca gat ttg gac cca tat gac   3811
Leu Val Ile Ile Ser Pro Ser Val Ala Asp Leu Asp Pro Tyr Asp
1100            1105                1110 aga tcc ctt cac tcg agg gtc ttc cct agc ggg aag tgc tca gga   3856
Arg Ser Leu His Ser Arg Val Phe Pro Ser Gly Lys Cys Ser Gly
1115            1120                1125 gta gcg gtg tct tct acc tac tgc tcc act aac cac gat tac acc   3901
Val Ala Val Ser Ser Thr Tyr Cys Ser Thr Asn His Asp Tyr Thr
1130            1135                1140 att tgg atg ccc gag aat ccg aga cta ggg atg tct tgt gac att   3946
Ile Trp Met Pro Glu Asn Pro Arg Leu Gly Met Ser Cys Asp Ile
1145            1150                1155 ttt acc aat agt agg ggg aag aga gca tcc aaa ggg agt gag act   3991
Phe Thr Asn Ser Arg Gly Lys Arg Ala Ser Lys Gly Ser Glu Thr
1160            1165                1170 tgc ggc ttt gta gat gaa aga ggc cta tat aag tct tta aaa gga   4036
Cys Gly Phe Val Asp Glu Arg Gly Leu Tyr Lys Ser Leu Lys Gly
1175            1180                1185 gca tgc aaa ctc aag tta tgt gga gtt cta gga ctt aga ctt atg   4081
Ala Cys Lys Leu Lys Leu Cys Gly Val Leu Gly Leu Arg Leu Met
1190            1195                1200 gat gga aca tgg gtc gcg atg caa aca tca aat gaa acc aaa tgg   4126
Asp Gly Thr Trp Val Ala Met Gln Thr Ser Asn Glu Thr Lys Trp
1205            1210                1215 tgc ccc ccc gat cag ttg gtg aac ctg cac gac ttt cgc tca gac   4171
Cys Pro Pro Asp Gln Leu Val Asn Leu His Asp Phe Arg Ser Asp
1220            1225                1230 gaa att gag cac ctt gtt gta gag gag ttg gtc agg aag aga gag   4216
Glu Ile Glu His Leu Val Val Glu Glu Leu Val Arg Lys Arg Glu
1235            1240                1245 gag tgt ctg gat gca cta gag tcc atc atg aca acc aag tca gtg   4261
Glu Cys Leu Asp Ala Leu Glu Ser Ile Met Thr Thr Lys Ser Val
1250            1255                1260 agt ttc aga cgt ccc agt cat tta aga aaa ctt gtc cct ggg ttt   4306
Ser Phe Arg Arg Pro Ser His Leu Arg Lys Leu Val Pro Gly Phe
1265            1270                1275 gga aaa gca tat acc ata ttc aac aag acc ttg atg gaa gcc gat   4351
Gly Lys Ala Tyr Thr Ile Phe Asn Lys Thr Leu Met Glu Ala Asp
1280            1285                1290 gct cac tac aag tca gtc aga act tgg aat gag atc ctc cct tca   4396
Ala His Tyr Lys Ser Val Arg Thr Trp Asn Glu Ile Leu Pro Ser
```

-continued

| | | | | | | | | | | |
|---|---|---|---|---|---|---|---|---|---|---|
| | | | 1295 | | | | 1300 | | 1305 | |

```
aaa ggg tgt tta aga gtt ggg ggg agg tgt cat cct cat gtg aac    4441
Lys Gly Cys Leu Arg Val Gly Gly Arg Cys His Pro His Val Asn
1310            1315                1320 ggg gtg ttt ttc aat ggt ata ata tta gga cct gac ggc aat gtc    4486
Gly Val Phe Phe Asn Gly Ile Ile Leu Gly Pro Asp Gly Asn Val
1325            1330                1335 tta atc cca gag atg caa tca tcc ctc ctc cag caa cat atg gag    4531
Leu Ile Pro Glu Met Gln Ser Ser Leu Leu Gln Gln His Met Glu
1340            1345                1350 ttg ttg gaa tcc tcg gtt atc ccc ctt gtg cac ccc ctg gca gac    4576
Leu Leu Glu Ser Ser Val Ile Pro Leu Val His Pro Leu Ala Asp
1355            1360                1365 ccg tct acc gtt ttc aag gac ggt gac gag gct gag gat ttt gtt    4621
Pro Ser Thr Val Phe Lys Asp Gly Asp Glu Ala Glu Asp Phe Val
1370            1375                1380 gaa gtt cac ctt ccc gat gtg cac aat cag gtc tca gga gtt gac    4666
Glu Val His Leu Pro Asp Val His Asn Gln Val Ser Gly Val Asp
1385            1390                1395 ttg ggt ctc ccg aac tgg ggg aag tat gta tta ctg agt gca ggg    4711
Leu Gly Leu Pro Asn Trp Gly Lys Tyr Val Leu Leu Ser Ala Gly
1400            1405                1410 gcc ctg act gcc ttg atg ttg ata att ttc ctg atg aca tgt tgt    4756
Ala Leu Thr Ala Leu Met Leu Ile Ile Phe Leu Met Thr Cys Cys
1415            1420                1425 aga aga gtc aat cga tca gaa cct acg caa cac aat ctc aga ggg    4801
Arg Arg Val Asn Arg Ser Glu Pro Thr Gln His Asn Leu Arg Gly
1430            1435                1440 aca ggg agg gag gtg tca gtc act ccc caa agc ggg aag atc ata    4846
Thr Gly Arg Glu Val Ser Val Thr Pro Gln Ser Gly Lys Ile Ile
1445            1450                1455 tct tca tgg gaa tca cac aag agt ggg ggt gag acc aga ctg        4888
Ser Ser Trp Glu Ser His Lys Ser Gly Gly Glu Thr Arg Leu
1460            1465                1470 tgaggactgg ccgtcctttc aacgatccaa gtcctgaaga tcacctcccc ttgggggtt 4948 cttttttgaaa aaaacctggg gttcaatagt cctcctcgaa ctccatgcaa ctgggtagat 5008 tcaagagtca tgagattttc attaatcctc tcagttgatc aagcaagatc atgtagattc 5068 tcataatagg ggagatcttc tagcagtttc agtgactaac ggtactttca ttctccagga 5128 actgacacca acagttgtag acaaaccacg gggtgtctcg ggtgactctg tgcttgggca 5188 cagacaaagg tcatggtgtg ttccatgata gcggactcag gatgagttaa ttgagagagg 5248 cagtcttcct cccgtgaagg acataagcag tagctcacaa tcatcccgcg tctcagcaaa 5308 gtgtgcataa ttataaagtg ctgggtcatc taagcttttc agtcgagaaa aaaacattag 5368 atcagaagaa caactggcaa cacttctcaa cctgagacct acttcaag atg ctc  gat 5425
                                                     Met Leu Asp
                                                              1475 cct gga gag gtc tat gat gac cct att gac cca atc gag tta gag     5470
Pro Gly Glu Val Tyr Asp Asp Pro Ile Asp Pro Ile Glu Leu Glu
         1480                1485                1490 gat gaa ccc aga gga acc ccc act gtc ccc aac atc ttg agg aac     5515
Asp Glu Pro Arg Gly Thr Pro Thr Val Pro Asn Ile Leu Arg Asn
    1495                1500                1505 tct gac tac aat ctc aac tct cct ttg ata gaa gat cct gct aga     5560
Ser Asp Tyr Asn Leu Asn Ser Pro Leu Ile Glu Asp Pro Ala Arg
    1510                1515                1520 cta atg tta gaa tgg tta aaa aca ggg aat aga cct tat cgg atg     5605
```

```
                Leu Met Leu Glu  Trp Leu Lys Thr  Gly Asn Arg Pro  Tyr Arg Met
                            1525             1530              1535 act cta aca gac  aat tgc tcc agg  tct ttc aga gtt  ttg aaa gat              5650
Thr Leu Thr Asp  Asn Cys Ser Arg  Ser Phe Arg Val  Leu Lys Asp
            1540             1545              1550 tat ttc aag aag  gta gat ttg ggt  tct ctc aag gtg  ggc gga atg              5695
Tyr Phe Lys Lys  Val Asp Leu Gly  Ser Leu Lys Val  Gly Gly Met
            1555             1560              1565 gct gca cag tca  atg att tct ctc  tgg tta tat ggt  gcc cac tct              5740
Ala Ala Gln Ser  Met Ile Ser Leu  Trp Leu Tyr Gly  Ala His Ser
            1570             1575              1580 gaa tcc aac agg  agc cgg aga tgt  ata aca gac ttg  gcc cat ttc              5785
Glu Ser Asn Arg  Ser Arg Arg Cys  Ile Thr Asp Leu  Ala His Phe
            1585             1590              1595 tat tcc aag tcg  tcc ccc ata gag  aag ctg ttg aat  ctc acg cta              5830
Tyr Ser Lys Ser  Ser Pro Ile Glu  Lys Leu Leu Asn  Leu Thr Leu
            1600             1605              1610 gga aat aga ggg  ctg aga atc ccc  cca gag gga gtg  tta agt tgc              5875
Gly Asn Arg Gly  Leu Arg Ile Pro  Pro Glu Gly Val  Leu Ser Cys
            1615             1620              1625 ctt gag agg gtt  gat tat gat aat  gca ttt gga agg  tat ctt gcc              5920
Leu Glu Arg Val  Asp Tyr Asp Asn  Ala Phe Gly Arg  Tyr Leu Ala
            1630             1635              1640 aac acg tat tcc  tct tac ttg ttc  ttc cat gta atc  acc tta tac              5965
Asn Thr Tyr Ser  Ser Tyr Leu Phe  Phe His Val Ile  Thr Leu Tyr
            1645             1650              1655 atg aac gcc cta  gac tgg gat gaa  gaa aag acc atc  cta gca tta              6010
Met Asn Ala Leu  Asp Trp Asp Glu  Glu Lys Thr Ile  Leu Ala Leu
            1660             1665              1670 tgg aaa gat tta  acc tca gtg gac  atc ggg aag gac  ttg gta aag              6055
Trp Lys Asp Leu  Thr Ser Val Asp  Ile Gly Lys Asp  Leu Val Lys
            1675             1680              1685 ttc aaa gac caa  ata tgg gga ctg  ccg atc gtg aca  aag gac ttt              6100
Phe Lys Asp Gln  Ile Trp Gly Leu  Pro Ile Val Thr  Lys Asp Phe
            1690             1695              1700 gtt tac tcc caa  agt tcc aat tgt  ctt ttt gac aga  aac tac aca              6145
Val Tyr Ser Gln  Ser Ser Asn Cys  Leu Phe Asp Arg  Asn Tyr Thr
            1705             1710              1715 ctt atg cta aaa  gaa ctt ttc ttg  tct cgc ttc aac  tcc tta atg              6190
Leu Met Leu Lys  Glu Leu Phe Leu  Ser Arg Phe Asn  Ser Leu Met
            1720             1725              1730 gtc ttg ctc tct  ccc cca gag ccc  cga tac tca gat  gac ttg ata              6235
Val Leu Leu Ser  Pro Pro Glu Pro  Arg Tyr Ser Asp  Asp Leu Ile
            1735             1740              1745 tct caa cta tgc  cag ctg tac att  gct ggg gat caa  gtc ttg tct              6280
Ser Gln Leu Cys  Gln Leu Tyr Ile  Ala Gly Asp Gln  Val Leu Ser
            1750             1755              1760 atg tgt gga aac  tcc ggc tat gaa  gtc atc aaa ata  ttg gag cca              6325
Met Cys Gly Asn  Ser Gly Tyr Glu  Val Ile Lys Ile  Leu Glu Pro
            1765             1770              1775 tat gtc gtg aat  agt tta gtc cag  aga gca gaa aag  ttt agg cct              6370
Tyr Val Val Asn  Ser Leu Val Gln  Arg Ala Glu Lys  Phe Arg Pro
            1780             1785              1790 ctc att cat tcc  ttg gga gac ttt  cct gta ttt ata  aaa gac aag              6415
Leu Ile His Ser  Leu Gly Asp Phe  Pro Val Phe Ile  Lys Asp Lys
            1795             1800              1805 gta agt caa ctt  gaa gag acg ttc  ggt ccc tgt gca  aga agg ttc              6460
Val Ser Gln Leu  Glu Glu Thr Phe  Gly Pro Cys Ala  Arg Arg Phe
            1810             1815              1820
```

```
ttt agg gct ctg gat caa ttc gac aac ata cat gac ttg gtt ttt       6505
Phe Arg Ala Leu Asp Gln Phe Asp Asn Ile His Asp Leu Val Phe
            1825                1830                1835 gtg tat ggc tgt tac agg cat tgg ggg cac cca tat ata gat tat       6550
Val Tyr Gly Cys Tyr Arg His Trp Gly His Pro Tyr Ile Asp Tyr
    1840                1845                1850 cga aag ggt ctg tca aaa cta tat gat cag gtt cac att aaa aaa       6595
Arg Lys Gly Leu Ser Lys Leu Tyr Asp Gln Val His Ile Lys Lys
        1855                1860                1865 gtg ata gat aag tcc tac cag gag tgc tta gca agc gac cta gcc       6640
Val Ile Asp Lys Ser Tyr Gln Glu Cys Leu Ala Ser Asp Leu Ala
            1870                1875                1880 agg agg atc ctt aga tgg ggt ttt gat aag tac tcc aag tgg tat       6685
Arg Arg Ile Leu Arg Trp Gly Phe Asp Lys Tyr Ser Lys Trp Tyr
                1885                1890                1895 ctg gat tca aga ttc cta gcc cga gac cac ccc ttg act ccc tat       6730
Leu Asp Ser Arg Phe Leu Ala Arg Asp His Pro Leu Thr Pro Tyr
    1900                1905                1910 atc aaa acc caa aca tgg cca ccc aaa cat att gta gac ttg gtg       6775
Ile Lys Thr Gln Thr Trp Pro Pro Lys His Ile Val Asp Leu Val
        1915                1920                1925 ggg gat aca tgg cac aag ctc ccg atc acg cag atc ttt gag att       6820
Gly Asp Thr Trp His Lys Leu Pro Ile Thr Gln Ile Phe Glu Ile
            1930                1935                1940 cct gaa tca atg gat ccg tca gaa ata ttg gat gac aaa tca cat       6865
Pro Glu Ser Met Asp Pro Ser Glu Ile Leu Asp Asp Lys Ser His
                1945                1950                1955 tct ttc acc aga acg aga cta gct tct tgg ctg tca gaa aac cga       6910
Ser Phe Thr Arg Thr Arg Leu Ala Ser Trp Leu Ser Glu Asn Arg
    1960                1965                1970 ggg gga cct gtt cct agc gaa aaa gtt att atc acg gcc ctg tct       6955
Gly Gly Pro Val Pro Ser Glu Lys Val Ile Ile Thr Ala Leu Ser
        1975                1980                1985 aag ccg cct gtc aat ccc cga gag ttt ctg agg tct ata gac ctc       7000
Lys Pro Pro Val Asn Pro Arg Glu Phe Leu Arg Ser Ile Asp Leu
            1990                1995                2000 gga gga ttg cca gat gaa gac ttg ata att ggc ctc aag cca aag       7045
Gly Gly Leu Pro Asp Glu Asp Leu Ile Ile Gly Leu Lys Pro Lys
                2005                2010                2015 gaa cgg gaa ttg aag att gaa ggt cga ttc ttt gct cta atg tca       7090
Glu Arg Glu Leu Lys Ile Glu Gly Arg Phe Phe Ala Leu Met Ser
    2020                2025                2030 tgg aat cta aga ttg tat ttt gtc atc act gaa aaa ctc ttg gcc       7135
Trp Asn Leu Arg Leu Tyr Phe Val Ile Thr Glu Lys Leu Leu Ala
        2035                2040                2045 aac tac atc ttg cca ctt ttt gac gcg ctg act atg aca gac aac       7180
Asn Tyr Ile Leu Pro Leu Phe Asp Ala Leu Thr Met Thr Asp Asn
            2050                2055                2060 ctg aac aag gtg ttt aaa aag ctg atc gac agg gtc acc ggg caa       7225
Leu Asn Lys Val Phe Lys Lys Leu Ile Asp Arg Val Thr Gly Gln
                2065                2070                2075 ggg ctt ttg gac tat tca agg gtc aca tat gca ttt cac ctg gac       7270
Gly Leu Leu Asp Tyr Ser Arg Val Thr Tyr Ala Phe His Leu Asp
    2080                2085                2090 tat gaa aag tgg aac aac cat caa aga tta gag tca aca gag gat       7315
Tyr Glu Lys Trp Asn Asn His Gln Arg Leu Glu Ser Thr Glu Asp
        2095                2100                2105 gta ttt tct gtc cta gat caa gtg ttt gga ttg aag aga gtg ttt       7360
Val Phe Ser Val Leu Asp Gln Val Phe Gly Leu Lys Arg Val Phe
            2110                2115                2120
```

| | | | | | | | | | | | | |
|---|---|---|---|---|---|---|---|---|---|---|---|---|
| tct | aga | aca | cac | gag | ttt | ttt | caa | aag | gcc | tgg | atc | tat | tat | tca | 7405 |
| Ser | Arg | Thr | His | Glu | Phe | Phe | Gln | Lys | Ala | Trp | Ile | Tyr | Tyr | Ser | |
| | | 2125 | | | | 2130 | | | | | 2135 | | | | |
| gac | aga | tca | gac | ctc | atc | ggg | tta | cgg | gag | gat | caa | ata | tac | tgc | 7450 |
| Asp | Arg | Ser | Asp | Leu | Ile | Gly | Leu | Arg | Glu | Asp | Gln | Ile | Tyr | Cys | |
| | | 2140 | | | | 2145 | | | | | 2150 | | | | |
| tta | gat | gcg | tcc | aac | ggc | cca | acc | tgt | tgg | aat | ggc | cag | gat | ggc | 7495 |
| Leu | Asp | Ala | Ser | Asn | Gly | Pro | Thr | Cys | Trp | Asn | Gly | Gln | Asp | Gly | |
| | | 2155 | | | | 2160 | | | | | 2165 | | | | |
| ggg | cta | gaa | ggc | tta | cgg | cag | aag | ggc | tgg | agt | cta | gtc | agc | tta | 7540 |
| Gly | Leu | Glu | Gly | Leu | Arg | Gln | Lys | Gly | Trp | Ser | Leu | Val | Ser | Leu | |
| | | 2170 | | | | 2175 | | | | | 2180 | | | | |
| ttg | atg | ata | gat | aga | gaa | tct | caa | atc | agg | aac | aca | aga | acc | aaa | 7585 |
| Leu | Met | Ile | Asp | Arg | Glu | Ser | Gln | Ile | Arg | Asn | Thr | Arg | Thr | Lys | |
| | | 2185 | | | | 2190 | | | | | 2195 | | | | |
| ata | cta | gct | caa | gga | gac | aac | cag | gtt | tta | tgt | ccg | aca | tat | atg | 7630 |
| Ile | Leu | Ala | Gln | Gly | Asp | Asn | Gln | Val | Leu | Cys | Pro | Thr | Tyr | Met | |
| | | 2200 | | | | 2205 | | | | | 2210 | | | | |
| ttg | tcg | cca | ggg | cta | tct | caa | gag | ggg | ctc | ctc | tat | gaa | ttg | gag | 7675 |
| Leu | Ser | Pro | Gly | Leu | Ser | Gln | Glu | Gly | Leu | Leu | Tyr | Glu | Leu | Glu | |
| | | 2215 | | | | 2220 | | | | | 2225 | | | | |
| aga | ata | tca | agg | aat | gca | ctt | tcg | ata | tac | aga | gcc | gtc | gag | gaa | 7720 |
| Arg | Ile | Ser | Arg | Asn | Ala | Leu | Ser | Ile | Tyr | Arg | Ala | Val | Glu | Glu | |
| | | 2230 | | | | 2235 | | | | | 2240 | | | | |
| ggg | gca | tct | aag | cta | ggg | ctg | atc | acc | aag | aaa | gag | agg | acc | atg | 7765 |
| Gly | Ala | Ser | Lys | Leu | Gly | Leu | Ile | Thr | Lys | Lys | Glu | Glu | Thr | Met | |
| | | 2245 | | | | 2250 | | | | | 2255 | | | | |
| tgt | agt | tat | gac | ttc | ctc | atc | tat | gga | aaa | acc | cct | ttg | ttt | aga | 7810 |
| Cys | Ser | Tyr | Asp | Phe | Leu | Ile | Tyr | Gly | Lys | Thr | Pro | Leu | Phe | Arg | |
| | | 2260 | | | | 2265 | | | | | 2270 | | | | |
| ggt | aac | ata | ttg | gtg | cct | gag | tcc | aaa | aga | tgg | gcc | aga | gtc | tct | 7855 |
| Gly | Asn | Ile | Leu | Val | Pro | Glu | Ser | Lys | Arg | Trp | Ala | Arg | Val | Ser | |
| | | 2275 | | | | 2280 | | | | | 2285 | | | | |
| tgc | gtc | tct | aat | gac | caa | ata | gtc | aac | ctc | gcc | aat | ata | atg | tcg | 7900 |
| Cys | Val | Ser | Asn | Asp | Gln | Ile | Val | Asn | Leu | Ala | Asn | Ile | Met | Ser | |
| | | 2290 | | | | 2295 | | | | | 2300 | | | | |
| aca | gtg | tcc | acc | aat | gcg | cta | aca | gtg | gca | caa | cac | tct | caa | tct | 7945 |
| Thr | Val | Ser | Thr | Asn | Ala | Leu | Thr | Val | Ala | Gln | His | Ser | Gln | Ser | |
| | | 2305 | | | | 2310 | | | | | 2315 | | | | |
| ttg | atc | aaa | ccg | atg | ggg | gat | ttt | ctg | ctc | atg | tca | gta | cag | gca | 7990 |
| Leu | Ile | Lys | Pro | Met | Gly | Asp | Phe | Leu | Leu | Met | Ser | Val | Gln | Ala | |
| | | 2320 | | | | 2325 | | | | | 2330 | | | | |
| gtc | ttt | cac | tac | ctg | cta | ttt | agc | cca | atc | tta | aag | gga | aga | gtt | 8035 |
| Val | Phe | His | Tyr | Leu | Leu | Phe | Ser | Pro | Ile | Leu | Lys | Gly | Arg | Val | |
| | | 2335 | | | | 2340 | | | | | 2345 | | | | |
| tac | aag | att | ctg | agc | gct | gaa | ggg | gat | agc | ttt | ctc | cta | gcc | atg | 8080 |
| Tyr | Lys | Ile | Leu | Ser | Ala | Glu | Gly | Asp | Ser | Phe | Leu | Leu | Ala | Met | |
| | | 2350 | | | | 2355 | | | | | 2360 | | | | |
| tca | agg | ata | atc | tat | cta | gat | cct | tct | ttg | gga | ggg | gta | tct | gga | 8125 |
| Ser | Arg | Ile | Ile | Tyr | Leu | Asp | Pro | Ser | Leu | Gly | Gly | Val | Ser | Gly | |
| | | 2365 | | | | 2370 | | | | | 2375 | | | | |
| atg | tcc | ctc | gga | aga | ttc | cat | ata | cga | cag | ttc | tca | gac | cct | gtc | 8170 |
| Met | Ser | Leu | Gly | Arg | Phe | His | Ile | Arg | Gln | Phe | Ser | Asp | Pro | Val | |
| | | 2380 | | | | 2385 | | | | | 2390 | | | | |
| tct | gaa | ggg | tta | tcc | ttc | tgg | aga | gag | atc | tgg | tta | agc | tcc | cac | 8215 |
| Ser | Glu | Gly | Leu | Ser | Phe | Trp | Arg | Glu | Ile | Trp | Leu | Ser | Ser | His | |
| | | 2395 | | | | 2400 | | | | | 2405 | | | | |
| gag | tcc | tgg | gtt | cac | gcg | ttg | tgt | caa | gag | gct | gga | aac | cca | gat | 8260 |
| Glu | Ser | Trp | Val | His | Ala | Leu | Cys | Gln | Glu | Ala | Gly | Asn | Pro | Asp | |

-continued

|  |  |  |  |
|---|---|---|---|
| 2410 | 2415 | 2420 | |

| ctt gga gag aga aca ctc gag agc ttc act cgc ctt cta gaa gat | 8305 |
| Leu Gly Glu Arg Thr Leu Glu Ser Phe Thr Arg Leu Leu Glu Asp | |
| 2425 2430 2435 | |

| cct acc acc tta aat atc aga gga ggg gcc agt cct acc att cta | 8350 |
| Pro Thr Thr Leu Asn Ile Arg Gly Gly Ala Ser Pro Thr Ile Leu | |
| 2440 2445 2450 | |

| ctc aag gat gca atc aga aag gct tta tat gac gag gtg gac aag | 8395 |
| Leu Lys Asp Ala Ile Arg Lys Ala Leu Tyr Asp Glu Val Asp Lys | |
| 2455 2460 2465 | |

| gtg gag aat tca gag ttt cga gag gca atc ctg ttg tcc aag acc | 8440 |
| Val Glu Asn Ser Glu Phe Arg Glu Ala Ile Leu Leu Ser Lys Thr | |
| 2470 2475 2480 | |

| cat aga gat aat ttt ata ctc ttc tta aca tct gtt gag cct ctg | 8485 |
| His Arg Asp Asn Phe Ile Leu Phe Leu Thr Ser Val Glu Pro Leu | |
| 2485 2490 2495 | |

| ttt cct cga ttt ctc agt gag cta ttc agt tcg tct ttt ttg gga | 8530 |
| Phe Pro Arg Phe Leu Ser Glu Leu Phe Ser Ser Ser Phe Leu Gly | |
| 2500 2505 2510 | |

| atc ccc gag tca atc att gga ttg ata caa aac tcc cga acg ata | 8575 |
| Ile Pro Glu Ser Ile Ile Gly Leu Ile Gln Asn Ser Arg Thr Ile | |
| 2515 2520 2525 | |

| aga agg cag ttt aga aag agt ctc tca aaa act tta gaa gaa tcc | 8620 |
| Arg Arg Gln Phe Arg Lys Ser Leu Ser Lys Thr Leu Glu Glu Ser | |
| 2530 2535 2540 | |

| ttc tac aac tca gag atc cac ggg att agt cgg atg acc cag aca | 8665 |
| Phe Tyr Asn Ser Glu Ile His Gly Ile Ser Arg Met Thr Gln Thr | |
| 2545 2550 2555 | |

| cct cag agg gtt ggg ggg gtg tgg cct tgc tct tca gag agg gca | 8710 |
| Pro Gln Arg Val Gly Gly Val Trp Pro Cys Ser Ser Glu Arg Ala | |
| 2560 2565 2570 | |

| gat cta ctt agg gag atc tct tgg gga aga aaa gtg gta ggc acg | 8755 |
| Asp Leu Leu Arg Glu Ile Ser Trp Gly Arg Lys Val Val Gly Thr | |
| 2575 2580 2585 | |

| aca gtt cct cac cct tct gag atg ttg ggg tta ctt ccc aag tcc | 8800 |
| Thr Val Pro His Pro Ser Glu Met Leu Gly Leu Leu Pro Lys Ser | |
| 2590 2595 2600 | |

| tct att tct tgc act tgt gga gca aca gga gga ggc aat cct aga | 8845 |
| Ser Ile Ser Cys Thr Cys Gly Ala Thr Gly Gly Gly Asn Pro Arg | |
| 2605 2610 2615 | |

| gtt tct gta tca gta ctc ccg tcc ttt gat cag tca ttt ttt tca | 8890 |
| Val Ser Val Ser Val Leu Pro Ser Phe Asp Gln Ser Phe Phe Ser | |
| 2620 2625 2630 | |

| cga ggc ccc cta aag ggg tac ttg ggc tcg tcc acc tct atg tcg | 8935 |
| Arg Gly Pro Leu Lys Gly Tyr Leu Gly Ser Ser Thr Ser Met Ser | |
| 2635 2640 2645 | |

| acc cag cta ttc cat gca tgg gaa aaa gtc act aat gtt cat gtg | 8980 |
| Thr Gln Leu Phe His Ala Trp Glu Lys Val Thr Asn Val His Val | |
| 2650 2655 2660 | |

| gtg aag aga gct cta tcg tta aaa gaa tct ata aac tgg ttc att | 9025 |
| Val Lys Arg Ala Leu Ser Leu Lys Glu Ser Ile Asn Trp Phe Ile | |
| 2665 2670 2675 | |

| act aga gat tcc aac ttg gct caa gct cta att agg aac att atg | 9070 |
| Thr Arg Asp Ser Asn Leu Ala Gln Ala Leu Ile Arg Asn Ile Met | |
| 2680 2685 2690 | |

| tct ctg aca ggc cct gat ttc cct cta gag gag gcc cct gtc ttc | 9115 |
| Ser Leu Thr Gly Pro Asp Phe Pro Leu Glu Glu Ala Pro Val Phe | |
| 2695 2700 2705 | |

| aaa agg acg ggg tca gcc ttg cat agg ttc aag tct gcc aga tac | 9160 |

-continued

| | | | | | | | | | | | | |
|---|---|---|---|---|---|---|---|---|---|---|---|---|
| Lys | Arg | Thr | Gly | Ser | Ala | Leu | His | Arg | Phe | Lys | Ser | Ala | Arg | Tyr |
| | | | 2710 | | | | 2715 | | | | 2720 | |

| agc | gaa | gga | ggg | tat | tct | tct | gtc | tgc | ccg | aac | ctc | ctc | tct | cat | 9205 |
| Ser | Glu | Gly | Gly | Tyr | Ser | Ser | Val | Cys | Pro | Asn | Leu | Leu | Ser | His | |
| | | | 2725 | | | | 2730 | | | | 2735 | | | |

| att | tct | gtt | agt | aca | gac | acc | atg | tct | gat | ttg | acc | caa | gac | ggg | 9250 |
| Ile | Ser | Val | Ser | Thr | Asp | Thr | Met | Ser | Asp | Leu | Thr | Gln | Asp | Gly | |
| | | | 2740 | | | | 2745 | | | | 2750 | | | |

| aag | aac | tac | gat | ttc | atg | ttc | cag | cca | ttg | atg | ctt | tat | gca | cag | 9295 |
| Lys | Asn | Tyr | Asp | Phe | Met | Phe | Gln | Pro | Leu | Met | Leu | Tyr | Ala | Gln | |
| | | | 2755 | | | | 2760 | | | | 2765 | | | |

| aca | tgg | aca | tca | gag | ctg | gta | cag | aga | gac | aca | agg | cta | aga | gac | 9340 |
| Thr | Trp | Thr | Ser | Glu | Leu | Val | Gln | Arg | Asp | Thr | Arg | Leu | Arg | Asp | |
| | | | 2770 | | | | 2775 | | | | 2780 | | | |

| tct | acg | ttt | cat | tgg | cac | ctc | cga | tgc | aac | agg | tgt | gtg | aga | ccc | 9385 |
| Ser | Thr | Phe | His | Trp | His | Leu | Arg | Cys | Asn | Arg | Cys | Val | Arg | Pro | |
| | | | 2785 | | | | 2790 | | | | 2795 | | | |

| att | gac | gac | gtg | acc | ctg | gag | acc | tct | cag | atc | ttc | gag | ttt | ccg | 9430 |
| Ile | Asp | Asp | Val | Thr | Leu | Glu | Thr | Ser | Gln | Ile | Phe | Glu | Phe | Pro | |
| | | | 2800 | | | | 2805 | | | | 2810 | | | |

| gat | gtg | tcg | aaa | aga | ata | tcc | aga | atg | gtt | tct | ggg | gct | gtg | cct | 9475 |
| Asp | Val | Ser | Lys | Arg | Ile | Ser | Arg | Met | Val | Ser | Gly | Ala | Val | Pro | |
| | | | 2815 | | | | 2820 | | | | 2825 | | | |

| cac | ttc | cag | agg | ctt | ccc | gat | atc | cgt | ctg | aga | cca | gga | gat | ttt | 9520 |
| His | Phe | Gln | Arg | Leu | Pro | Asp | Ile | Arg | Leu | Arg | Pro | Gly | Asp | Phe | |
| | | | 2830 | | | | 2835 | | | | 2840 | | | |

| gaa | tct | cta | agc | ggt | aga | gaa | aag | tct | cac | cat | atc | gga | tca | gct | 9565 |
| Glu | Ser | Leu | Ser | Gly | Arg | Glu | Lys | Ser | His | His | Ile | Gly | Ser | Ala | |
| | | | 2845 | | | | 2850 | | | | 2855 | | | |

| cag | ggg | ctc | tta | tac | tca | atc | tta | gtg | gca | att | cac | gac | tca | gga | 9610 |
| Gln | Gly | Leu | Leu | Tyr | Ser | Ile | Leu | Val | Ala | Ile | His | Asp | Ser | Gly | |
| | | | 2860 | | | | 2865 | | | | 2870 | | | |

| tac | aat | gat | gga | acc | atc | ttc | cct | gcc | aac | ata | tac | ggc | aag | gtt | 9655 |
| Tyr | Asn | Asp | Gly | Thr | Ile | Phe | Pro | Ala | Asn | Ile | Tyr | Gly | Lys | Val | |
| | | | 2875 | | | | 2880 | | | | 2885 | | | |

| tcc | cct | aga | gac | tat | ttg | aga | ggg | ctc | gca | agg | gga | gta | ttg | ata | 9700 |
| Ser | Pro | Arg | Asp | Tyr | Leu | Arg | Gly | Leu | Ala | Arg | Gly | Val | Leu | Ile | |
| | | | 2890 | | | | 2895 | | | | 2900 | | | |

| gga | tcc | tcg | att | tgc | ttc | ttg | aca | aga | atg | aca | aat | atc | aat | att | 9745 |
| Gly | Ser | Ser | Ile | Cys | Phe | Leu | Thr | Arg | Met | Thr | Asn | Ile | Asn | Ile | |
| | | | 2905 | | | | 2910 | | | | 2915 | | | |

| aat | aga | cct | ctt | gaa | ttg | atc | tca | ggg | gta | atc | tca | tat | att | ctc | 9790 |
| Asn | Arg | Pro | Leu | Glu | Leu | Ile | Ser | Gly | Val | Ile | Ser | Tyr | Ile | Leu | |
| | | | 2920 | | | | 2925 | | | | 2930 | | | |

| ctg | agg | cta | gat | aac | cat | ccc | tcc | ttg | tac | ata | atg | ctc | aga | gaa | 9835 |
| Leu | Arg | Leu | Asp | Asn | His | Pro | Ser | Leu | Tyr | Ile | Met | Leu | Arg | Glu | |
| | | | 2935 | | | | 2940 | | | | 2945 | | | |

| ccg | tct | ctt | aga | gga | gag | ata | ttt | tct | atc | cct | cag | aaa | atc | ccc | 9880 |
| Pro | Ser | Leu | Arg | Gly | Glu | Ile | Phe | Ser | Ile | Pro | Gln | Lys | Ile | Pro | |
| | | | 2950 | | | | 2955 | | | | 2960 | | | |

| gcc | gct | tat | cca | acc | act | atg | aaa | gaa | ggc | aac | aga | tca | atc | ttg | 9925 |
| Ala | Ala | Tyr | Pro | Thr | Thr | Met | Lys | Glu | Gly | Asn | Arg | Ser | Ile | Leu | |
| | | | 2965 | | | | 2970 | | | | 2975 | | | |

| tgt | tat | ctc | caa | cat | gtg | cta | cgc | tat | gag | cga | gag | ata | atc | acg | 9970 |
| Cys | Tyr | Leu | Gln | His | Val | Leu | Arg | Tyr | Glu | Arg | Glu | Ile | Ile | Thr | |
| | | | 2980 | | | | 2985 | | | | 2990 | | | |

| gcg | tct | cca | gag | aat | gac | tgg | cta | tgg | atc | ttt | tca | gac | ttt | aga | 10015 |
| Ala | Ser | Pro | Glu | Asn | Asp | Trp | Leu | Trp | Ile | Phe | Ser | Asp | Phe | Arg | |
| | | | 2995 | | | | 3000 | | | | 3005 | | | |

| | |
|---|---|
| agt gcc aaa atg acg tac cta acc ctc att act tac cag tct cat<br>Ser Ala Lys Met Thr Tyr Leu Thr Leu Ile Thr Tyr Gln Ser His<br>3010                       3015                       3020 | 10060 |
| ctt cta ctc cag agg gtt gag aga aac cta tct aag agt atg aga<br>Leu Leu Leu Gln Arg Val Glu Arg Asn Leu Ser Lys Ser Met Arg<br>3025                       3030                       3035 | 10105 |
| gat aac ctg cga caa ttg agt tcc ttg atg agg cag gtg ctg ggc<br>Asp Asn Leu Arg Gln Leu Ser Ser Leu Met Arg Gln Val Leu Gly<br>3040                       3045                       3050 | 10150 |
| ggg cac gga gaa gat acc tta gag tca gac gac aac att caa cga<br>Gly His Gly Glu Asp Thr Leu Glu Ser Asp Asp Asn Ile Gln Arg<br>3055                       3060                       3065 | 10195 |
| ctg cta aaa gac tct tta cga agg aca aga tgg gtg gat caa gag<br>Leu Leu Lys Asp Ser Leu Arg Arg Thr Arg Trp Val Asp Gln Glu<br>3070                       3075                       3080 | 10240 |
| gtg cgc cat gca gct aga acc atg act gga gat tac agc ccc aac<br>Val Arg His Ala Ala Arg Thr Met Thr Gly Asp Tyr Ser Pro Asn<br>3085                       3090                       3095 | 10285 |
| aag aag gtg tcc cgt aag gta gga tgt tca gaa tgg gtc tgc tct<br>Lys Lys Val Ser Arg Lys Val Gly Cys Ser Glu Trp Val Cys Ser<br>3100                       3105                       3110 | 10330 |
| gct caa cag gtt gca gtc tct acc tca gca aac ccg gcc cct gtc<br>Ala Gln Gln Val Ala Val Ser Thr Ser Ala Asn Pro Ala Pro Val<br>3115                       3120                       3125 | 10375 |
| tcg gag ctt gac ata agg gcc ctc tct aag agg ttc cag aac cct<br>Ser Glu Leu Asp Ile Arg Ala Leu Ser Lys Arg Phe Gln Asn Pro<br>3130                       3135                       3140 | 10420 |
| ttg atc tcg ggc ttg aga gtg gtt cag tgg gca acc ggt gct cat<br>Leu Ile Ser Gly Leu Arg Val Val Gln Trp Ala Thr Gly Ala His<br>3145                       3150                       3155 | 10465 |
| tat aag ctt aag cct att cta gat gat ctc aat gtt ttc ccc tct<br>Tyr Lys Leu Lys Pro Ile Leu Asp Asp Leu Asn Val Phe Pro Ser<br>3160                       3165                       3170 | 10510 |
| ctc tgc ctt gta gtt ggg gac ggg tca ggg ggg ata tca agg gca<br>Leu Cys Leu Val Val Gly Asp Gly Ser Gly Gly Ile Ser Arg Ala<br>3175                       3180                       3185 | 10555 |
| gtc ctc aac atg ttt cca gat gcc aag ctt gtg ttc aac agt ctc<br>Val Leu Asn Met Phe Pro Asp Ala Lys Leu Val Phe Asn Ser Leu<br>3190                       3195                       3200 | 10600 |
| tta gag gtg aat gac ctg atg gct tcc gga aca cat cca ctg cct<br>Leu Glu Val Asn Asp Leu Met Ala Ser Gly Thr His Pro Leu Pro<br>3205                       3210                       3215 | 10645 |
| cct tca gca atc atg agg gga gga aat ggt atc gtc tcc aga gtg<br>Pro Ser Ala Ile Met Arg Gly Gly Asn Gly Ile Val Ser Arg Val<br>3220                       3225                       3230 | 10690 |
| ata gat ttt gac tca atc tgg gaa aaa ccg tcc gac ttg aga aac<br>Ile Asp Phe Asp Ser Ile Trp Glu Lys Pro Ser Asp Leu Arg Asn<br>3235                       3240                       3245 | 10735 |
| ttg gca acc tgg aaa tac ttc cag tca gtc caa aag cag gtc aac<br>Leu Ala Thr Trp Lys Tyr Phe Gln Ser Val Gln Lys Gln Val Asn<br>3250                       3255                       3260 | 10780 |
| atg tcc tat gac ctc att att tgc gat gca gaa gtt act gac att<br>Met Ser Tyr Asp Leu Ile Ile Cys Asp Ala Glu Val Thr Asp Ile<br>3265                       3270                       3275 | 10825 |
| gca tct atc aac cgg ata acc ctg tta atg tcc gat ttt gca ttg<br>Ala Ser Ile Asn Arg Ile Thr Leu Leu Met Ser Asp Phe Ala Leu<br>3280                       3285                       3290 | 10870 |
| tct ata gat gga cca ctc tat ttg gtc ttc aaa act tat ggg act<br>Ser Ile Asp Gly Pro Leu Tyr Leu Val Phe Lys Thr Tyr Gly Thr<br>3295                       3300                       3305 | 10915 |

-continued

| | | | | | | | | | | | | | |
|---|---|---|---|---|---|---|---|---|---|---|---|---|---|
| atg | cta | gta | aat | cca | aac | tac | aag | gct | att | caa | cac | ctg | tca | aga | 10960 |
| Met | Leu | Val | Asn | Pro | Asn | Tyr | Lys | Ala | Ile | Gln | His | Leu | Ser | Arg |
| | | | 3310 | | | | 3315 | | | | 3320 | | | gcg ttc ccc tcg gtc aca ggg ttt atc acc caa gta act tcg tct    11005
Ala Phe Pro Ser Val Thr Gly Phe Ile Thr Gln Val Thr Ser Ser
            3325            3330            3335 ttt tca tct gag ctc tac ctc cga ttc tcc aaa cga ggg aag ctt    11050
Phe Ser Ser Glu Leu Tyr Leu Arg Phe Ser Lys Arg Gly Lys Leu
            3340            3345            3350 ttc aga gat gct gag tac ttg acc tct tcc acc ctt cga gaa atg    11095
Phe Arg Asp Ala Glu Tyr Leu Thr Ser Ser Thr Leu Arg Glu Met
            3355            3360            3365 agc ctt gtg tta ttc aat tgt agc agc ccc aag agt gag atg cag    11140
Ser Leu Val Leu Phe Asn Cys Ser Ser Pro Lys Ser Glu Met Gln
            3370            3375            3380 aga gct cgt tcc ttg aac tat cag gat ctt gtg aga gga ttt cct    11185
Arg Ala Arg Ser Leu Asn Tyr Gln Asp Leu Val Arg Gly Phe Pro
            3385            3390            3395 gaa gaa atc ata tca aat cct tac aat gag atg atc ata act ctg    11230
Glu Glu Ile Ile Ser Asn Pro Tyr Asn Glu Met Ile Ile Thr Leu
            3400            3405            3410 att gac agt gat gta gaa tct ttt cta gtc cac aag atg gtt gat    11275
Ile Asp Ser Asp Val Glu Ser Phe Leu Val His Lys Met Val Asp
            3415            3420            3425 gat ctt gag tta cag agg gga act ctg tct aaa gtg gct atc att    11320
Asp Leu Glu Leu Gln Arg Gly Thr Leu Ser Lys Val Ala Ile Ile
            3430            3435            3440 ata gcc atc atg ata gtt ttc tcc aac aga gtc ttc aac gtt tcc    11365
Ile Ala Ile Met Ile Val Phe Ser Asn Arg Val Phe Asn Val Ser
            3445            3450            3455 aaa ccc cta act gac ccc ttg ttc tat cca ccg tct gat ccc aaa    11410
Lys Pro Leu Thr Asp Pro Leu Phe Tyr Pro Pro Ser Asp Pro Lys
            3460            3465            3470 atc ctg agg cac ttc aac ata tgt cgc agt act atg atg tat cta    11455
Ile Leu Arg His Phe Asn Ile Cys Arg Ser Thr Met Met Tyr Leu
            3475            3480            3485 tct act gct tta ggt gac gtc cct agc ttc gca aga ctt cac gac    11500
Ser Thr Ala Leu Gly Asp Val Pro Ser Phe Ala Arg Leu His Asp
            3490            3495            3500 ctg tat aac aga cct ata act tat tac ttc aga aag caa ttc att    11545
Leu Tyr Asn Arg Pro Ile Thr Tyr Tyr Phe Arg Lys Gln Phe Ile
            3505            3510            3515 cga ggg aac gtt tat cta tct tgg agt tgg tcc aac gac acc tca    11590
Arg Gly Asn Val Tyr Leu Ser Trp Ser Trp Ser Asn Asp Thr Ser
            3520            3525            3530 gtg ttc aaa agg gta gcc tgt aat tct agc ctg agt ctg tca tct    11635
Val Phe Lys Arg Val Ala Cys Asn Ser Ser Leu Ser Leu Ser Ser
            3535            3540            3545 cac tgg atc agg ttg att tac aag ata gtg aag gct acc aga ctc    11680
His Trp Ile Arg Leu Ile Tyr Lys Ile Val Lys Ala Thr Arg Leu
            3550            3555            3560 gtt ggc agc atc aag gat cta tcc aga gaa gtg gaa aga cac ctt    11725
Val Gly Ser Ile Lys Asp Leu Ser Arg Glu Val Glu Arg His Leu
            3565            3570            3575 cat agg tac aac agg tgg atc acc cta gag gat atc aga tct aga    11770
His Arg Tyr Asn Arg Trp Ile Thr Leu Glu Asp Ile Arg Ser Arg
            3580            3585            3590 tca tcc cta cta gac tac agt tgc ctg                            11817
Ser Ser Leu Leu Asp Tyr Ser Cys Leu

```
                3595          3600
gcctgcccat gctaagactc ttgtgtgatg tatcttgaaa aaaacaagat cctaaatctg    11877
aacctttggt tgtttgattg tttttctcat ttttgttgtt tatttgttaa gcgt          11931
```

<210> SEQ ID NO 2
<211> LENGTH: 450
<212> TYPE: PRT
<213> ORGANISM: rabies virus

<400> SEQUENCE: 2

```
Met Asp Ala Asp Lys Ile Val Phe Lys Val Asn Asn Gln Val Val Ser
1               5                   10                  15

Leu Lys Pro Glu Ile Ile Val Asp Gln His Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asp Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Val Ile
                85                  90                  95

Ala Arg Lys Gly Asp Lys Ile Thr Pro Gly Ser Leu Val Glu Ile Lys
            100                 105                 110

Arg Thr Asp Val Glu Gly Asn Trp Ala Leu Thr Gly Gly Met Glu Leu
        115                 120                 125

Thr Arg Asp Pro Thr Val Pro Glu His Ala Ser Leu Val Gly Leu Leu
    130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
            180                 185                 190

Met Cys Ala Asn Trp Ser Thr Ile Pro Asn Phe Arg Phe Leu Ala Gly
        195                 200                 205

Thr Tyr Asp Met Phe Phe Ser Arg Ile Glu His Leu Tyr Ser Ala Ile
    210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
            260                 265                 270

Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350
```

```
Gly Thr Phe Glu Arg Arg Phe Arg Asp Glu Lys Glu Leu Gln Glu
        355                 360                 365

Tyr Glu Ala Ala Glu Leu Thr Lys Thr Asp Val Ala Leu Ala Asp Asp
    370                 375                 380

Gly Thr Val Asn Ser Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
        435                 440                 445

Asp Ser
    450

<210> SEQ ID NO 3
<211> LENGTH: 297
<212> TYPE: PRT
<213> ORGANISM: rabies virus

<400> SEQUENCE: 3

Met Ser Lys Ile Phe Val Asn Pro Ser Ala Ile Arg Ala Gly Leu Ala
1               5                   10                  15

Asp Leu Glu Met Ala Glu Glu Thr Val Asp Leu Ile Asn Arg Asn Ile
            20                  25                  30

Glu Asp Asn Gln Ala His Leu Gln Gly Glu Pro Ile Glu Val Asp Asn
        35                  40                  45

Leu Pro Glu Asp Met Gly Arg Leu His Leu Asp Asp Gly Lys Ser Pro
    50                  55                  60

Asn Pro Gly Glu Met Ala Lys Val Gly Glu Gly Lys Tyr Arg Glu Asp
65                  70                  75                  80

Phe Gln Met Asp Glu Gly Glu Asp Leu Ser Phe Leu Phe Gln Ser Tyr
                85                  90                  95

Leu Glu Asn Val Gly Val Gln Ile Val Arg Gln Met Arg Ser Gly Glu
            100                 105                 110

Arg Phe Leu Lys Ile Trp Ser Gln Thr Val Glu Glu Ile Ile Ser Tyr
        115                 120                 125

Val Ala Val Asn Phe Pro Asn Pro Pro Gly Lys Ser Ser Glu Asp Lys
    130                 135                 140

Ser Thr Gln Thr Thr Gly Arg Glu Leu Lys Lys Glu Thr Thr Pro Thr
145                 150                 155                 160

Pro Ser Gln Arg Glu Ser Gln Ser Ser Lys Ala Arg Met Ala Ala Gln
                165                 170                 175

Ile Ala Ser Gly Pro Pro Ala Leu Glu Trp Ser Ala Thr Asn Glu Glu
            180                 185                 190

Asp Asp Leu Ser Val Glu Ala Glu Ile Ala His Gln Ile Ala Glu Ser
        195                 200                 205

Phe Ser Lys Lys Tyr Lys Phe Pro Ser Arg Ser Ser Gly Ile Leu Leu
    210                 215                 220

Tyr Asn Phe Glu Gln Leu Lys Met Asn Leu Asp Asp Ile Val Lys Glu
225                 230                 235                 240

Ala Lys Asn Val Pro Gly Val Thr Arg Leu Ala His Asp Gly Ser Lys
                245                 250                 255

Leu Pro Leu Arg Cys Val Leu Gly Trp Val Ala Leu Ala Asn Pro Lys
```

```
            260                 265                 270

Lys Phe Gln Leu Leu Val Glu Ser Asp Lys Leu Ser Lys Ile Met Gln
        275                 280                 285

Asp Asp Leu Asn Arg Tyr Thr Ser Cys
    290                 295

<210> SEQ ID NO 4
<211> LENGTH: 202
<212> TYPE: PRT
<213> ORGANISM: rabies virus
<400> SEQUENCE: 4

Met Asn Phe Leu Arg Lys Ile Val Lys Asn Cys Arg Asp Glu Asp Thr
1               5                   10                  15

Gln Lys Pro Ser Pro Val Ser Ala Pro Leu Asp Asp Asp Asp Leu Trp
            20                  25                  30

Leu Pro Pro Pro Glu Tyr Val Pro Leu Lys Glu Leu Thr Ser Lys Lys
        35                  40                  45

Asn Met Arg Asn Phe Cys Ile Asn Gly Gly Val Lys Val Cys Ser Pro
    50                  55                  60

Asn Gly Tyr Ser Phe Arg Ile Leu Arg His Ile Leu Lys Ser Phe Asp
65                  70                  75                  80

Glu Ile Tyr Ser Gly Asn His Arg Met Ile Gly Leu Ala Lys Val Val
                85                  90                  95

Ile Gly Leu Ala Leu Ser Gly Ser Pro Val Pro Glu Gly Met Asn Trp
            100                 105                 110

Val Tyr Lys Leu Arg Arg Thr Phe Ile Phe Gln Trp Ala Asp Ser Arg
        115                 120                 125

Gly Pro Leu Glu Gly Glu Glu Leu Glu Tyr Ser Gln Glu Ile Thr Trp
    130                 135                 140

Asp Asp Asp Thr Glu Phe Val Gly Leu Gln Ile Arg Val Ile Ala Lys
145                 150                 155                 160

Gln Cys His Ile Gln Gly Arg Ile Trp Cys Ile Asn Met Asn Pro Arg
                165                 170                 175

Ala Cys Gln Leu Trp Ser Asp Met Ser Leu Gln Thr Gln Arg Ser Glu
            180                 185                 190

Glu Asp Lys Asp Ser Ser Leu Leu Leu Glu
        195                 200

<210> SEQ ID NO 5
<211> LENGTH: 524
<212> TYPE: PRT
<213> ORGANISM: rabies virus
<400> SEQUENCE: 5

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
```

-continued

```
                    85                  90                  95
Val Thr Thr Thr Phe Lys Arg Lys His Phe Arg Pro Thr Pro Asp Ala
                100                 105                 110
Cys Arg Ala Ala Tyr Asn Trp Lys Met Ala Gly Asp Pro Arg Tyr Glu
            115                 120                 125
Glu Ser Leu His Asn Pro Tyr Pro Asp Tyr His Trp Leu Arg Thr Val
        130                 135                 140
Lys Thr Thr Lys Glu Ser Leu Val Ile Ile Ser Pro Ser Val Ala Asp
145                 150                 155                 160
Leu Asp Pro Tyr Asp Arg Ser Leu His Ser Arg Val Phe Pro Ser Gly
                165                 170                 175
Lys Cys Ser Gly Val Ala Val Ser Ser Thr Tyr Cys Ser Thr Asn His
            180                 185                 190
Asp Tyr Thr Ile Trp Met Pro Glu Asn Pro Arg Leu Gly Met Ser Cys
        195                 200                 205
Asp Ile Phe Thr Asn Ser Arg Gly Lys Arg Ala Ser Lys Gly Ser Glu
    210                 215                 220
Thr Cys Gly Phe Val Asp Glu Arg Gly Leu Tyr Lys Ser Leu Lys Gly
225                 230                 235                 240
Ala Cys Lys Leu Lys Leu Cys Gly Val Leu Gly Leu Arg Leu Met Asp
                245                 250                 255
Gly Thr Trp Val Ala Met Gln Thr Ser Asn Glu Thr Lys Trp Cys Pro
            260                 265                 270
Pro Asp Gln Leu Val Asn Leu His Asp Phe Arg Ser Asp Glu Ile Glu
        275                 280                 285
His Leu Val Val Glu Glu Leu Val Arg Lys Arg Glu Glu Cys Leu Asp
    290                 295                 300
Ala Leu Glu Ser Ile Met Thr Thr Lys Ser Val Ser Phe Arg Arg Pro
305                 310                 315                 320
Ser His Leu Arg Lys Leu Val Pro Gly Phe Gly Lys Ala Tyr Thr Ile
                325                 330                 335
Phe Asn Lys Thr Leu Met Glu Ala Asp Ala His Tyr Lys Ser Val Arg
            340                 345                 350
Thr Trp Asn Glu Ile Leu Pro Ser Lys Gly Cys Leu Arg Val Gly Gly
        355                 360                 365
Arg Cys His Pro His Val Asn Gly Val Phe Phe Asn Gly Ile Ile Leu
    370                 375                 380
Gly Pro Asp Gly Asn Val Leu Ile Pro Glu Met Gln Ser Ser Leu Leu
385                 390                 395                 400
Gln Gln His Met Glu Leu Leu Glu Ser Ser Val Ile Pro Leu Val His
                405                 410                 415
Pro Leu Ala Asp Pro Ser Thr Val Phe Lys Asp Gly Asp Glu Ala Glu
            420                 425                 430
Asp Phe Val Glu Val His Leu Pro Asp Val His Asn Gln Val Ser Gly
        435                 440                 445
Val Asp Leu Gly Leu Pro Asn Trp Gly Lys Tyr Val Leu Leu Ser Ala
    450                 455                 460
Gly Ala Leu Thr Ala Leu Met Leu Ile Ile Phe Leu Met Thr Cys Cys
465                 470                 475                 480
Arg Arg Val Asn Arg Ser Glu Pro Thr Gln His Asn Leu Arg Gly Thr
                485                 490                 495
Gly Arg Glu Val Ser Val Thr Pro Gln Ser Gly Lys Ile Ile Ser Ser
            500                 505                 510
```

-continued

```
Trp Glu Ser His Lys Ser Gly Gly Glu Thr Arg Leu
        515                 520

<210> SEQ ID NO 6
<211> LENGTH: 2127
<212> TYPE: PRT
<213> ORGANISM: rabies virus

<400> SEQUENCE: 6

Met Leu Asp Pro Gly Glu Val Tyr Asp Asp Pro Ile Asp Pro Ile Glu
1               5                   10                  15

Leu Glu Asp Glu Pro Arg Gly Thr Pro Thr Val Pro Asn Ile Leu Arg
            20                  25                  30

Asn Ser Asp Tyr Asn Leu Asn Ser Pro Leu Ile Glu Asp Pro Ala Arg
        35                  40                  45

Leu Met Leu Glu Trp Leu Lys Thr Gly Asn Arg Pro Tyr Arg Met Thr
    50                  55                  60

Leu Thr Asp Asn Cys Ser Arg Ser Phe Arg Val Leu Lys Asp Tyr Phe
65                  70                  75                  80

Lys Lys Val Asp Leu Gly Ser Leu Lys Val Gly Gly Met Ala Ala Gln
                85                  90                  95

Ser Met Ile Ser Leu Trp Leu Tyr Gly Ala His Ser Glu Ser Asn Arg
            100                 105                 110

Ser Arg Arg Cys Ile Thr Asp Leu Ala His Phe Tyr Ser Lys Ser Ser
        115                 120                 125

Pro Ile Glu Lys Leu Leu Asn Leu Thr Leu Gly Asn Arg Gly Leu Arg
    130                 135                 140

Ile Pro Pro Glu Gly Val Leu Ser Cys Leu Glu Arg Val Asp Tyr Asp
145                 150                 155                 160

Asn Ala Phe Gly Arg Tyr Leu Ala Asn Thr Tyr Ser Ser Tyr Leu Phe
                165                 170                 175

Phe His Val Ile Thr Leu Tyr Met Asn Ala Leu Asp Trp Asp Glu Glu
            180                 185                 190

Lys Thr Ile Leu Ala Leu Trp Lys Asp Leu Thr Ser Val Asp Ile Gly
        195                 200                 205

Lys Asp Leu Val Lys Phe Lys Asp Gln Ile Trp Gly Leu Pro Ile Val
    210                 215                 220

Thr Lys Asp Phe Val Tyr Ser Gln Ser Ser Asn Cys Leu Phe Asp Arg
225                 230                 235                 240

Asn Tyr Thr Leu Met Leu Lys Glu Leu Phe Leu Ser Arg Phe Asn Ser
                245                 250                 255

Leu Met Val Leu Leu Ser Pro Pro Glu Pro Arg Tyr Ser Asp Asp Leu
            260                 265                 270

Ile Ser Gln Leu Cys Gln Leu Tyr Ile Ala Gly Asp Gln Val Leu Ser
        275                 280                 285

Met Cys Gly Asn Ser Gly Tyr Glu Val Ile Lys Ile Leu Glu Pro Tyr
    290                 295                 300

Val Val Asn Ser Leu Val Gln Arg Ala Glu Lys Phe Arg Pro Leu Ile
305                 310                 315                 320

His Ser Leu Gly Asp Phe Pro Val Phe Ile Lys Asp Lys Val Ser Gln
                325                 330                 335

Leu Glu Glu Thr Phe Gly Pro Cys Ala Arg Arg Phe Phe Arg Ala Leu
            340                 345                 350

Asp Gln Phe Asp Asn Ile His Asp Leu Val Phe Val Tyr Gly Cys Tyr
```

-continued

```
                355                 360                 365
Arg His Trp Gly His Pro Tyr Ile Asp Tyr Arg Lys Gly Leu Ser Lys
    370                 375                 380

Leu Tyr Asp Gln Val His Ile Lys Lys Val Ile Asp Lys Ser Tyr Gln
385                 390                 395                 400

Glu Cys Leu Ala Ser Asp Leu Ala Arg Arg Ile Leu Arg Trp Gly Phe
                405                 410                 415

Asp Lys Tyr Ser Lys Trp Tyr Leu Asp Ser Arg Phe Leu Ala Arg Asp
            420                 425                 430

His Pro Leu Thr Pro Tyr Ile Lys Thr Gln Thr Trp Pro Pro Lys His
        435                 440                 445

Ile Val Asp Leu Val Gly Asp Thr Trp His Lys Leu Pro Ile Thr Gln
    450                 455                 460

Ile Phe Glu Ile Pro Glu Ser Met Asp Pro Ser Glu Ile Leu Asp Asp
465                 470                 475                 480

Lys Ser His Ser Phe Thr Arg Thr Arg Leu Ala Ser Trp Leu Ser Glu
                485                 490                 495

Asn Arg Gly Gly Pro Val Pro Ser Glu Lys Val Ile Ile Thr Ala Leu
            500                 505                 510

Ser Lys Pro Pro Val Asn Pro Arg Glu Phe Leu Arg Ser Ile Asp Leu
        515                 520                 525

Gly Gly Leu Pro Asp Glu Asp Leu Ile Ile Gly Leu Lys Pro Lys Glu
    530                 535                 540

Arg Glu Leu Lys Ile Glu Gly Arg Phe Ala Leu Met Ser Trp Asn
545                 550                 555                 560

Leu Arg Leu Tyr Phe Val Ile Thr Glu Lys Leu Leu Ala Asn Tyr Ile
                565                 570                 575

Leu Pro Leu Phe Asp Ala Leu Thr Met Thr Asp Asn Leu Asn Lys Val
            580                 585                 590

Phe Lys Lys Leu Ile Asp Arg Val Thr Gly Gln Gly Leu Leu Asp Tyr
        595                 600                 605

Ser Arg Val Thr Tyr Ala Phe His Leu Asp Tyr Glu Lys Trp Asn Asn
    610                 615                 620

His Gln Arg Leu Glu Ser Thr Glu Asp Val Phe Ser Val Leu Asp Gln
625                 630                 635                 640

Val Phe Gly Leu Lys Arg Val Phe Ser Arg Thr His Glu Phe Phe Gln
                645                 650                 655

Lys Ala Trp Ile Tyr Tyr Ser Asp Arg Ser Asp Leu Ile Gly Leu Arg
            660                 665                 670

Glu Asp Gln Ile Tyr Cys Leu Asp Ala Ser Asn Gly Pro Thr Cys Trp
        675                 680                 685

Asn Gly Gln Asp Gly Gly Leu Glu Gly Leu Arg Gln Lys Gly Trp Ser
    690                 695                 700

Leu Val Ser Leu Leu Met Ile Asp Arg Glu Ser Gln Ile Arg Asn Thr
705                 710                 715                 720

Arg Thr Lys Ile Leu Ala Gln Gly Asp Asn Gln Val Leu Cys Pro Thr
                725                 730                 735

Tyr Met Leu Ser Pro Gly Leu Ser Gln Glu Gly Leu Leu Tyr Glu Leu
            740                 745                 750

Glu Arg Ile Ser Arg Asn Ala Leu Ser Ile Tyr Arg Ala Val Glu Glu
        755                 760                 765

Gly Ala Ser Lys Leu Gly Leu Ile Thr Lys Lys Glu Glu Thr Met Cys
    770                 775                 780
```

-continued

Ser Tyr Asp Phe Leu Ile Tyr Gly Lys Thr Pro Leu Phe Arg Gly Asn
785                 790                 795                 800

Ile Leu Val Pro Glu Ser Lys Arg Trp Ala Arg Val Ser Cys Val Ser
            805                 810                 815

Asn Asp Gln Ile Val Asn Leu Ala Asn Ile Met Ser Thr Val Ser Thr
            820                 825                 830

Asn Ala Leu Thr Val Ala Gln His Ser Gln Ser Leu Ile Lys Pro Met
            835                 840                 845

Gly Asp Phe Leu Leu Met Ser Val Gln Ala Val Phe His Tyr Leu Leu
850                 855                 860

Phe Ser Pro Ile Leu Lys Gly Arg Val Tyr Lys Ile Leu Ser Ala Glu
865                 870                 875                 880

Gly Asp Ser Phe Leu Leu Ala Met Ser Arg Ile Ile Tyr Leu Asp Pro
                885                 890                 895

Ser Leu Gly Gly Val Ser Gly Met Ser Leu Gly Arg Phe His Ile Arg
                900                 905                 910

Gln Phe Ser Asp Pro Val Ser Glu Gly Leu Ser Phe Trp Arg Glu Ile
                915                 920                 925

Trp Leu Ser Ser His Glu Ser Trp Val His Ala Leu Cys Gln Glu Ala
            930                 935                 940

Gly Asn Pro Asp Leu Gly Glu Arg Thr Leu Glu Ser Phe Thr Arg Leu
945                 950                 955                 960

Leu Glu Asp Pro Thr Thr Leu Asn Ile Arg Gly Gly Ala Ser Pro Thr
                965                 970                 975

Ile Leu Leu Lys Asp Ala Ile Arg Lys Ala Leu Tyr Asp Glu Val Asp
                980                 985                 990

Lys Val Glu Asn Ser Glu Phe Arg  Glu Ala Ile Leu Leu  Ser Lys Thr
                995                 1000                1005

His Arg Asp Asn Phe Ile Leu  Phe Leu Thr Ser Val  Glu Pro Leu
    1010                1015                1020

Phe Pro Arg Phe Leu Ser Glu  Leu Phe Ser Ser Ser  Phe Leu Gly
    1025                1030                1035

Ile Pro Glu Ser Ile Ile Gly  Leu Ile Gln Asn Ser  Arg Thr Ile
    1040                1045                1050

Arg Arg Gln Phe Arg Lys Ser  Leu Ser Lys Thr Leu  Glu Glu Ser
    1055                1060                1065

Phe Tyr Asn Ser Glu Ile His  Gly Ile Ser Arg Met  Thr Gln Thr
    1070                1075                1080

Pro Gln Arg Val Gly Gly Val  Trp Pro Cys Ser Ser  Glu Arg Ala
    1085                1090                1095

Asp Leu Leu Arg Glu Ile Ser  Trp Gly Arg Lys Val  Val Gly Thr
    1100                1105                1110

Thr Val Pro His Pro Ser Glu  Met Leu Gly Leu Leu  Pro Lys Ser
    1115                1120                1125

Ser Ile Ser Cys Thr Cys Gly  Ala Thr Gly Gly Gly  Asn Pro Arg
    1130                1135                1140

Val Ser Val Ser Val Leu Pro  Ser Phe Asp Gln Ser  Phe Phe Ser
    1145                1150                1155

Arg Gly Pro Leu Lys Gly Tyr  Leu Gly Ser Ser Thr  Ser Met Ser
    1160                1165                1170

Thr Gln Leu Phe His Ala Trp  Glu Lys Val Thr Asn  Val His Val
    1175                1180                1185

```
Val Lys Arg Ala Leu Ser Leu Lys Glu Ser Ile Asn Trp Phe Ile
1190             1195             1200

Thr Arg Asp Ser Asn Leu Ala Gln Ala Leu Ile Arg Asn Ile Met
1205             1210             1215

Ser Leu Thr Gly Pro Asp Phe Pro Leu Glu Glu Ala Pro Val Phe
1220             1225             1230

Lys Arg Thr Gly Ser Ala Leu His Arg Phe Lys Ser Ala Arg Tyr
1235             1240             1245

Ser Glu Gly Gly Tyr Ser Ser Val Cys Pro Asn Leu Leu Ser His
1250             1255             1260

Ile Ser Val Ser Thr Asp Thr Met Ser Asp Leu Thr Gln Asp Gly
1265             1270             1275

Lys Asn Tyr Asp Phe Met Phe Gln Pro Leu Met Leu Tyr Ala Gln
1280             1285             1290

Thr Trp Thr Ser Glu Leu Val Gln Arg Asp Thr Arg Leu Arg Asp
1295             1300             1305

Ser Thr Phe His Trp His Leu Arg Cys Asn Arg Cys Val Arg Pro
1310             1315             1320

Ile Asp Asp Val Thr Leu Glu Thr Ser Gln Ile Phe Glu Phe Pro
1325             1330             1335

Asp Val Ser Lys Arg Ile Ser Arg Met Val Ser Gly Ala Val Pro
1340             1345             1350

His Phe Gln Arg Leu Pro Asp Ile Arg Leu Arg Pro Gly Asp Phe
1355             1360             1365

Glu Ser Leu Ser Gly Arg Glu Lys Ser His His Ile Gly Ser Ala
1370             1375             1380

Gln Gly Leu Leu Tyr Ser Ile Leu Val Ala Ile His Asp Ser Gly
1385             1390             1395

Tyr Asn Asp Gly Thr Ile Phe Pro Ala Asn Ile Tyr Gly Lys Val
1400             1405             1410

Ser Pro Arg Asp Tyr Leu Arg Gly Leu Ala Arg Gly Val Leu Ile
1415             1420             1425

Gly Ser Ser Ile Cys Phe Leu Thr Arg Met Thr Asn Ile Asn Ile
1430             1435             1440

Asn Arg Pro Leu Glu Leu Ile Ser Gly Val Ile Ser Tyr Ile Leu
1445             1450             1455

Leu Arg Leu Asp Asn His Pro Ser Leu Tyr Ile Met Leu Arg Glu
1460             1465             1470

Pro Ser Leu Arg Gly Glu Ile Phe Ser Ile Pro Gln Lys Ile Pro
1475             1480             1485

Ala Ala Tyr Pro Thr Thr Met Lys Glu Gly Asn Arg Ser Ile Leu
1490             1495             1500

Cys Tyr Leu Gln His Val Leu Arg Tyr Glu Arg Glu Ile Ile Thr
1505             1510             1515

Ala Ser Pro Glu Asn Asp Trp Leu Trp Ile Phe Ser Asp Phe Arg
1520             1525             1530

Ser Ala Lys Met Thr Tyr Leu Thr Leu Ile Thr Tyr Gln Ser His
1535             1540             1545

Leu Leu Leu Gln Arg Val Glu Arg Asn Leu Ser Lys Ser Met Arg
1550             1555             1560

Asp Asn Leu Arg Gln Leu Ser Ser Leu Met Arg Gln Val Leu Gly
1565             1570             1575

Gly His Gly Glu Asp Thr Leu Glu Ser Asp Asp Asn Ile Gln Arg
```

-continued

```
              1580                1585                1590

Leu Leu Lys Asp Ser Leu Arg Arg Thr Arg Trp Val Asp Gln Glu
    1595                1600                1605

Val Arg His Ala Ala Arg Thr Met Thr Gly Asp Tyr Ser Pro Asn
    1610                1615                1620

Lys Lys Val Ser Arg Lys Val Gly Cys Ser Glu Trp Val Cys Ser
    1625                1630                1635

Ala Gln Gln Val Ala Val Ser Thr Ser Ala Asn Pro Ala Pro Val
    1640                1645                1650

Ser Glu Leu Asp Ile Arg Ala Leu Ser Lys Arg Phe Gln Asn Pro
    1655                1660                1665

Leu Ile Ser Gly Leu Arg Val Val Gln Trp Ala Thr Gly Ala His
    1670                1675                1680

Tyr Lys Leu Lys Pro Ile Leu Asp Asp Leu Asn Val Phe Pro Ser
    1685                1690                1695

Leu Cys Leu Val Val Gly Asp Gly Ser Gly Gly Ile Ser Arg Ala
    1700                1705                1710

Val Leu Asn Met Phe Pro Asp Ala Lys Leu Val Phe Asn Ser Leu
    1715                1720                1725

Leu Glu Val Asn Asp Leu Met Ala Ser Gly Thr His Pro Leu Pro
    1730                1735                1740

Pro Ser Ala Ile Met Arg Gly Gly Asn Gly Ile Val Ser Arg Val
    1745                1750                1755

Ile Asp Phe Asp Ser Ile Trp Glu Lys Pro Ser Asp Leu Arg Asn
    1760                1765                1770

Leu Ala Thr Trp Lys Tyr Phe Gln Ser Val Gln Lys Gln Val Asn
    1775                1780                1785

Met Ser Tyr Asp Leu Ile Ile Cys Asp Ala Glu Val Thr Asp Ile
    1790                1795                1800

Ala Ser Ile Asn Arg Ile Thr Leu Leu Met Ser Asp Phe Ala Leu
    1805                1810                1815

Ser Ile Asp Gly Pro Leu Tyr Leu Val Phe Lys Thr Tyr Gly Thr
    1820                1825                1830

Met Leu Val Asn Pro Asn Tyr Lys Ala Ile Gln His Leu Ser Arg
    1835                1840                1845

Ala Phe Pro Ser Val Thr Gly Phe Ile Thr Gln Val Thr Ser Ser
    1850                1855                1860

Phe Ser Ser Glu Leu Tyr Leu Arg Phe Ser Lys Arg Gly Lys Leu
    1865                1870                1875

Phe Arg Asp Ala Glu Tyr Leu Thr Ser Ser Thr Leu Arg Glu Met
    1880                1885                1890

Ser Leu Val Leu Phe Asn Cys Ser Ser Pro Lys Ser Glu Met Gln
    1895                1900                1905

Arg Ala Arg Ser Leu Asn Tyr Gln Asp Leu Val Arg Gly Phe Pro
    1910                1915                1920

Glu Glu Ile Ile Ser Asn Pro Tyr Asn Glu Met Ile Ile Thr Leu
    1925                1930                1935

Ile Asp Ser Asp Val Glu Ser Phe Leu Val His Lys Met Val Asp
    1940                1945                1950

Asp Leu Glu Leu Gln Arg Gly Thr Leu Ser Lys Val Ala Ile Ile
    1955                1960                1965

Ile Ala Ile Met Ile Val Phe Ser Asn Arg Val Phe Asn Val Ser
    1970                1975                1980
```

-continued

Lys Pro Leu Thr Asp Pro Leu Phe Tyr Pro Pro Ser Asp Pro Lys
    1985                1990                1995

Ile Leu Arg His Phe Asn Ile Cys Arg Ser Thr Met Met Tyr Leu
    2000                2005                2010

Ser Thr Ala Leu Gly Asp Val Pro Ser Phe Ala Arg Leu His Asp
    2015                2020                2025

Leu Tyr Asn Arg Pro Ile Thr Tyr Tyr Phe Arg Lys Gln Phe Ile
    2030                2035                2040

Arg Gly Asn Val Tyr Leu Ser Trp Ser Trp Ser Asn Asp Thr Ser
    2045                2050                2055

Val Phe Lys Arg Val Ala Cys Asn Ser Ser Leu Ser Leu Ser Ser
    2060                2065                2070

His Trp Ile Arg Leu Ile Tyr Lys Ile Val Lys Ala Thr Arg Leu
    2075                2080                2085

Val Gly Ser Ile Lys Asp Leu Ser Arg Glu Val Glu Arg His Leu
    2090                2095                2100

His Arg Tyr Asn Arg Trp Ile Thr Leu Glu Asp Ile Arg Ser Arg
    2105                2110                2115

Ser Ser Leu Leu Asp Tyr Ser Cys Leu
    2120                2125

<210> SEQ ID NO 7
<211> LENGTH: 11930
<212> TYPE: DNA
<213> ORGANISM: artificial sequence
<220> FEATURE:
<223> OTHER INFORMATION: Recombinant ERA rabies virus genome
<220> FEATURE:
<221> NAME/KEY: misc_feature
<222> LOCATION: (1)..(58)
<223> OTHER INFORMATION: Leader region
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (4963)..(5361)
<223> OTHER INFORMATION: Psi region
<220> FEATURE:
<221> NAME/KEY: misc_feature
<222> LOCATION: (5416)..(11796)
<220> FEATURE:
<221> NAME/KEY: misc_feature
<222> LOCATION: (11861)..(11930)
<223> OTHER INFORMATION: Trailer region

<400> SEQUENCE: 7
acgcttaaca accagatcaa agaaaaaaca gacattgtca attgcaaagc aaaaatgtaa 60
cacccctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300
aatgcagttt tttgaggggga catgtccgga agactggacc agctatggaa tcgtgattgc 360

-continued

```
acgaaaagga gataagatca ccccaggttc tctggtggag ataaaacgta ctgatgtaga      420
agggaattgg gctctgacag gaggcatgga actgacaaga gaccccactg tccctgagca      480
tgcgtcctta gtcggtcttc tcttgagtct gtataggttg agcaaaatat ccgggcaaaa      540
cactggtaac tataagacaa acattgcaga caggatagag cagattttg agacagcccc      600 ttttgttaaa atcgtggaac accatactct aatgacaact cacaaaatgt gtgctaattg      660
gagtactata ccaaacttca gattttggc cggaacctat gacatgtttt tctcccggat      720
tgagcatcta tattcagcaa tcagagtggg cacagttgtc actgcttatg aagactgttc      780
aggactggta tcatttactg ggttcataaa acaaatcaat ctcaccgcta gagaggcaat      840
actatatttc ttccacaaga actttgagga agagataaga agaatgtttg agccagggca      900
ggagacagct gttcctcact cttatttcat ccacttccgt tcactaggct tgagtgggaa      960
atctccttat tcatcaaatg ctgttggtca cgtgttcaat ctcattcact ttgtaggatg     1020
ctatatgggt caagtcagat ccctaaatgc aacggttatt gctgcatgtg ctcctcatga     1080
aatgtctgtt ctaggggct atctgggaga ggaattcttc gggaaaggga catttgaaag     1140
aagattcttc agagatgaga aagaacttca agaatacgag gcggctgaac tgacaaagac     1200
tgacgtagca ctggcagatg atggaactgt caactctgac gacgaggact acttctcagg     1260
tgaaaccaga agtccggagg ctgtttatac tcgaatcatg atgaatggag gtcgactaaa     1320
gagatctcac atacggagat atgtctcagt cagttccaat catcaagccc gtccaaactc     1380
attcgccgag tttctaaaca agacatattc gagtgactca taagaagttg aacaacaaaa     1440
tgccggaaat ctacggattg tgtatatcca tcatgaaaaa aactaacacc cctcctttcg     1500
aaccatccca acatgagca agatctttgt caatcctagt gctattagag ccggtctggc     1560
cgatcttgag atggctgaag aaactgttga tctgatcaat agaaatatcg aagacaatca     1620
ggctcatctc caaggggaac ccatagaagt ggacaatctc cctgaggata tggggcgact     1680
tcacctggat gatggaaaat cgcccaaccc tggtgagatg gccaaggtgg gagaaggcaa     1740
gtatcgagag gactttcaga tggatgaagg agaggatctt agcttcctgt tccagtcata     1800
cctggaaaat gttggagtcc aaatagtcag acaaatgagg tcaggagaga gatttctcaa     1860
gatatggtca cagaccgtag aagagattat atcctatgtc gcggtcaact ttcccaaccc     1920
tccaggaaag tcttcagagg ataaatcaac ccagactact ggccgagagc tcaagaagga     1980
gacaacaccc actccttctc agagagaaag ccaatcatcg aaagccagga tggcggctca     2040
aattgcttct ggccctccag cccttgaatg gtcggccacc aatgaagagg atgatctatc     2100
agtggaggct gagatcgctc accagattgc agaaagtttc tccaaaaaat ataagtttcc     2160
ctctcgatcc tcagggatac tcttgtataa ttttgagcaa ttgaaaatga accttgatga     2220
tatagttaaa gaggcaaaaa atgtaccagg tgtgacccgt ttagcccatg acgggtccaa     2280 actccccta agatgtgtac tgggatgggt cgctttggcc aaccctaaga aattccagtt     2340
gttagtcgaa tccgacaagc tgagtaaaat catgcaagat gacttgaatc gctatacatc     2400
ttgctaaccg aacctctcca ctcagtccct ctagacaata agtccgaga tgtcctaaag     2460 tcaacatgaa aaaacaggc aacaccactg ataaaatgaa ctttctacgt aagatagtga     2520
aaaattgcag ggacgaggac actcaaaaac cctctcccgt gtcagcccct ctggatgacg     2580
atgacttgtg gcttccaccc cctgaatacg tcccgctgaa agaacttaca agcaagaaga     2640
acatgaggaa cttttgtatc aacggagggg ttaaagtgtg tagcccgaat ggttactcgt     2700
```

-continued

```
tcaggatcct gcggcacatt ctgaaatcat tcgacgagat atattctggg aatcatagga    2760
tgatcgggtt agccaaagta gttattggac tggctttgtc aggatctcca gtccctgagg    2820
gcatgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag ggcagaatct    3000
ggtgtatcaa catgaacccg agagcatgtc aactatggtc tgacatgtct cttcagacac    3060
aaaggtccga agaggacaaa gattcctctc tgcttctaga ataatcagat tatatcccgc    3120
aaatttatca cttgtttacc tctggaggag agaacatatg ggctcaactc caacccttgg    3180
gagcaatata acaaaaaaca tgttatggtg ccattaaacc gctgcatttc atcaaagtca    3240
agttgattac ctttacattt tgatcctctt ggatgtgaaa aaaactatta acatccctca    3300
aaagactcaa ggaaagatgg ttcctcaggc tctcctgttt gtacccttc tggttttcc     3360 attgtgtttt gggaaattcc ctatttacac gataccagac aagcttggtc cctggagccc    3420
gattgacata catcaccctca gctgcccaaa caatttggta gtggaggacg aaggatgcac    3480
caacctgtca gggttctcct acatggaact taaagttgga tacatcttag ccataaaaat    3540
gaacgggttc acttgcacag gcgttgtgac ggaggctgaa acctatacta acttcgttgg    3600
ttatgtcaca accacgttca aaagaaagca tttccgccca acaccagatg catgtagagc    3660
cgcgtacaac tggaagatgg ccggtgaccc cagatatgaa gagtctctac acaatccgta    3720
ccctgactac cactggcttc gaactgtaaa aaccaccaag gagtctctcg ttatcatatc    3780
tccaagtgtg gcagatttgg acccatatga cagatcccctt cactcgaggg tcttccctag    3840
cgggaagtgc tcaggagtag cggtgtcttc tacctactgc tccactaacc acgattacac    3900
catttggatg cccgagaatc cgagactagg gatgtcttgt gacattttta ccaatagtag    3960
ggggaagaga gcatccaaag ggagtgagac ttgcggcttt gtagatgaaa gaggcctata    4020
taagtcttta aaaggagcat gcaaactcaa gttatgtgga gttctaggac ttagacttat    4080
ggatggaaca tgggtcgcga tgcaaacatc aaatgaaacc aaatggtgcc cccccgatca    4140
gttggtgaac ctgcacgact ttcgctcaga cgaaattgag caccttgttg tagaggagtt    4200
ggtcaggaag agagaggagt gtctggatgc actagagtcc atcatgacaa ccaagtcagt    4260
gagtttcaga cgtcccagtc atttaagaaa acttgtccct gggtttggaa aagcatatac    4320
catattcaac aagaccttga tggaagccga tgctcactac aagtcagtca gaacttggaa    4380
tgagatcctc ccttcaaaag ggtgtttaag agttgggggg aggtgtcatc ctcatgtgaa    4440
cggggtgttt ttcaatggta taatattagg acctgacggc aatgtcttaa tcccagagat    4500
gcaatcatcc ctcctccagc aacatatgga gttgttggaa tcctcggtta tcccccttgt    4560 gcacccctg gcagacccgt ctaccgtttt caaggacggt gacgaggctg aggattttgt    4620
tgaagttcac cttcccgatg tgcacaatca ggtctcagga gttgacttgg gtctcccgaa    4680
ctgggggaag tatgtattac tgagtgcagg ggccctgact gccttgatgt tgataatttt    4740
cctgatgaca tgttgtagaa gagtcaatcg atcagaacct acgcaacaca atctcagagg    4800
gacagggagg gaggtgtcag tcactcccca aagcgggaag atcatatctt catgggaatc    4860
acacaagagt gggggtgaga ccagactgtg aggactggcc gtcctttcaa cgatccaagt    4920
cctgaagatc acctcccctt gggggttct ttttgaaaaa aacctggggtt caatagtcct    4980 cctcgaactc catgcaactg ggtagattca agagtcatga gatttcatt aatcctctca    5040 gttgatcaag caagatcatg tagattctca taataggga gatcttctag cagtttcagt    5100
```

```
gactaacggt actttcattc tccaggaact gacaccaaca gttgtagaca aaccacgggg    5160
tgtctcgggt gactctgtgc ttgggcacag acaaaggtca tggtgtgttc catgatagcg    5220
gactcaggat gagttaattg agagaggcag tcttcctccc gtgaaggaca taagcagtag    5280
ctcacaatca tcccgcgtct cagcaaagtg tgcataatta taaagtgctg ggtcatctaa    5340
gcttttcagt cgagaaaaaa acattagatc agaagaacaa ctggcaacac ttctcaacct    5400
gagacctact tcaagatgct cgatcctgga gaggtctatg atgaccctat tgacccaatc    5460
gagttagagg atgaacccag aggaaccccc actgtcccca acatcttgag gaactctgac    5520
tacaatctca actctccttt gatagaagat cctgctagac taatgttaga atggttaaaa    5580
acagggaata gaccttatcg gatgactcta acagacaatt gctccaggtc tttcagagtt    5640
ttgaaagatt atttcaagaa ggtagatttg ggttctctca aggtgggcgg aatggctgca    5700
cagtcaatga tttctctctg gttatatggt gcccactctg aatccaacag gagccggaga    5760
tgtataacag acttggccca tttctattcc aagtcgtccc ccatagagaa gctgttgaat    5820
ctcacgctag gaaatagagg gctgagaatc cccccagagg gagtgttaag ttgccttgag    5880
agggttgatt atgataatgc atttggaagg tatcttgcca acacgtattc ctcttacttg    5940
ttcttccatg taatcacctt atacatgaac gccctagact gggatgaaga aaagaccatc    6000
ctagcattat ggaaagattt aacctcagtg gacatcggga aggacttggt aaagttcaaa    6060
gaccaaatat ggggactgcc gatcgtgaca aaggactttg tttactccca aagttccaat    6120 tgtcttttg acagaaacta cacacttatg ctaaaagaac ttttcttgtc tcgcttcaac    6180
tccttaatgg tcttgctctc tccccagag ccccgatact cagatgactt gatatctcaa    6240
ctatgccagc tgtacattgc tggggatcaa gtcttgtcta tgtgtggaaa ctccggctat    6300
gaagtcatca aaatattgga gccatatgtc gtgaatagtt tagtccagag agcagaaaag    6360
tttaggcctc tcattcattc cttgggagac tttcctgtat ttataaaaga caaggtaagt    6420
caacttgaag agacgttcgg tccctgtgca agaaggttct ttagggctct ggatcaattc    6480
gacaacatac atgacttggt ttttgtgtat ggctgttaca ggcattgggg gcacccatat    6540
atagattatc gaaagggtct gtcaaaacta tatgatcagg ttcacattaa aaaagtgata    6600
gataagtcct accaggagtg cttagcaagc gacctagcca ggaggatcct tagatggggt    6660
tttgataagt actccaagtg gtatctggat tcaagattcc tagcccgaga ccacccttg    6720 actccctata tcaaaaccca aacatggcca cccaaacata ttgtagactt ggtgggggat    6780
acatggcaca agctcccgat cacgcagatc tttgagattc ctgaatcaat ggatccgtca    6840
gaaatattgg atgacaaatc acattctttc accagaacga gactagcttc ttggctgtca    6900
gaaaaccgag ggggacctgt tcctagcgaa aaagttatta tcacggccct gtctaagccg    6960
cctgtcaatc cccgagagtt tctgaggtct atagacctcg gaggattgcc agatgaagac    7020
ttgataattg gcctcaagcc aaaggaacgg gaattgaaga ttgaaggtcg attctttgct    7080
ctaatgtcat ggaatctaag attgtatttt gtcatcactg aaaaactctt ggccaactac    7140
atcttgccac ttttgacgc gctgactatg acagacaacc tgaacaaggt gtttaaaaag    7200
ctgatcgaca gggtcaccgg gcaagggctt ttggactatt caagggtcac atatgcattt    7260
cacctggact atgaaaagtg gaacaaccat caaagattag agtcaacaga ggatgtattt    7320
tctgtcctag atcaagtgtt tggattgaag agagtgtttt ctagaacaca cgagtttttt    7380
caaaaggcct ggatctatta ttcagacaga tcagacctca tcgggttacg ggaggatcaa    7440
```

```
atatactgct tagatgcgtc caacggccca acctgttgga atggccagga tggcgggcta    7500
gaaggcttac ggcagaaggg ctggagtcta gtcagcttat tgatgataga tagagaatct    7560
caaatcagga acacaagaac caaaatacta gctcaaggag acaaccaggt tttatgtccg    7620
acatatatgt tgtcgccagg gctatctcaa gaggggctcc tctatgaatt ggagagaata    7680
tcaaggaatg cactttcgat atacagagcc gtcgaggaag gggcatctaa gctagggctg    7740
atcaccaaga aagaagagac catgtgtagt tatgacttcc tcatctatgg aaaaacccct    7800
ttgtttagag gtaacatatt ggtgcctgag tccaaaagat gggccagagt ctcttgcgtc    7860
tctaatgacc aaatagtcaa cctcgccaat ataatgtcga cagtgtccac caatgcgcta    7920
acagtggcac aacactctca atctttgatc aaaccgatgg gggattttct gctcatgtca    7980
gtacaggcag tctttcacta cctgctattt agcccaatct taaagggaag agtttacaag    8040
attctgagcg ctgaagggga tagctttctc ctagccatgt caaggataat ctatctagat    8100
ccttctttgg gaggggtatc tggaatgtcc ctcggaagat tccatatacg acagttctca    8160
gaccctgtct ctgaagggtt atccttctgg agagagatct ggttaagctc ccacgagtcc    8220
tgggttcacg cgttgtgtca agaggctgga aacccagatc ttggagagag aacactcgag    8280
agcttcactc gccttctaga agatcctacc accttaaata tcagaggagg ggccagtcct    8340
accattctac tcaaggatgc aatcagaaag gctttatatg acgaggtgga caaggtggag    8400
aattcagagt ttcgagaggc aatcctgttg tccaagaccc atagagataa ttttatactc    8460
ttcttaacat ctgttgagcc tctgtttcct cgatttctca gtgagctatt cagttcgtct    8520
tttttgggaa tccccgagtc aatcattgga ttgatacaaa actcccgaac gataagaagg    8580
cagtttagaa agagtctctc aaaaacttta gaagaatcct tctacaactc agagatccac    8640
gggattagtc ggatgaccca gacacctcag agggttgggg gggtgtggcc ttgctcttca    8700
gagagggcag atctacttag ggagatctct tggggaagaa aagtggtagg cacgacagtt    8760
cctcacccct ctgagatgtt ggggttactt cccaagtcct ctatttcttg cacttgtgga    8820
gcaacaggag gaggcaatcc tagagttttct gtatcagtac tcccgtccctt tgatcagtca    8880 tttttttcac gaggccccct aaaggggtac ttgggctcgt ccacctctat gtcgacccag    8940
ctattccatg catgggaaaa agtcactaat gttcatgtgg tgaagagagc tctatcgtta    9000
aaagaatcta taaactggtt cattactaga gattccaact tggctcaagc tctaattagg    9060
aacattatgt ctctgacagg ccctgatttc cctctagagg aggcccctgt cttcaaaagg    9120
acggggtcag ccttgcatag gttcaagtct gccagataca gcgaaggagg gtattcttct    9180
gtctgcccga acctcctctc tcatatttct gttagtacag acaccatgtc tgatttgacc    9240
caagacggga agaactacga tttcatgttc cagccattga tgctttatgc acagacatgg    9300
acatcagagc tggtacagag agacacaagg ctaagagact ctacgtttca ttggcacctc    9360
cgatgcaaca ggtgtgtgag acccattgac gacgtgaccc tggagacctc tcagatcttc    9420
gagtttccgg atgtgtcgaa aagaatatcc agaatggttt ctggggctgt gcctcacttc    9480
cagaggcttc ccgatatccg tctgagacca ggagattttg aatctctaag cggtagagaa    9540
aagtctcacc atatcggatc agctcagggg ctcttatact caatcttagt ggcaattcac    9600
gactcaggat acaatgatgg aaccatcttc cctgccaaca tatacggcaa ggtttcccct    9660
agagactatt tgagagggct cgcaagggga gtattgatag gatcctcgat ttgcttcttg    9720
acaagaatga caaatatcaa tattaataga cctcttgaat tgatctcagg ggtaatctca    9780
tatattctcc tgaggctaga taaccatccc tccttgtaca taatgctcag agaaccgtct    9840
```

```
cttagaggag agatattttc tatccctcag aaaatccccg ccgcttatcc aaccactatg    9900
aaagaaggca acagatcaat cttgtgttat ctccaacatg tgctacgcta tgagcgagag    9960
ataatcacgg cgtctccaga gaatgactgg ctatggatct tttcagactt tagaagtgcc   10020
aaaatgacgt acctaacccct cattacttac cagtctcatc ttctactcca gagggttgag   10080
agaaacctat ctaagagtat gagagataac ctgcgacaat tgagttcctt gatgaggcag   10140
gtgctgggcg ggcacggaga agatacctta gagtcagacg acaacattca acgactgcta   10200
aaagactctt tacgaaggac aagatggggtg gatcaagagg tgcgccatgc agctagaacc   10260
atgactggag attacagccc caacaagaag gtgtcccgta aggtaggatg ttcagaatgg   10320
gtctgctctg ctcaacaggt tgcagtctct acctcagcaa acccggcccc tgtctcggag   10380
cttgacataa gggccctctc taagaggttc cagaaccctt tgatctcggg cttgagagtg   10440
gttcagtggg caaccggtgc tcattataag cttaagccta ttctagatga tctcaatgtt   10500
ttcccctctc tctgccttgt agttggggac gggtcagggg ggatatcaag ggcagtcctc   10560
aacatgtttc cagatgccaa gcttgtgttc aacagtctct tagaggtgaa tgacctgatg   10620
gcttccggaa cacatccact gcctccttca gcaatcatga ggggaggaaa tggtatcgtc   10680
tccagagtga tagattttga ctcaatctgg gaaaaaccgt ccgacttgag aaacttggca   10740
acctggaaat acttccagtc agtccaaaag caggtcaaca tgtcctatga cctcattatt   10800
tgcgatgcag aagttactga cattgcatct atcaaccgga taaccctgtt aatgtccgat   10860
tttgcattgt ctatagatgg accactctat ttggtcttca aaacttatgg gactatgcta   10920
gtaaatccaa actacaaggc tattcaacac ctgtcaagag cgttccccctc ggtcacaggg   10980 tttatcaccc aagtaacttc gtctttttca tctgagctct acctccgatt ctccaaacga   11040
gggaagcttt tcagagatgc tgagtacttg acctcttcca cccttcgaga aatgagcctt   11100
gtgttattca attgtagcag ccccaagagt gagatgcaga gagctcgttc cttgaactat   11160
caggatcttg tgagaggatt tcctgaagaa atcatatcaa atccttacaa tgagatgatc   11220
ataactctga ttgacagtga tgtagaatct tttctagtcc acaagatggt tgatgatctt   11280
gagttacaga ggggaactct gtctaaagtg gctatcatta tagccatcat gatagttttc   11340
tccaacagag tcttcaacgt ttccaaaccc taactgacc ccttgttcta tccaccgtct   11400
gatcccaaaa tcctgaggca cttcaacata tgtcgcagta ctatgatgta tctatctact   11460
gctttaggtg acgtccctag cttcgcaaga cttcacgacc tgtataacag acctataact   11520
tattacttca gaaagcaatt cattcgaggg aacgtttatc tatcttggag ttggtccaac   11580
gacacctcag tgttcaaaag ggtagcctgt aattctagcc tgagtctgtc atctcactgg   11640
atcaggttga tttacaagat agtgaaggct accagactcg ttggcagcat caaggatcta   11700
tccagagaag tggaaagaca ccttcatagg tacaacaggt ggatcaccct agaggatatc   11760
agatctagat catccctact agactacagt tgcctgtgaa ccggatactc ctggaagcct   11820
gcccatgcta agactcttgt gtgatgtatc ttgaaaaaaa caagatccta aatctgaacc   11880
tttggttgtt tgattgtttt tctcattttt gttgtttatt tgttaagcgt              11930
```

<210> SEQ ID NO 8
<211> LENGTH: 11930
<212> TYPE: DNA
<213> ORGANISM: artificial sequence
<220> FEATURE:
<223> OTHER INFORMATION: Recombinant ERAg3 rabies virus genome
<220> FEATURE:

```
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (5416)..(11796)

<400> SEQUENCE: 8
```

| | | | | | |
|---|---|---|---|---|---|
| acgcttaaca | accagatcaa | agaaaaaaca | gacattgtca | attgcaaagc | aaaaatgtaa | 60 |
| caccccctaca | atggatgccg | acaagattgt | attcaaagtc | aataatcagg | tggtctcttt | 120 |
| gaagcctgag | attatcgtgg | atcaacatga | gtacaagtac | cctgccatca | agatttgaa | 180 |
| aaagccctgt | ataaccctag | gaaaggctcc | cgatttaaat | aaagcataca | agtcagtttt | 240 |
| gtcaggcatg | agcgccgcca | aacttgatcc | tgacgatgta | tgttcctatt | tggcagcggc | 300 |
| aatgcagttt | tttgagggga | catgtccgga | agactggacc | agctatggaa | tcgtgattgc | 360 |
| acgaaaagga | gataagatca | ccccaggttc | tctggtggag | ataaaacgta | ctgatgtaga | 420 |
| agggaattgg | gctctgacag | gaggcatgga | actgacaaga | gaccccactg | tccctgagca | 480 |
| tgcgtcctta | gtcggtcttc | tcttgagtct | gtataggttg | agcaaaatat | ccggcaaaa | 540 |
| cactggtaac | tataagacaa | acattgcaga | caggatagag | cagattttg | agacagcccc | 600 |
| ttttgttaaa | atcgtggaac | accatactct | aatgacaact | cacaaaatgt | gtgctaattg | 660 |
| gagtactata | ccaaacttca | gattttttggc | cggaacctat | gacatgtttt | tctcccggat | 720 |
| tgagcatcta | tattcagcaa | tcagagtggg | cacagttgtc | actgcttatg | aagactgttc | 780 |
| aggactggta | tcatttactg | ggttcataaa | acaaatcaat | ctcaccgcta | gagaggcaat | 840 |
| actatattc | ttccacaaga | actttgagga | agagataaga | agaatgtttg | agccagggca | 900 |
| ggagacagct | gttcctcact | cttatttcat | ccacttccgt | tcactaggct | tgagtgggaa | 960 |
| atctccttat | tcatcaaatg | ctgttggtca | cgtgttcaat | ctcattcact | tgtaggatg | 1020 |
| ctatatgggt | caagtcagat | ccctaaatgc | aacggttatt | gctgcatgtg | ctcctcatga | 1080 |
| aatgtctgtt | ctaggggct | atctgggaga | ggaattcttc | gggaaaggga | catttgaaag | 1140 |
| aagattcttc | agagatgaga | agaacttca | agaatacgag | gcggctgaac | tgacaaagac | 1200 |
| tgacgtagca | ctggcagatg | atggaactgt | caactctgac | gacgaggact | acttctcagg | 1260 |
| tgaaaccaga | agtccggagg | ctgttttatac | tcgaatcatg | atgaatggag | tcgactaaa | 1320 |
| gagatctcac | atacggagat | atgtctcagt | cagttccaat | catcaagccc | gtccaaactc | 1380 |
| attcgccgag | tttctaaaca | agacatattc | gagtgactca | aagaagttg | aacaacaaaa | 1440 |
| tgccggaaat | ctacggattg | tgtatatcca | tcatgaaaaa | aactaacacc | cctcctttcg | 1500 |
| aaccatccca | aacatgagca | agatctttgt | caatcctagt | gctattagag | ccggtctggc | 1560 |
| cgatcttgag | atggctgaag | aaactgttga | tctgatcaat | agaaatatcg | aagacaatca | 1620 |
| ggctcatctc | caaggggaac | ccatagaagt | ggacaatctc | cctgaggata | tggggcgact | 1680 |
| tcacctggat | gatggaaaat | cgcccaaccc | tggtgagatg | gccaaggtgg | agaaggcaa | 1740 |
| gtatcgagag | gactttcaga | tggatgaagg | agaggatctt | agcttcctgt | tccagtcata | 1800 |
| cctggaaaat | gttggagtcc | aaatagtcag | acaaatgagg | tcaggagaga | gatttctcaa | 1860 |

```
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcaggatac tcttgtataa ttttgagcaa ttgaaaatga accttgatga   2220
tatagttaaa gaggcaaaaa atgtaccagg tgtgacccgt ttagcccatg acgggtccaa   2280 actccccta agatgtgtac tgggatgggt cgctttggcc aaccctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
acatgaggaa cttttgtatc aacggagggg ttaaagtgtg tagcccgaat ggttactcgt   2700
tcaggatcct gcggcacatt ctgaaatcat cgacgagat atattctggg aatcatagga   2760
tgatcgggtt agccaaagta gttattggac tggctttgtc aggatctcca gtccctgagg   2820
gcatgaactg gtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagaatct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caaccctggg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagccc   3420
gattgacata catcacctca gctgcccaaa caatttggta gtggaggacg aaggatgcac   3480
caacctgtca gggttctcct acatggaact taaagttgga tacatcttag ccataaaaat   3540
gaacgggttc acttgcacag gcgttgtgac ggaggctgaa acctatacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cactggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacatttta ccaatagtag   3960 ggggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtcgcga tgcaaacatc aaatgaaacc aaatggtgcc ccccgatca   4140 gttggtgaac ctgcacgact ttcgctcaga cgaaattgag cacctgttg tagaggagtt   4200 ggtcaggaag agagaggagt gtctggatgc actagagtcc atcatgacaa ccaagtcagt   4260
```

```
gagtttcaga cgtcccagtc atttaagaaa acttgtccct gggtttggaa aagcatatac    4320
catattcaac aagaccttga tggaagccga tgctcactac aagtcagtcg agacttggaa    4380
tgagatcctc ccttcaaaag ggtgtttaag agttgggggg aggtgtcatc ctcatgtgaa    4440
cggggtgttt ttcaatggta taatattagg acctgacggc aatgtcttaa tcccagagat    4500
gcaatcatcc ctcctccagc aacatatgga gttgttggaa tcctcggtta tcccccttgt    4560
gcaccccctg gcagacccgt ctaccgtttt caaggacggt gacgaggctg aggattttgt    4620
tgaagttcac cttcccgatg tgcacaatca ggtctcagga gttgacttgg gtctcccgaa    4680
ctgggggaag tatgtattac tgagtgcagg ggccctgact gccttgatgt tgataatttt    4740
cctgatgaca tgttgtagaa gagtcaatcg atcagaacct acgcaacaca atctcagagg    4800
gacagggagg gaggtgtcag tcactcccca aagcgggaag atcatatctt catgggaatc    4860
acacaagagt gggggtgaga ccagactgtg aggactggcc gtcctttcaa ctatccaagt    4920
cctgaagatc acctccccct tgggggttct ttttgaaaaa aacctgggtt caatagtcct    4980
cctcgaactc catgcaactg ggtagattca agagtcatga gattttcatt aatcctctca    5040
gttgatcaag caagatcatg tagattctca taatagggga gatcttctag cagtttcagt    5100
gactaacggt actttcattc tccaggaact gacaccaaca gttgtagaca aaccacgggg    5160
tgtctcgggt gactctgtgc ttgggcacag acaaaggtca tggtgtgttc catgatagcg    5220
gactcaggat gagttaattg agagaggcag tcttcctccc gtgaaggaca taagcagtag    5280
ctcacaatca tcccgcgtct cagcaaagtg tgcataatta taaagtgctg ggtcatctaa    5340
gcttttcagt cgagaaaaaa acattagatc agaagaacaa ctggcaacac ttctcaacct    5400
gagacctact tcaagatgct cgatcctgga gaggtctatg atgacccata tgacccaatc    5460
gagttagagg atgaacccag aggaaccccc actgtcccca acatcttgag gaactctgac    5520
tacaatctca actctccttt gatagaagat cctgctagac taatgttaga atggttaaaa    5580
acagggaata gaccttatcg gatgactcta acagacaatt gctccaggtc tttcagagtt    5640
ttgaaagatt atttcaagaa ggtagatttg ggttctctca aggtgggcgg aatggctgca    5700
cagtcaatga tttctctctg gttatatggt gcccactctg aatccaacag gagccggaga    5760
tgtataacag acttggccca tttctattcc aagtcgtccc ccatagagaa gctgttgaat    5820
ctcacgctag gaaatagagg gctgagaatc cccccagagg gagtgttaag ttgccttgag    5880
agggttgatt atgataatgc atttggaagg tatcttgcca acacgtattc ctcttacttg    5940
ttcttccatg taatcaccct atacatgaac gccctagact gggatgaaga aaagaccatc    6000
ctagcattat ggaaagattt aacctcagtg gacatcggga aggacttggt aaagttcaaa    6060
gaccaaatat ggggactgcc gatcgtgaca aaggactttg tttactccca aagttccaat    6120
tgtcttttg acagaaacta cacacttatg ctaaaagaac ttttcttgtc tcgcttcaac    6180
tccttaatgg tcttgctctc tccccagag ccccgatact cagatgactt gatatctcaa    6240
ctatgccagc tgtacattgc tgggatcaa gtcttgtcta tgtgtggaaa ctccggctat    6300
gaagtcatca aaatattgga gccatatgtc gtgaatagtt tagtccagag agcagaaaag    6360
tttaggcctc tcattcattc cttgggagac tttcctgtat ttataaaaga caaggtaagt    6420
caacttgaag agacgttcgg tccctgtgca agaaggttct ttagggctct ggatcaattc    6480
gacaacatac atgacttggt ttttgtgtat ggctgttaca ggcattgggg cacccatat    6540
atagattatc gaaagggtct gtcaaaacta tatgatcagg ttcacattaa aaaagtgata    6600
```

```
gataagtcct accaggagtg cttagcaagc gacctagcca ggaggatcct tagatggggt    6660
tttgataagt actccaagtg gtatctggat tcaagattcc tagcccgaga ccaccccttg    6720
actccttata tcaaaaccca aacatggcca cccaaacata ttgtagactt ggtgggggat    6780
acatggcaca agctcccgat cacgcagatc tttgagattc ctgaatcaat ggatccgtca    6840
gaaatattgg atgacaaatc acattctttc accagaacga gactagcttc ttggctgtca    6900
gaaaaccgag ggggacctgt tcctagcgaa aaagttatta tcacggccct gtctaagccg    6960
cctgtcaatc cccgagagtt tctgaggtct atagacctcg gaggattgcc agatgaagac    7020
ttgataattg gcctcaagcc aaaggaacgg gaattgaaga ttgaaggtcg attctttgct    7080
ctaatgtcat ggaatctaag attgtatttt gtcatcactg aaaaactctt ggccaactac    7140
atcttgccac ttttttgacgc gctgactatg acagacaacc tgaacaaggt gtttaaaaag    7200
ctgatcgaca gggtcaccgg gcaagggctt ttggactatt caagggtcac atatgcattt    7260
cacctggact atgaaaagtg gaacaaccat caaagattag agtcaacaga ggatgtattt    7320
tctgtcctag atcaagtgtt tggattgaag agagtgtttt ctagaacaca cgagtttttt    7380
caaaaggcct ggatctatta ttcagacaga tcagacctca tcgggttacg ggaggatcaa    7440
atatactgct tagatgcgtc caacggccca acctgttgga atggccagga tggcgggcta    7500
gaaggcttac ggcagaaggg ctggagtcta gtcagcttat tgatgataga tagagaatct    7560
caaatcagga acacaagaac caaaatacta gctcaaggag acaaccaggt tttatgtccg    7620
acatatatgt tgtcgccagg gctatctcaa gagggctcc tctatgaatt ggagagaata    7680
tcaaggaatg cactttcgat atacagagcc gtcgaggaag gggcatctaa gctagggctg    7740
atcatcaaga aagaagagac catgtgtagt tatgacttcc tcatctatgg aaaaaccccct    7800
ttgtttagag gtaacatatt ggtgcctgag tccaaaagat gggccagagt ctcttgcgtc    7860
tctaatgacc aaatagtcaa cctcgccaat ataatgtcga cagtgtccac caatgcgcta    7920
acagtggcac aacactctca atctttgatc aaaccgatga gggattttct gctcatgtca    7980
gtacaggcag tctttcacta cctgctattt agcccaatct taaagggaag agtttacaag    8040
attctgagcg ctgaagggga tagctttctc ctagccatgt caaggataat ctatctagat    8100
ccttctttgg gagggtatc tggaatgtcc ctcggaagat tccatatacg acagttctca    8160
gaccctgtct ctgaagggtt atccttctgg agagagatct ggttaagctc ccacgagtcc    8220
tggattcacg cgttgtgtca agaggctgga aacccagatc ttggagagag aacactcgag    8280
agcttcactc gccttctaga agatcctacc accttaaata tcagaggagg ggccagtcct    8340
accattctac tcaaggatgc aatcagaaag gctttatatg acgaggtgga caaggtggag    8400
aattcagagt ttcgagaggc aatcctgttg tccaagaccc atagagataa ttttatactc    8460
ttcttaacat ctgttgagcc tctgtttcct cgatttctca gtgagctatt cagttcgtct    8520
tttttgggaa tccccgagtc aatcattgga ttgatacaaa actcccgaac gataagaagg    8580
cagtttagaa agagtctctc aaaaactta gaagaatcct tctacaactc agagatccac    8640
gggattagtc ggatgaccca gacacctcag aggtttgggg ggtgtggcc ttgctcttca    8700
gagagggcag atctacttag ggagatctct tggggaagaa aagtggtagg cacgacagtt    8760
cctcacccctt ctgagatgtt ggggttactt cccaagtcct ctatttcttg cacttgtgga    8820
gcaacaggag gaggcaatcc tagagttct gtatcagtac tcccgtcctt tgatcagtca    8880
ttttttttcac gaggccccct aaaggggtac ttgggctcgt ccacctctat gtcgacccag    8940
ctattccatg catgggaaaa agtcactaat gttcatgtgg tgaagagagc tctatcgtta    9000
```

```
aaagaatcta taaactggtt cattactaga gattccaact tggctcaagc tctaattagg   9060
aacattatgt ctctgacagg ccctgatttc cctctagagg aggcccctgt cttcaaaagg   9120
acggggtcag ccttgcatag gttcaagtct gccagataca gcgaaggagg gtattcttct   9180
gtctgcccga acctcctctc tcatatttct gttagtacag acaccatgtc tgatttgacc   9240
caagacggga agaactacga tttcatgttc cagccattga tgctttatgc acagacatgg   9300
acatcagagc tggtacagag agacacaagg ctaagagact ctacgtttca ttggcacctc   9360
cgatgcaaca ggtgtgtgag acccattgac gacgtgaccc tggagacctc tcagatcttc   9420
gagtttccgg atgtgtcgaa aagaatatcc agaatggttt ctgggctgt  gcctcacttc   9480 cagaggcttc ccgatatccg tctgagacca ggagattttg aatctctaag cggtagagaa   9540
aagtctcacc atatcggatc agctcagggg ctcttatact caatcttagt ggcaattcac   9600
gactcaggat acaatgatgg aaccatcttc cctgtcaaca tacgacaa  ggtttcccct    9660 agagactatt tgagagggct cgcaagggga gtattgatag gatcctcgat ttgcttcttg   9720
acaagaatga caaatatcaa tattaataga cctcttgaat tgatctcagg ggtaatctca   9780
tatattctcc tgaggctaga taaccatccc tccttgtaca taatgctcag agaaccgtct   9840
cttagaggag agatattttc tatccctcag aaaatccccg ccgcttatcc aaccactatg   9900
aaagaaggca acagatcaat cttgtgttat ctccaacatg tgctacgcta tgagcgagag   9960
ataatcacgg cgtctccaga gaatgactgg ctatggatct tttcagactt tagaagtgcc  10020
aaaatgacgt acctaaccct cattacttac cagtctcatc ttctactcca gagggttgag  10080
agaaacctat ctaagagtat gagagataac ctgcgacaat tgagttcctt gatgaggcag  10140
gtgctgggcg ggcacggaga agataccta  gagtcagacg acaacattca acgactgcta  10200
aaagactctt tacgaaggac aagatgggtg gatcaagagg tgcgccatgc agctagaacc  10260
atgactggag attacagccc caacaagaag gtgtcccgta aggtaggatg ttcagaatgg  10320
gtctgctctg ctcaacaggt tgcagtctct acctcagcaa acccggcccc tgtctcggag  10380
cttgacataa gggccctctc taagaggttc cagaacccct tgatctcggg cttgagagtg  10440
gttcagtggg caaccggtgc tcattataag cttaagccta ttctagatga tctcaatgtt  10500
ttcccatctc tctgccttgt agttggggac gggtcagggg ggatatcaag gcagtcctc   10560 aacatgtttc cagatgccaa gcttgtgttc aacagtctct tagaggtgaa tgacctgatg  10620
gcttccggaa cacatccact gcctccttca gcaatcatga gggaggaaa  tgatatcgtc  10680 tccagagtga tagattttga ctcaatctgg gaaaaaccgt ccgacttgag aaacttggca  10740
acctggaaat acttccagtc agtccaaaag caggtcaaca tgtcctatga cctcattatt  10800
tgcgatgcag aagttactga cattgcatct atcaaccgga taaccctgtt aatgtccgat  10860
tttgcattgt ctatagatgg accactctat ttggtcttca aaacttatgg gactatgcta  10920
gtaaatccaa actacaaggc tattcaacac ctgtcaagag cgttcccctc ggtcacaggg  10980
tttatcaccc aagtaacttc gtcttttca tctgagctct acctccgatt ctccaaacga  11040
gggaagtttt tcagagatgc tgagtacttg acctcttcca cccttcgaga aatgagcctt  11100
gtgttattca attgtagcag ccccaagagt gagatgcaga gagctcgttc cttgaactat  11160
caggatcttg tgagaggatt tcctgaagaa atccatatcaa atccttacaa tgagatgatc  11220
ataactctga ttgacagtga tgtagaatct tttctagtcc acaagatggt tgatgatcttt  11280 gagttacaga ggggaactct gtctaaagtg gctatcatta tagccatcat gatagttttc  11340
```

-continued

```
tccaacagag tcttcaacgt ttccaaaccc ctaactgacc ccttgttcta tccaccgtct    11400
gatcccaaaa tcctgaggca cttcaacata tgttgcagta ctatgatgta tctatctact    11460
gctttaggtg acgtccctag cttcgcaaga cttcacgacc tgtataacag acctataact    11520
tattacttca gaaagcaatt cattcgaggg aacgtttatc tatcttggag ttggtccaac    11580
gacacctcag tgttcaaaag ggtagcctgt aattctagcc tgagtctgtc atctcactgg    11640
atcaggttga tttacaagat agtgaagact accagactcg ttggcagcat caaggatcta    11700
tccagagaag tggaaagaca ccttcatagg tacaacaggt ggatcaccct agaggatatc    11760
agatctagat catccctact agactacagt tgcctgtgaa ccggatactc ctggaagcct    11820
gcccatgcta agactcttgt gtgatgtatc ttgaaaaaaa caagatccta aatctgaacc    11880
tttggttgtt tgattgtttt tctcattttt gttgtttatt tgttaagcgt              11930
```

```
<210> SEQ ID NO 9
<211> LENGTH: 11577
<212> TYPE: DNA
<213> ORGANISM: artificial sequence
<220> FEATURE:
<223> OTHER INFORMATION: recombinant ERA- rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (5063)..(11443)
```

\<400\> SEQUENCE: 9

```
acgcttaaca accagatcaa agaaaaaaca gacattgtca attgcaaagc aaaaatgtaa      60
cacccctaca atggatgccg acaagattgt attcaaagtc aataatcagg tggtctcttt     120
gaagcctgag attatcgtgg atcaacatga gtacaagtac cctgccatca aagatttgaa     180 aaagcccctgt ataaccctag gaaaggctcc cgatttaaat aaagcataca agtcagtttt    240
gtcaggcatg agcgccgcca aacttgatcc tgacgatgta tgttcctatt tggcagcggc     300
aatgcagttt tttgagggga catgtccgga agactggacc agctatggaa tcgtgattgc     360
acgaaaagga gataagatca ccccaggttc tctggtggag ataaaacgta ctgatgtaga     420
agggaattgg gctctgacag gaggcatgga actgacaaga accccactg tccctgagca      480 tgcgtcctta gtcggtcttc tcttgagtct gtataggttg agcaaaatat ccgggcaaaa     540
cactggtaac tataagacaa acattgcaga caggatagag cagattttg agacagcccc     600 ttttgttaaa atcgtggaac accatactct aatgacaact cacaaaatgt gtgctaattg     660
gagtactata ccaaacttca gattttggc cggaacctat gacatgtttt tctcccggat      720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg    1020
```

```
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctccttttcg   1500 aaccatccca acatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
acatgaggaa cttttgtatc aacggagggg ttaaagtgtg tagcccgaat ggttactcgt   2700
tcaggatcct gcggcacatt ctgaaatcat tcgacgagat atattctggg aatcatagga   2760
tgatcgggtt agtcaaagta gttattggac tggctttgtc aggatctcca gtccctgagg   2820
gcatgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcga ttgcaaata agagtgattg caaaacagtg tcatatccag gcagaatct   3000 ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac cttacatttt tgatcctctt ggatgtgaaa aaaactatta acatccctca   3300
aaagactcaa ggaaagatgg ttcctcaggc tctcctgttt gtaccccttc tggttttttcc   3360 attgtgtttt gggaaattcc ctatttacac gataccagac aagcttggtc cctggagccc   3420
```

```
gattgacata catcacctca gctgcccaaa caatttggta gtggaggacg aaggatgcac    3480
caacctgtca gggttctcct acatggaact taaagttgga tacatcttag ccataaaaat    3540
gaacgggttc acttgcacag gcgttgtgac ggaggctgaa acctacacta acttcgttgg    3600
ttatgtcaca accacgttca aaagaaagca tttccgccca acaccagatg catgtagagc    3660
cgcgtacaac tggaagatgg ccggtgaccc cagatatgaa gagtctctac acaatccgta    3720
ccctgactac cactggcttc gaactgtaaa aaccaccaag gagtctctcg ttatcatatc    3780
tccaagtgtg gcagatttgg acccatatga cagatcccTT cactcgaggg tcttccctag    3840
cgggaagtgc tcaggagtag cggtgtcttc tacctactgc tccactaacc acgattacac    3900
catttggatg cccgagaatc cgagactagg gatgtcttgt gacatttttA ccaatagtag    3960
agggaagaga gcatccaaag ggagtgagac ttgcggcttt gtagatgaaa gaggcctata    4020
taagtcttta aaaggagcat gcaaactcaa gttatgtgga gttctaggac ttagacttat    4080
ggatggaaca tgggtcgcga tgcaaacatc aaatgaaacc aaatggtgcc ctcccgatca    4140
gttggtgaac ctgcacgact ttcgctcaga cgaaattgag caccttgttg tagaggagtt    4200
ggtcaggaag agagaggagt gtctggatgc actagagtcc atcatgacaa ccaagtcagt    4260
gagtttcaga cgtctcagtc atttaagaaa acttgtccct gggtttggaa aagcatatac    4320
catattcaac aagaccttga tggaagccga tgctcactac aagtcagtca gaacttggaa    4380
tgagatcctc ccttcaaaag ggtgtttaag agttgggggg aggtgtcatc ctcatgtgaa    4440
cggggtgttt ttcaatggta taatattagg acctgacgg aatgtcttaa tcccagagat    4500
gcaatcatcc ctcctccagc aacatatgga gttgttggaa tcctcggtta tcccccttgt    4560
gcaccccctg gcagacccgt ctaccgtttt caaggacggt gacgaggctg aggattttgt    4620
tgaagttcac cttcccgatg tgcacaatca ggtctcagga gttgacttgg gtctcccgaa    4680
ctgggggaag tatgtattac tgagtgcagg ggccctgact gccttgatgt tgataattTT    4740
cctgatgaca tgttgtagaa gagtcaatcg atcagaacct acgcaacaca atctcagagg    4800
gacagggagg gaggtgtcag tcactcccca aagcgggaag atcatatctt catgggaatc    4860
acacaagagt gggggtgaga ccagactgtg aggactggcc gtcctttcaa ctatccaagt    4920
cctgaagatc acctccccctt gggggttca tcatgaaaaa aactaacacc cctcctttcg    4980
ctgcagtttg gtaccgtcga gaaaaaaaca ttagatcaga agaacaactg caacacttc    5040 tcaacctgag acctacttca agatgctcga tcctggagag gtctatgatg accctattga    5100
cccaatcgag ttagaggatg aacccagagg aacccccact gtccccaaca tcttgaggaa    5160
ctctgactac aatctcaact ctcctttgat agaagatcct gctagactaa tgttagaatg    5220
gttaaaaaca gggaatagac cttatcggat gactctaaca gacaattgct ccaggtcttt    5280
cagagttttg aaagattatt tcaagaaggt agatttgggt tctctcaagg tgggcggaat    5340
ggctgcacag tcaatgattt ctctctggtt atatggtgcc cactctgaat ccaacaggag    5400
ccggagatgt ataacagact tggcccattt ctattccaag tcgtccccca tagagaagct    5460
gttgaatctc acgctaggaa atagagggct gagaatcccc ccagagggag tgttaagttg    5520
ccttgagagg gttgattatg ataatgcatt tggaaggtat cttgccaaca cgtattcctc    5580
ttacttgttc ttccatgtaa tcaccttata catgaacgcc ctagactggg atgaagaaaa    5640
gaccatccta gcattatgga aagatttaac ctcagtggac atcggaaagg acttggtaaa    5700
gttcaaagac caaatatggg gactgctgat cgtgacaaag gactttgttt actcccaaag    5760
```

```
ttccaattgt cttttttgaca gaaactacac acttatgcta aaagatcttt tcttgtctcg   5820
cttcaactcc ttaatggtct tgctctctcc cccagagccc cgatactcag atgacttgat   5880
atctcaacta tgccagctgt acattgctgg ggatcaagtc ttgtctatgt gtggaaactc   5940
cggctatgaa gtcatcaaaa tattggagcc atatgtcgtg aatagtttag tccagagagc   6000
agaaaagttt aggcctctca ttcattcctt gggagacttt cctgtattta taaaagacaa   6060
ggtaagtcaa cttgaagaga cgttcggtcc ctgtgcaaga aggttcttta gggctctgga   6120
tcaattcgac aacatacatg acttggtttt tgtgtatggc tgttacaggc attggggca    6180
cccatatata gattatcgaa agggtctgtc aaaactatat gatcaggttc acattaaaaa   6240
agtgatagat aagtcctacc aggagtgctt agcaagcgac ctagccagga ggatccttag   6300
atgggggtttt gataagtact ccaagtggta tctggattca agattcctag cccgagacca   6360
cccccttgact ccttatatca aaacccaaac atggccaccc aaacatattg tagacttggt   6420
gggggataca tggcacaagc tcccgatcac gcagatcttt gagattcctg aatcaatgga   6480
tccgtcagaa atattggatg acaaatcaca ttcttttcacc agaacgagac tagcttcttg   6540
gctgtcagaa aaccgagggg gacctgttcc tagcgaaaaa gttattatca cggccctgtc   6600
taagccgcct gtcaatcccc gagagtttct gaggtctata gacctcggag gattgccaga   6660
tgaagacttg ataattggcc tcaagccaaa ggaacgggaa ttgaagattg aaggtcgatt   6720
ctttgctcta atgtcatgga atctaagatt gtatttttgtc atcactgaaa aactcttggc   6780
caactcatc ttgccacttt ttgacgcgct gactatgaca gacaacctga caaggtgtt    6840
taaaaagctg atcgacaggg tcaccgggca agggcttttg gactattcaa gggtcacata   6900
tgcatttcac ctggactatg aaaagtggaa caaccatcaa agattagagt caacagagga   6960
tgtattttct gtcctagatc aagtgtttgg attgaagaga gtgttttcta gaacacacga   7020
gttttttcaa aaggcctgga tctattattc agacagatca gacctcatcg ggttacggga   7080
ggatcaaata tactgcttag atgcgtccaa cggcccaacc tgttggaatg ccaggatgg    7140
cgggctagaa ggcttacggc agaagggctg gagtctagtc agcttattga tgatagatag   7200
agaatctcaa atcaggaaca caagaaccaa aatactagct caaggagaca accaggtttt   7260
atgtccgaca tatatgttgt cgccagggct atctcaagag gggctcctct atgaattgga   7320
gagaatatca aggaatgcac tttcgatata cagagccgtc gaggaagggg catctaagct   7380
agggctgatc atcaagaaag aagagaccat gtgtagttat gacttcctca tctatggaaa   7440
aacccctttg tttagaggta acatattggt gcctgagtcc aaaagatggg ccagagtctc   7500
ttgcgtctct aatgaccaaa tagtcaacct cgccaatata atgtcgacag tgtccaccaa   7560
tgcgctaaca gtggcacaac actctcaatc tttgatcaaa ccgatgaggg atttctgct   7620
catgtcagta caggcagtct ttcactacct gctatttagc ccaatcttaa agggaagagt   7680
ttacaagatt ctgagcgctg aagggatag ctttctccta gccatgtcaa ggataatcta    7740
tctagatcct tctttgggag gggtatctgg aatgtccctc ggaagattcc atatacgaca   7800
gttctcagac cctgtctctg aagggttatc cttctggaga gagatctggt taagctccca   7860
cgagtcctgg attcacgcgt tgtgtcaaga ggctggaaac ccagatcttg gagagagaac   7920
actcgagagc ttcactcgcc ttctagaaga tcctaccacc ttaaaatatca gaggagggc    7980
cagtcctacc attctactca aggatgcaat cagaaaggct ttatatgacg aggtggacaa   8040
ggtggagaat tcagagtttc gagaggcaat cctgttgtcc aagacccata gagataattt   8100
tatactcttc ttaacatctg ttgagcctct gtttcctcga tttctcagtg agctattcag   8160
```

```
ttcgtctttt ttgggaatcc ccgagtcaat cattggattg atacaaaact cccgaacgat    8220
aagaaggcag tttagaaaga gtctctcaaa aactttagaa gaatccttct acaactcaga    8280
gatccacggg attagtcgga tgacccagac acctcagagg gttgggggggg tgtggccttg   8340 ctcttcagag agggcagatc tacttaggga gatctcttgg ggaagaaaag tggtaggcac    8400
gacagttcct caccctttctg agatgttggg gttacttccc aagtcctcta tttcttgcac   8460
ttgtggagca acaggaggag gcaatcctag agtttctgta tcagtactcc cgtcctttga   8520
tcagtcattt ttttcacgag gcccctaaa ggggtacttg ggctcgtcca cctctatgtc    8580
gacccagcta ttccatgcat gggaaaaagt cactaatgtt catgtggtga agagagctct   8640
atcgttaaaa gaatctataa actggttcat tactagagat tccaacttgg ctcaagctct   8700
aattaggaac attatgtctc tgacaggccc tgatttccct ctagaggagg ccctgtcctt   8760
caaaaggacg gggtcagcct tgcataggtt caagtctgcc agatacagcg aaggagggta   8820
ttcttctgtc tgcccgaacc tcctctctca tatttctgtt agtacagaca ccatgtctga   8880
tttgacccaa gacgggaaga actacgattt catgttccag ccattgatgc tttatgcaca   8940
gacatggaca tcagagctgg tacagagaga cacaaggcta agagactcta cgtttcattg   9000
gcacctccga tgcaacaggt gtgtgagacc cattgacgac gtgaccctgg agacctctca   9060
gatcttcgag tttccggatg tgtcgaaaag aatatccaga atggtttctg gggctgtgcc   9120
tcacttccag aggcttcccg atatccgtct gagaccagga gatttgaat ctctaagcgg    9180 tagagaaaag tctcaccata tcggatcagc tcaggggctc ttatactcaa tcttagtggc   9240
aattcacgac tcaggataca atgatggaac catcttccct gtcaacatat acgacaaggt   9300
ttcccctaga gactatttga gagggctcgc aaggggagta ttgataggat cctcgatttg   9360
cttcttgaca agaatgacaa atatcaatat taatagacct cttgaattga tctcaggggt   9420
aatctcatat attctcctga ggctagataa ccatccctcc ttgtacataa tgctcagaga   9480
accgtctctt agaggagaga tattttctat ccctcagaaa atccccgccg cttatccaac   9540
cactatgaaa gaaggcaaca gatcaatctt gtgttatctc caacatgtgc tacgctatga   9600
gcgagagata atcacggcgt ctccagagaa tgactggcta tggatctttt cagactttag   9660
aagtgccaaa atgacgtacc taaccctcat tacttaccag tctcatcttc tactccagag   9720
ggttgagaga aacctatcta agagtatgag agataacctg cgacaattga gttccttgat   9780
gaggcaggtg ctgggcgggc acggagaaga taccttagag tcagacgaca acattcaacg   9840
actgctaaaa gactctttac gaaggacaag atgggtggat caagaggtgc gccatgcagc   9900
tagaaccatg actggagatt acagccccaa caagaaggtg tcccgtaagg taggatgttc   9960
agaatgggtc tgctctgctc aacaggttgc agtctctacc tcagcaaacc cggcccctgt   10020
ctcggagctt gacataaggg ccctctctaa gaggttccag aacccttttga tctcgggctt   10080 gagagtggtt cagtgggcaa ccggtgctca ttataagctt aagcctattc tagatgatct   10140
caatgttttc ccatctctct gccttgtagt tgggacggg tcaggggga tatcaagggc     10200 agtcctcaac atgtttccag atgccaagct tgtgttcaac agtctcttag aggtgaatga   10260
cctgatggct tccggaacac atccactgcc tccttcagca atcatgaggg gaggaaatga   10320
tatcgtctcc agagtgatag atttttgactc aatctgggaa aaaccgtccg acttgagaaa   10380
cttggcaacc tggaaatact tccagtcagt ccaaaagcag gtcaacatgt cctatgacct   10440
cattatttgc gatgcagaag ttactgacat tgcatctatc aaccgataa ccctgttaat     10500
```

-continued

```
gtccgatttt gcattgtcta tagatggacc actctatttg gtcttcaaaa cttatgggac    10560
tatgctagta aatccaaact acaaggctat tcaacacctg tcaagagcgt tccccctcggt   10620 cacagggttt atcacccaag taacttcgtc ttttttcatct gagctctacc tccgattctc   10680
caaacgaggg aagttttttca gagatgctga gtacttgacc tcttccaccc ttcgagaaat   10740
gagccttgtg ttattcaatt gtagcagccc caagagtgag atgcagagag ctcgttcctt   10800
gaactatcag gatcttgtga gaggatttcc tgaagaaatc atatcaaatc cttacaatga   10860
gatgatcata actctgattg acagtgatgt agaatctttt ctagtccaca agatggttga   10920
tgatcttgag ttacagaggg gaactctgtc taaagtggct atcattatag ccatcatgat   10980
agttttctcc aacagagtct tcaacgtttc caaaccccta actgacccct tgttctatcc   11040
accgtctgat cccaaaatcc tgaggcactt caacatatgt tgcagtacta tgatgtatct   11100
atctactgct ttaggtgacg tccctagctt cgcaagactt cacgacctgt ataacagacc   11160
tataacttat tacttcagaa agcaattcat tcgagggaac gtttatctat cttggagttg   11220
gtccaacgac acctcagtgt tcaaaagggt agcctgtaat tctagcctga gtctgtcatc   11280
tcactggatc aggttgattt acaagatagt gaagactacc agactcgttg gcagcatcaa   11340
ggatctatcc agagaagtgg aaagacacct tcataggtac aacaggtgga tcaccctaga   11400
ggatatcaga tctagatcat ccctactaga ctacagttgc ctgtgatccg gatactcctg   11460
gaagcctgcc catgctaaga ctcttgtgtg atgtatcttg aaaaaaacaa gatcctaaat   11520 ctgaacccttt ggttgtttga ttgttttttct catttttgtt gtttatttgt taagcgt     11577
```

<210> SEQ ID NO 10
<211> LENGTH: 13150
<212> TYPE: DNA
<213> ORGANISM: artificial sequence
<220> FEATURE:
<223> OTHER INFORMATION: Recombinant ERA-2G rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (4988)..(6559)
<220> FEATURE:
<221> NAME/KEY: misc_feature
<222> LOCATION: (6636)..(13016)

<400> SEQUENCE: 10

```
acgcttaaca accagatcaa agaaaaaaca gacattgtca attgcaaagc aaaaatgtaa       60 caccccctaca atggatgccg acaagattgt attcaaagtc aataatcagg tggtctcttt     120
gaagcctgag attatcgtgg atcaacatga gtacaagtac cctgccatca agatttgaa      180 aaagccctgt ataaccctag gaaaggctcc cgatttaaat aaagcataca agtcagtttt     240
gtcaggcatg agcgccgcca aacttgatcc tgacgatgta tgttcctatt tggcagcggc    300
aatgcagttt ttgagggga catgtccgga agactggacc agctatggaa tcgtgattgc     360
acgaaaagga gataagatca cccccaggttc tctggtggag ataaaacgta ctgatgtaga    420
agggaattgg gctctgacag gaggcatgga actgacaaga gaccccactg tccctgagca    480
```

```
tgcgtcctta gtcggtcttc tcttgagtct gtataggttg agcaaaatat ccgggcaaaa      540
cactggtaac tataagacaa acattgcaga caggatagag cagattttg  agacagcccc      600 ttttgttaaa atcgtggaac accatactct aatgacaact cacaaaatgt gtgctaattg      660
gagtactata ccaaacttca gattttggc  cggaacctat gacatgtttt tctcccggat      720
tgagcatcta tattcagcaa tcagagtggg cacagttgtc actgcttatg aagactgttc      780
aggactggta tcatttactg ggttcataaa acaaatcaat ctcaccgcta gagaggcaat      840
actatatttc ttccacaaga actttgagga agagataaga agaatgtttg agccagggca      900
ggagacagct gttcctcact cttatttcat ccacttccgt tcactaggct tgagtgggaa      960
atctccttat tcatcaaatg ctgttggtca cgtgttcaat ctcattcact ttgtaggatg      1020
ctatatgggt caagtcagat ccctaaatgc aacggttatt gctgcatgtg ctcctcatga     1080
aatgtctgtt ctaggggct  atctgggaga ggaattcttc gggaaaggga catttgaaag     1140
aagattcttc agagatgaga aagaacttca agaatacgag gcggctgaac tgacaaagac     1200
tgacgtagca ctggcagatg atggaactgt caactctgac gacgaggact acttctcagg     1260
tgaaaccaga agtccggagg ctgtttatac tcgaatcatg atgaatggag gtcgactaaa     1320
gagatctcac atacggagat atgtctcagt cagttccaat catcaagccc gtccaaactc     1380
attcgccgag tttctaaaca agacatattc gagtgactca taagaagttg aataacaaaa     1440
tgccggaaat ctacgattg  tgtatatcca tcatgaaaaa aactaacacc cctcctttcg     1500
aaccatccca aacatgagca agatctttgt caatcctagt gctattagag ccggtctggc     1560
cgatcttgag atggctgaag aaactgttga tctgatcaat agaaatatcg aagacaatca     1620
ggctcatctc caagggaac  ccatagaagt ggacaatctc cctgaggata tggggcgact     1680
tcacctggat gatggaaaat cgcccaaccc tggtgagatg gccaaggtgg gagaaggcaa     1740
gtatcgagag gactttcaga tggatgaagg agaggatcct agcttcctgt tccagtcata     1800
cctggaaaat gttggagtcc aaatagtcag acaaatgagg tcaggagaga gatttctcaa     1860
gatatggtca cagaccgtag aagagattat atcctatgtc gcggtcaact ttcccaaccc     1920
tccaggaaag tcttcagagg ataaatcaac ccagactact ggccgagagc tcaagaagga     1980
gacaacaccc actccttctc agagagaaag ccaatcatcg aaagccagga tggcggctca     2040
aattgcttct ggccctccag cccttgaatg gtcggccacc aatgaagagg atgatctatc     2100
agtggaggct gagatcgctc accagattgc agaaagtttc tccaaaaaat ataagtttcc     2160
ctctcgatcc tcagggatac tcttgtataa ttttgagcaa ttgaaaatga accttgatga     2220
tatagttaaa gaggcaaaaa atgtaccagg tgtgacccgt ttagcccatg acgggtccaa     2280
actcccccta agatgtgtac tgggatgggt cgctttggcc aactctaaga aattccagtt     2340
gttagtcgaa tccgacaagc tgagtaaaat catgcaagat gacttgaatc gctatacatc     2400
ttgctaaccg aacctctcca ctcagtccct ctagacaata aagtccgaga tgtcctaaag     2460
tcaacatgaa aaaacaggc  aacaccactg ataaaatgaa ctttctacgt aagatagtga     2520
aaaattgcag ggacgaggac actcaaaaac cctctcccgt gtcagcccct ctggatgacg     2580
atgacttgtg gcttccaccc cctgaatacg tcccgctgaa agaacttaca agcaagaaga     2640
acatgaggaa cttttgtatc aacggagggg ttaaagtgtg tagcccgaat ggttactcgt     2700
tcaggatcct gcggcacatt ctgaaatcat tcgacgagat atattctggg aatcatagga     2760
tgatcgggtt agtcaaagta gttattggac tggctttgtc aggatctcca gtccctgagg     2820
```

```
gcatgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag ggcagaatct    3000
ggtgtatcaa catgaacccg agagcatgtc aactatggtc tgacatgtct cttcagacac    3060
aaaggtccga agaggacaaa gattcctctc tgcttctaga ataatcagat tatatcccgc    3120
aaatttatca cttgtttacc tctggaggag agaacatatg ggctcaactc caacccttgg    3180
gagcaatata acaaaaaaca tgttatggtg ccattaaacc gctgcatttc atcaaagtca    3240
agttgattac ctttacattt tgatcctctt ggatgtgaaa aaaactatta acatccctca    3300
aaagactcaa ggaaagatgg ttcctcaggc tctcctgttt gtacccctttc tggttttttcc   3360
attgtgtttt gggaaattcc ctatttacac gataccagac aagcttggtc cctggagccc    3420
gattgacata catcacctca gctgcccaaa caatttggta gtggaggacg aaggatgcac    3480
caacctgtca gggttctcct acatggaact taaagttgga tacatcttag ccataaaaat    3540
gaacgggttc acttgcacag gcgttgtgac ggaggctgaa acctacacta acttcgttgg    3600
ttatgtcaca accacgttca aaagaaagca tttccgccca acaccagatg catgtagagc    3660
cgcgtacaac tggaagatgg ccggtgaccc cagatatgaa gagtctctac acaatccgta    3720
ccctgactac cactggcttc gaactgtaaa aaccaccaag gagtctctcg ttatcatatc    3780
tccaagtgtg gcagatttgg acccatatga cagatcccctt cactcgaggg tcttccctag    3840
cgggaagtgc tcaggagtag cggtgtcttc tacctactgc tccactaacc acgattacac    3900
catttggatg cccgagaatc cgagactagg gatgtcttgt gacattttta ccaatagtag    3960
agggaagaga gcatccaaag ggagtgagac ttgcggcttt gtagatgaaa gaggcctata    4020
taagtcttta aaaggagcat gcaaactcaa gttatgtgga gttctaggac ttagacttat    4080
ggatggaaca tgggtcgcga tgcaaacatc aaatgaaacc aaatggtgcc ctcccgatca    4140
gttggtgaac ctgcacgact ttcgctcaga cgaaattgag caccttgttg tagaggagtt    4200
ggtcaggaag agagaggagt gtctggatgc actagagtcc atcatgacaa ccaagtcagt    4260
gagtttcaga cgtctcagtc atttaagaaa acttgtccct gggtttggaa aagcatatac    4320
catattcaac aagaccttga tggaagccga tgctcactac aagtcagtca gaacttggaa    4380
tgagatcctc ccttcaaaag ggtgtttaag agttgggggg aggtgtcatc ctcatgtgaa    4440
cggggtgttt ttcaatggta taatattagg acctgacggc aatgtcttaa tcccagagat    4500
gcaatcatcc ctcctccagc aacatatgga gttgttggaa tcctcggtta tcccccttgt    4560
gcacccctg gcagacccgt ctaccgtttt caaggacggt gacgaggctg aggattttgt    4620
tgaagttcac cttcccgatg tgcacaatca ggtctcagga gttgacttgg gtctcccgaa    4680
ctgggggaag tatgtattac tgagtgcagg ggccctgact gccttgatgt tgataatttt    4740
cctgatgaca tgttgtagaa gagtcaatcg atcagaacct acgcaacaca atctcagagg    4800
gacagggagg gaggtgtcag tcactcccca aagcgggaag atcatatctt catgggaatc    4860
acacaagagt gggggtgaga ccagactgtg aggactggcc gtcctttcaa ctatccaagt    4920
cctgaagatc acctcccctt gggggttca tcatgaaaaa actaacacc cctcctttcg    4980
ctgcaggatg gttcctcagg ctctcctgtt tgtacccctt ctggtttttc cattgtgttt    5040
tgggaaattc cctatttaca cgataccaga caagcttggt ccctggagcc cgattgacat    5100
acatcacctc agctgcccaa acaatttggt agtggaggac gaaggatgca ccaacctgtc    5160
agggttctcc tacatggaac ttaaagttgg atacatctta gccataaaaa tgaacgggtt    5220
```

```
cacttgcaca ggcgttgtga cggaggctga aacctacact aacttcgttg gttatgtcac    5280
aaccacgttc aaaagaaagc atttccgccc aacaccagat gcatgtagag ccgcgtacaa    5340
ctggaagatg gccggtgacc ccagatatga agagtctcta cacaatccgt accctgacta    5400
ccactggctt cgaactgtaa aaaccaccaa ggagtctctc gttatcatat ctccaagtgt    5460
ggcagatttg gacccatatg acagatccct tcactcgagg gtcttcccta gcgggaagtg    5520
ctcaggagta gcggtgtctt ctacctactg ctccactaac cacgattaca ccatttggat    5580
gcccgagaat ccgagactag ggatgtcttg tgacattttt accaatagta gagggaagag    5640
agcatccaaa gggagtgaga cttgcggctt tgtagatgaa agaggcctat ataagtcttt    5700
aaaaggagca tgcaaactca agttatgtgg agttctagga cttagactta tggatggaac    5760
atgggtcgcg atgcaaacat caaatgaaac caaatggtgc cctcccgatc agttggtgaa    5820
cctgcacgac tttcgctcag acgaaattga gcaccttgtt gtagaggagt tggtcaggaa    5880
gagagaggag tgtctggatg cactagagtc catcatgaca accaagtcag tgagtttcag    5940
acgtctcagt catttaagaa aacttgtccc tgggtttgga aaagcatata ccatattcaa    6000
caagaccttg atggaagccg atgctcacta caagtcagtc agaacttgga atgagatcct    6060
cccttcaaaa gggtgtttaa gagttggggg gaggtgtcat cctcatgtga acggggtgtt    6120
tttcaatggt ataatattag acctgacgg caatgtctta atcccagaga tgcaatcatc    6180
cctcctccag caacatatgg agttgttgga atcctcggtt atccccttg tgcacccct    6240 ggcagacccg tctaccgttt tcaaggacgg tgacgaggct gaggattttg ttgaagttca    6300
ccttcccgat gtgcacaatc aggtctcagg agttgacttg ggtctcccga actgggggaa    6360
gtatgtatta ctgagtgcag gggccctgac tgccttgatg ttgataattt tcctgatgac    6420
atgttgtaga agagtcaatc gatcagaacc tacgcaacac aatctcagag ggacagggag    6480
ggaggtgtca gtcactcccc aaagcgggaa gatcatatct tcatgggaat cacacaagag    6540
tgggggtgag accagactgt gaggtaccgt cgagaaaaaa acattagatc agaagaacaa    6600
ctggcaacac ttctcaacct gagacctact tcaagatgct cgatcctgga gaggtctatg    6660
atgaccctat tgacccaatc gagttagagg atgaacccag aggaaccccc actgtcccca    6720
acatcttgag gaactctgac tacaatctca actctccttt gatagaagat cctgctagac    6780
taatgttaga atggttaaaa acagggaata gaccttatcg gatgactcta acagacaatt    6840
gctccaggtc tttcagagtt ttgaaagatt atttcaagaa ggtagatttg ggttctctca    6900
aggtgggcgg aatggctgca cagtcaatga tttctctctg gttatatggt gcccactctg    6960
aatccaacag gagccggaga tgtataacag acttggccca tttctattcc aagtcgtccc    7020
ccatagagaa gctgttgaat ctcacgctag gaaatagagg gctgagaatc cccccagagg    7080
gagtgttaag ttgccttgag agggttgatt atgataatgc atttggaagg tatcttgcca    7140
acacgtattc ctcttacttg ttcttccatg taatcaccct atacatgaac gccctagact    7200
gggatgaaga aaagaccatc ctagcattat ggaaagattt aacctcagtg gacatcggga    7260
aggacttggt aaagttcaaa gaccaaatat ggggactgct gatcgtgaca aaggactttg    7320
tttactccca aagttccaat tgtctttttg acagaaacta cacacttatg ctaaaagatc    7380
ttttcttgtc tcgcttcaac tccttaatgg tcttgctctc tccccagag ccccgatact    7440 cagatgactt gatatctcaa ctatgccagc tgtacattgc tggggatcaa gtcttgtcta    7500
tgtgtggaaa ctccggctat gaagtcatca aaatattgga gccatatgtc gtgaatagtt    7560
```

```
tagtccagag agcagaaaag tttaggcctc tcattcattc cttgggagac tttcctgtat    7620
ttataaaaga caaggtaagt caacttgaag agacgttcgg tccctgtgca agaaggttct    7680
ttagggctct ggatcaattc gacaacatac atgacttggt ttttgtgtat ggctgttaca    7740
ggcattgggg gcacccatat atagattatc gaaagggtct gtcaaaacta tatgatcagg    7800
ttcacattaa aaagtgata gataagtcct accaggagtg cttagcaagc gacctagcca    7860
ggaggatcct tagatggggt tttgataagt actccaagtg gtatctggat tcaagattcc    7920
tagcccgaga ccacccttg actccttata tcaaaaccca aacatggcca cccaaacata    7980
ttgtagactt ggtgggggat acatggcaca agctcccgat cacgcagatc tttgagattc    8040
ctgaatcaat ggatccgtca gaaatattgg atgacaaatc acattctttc accagaacga    8100
gactagcttc ttggctgtca gaaaaccgag ggggacctgt tcctagcgaa aaagttatta    8160
tcacggcct gtctaagccg cctgtcaatc cccgagagtt tctgaggtct atagacctcg    8220
gaggattgcc agatgaagac ttgataattg gcctcaagcc aaaggaacgg gaattgaaga    8280
ttgaaggtcg attctttgct ctaatgtcat ggaatctaag attgtatttt gtcatcactg    8340
aaaaactctt ggccaactac atcttgccac tttttgacgc gctgactatg acagacaacc    8400
tgaacaaggt gtttaaaaag ctgatcgaca gggtcaccgg gcaagggctt ttggactatt    8460
caagggtcac atatgcattt cacctggact atgaaaagtg gaacaaccat caagattag    8520
agtcaacaga ggatgtattt tctgtcctag atcaagtgtt tggattgaag agagtgtttt    8580
ctagaacaca cgagttttt caaaaggcct ggatctatta ttcagacaga tcagacctca    8640
tcgggttacg ggaggatcaa atatactgct tagatgcgtc caacggccca acctgttgga    8700
atggccagga tggcgggcta gaaggcttac ggcagaaggg ctggagtcta gtcagcttat    8760
tgatgataga tagagaatct caaatcagga acacaagaac caaaatacta gctcaaggag    8820
acaaccaggt tttatgtccg acatatatgt tgtcgccagg gctatctcaa gagggctcc    8880
tctatgaatt ggagagaata tcaaggaatg cactttcgat atacagagcc gtcgaggaag    8940
gggcatctaa gctagggctg atcatcaaga agaagagac catgtgtagt tatgacttcc    9000
tcatctatgg aaaaaccct tgtttagag gtaacatatt ggtgcctgag tccaaaagat    9060
gggccagagt ctcttgcgtc tctaatgacc aaatagtcaa cctcgccaat ataatgtcga    9120
cagtgtccac caatgcgcta acagtggcac aacactctca atctttgatc aaaccgatga    9180
gggatttttct gctcatgtca gtacaggcag tctttcacta cctgctattt agcccaatct    9240
taaagggaag agtttacaag attctgagcg ctgaagggga tagctttctc ctagccatgt    9300
caaggataat ctatctagat ccttctttgg gaggggtatc tggaatgtcc ctcggaagat    9360
tccatatacg acagttctca gaccctgtct ctgaagggt atccttctgg agagagatct    9420
ggttaagctc ccacgagtcc tggattcacg cgttgtgtca agaggctgga aacccagatc    9480
ttggagagag aacactcgag agcttcactc gccttctaga agatcctacc accttaaata    9540
tcagaggagg ggccagtcct accattctac tcaaggatgc aatcagaaag gctttatatg    9600
acgaggtgga caaggtggag aattcagagt ttcgagaggc aatcctgttg tccaagaccc    9660
atagagataa ttttatactc ttcttaacat ctgttgagcc tctgtttcct cgatttctca    9720
gtgagctatt cagttcgtct ttttttggaa tccccgagtc aatcattgga ttgatacaaa    9780
actcccgaac gataagaagg cagtttagaa agagtctctc aaaaactta gaagaatcct    9840
tctacaactc agagatccac gggattagtc ggatgaccca gacacctcag agggttgggg    9900
gggtgtggcc ttgctcttca gagagggcag atctacttag ggagatctct tggggaagaa    9960
```

```
aagtggtagg cacgacagtt cctcaccctt ctgagatgtt ggggttactt cccaagtcct   10020
ctatttcttg cacttgtgga gcaacaggag gaggcaatcc tagagtttct gtatcagtac   10080
tcccgtcctt tgatcagtca ttttttttcac gaggcccct aaaggggtac ttgggctcgt   10140
ccacctctat gtcgacccag ctattccatg catgggaaaa agtcactaat gttcatgtgg   10200
tgaagagagc tctatcgtta aaagaatcta taaactggtt cattactaga gattccaact   10260
tggctcaagc tctaattagg aacattatgt ctctgacagg ccctgatttc cctctagagg   10320
aggcccctgt cttcaaaagg acggggtcag ccttgcatag gttcaagtct gccagataca   10380
gcgaaggagg gtattcttct gtctgcccga acctcctctc tcatatttct gttagtacag   10440
acaccatgtc tgatttgacc caagacggga agaactacga tttcatgttc cagccattga   10500
tgctttatgc acagacatgg acatcagagc tggtacagag agacacaagg ctaagagact   10560
ctacgtttca ttggcacctc cgatgcaaca ggtgtgtgag acccattgac gacgtgaccc   10620
tggagacctc tcagatcttc gagtttccgg atgtgtcgaa aagaatatcc agaatggttt   10680
ctggggctgt gcctcacttc cagaggcttc ccgatatccg tctgagacca ggagattttg   10740
aatctctaag cggtagagaa aagtctcacc atatcggatc agctcagggg ctcttatact   10800
caatcttagt ggcaattcac gactcaggat acaatgatgg aaccatcttc cctgtcaaca   10860
tatacgacaa ggtttcccct agagactatt tgagagggct cgcaagggga gtattgatag   10920
gatcctcgat ttgcttcttg acaagaatga caaatatcaa tattaataga cctcttgaat   10980
tgatctcagg ggtaatctca tatattctcc tgaggctaga taaccatccc tccttgtaca   11040
taatgctcag agaaccgtct cttagaggag agatattttc tatccctcag aaaatccccg   11100
ccgcttatcc aaccactatg aaagaaggca acagatcaat cttgtgttat ctccaacatg   11160
tgctacgcta tgagcgagag ataatcacgg cgtctccaga gaatgactgg ctatggatct   11220
tttcagactt tagaagtgcc aaaatgacgt acctaaccct cattacttac cagtctcatc   11280
ttctactcca gagggttgag agaaacctat ctaagagtat gagagataac ctgcgacaat   11340
tgagttcctt tgatgaggcag gtgctgggcg ggcacggaga agatacctta gagtcagacg   11400
acaacattca acgactgcta aaagactctt tacgaaggac aagatgggtg gatcaagagg   11460
tgcgccatgc agctagaacc atgactggag attacagccc caacaagaag gtgtcccgta   11520
aggtaggatg ttcagaatgg gtctgctctg ctcaacaggt tgcagtctct acctcagcaa   11580
acccggcccc tgtctcggag cttgacataa gggccctctc taagaggttc cagaacccctt   11640 tgatctcggg cttgagagtg gttcagtggg caaccggtgc tcattataag cttaagccta   11700
ttctagatga tctcaatgtt ttcccatctc tctgccttgt agttggggac gggtcagggg   11760
ggatatcaag ggcagtcctc aacatgtttc cagatgccaa gcttgtgttc aacagtctct   11820
tagaggtgaa tgacctgatg gcttccggaa cacatccact gcctccttca gcaatcatga   11880
ggggaggaaa tgatatcgtc tccagagtga tagattttga ctcaatctgg gaaaaaccgt   11940
ccgacttgag aaacttggca acctggaaat acttccagtc agtccaaaag caggtcaaca   12000
tgtcctatga cctcattatt tgcgatgcag aagttactga cattgcatct atcaaccgga   12060
taaccctgtt aatgtccgat tttgcattgt ctatagatgg accactctat ttggtcttca   12120
aaacttatgg gactatgcta gtaaatccaa actacaaggc tattcaacac ctgtcaagag   12180
cgttcccctc ggtcacaggg tttatcaccc aagtaacttc gtcttttttca tctgagctct   12240 acctccgatt ctccaaacga gggaagtttt tcagagatgc tgagtacttg acctcttcca   12300
```

-continued

```
ccccttcgaga aatgagcctt gtgttattca attgtagcag ccccaagagt gagatgcaga    12360
gagctcgttc cttgaactat caggatcttg tgagaggatt tcctgaagaa atcatatcaa    12420
atccttacaa tgagatgatc ataactctga ttgacagtga tgtagaatct tttctagtcc    12480
acaagatggt tgatgatctt gagttacaga ggggaactct gtctaaagtg gctatcatta    12540
tagccatcat gatagttttc tccaacagag tcttcaacgt ttccaaaccc ctaactgacc    12600
ccttgttcta tccaccgtct gatcccaaaa tcctgaggca cttcaacata tgttgcagta    12660
ctatgatgta tctatctact gctttaggtg acgtccctag cttcgcaaga cttcacgacc    12720
tgtataacag acctataact tattacttca gaaagcaatt cattcgaggg aacgtttatc    12780
tatcttggag ttggtccaac gacacctcag tgttcaaaag ggtagcctgt aattctagcc    12840
tgagtctgtc atctcactgg atcaggttga tttacaagat agtgaagact accagactcg    12900
ttggcagcat caaggatcta tccagagaag tggaaagaca ccttcatagg tacaacaggt    12960
ggatcaccct agaggatatc agatctagat catccctact agactacagt tgcctgtgat    13020
ccggatactc ctggaagcct gcccatgcta agactcttgt gtgatgtatc ttgaaaaaaa    13080
caagatccta aatctgaacc tttggttgtt tgattgtttt tctcattttt gttgtttatt    13140
tgttaagcgt                                                           13150
```

<210> SEQ ID NO 11
<211> LENGTH: 12266
<212> TYPE: DNA
<213> ORGANISM: artificial sequence
<220> FEATURE:
<223> OTHER INFORMATION: Recombinant ERAgreen rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (4993)..(5673)
<220> FEATURE:
<221> NAME/KEY: misc_feature
<222> LOCATION: (5752)..(12132)

<400> SEQUENCE: 11
acgcttaaca accagatcaa agaaaaaaca gacattgtca attgcaaagc aaaaatgtaa 60
cacccctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300
aatgcagttt tttgagggga catgtccgga agactggacc agctatggaa tcgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540
cactggtaac tataagacaa acattgcaga caggatagag cagatttttg agacagcccc 600
ttttgttaaa atcgtggaac accatactct aatgacaact cacaaaatgt gtgctaattg 660

```
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctaggggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatcttgt caatcctagt gctattagag ccggtctggc   1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg agaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcaggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
acatgaggaa cttttgtatc aacggagggg ttaaagtgtg tagcccgaat ggttactcgt   2700
tcaggatcct gcggcacatt ctgaaatcat tcgacgagat atattctggg aatcatagga   2760
tgatcgggtt agtcaaagta gttattggac tggctttgtc aggatctcca gtccctgagg   2820
gcatgaactg ggtatacaaa ttgaggagaa ccttttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagaatct   3000
```

```
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg gctcaactc caacccttgg    3180 gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggttttcc    3360 attgtgtttt gggaaattcc ctatttacac gataccagac aagcttggtc cctggagccc   3420
gattgacata catcacctca gctgcccaaa caatttggta gtggaggacg aaggatgcac   3480
caacctgtca gggttctcct acatggaact aaagttgga tacatcttag ccataaaaat    3540
gaacgggttc acttgcacag cgttgtgac ggaggctgaa acctcacta acttcgttgg     3600 ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cactggcttc gaactgtaaa aaccaccaag gagtctctcg ttatcatatc   3780
tccaagtgtg gcagatttgg acccatatga cagatcccct cactcgaggg tcttccctag   3840
cgggaagtgc tcaggagtag cggtgtcttc tacctactgc tccactaacc acgattacac   3900
catttggatg cccgagaatc cgagactagg gatgtcttgt gacatttta ccaatagtag    3960 agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtcgcga tgcaaacatc aaatgaaacc aaatggtgcc ctcccgatca   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtca gaacttggaa   4380
tgagatcctc ccttcaaaag ggtgtttaag agttggggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tccccttgt    4560 gcaccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgtg aggactggcc gtccttttcaa ctatccaagt   4920 cctgaagatc acctcccctt gggggttca tcatgaaaaa actaacacc cctccttcg      4980 ctgcaggcca ccatgggcgt gatcaagccc gacatgaaga tcaagctgcg gatggagggc   5040
gccgtgaacg gccacaaatt cgtgatcgag ggcgacggga aaggcaagcc ctttgagggt   5100
aagcagacta tggacctgac cgtgatcgag ggcgcccccc tgcccttcgc ttatgacatt   5160
ctcaccaccg tgttcgacta cggtaaccgt gtcttcgcca agtacccaa ggacatccct    5220 gactacttca agcagacctt ccccgagggc tactcgtggg agcgaagcat gacatacgag   5280
gaccagggaa tctgtatcgc tacaaacgac atcaccatga tgaagggtgt ggacgactgc   5340
ttcgtgtaca aaatccgctt cgacggggtc aacttccctg ctaatggccc ggtgatgcag   5400
```

```
cgcaagaccc taaagtggga gcccagtacc gagaagatgt acgtgcggga cggcgtactg    5460
aagggcgatg ttaatatggc actgctcttg gagggaggcg gccactaccg ctgcgacttc    5520
aagaccacct acaaagccaa gaaggtggtg cagcttcccg actaccactt cgtggaccac    5580
cgcatcgaga tcgtgagcca cgacaaggac tacaacaaag tcaagctgta cgagcacgcc    5640
gaagcccaca gcggactacc ccgccaggcc ggctaatagg taccgtcgag aaaaaaacat    5700
tagatcagaa gaacaactgg caacacttct caacctgaga cctacttcaa gatgctcgat    5760
cctggagagg tctatgatga ccctattgac ccaatcgagt tagaggatga acccagagga    5820 accccccactg tccccaacat cttgaggaac tctgactaca atctcaactc tcctttgata    5880
gaagatcctg ctagactaat gttagaatgg ttaaaaacag ggaatagacc ttatcggatg    5940
actctaacag acaattgctc caggtctttc agagttttga aagattattt caagaaggta    6000
gatttgggtt ctctcaaggt gggcggaatg gctgcacagt caatgatttc tctctggtta    6060
tatggtgccc actctgaatc caacaggagc cggagatgta taacagactt ggcccatttc    6120
tattccaagt cgtcccccat agagaagctg ttgaatctca cgctaggaaa tagagggctg    6180
agaatccccc cagagggagt gttaagttgc cttgagaggg ttgattatga taatgcattt    6240
ggaaggtatc ttgccaacac gtattcctct tacttgttct tccatgtaat caccttatac    6300
atgaacgccc tagactggga tgaagaaaag accatcctag cattatggaa agatttaacc    6360
tcagtggaca tcgggaagga cttggtaaag ttcaaagacc aaatatgggg actgctgatc    6420
gtgacaaagg actttgttta ctcccaaagt tccaattgtc tttttgacag aaactacaca    6480
cttatgctaa aagatctttt cttgtctcgc ttcaactcct taatggtctt gctctctccc    6540
ccagagcccc gatactcaga tgacttgata tctcaactat gccagctgta cattgctggg    6600
gatcaagtct tgtctatgtg tggaaactcc ggctatgaag tcatcaaaat attggagcca    6660
tatgtcgtga atagtttagt ccagagagca gaaaagttta ggcctctcat tcattccttg    6720
ggagactttc ctgtatttat aaaagacaag gtaagtcaac ttgaagagac gttcggtccc    6780
tgtgcaagaa ggttctttag ggctctggat caattcgaca acatacatga cttggttttt    6840
gtgtatggct gttacaggca ttgggggcac ccatatatag attatcgaaa gggtctgtca    6900
aaactatatg atcaggttca cattaaaaaa gtgatagata agtcctacca ggagtgctta    6960
gcaagcgacc tagccaggag gatccttaga tggggttttg ataagtactc caagtggtat    7020
ctggattcaa gattcctagc ccgagaccac cccttgactc cttatatcaa aacccaaaca    7080
tggccaccca acatattgt agacttggtg ggggatacat ggcacaagct cccgatcacg    7140
cagatctttg agattcctga atcaatggat ccgtcagaaa tattggatga caaatcacat    7200
tctttcacca gaacgagact agcttcttgg ctgtcagaaa accgaggggg acctgttcct    7260
agcgaaaaag ttattatcac ggccctgtct aagccgcctg tcaatccccg agagtttctg    7320
aggtctatag acctcggagg attgccagat gaagacttga taattggcct caagccaaag    7380
gaacgggaat tgaagattga aggtcgattc tttgctctaa tgtcatggaa tctaagattg    7440
tattttgtca tcactgaaaa actcttggcc aactacatct gccactttt tgacgcgctg    7500 actatgacag acaacctgaa caaggtgttt aaaaagctga tcgacagggt caccgggcaa    7560
gggcttttgg actattcaag ggtcacatat gcatttcacc tggactatga aaagtggaac    7620
aaccatcaaa gattagagtc aacagaggat gtatttctg tcctagatca agtgtttgga    7680
ttgaagagag tgttttctag aacacacgag ttttttcaaa aggcctggat ctattattca    7740
```

```
gacagatcag acctcatcgg gttacgggag gatcaaatat actgcttaga tgcgtccaac    7800
ggcccaacct gttggaatgg ccaggatggc gggctagaag gcttacggca gaagggctgg    7860
agtctagtca gcttattgat gatagataga gaatctcaaa tcaggaacac aagaaccaaa    7920
atactagctc aaggagacaa ccaggtttta tgtccgacat atatgttgtc gccagggcta    7980
tctcaagagg ggctcctcta tgaattggag agaatatcaa ggaatgcact ttcgatatac    8040
agagccgtcg aggaaggggc atctaagcta gggctgatca tcaagaaaga agagaccatg    8100
tgtagttatg acttcctcat ctatggaaaa acccctttgt ttagaggtaa catattggtg    8160
cctgagtcca aaagatgggc cagagtctct tgcgtctcta atgaccaaat agtcaacctc    8220
gccaatataa tgtcgacagt gtccaccaat gcgctaacag tggcacaaca ctctcaatct    8280
ttgatcaaac cgatgaggga ttttctgctc atgtcagtac aggcagtctt tcactacctg    8340
ctatttagcc caatcttaaa gggaagagtt tacaagattc tgagcgctga aggggatagc    8400
tttctcctag ccatgtcaag gataatctat ctagatcctt ctttgggagg ggtatctgga    8460
atgtccctcg gaagattcca tatacgacag ttctcagacc ctgtctctga agggttatcc    8520
ttctggagag agatctggtt aagctcccac gagtcctgga ttcacgcgtt gtgtcaagag    8580
gctggaaacc cagatcttgg agagagaaca ctcgagagct tcactcgcct tctagaagat    8640
cctaccacct aaatatcag aggaggggcc agtcctacca ttctactcaa ggatgcaatc    8700
agaaaggctt tatatgacga ggtggacaag gtggagaatt cagagtttcg agaggcaatc    8760
ctgttgtcca agaccatag agataatttt tactcttct taacatctgt tgagcctctg    8820
tttcctcgat ttctcagtga gctattcagt tcgtcttttt tgggaatccc cgagtcaatc    8880
attggattga tacaaaactc ccgaacgata agaaggcagt ttagaaagag tctctcaaaa    8940
actttagaag aatccttcta caactcagag atccacggga ttagtcggat gacccagaca    9000
cctcagaggg ttggggggt gtggccttgc tcttcagaga gggcagatct acttagggag    9060
atctcttggg gaagaaaagt ggtaggcacg acagttcctc acccttctga gatgttgggg    9120
ttacttccca gtcctctat ttcttgcact tgtggagcaa caggaggagg caatcctaga    9180
gtttctgtat cagtactccc gtcctttgat cagtcatttt tttcacgagg cccctaaag    9240
gggtacttgg gctcgtccac ctctatgtcg acccagctat tccatgcatg ggaaaaagtc    9300
actaatgttc atgtggtgaa gagagctcta tcgttaaaag aatctataaa ctggttcatt    9360
actagagatt ccaacttggc tcaagctcta attaggaaca ttatgtctct gacaggccct    9420
gatttccctc tagaggaggc ccctgtcttc aaaaggacgg ggtcagcctt gcataggttc    9480
aagtctgcca gatacagcga aggagggtat tcttctgtct gcccgaacct cctctctcat    9540
atttctgtta gtacagacac catgtctgat ttgacccaag acgggaagaa ctacgatttc    9600
atgttccagc cattgatgct ttatgcacag acatggacat cagagctggt acagagagac    9660
acaaggctaa gagactctac gtttcattgg cacctccgat gcaacaggtg tgtgagaccc    9720
attgacgacg tgaccctgga gacctctcag atcttcgagt ttccggatgt gtcgaaaaga    9780
atatccagaa tggtttctgg ggctgtgcct cacttccaga ggcttcccga tatccgtctg    9840
agaccaggag attttgaatc tctaagcggt agagaaaagt ctcaccatat cggatcagct    9900
caggggctct tatactcaat cttagtggca attcacgact caggatacaa tgatggaacc    9960
atcttccctg tcaacatata cgacaaggtt tcccctagag actatttgag agggctcgca   10020
aggggagtat tgataggatc ctcgatttgc ttccttgacaa gaatgacaaa tatcaatatt   10080
aatagacctc ttgaattgat ctcaggggta atctcatata ttctcctgag gctagataac   10140
```

```
catccctcct tgtacataat gctcagagaa ccgtctctta gaggagagat attttctatc    10200
cctcagaaaa tccccgccgc ttatccaacc actatgaaag aaggcaacag atcaatcttg    10260
tgttatctcc aacatgtgct acgctatgag cgagagataa tcacggcgtc tccagagaat    10320
gactggctat ggatcttttc agactttaga agtgccaaaa tgacgtacct aaccctcatt    10380
acttaccagt ctcatcttct actccagagg gttgagagaa acctatctaa gagtatgaga    10440
gataacctgc gacaattgag ttccttgatg aggcaggtgc tgggcgggca cggagaagat    10500
accttagagt cagacgacaa cattcaacga ctgctaaaag actctttacg aaggacaaga    10560
tgggtggatc aagaggtgcg ccatgcagct agaaccatga ctggagatta cagccccaac    10620
aagaaggtgt cccgtaaggt aggatgttca gaatgggtct gctctgctca acaggttgca    10680
gtctctacct cagcaaaccc ggcccctgtc tcggagcttg acataagggc cctctctaag    10740
aggttccaga acccttttgat ctcgggcttg agagtggttc agtgggcaac cggtgctcat    10800
tataagctta agcctattct agatgatctc aatgttttcc catctctctg ccttgtagtt    10860
ggggacgggt caggggggat atcaagggca gtcctcaaca tgtttccaga tgccaagctt    10920
gtgttcaaca gtctcttaga ggtgaatgac ctgatggctt ccggaacaca tccactgcct    10980
ccttcagcaa tcatgagggg aggaaatgat atcgtctcca gagtgataga ttttgactca    11040
atctgggaaa aaccgtccga cttgagaaac ttggcaacct ggaaatactt ccagtcagtc    11100
caaaagcagg tcaacatgtc ctatgacctc attatttgcg atgcagaagt tactgacatt    11160
gcatctatca accggataac cctgttaatg tccgattttg cattgtctat agatggacca    11220
ctctatttgg tcttcaaaac ttatgggact atgctagtaa atccaaacta caaggctatt    11280
caacacctgt caagagcgtt cccctcggtc acagggttta tcacccaagt aacttcgtct    11340
ttttcatctg agctctacct ccgattctcc aaacgaggga agttttcag agatgctgag    11400
tacttgacct cttccaccct tcgagaaatg agccttgtgt tattcaattg tagcagcccc    11460
aagagtgaga tgcagagagc tcgttccttg aactatcagg atcttgtgag aggatttcct    11520
gaagaaatca tatcaaatcc ttacaatgag atgatcataa ctctgattga cagtgatgta    11580
gaatcttttc tagtccacaa gatggttgat gatcttgagt tacagagggg aactctgtct    11640
aaagtggcta tcattatagc catcatgata gttttctcca acagagtctt caacgtttcc    11700
aaaccccctaa ctgacccctt gttctatcca ccgtctgatc ccaaaatcct gaggcacttc    11760
aacatatgtt gcagtactat gatgtatcta tctactgctt taggtgacgt ccctagcttc    11820
gcaagacttc acgacctgta taacagacct ataacttatt acttcagaaa gcaattcatt    11880
cgagggaacg tttatctatc ttggagttgg tccaacgaca cctcagtgtt caaaagggta    11940
gcctgtaatt ctagcctgag tctgtcatct cactggatca ggttgattta caagatagtg    12000
aagactacca gactcgttgg cagcatcaag gatctatcca gagaagtgga aagacacctt    12060
cataggtaca acaggtggat caccctagag gatatcagat ctagatcatc cctactagac    12120
tacagttgcc tgtgatccgg atactcctgg aagcctgccc atgctaagac tcttgtgtga    12180
tgtatcttga aaaaaacaag atcctaaatc tgaacctttg gttgtttgat tgttttctc     12240
attttttgttg tttatttgtt aagcgt                                        12266
```

<210> SEQ ID NO 12
<211> LENGTH: 10288
<212> TYPE: DNA
<213> ORGANISM: artificial sequence
<220> FEATURE:

-continued

```
<223> OTHER INFORMATION: Recombinant ERA-G rabies virus
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3774)..(10154)

<400> SEQUENCE: 12
acgcttaaca accagatcaa agaaaaaaca gacattgtca attgcaaagc aaaaatgtaa      60 caccccctaca atggatgccg acaagattgt attcaaagtc aataatcagg tggtctcttt     120
gaagcctgag attatcgtgg atcaacatga gtacaagtac cctgccatca agatttgaa     180 aaagccctgt ataaccctag aaaggctcc cgatttaaat aaagcataca agtcagtttt     240
gtcaggcatg agcgccgcca acttgatcc tgacgatgta tgttcctatt ggcagcggc      300 aatgcagttt tttgagggga catgtccgga agactggacc agctatggaa tcgtgattgc     360
acgaaaagga gataagatca ccccaggttc tctggtggag ataaaacgta ctgatgtaga     420
agggaattgg gctctgacag gaggcatgga actgacaaga gaccccactg tccctgagca     480
tgccgtccta gtcggtcttc tcttgagtct gtataggttg agcaaaatat ccgggcaaaa     540
cactggtaac tataagacaa acattgcaga caggatagag cagattttttg agacagcccc     600 ttttgttaaa atcgtggaac accatactct aatgacaact cacaaaatgt gtgctaattg     660
gagtactata ccaaacttca gatttttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga agaatgtttg agccagggca     900
ggagacagct gttcctcact cttatttcat ccacttccgt tcactaggct tgagtgggaa     960
atctccttat tcatcaaatg ctgttggtca cgtgttcaat ctcattcact tgtaggatg    1020 ctatatgggt caagtcagat ccctaaatgc aacggttatt gctgcatgtg ctcctcatga    1080
aatgtctgtt ctaggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact acttctcagg    1260
tgaaaccaga agtccggagg ctgttttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taagaagttg aataacaaaa    1440
tgccggaaat ctacgattg tgtatatcca tcatgaaaaa aactaacacc cctcctttcg    1500
aaccatccca acatgagca agatctttgt caatcctagt gctattagag ccggtctggc    1560
cgatcttgag atggctgaag aaactgttga tctgatcaat agaaatatcg aagacaatca    1620
ggctcatctc caaggggaac ccatagaagt ggacaatctc cctgaggata tggggcgact    1680
tcacctggat gatggaaaat cgcccaaccc tggtgagatg gccaaggtgg agaaggcaa    1740 gtatcgagag gactttcaga tggatgaagg agaggatcct agcttcctgt ccagtcata    1800 cctgaaaaat gttggagtcc aaatagtcag acaaatgagg tcaggagaga gatttctcaa    1860
gatatggtca cagaccgtag aagagattat atcctatgtc gcggtcaact ttcccaaccc    1920
```

```
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaacaggc aacaccactg ataaaatgaa ctttctacgt aagatagtga   2520
aaaattgcag ggacgaggac actcaaaaac cctctcccgt gtcagcccct ctggatgacg   2580
atgacttgtg gcttccaccc cctgaatacg tcccgctgaa agaacttaca agcaagaaga   2640
acatgaggaa cttttgtatc aacggagggg ttaaagtgtg tagcccgaat ggttactcgt   2700
tcaggatcct gcggcacatt ctgaaatcat tcgacgagat atattctggg aatcatagga   2760
tgatcgggtt agtcaaagta gttattggac tggctttgtc aggatctcca gtccctgagg   2820
gcatgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagaatct   3000
ggtgtatcaa catgaacccg agagcatgtc aactatggtc tgacatgtct cttcagacac   3060
aaaggtccga gaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactaaca cccctctgca   3300
gtttggtacc ttgaaaaaaa cctgggttca atagtcctcc ttgaactcca tgcaactggg   3360
tagattcaag agtcatgaga ttttcattaa tcctctcagt tgatcaagca agatcatgta   3420
gattctcata ataggggaga tcttctagca gtttcagtga ctaacggtac tttcattctc   3480
caggaactga caccaacagt tgtagacaaa ccacggggtg tctcgggtga ctctgtgctt   3540
gggcacagac aaaggtcatg gtgtgttcca tgatagcgga ctcaggatga gttaattgag   3600
agaggcagtc ttcctcccgt gaaggacata agcagtagct cacaatcatc tcgcgtctca   3660
gcaaagtgtg cataattata aagtgctggg tcatctaagc ttttcagtcg agaaaaaaac   3720
attagatcag aagaacaact ggcaacactt ctcaacctga gacctacttc aagatgctcg   3780
atcctggaga ggtctatgat gaccctattg acccaatcga gttagaggat gaacccagag   3840 gaaccccac tgtccccaac atcttgagga actctgacta caatctcaac tctcctttga   3900
tagaagatcc tgctagacta atgttagaat ggttaaaaac agggaataga ccttatcgga   3960
tgactctaac agacaattgc tccaggtctt tcagagtttt gaaagattat ttcaagaagg   4020
tagatttggg ttctctcaag gtgggcgaa tggctgcaca gtcaatgatt tctctctggt   4080
tatatggtgc ccactctgaa tccaacagga gccggagatg tataacagac ttggcccatt   4140
tctattccaa gtcgtccccc atagagaagc tgttgaatct cacgctagga aatagagggc   4200
tgagaatccc cccagaggga gtgttaagtt gccttgagag ggttgattat gataatgcat   4260
```

```
ttggaaggta tcttgccaac acgtattcct cttacttgtt cttccatgta atcaccttat   4320
acatgaacgc cctagactgg gatgaagaaa agaccatcct agcattatgg aaagatttaa   4380
cctcagtgga catcgggaag gacttggtaa agttcaaaga ccaaatatgg ggactgctga   4440
tcgtgacaaa ggactttgtt tactcccaaa gttccaattg tcttttttgac agaaactaca  4500 cacttatgct aaaagatctt ttcttgtctc gcttcaactc cttaatggtc ttgctctctc   4560
ccccagagcc ccgatactca gatgacttga tatctcaact atgccagctg tacattgctg   4620
gggatcaagt cttgtctatg tgtggaaact ccggctatga agtcatcaaa atattggagc   4680
catatgtcgt gaatagttta gtccagagag cagaaaagtt taggcctctc attcattcct   4740
tgggagactt tcctgtattt ataaaagaca aggtaagtca acttgaagag cgttcggtc    4800 cctgtgcaag aaggttcttt agggctctgg atcaattcga caacatacat gacttggttt   4860
ttgtgtatgg ctgttacagg cattgggggc acccatatat agattatcga aagggtctgt   4920
caaaactata tgatcaggtt cacattaaaa aagtgataga taagtcctac caggagtgct   4980
tagcaagcga cctagccagg aggatcctta gatggggttt tgataagtac tccaagtggt   5040
atctggattc aagattccta gcccgagacc accccttgac tccttatatc aaaacccaaa   5100
catggccacc caaacatatt gtagacttgg tgggggatac atggcacaag ctcccgatca   5160
cgcagatctt tgagattcct gaatcaatgg atccgtcaga aatattggat gacaaatcac   5220
attctttcac cagaacgaga ctagcttctt ggctgtcaga aaaccgaggg ggacctgttc   5280
ctagcgaaaa agttattatc acggcccgt ctaagccgcc tgtcaatccc cgagagtttc     5340
tgaggtctat agacctcgga ggattgccag atgaagactt gataattggc ctcaagccaa   5400
aggaacggga attgaagatt gaaggtcgat tctttgctct aatgtcatgg aatctaagat   5460
tgtattttgt catcactgaa aaactcttgg ccaactacat cttgccactt tttgacgcgc   5520
tgactatgac agacaacctg aacaaggtgt taaaaagct gatcgacagg gtcaccgggc    5580
aagggctttt ggactattca agggtcacat atgcatttca cctggactat gaaaagtgga   5640
acaaccatca aagattagag tcaacagagg atgtattttc tgtcctagat caagtgtttg   5700
gattgaagag agtgttttct agaacacacg agtttttca aaaggcctgg atctattatt    5760
cagacagatc agacctcatc gggttacggg aggatcaaat atactgctta gatgcgtcca   5820
acggcccaac ctgttggaat ggccaggatg gcgggctaga aggcttacgg cagaagggct   5880
ggagtctagt cagcttattg atgatagata gagaatctca aatcaggaac acaagaacca   5940
aaatactagc tcaaggagac aaccaggttt tatgtccgac atatatgttg tcgccagggc   6000
tatctcaaga ggggctcctc tatgaattgg agagaatatc aaggaatgca ctttcgatat   6060
acagagccgt cgaggaaggg gcatctaagc tagggctgat catcaagaaa gagagacca    6120 tgtgtagtta tgacttcctc atctatggaa aaaccccttt gtttagaggt aacatattgg    6180
tgcctgagtc caaaagatgg gccagagtct cttgcgtctc taatgaccaa atagtcaacc   6240
tcgccaatat aatgtcgaca gtgtccacca atgcgctaac agtggcacaa cactctcaat   6300
ctttgatcaa accgatgagg gattttctgc tcatgtcagt acaggcagtc tttcactacc   6360
tgctatttag cccaatctta aagggaagag tttacaagat tctgagcgct gaaggggata   6420
gctttctcct agccatgtca aggataatct atctagatcc ttctttggga ggggtatctg    6480
gaatgtccct cggaagattc catatacgac agttctcaga ccctgtctct gaagggttat   6540
ccttctggag agagatctgg ttaagctccc acgagtcctg gattcacgcg ttgtgtcaag   6600
aggctggaaa cccagatctt ggagagagaa cactcgagag cttcactcgc cttctagaag   6660
```

```
atcctaccac cttaaatatc agaggagggg ccagtcctac cattctactc aaggatgcaa    6720
tcagaaaggc tttatatgac gaggtggaca aggtggagaa ttcagagttt cgagaggcaa    6780
tcctgttgtc caagacccat agagataatt ttatactctt cttaacatct gttgagcctc    6840
tgtttcctcg atttctcagt gagctattca gttcgtcttt tttgggaatc cccgagtcaa    6900
tcattggatt gatacaaaac tcccgaacga taagaaggca gtttagaaag agtctctcaa    6960
aaactttaga agaatccttc tacaactcag agatccacgg gattagtcgg atgacccaga    7020 caccctcagag ggttgggggg gtgtggcctt gctcttcaga gagggcagat ctacttaggg    7080
agatctcttg gggaagaaaa gtggtaggca cgacagttcc tcacccttct gagatgttgg    7140
ggttacttcc caagtcctct atttcttgca cttgtggagc aacaggagga ggcaatccta    7200
gagtttctgt atcagtactc ccgtcctttg atcagtcatt ttttcacga ggccccctaa     7260 aggggtactt gggctcgtcc acctctatgt cgacccagct attccatgca tgggaaaaag    7320
tcactaatgt tcatgtggtg aagagagctc tatcgttaaa agaatctata aactggttca    7380
ttactagaga ttccaacttg gctcaagctc taattaggaa cattatgtct ctgacaggcc    7440
ctgatttccc tctagaggag gcccctgtct tcaaaaggac ggggtcagcc ttgcataggt    7500
tcaagtctgc cagatacagc gaaggagggt attcttctgt ctgcccgaac ctcctctctc    7560
atatttctgt tagtacagac accatgtctg atttgaccca agacgggaag aactacgatt    7620
tcatgttcca gccattgatg ctttatgcac agacatggac atcagagctg gtacagagag    7680
acacaaggct aagagactct acgtttcatt ggcacctccg atgcaacagg tgtgtgagac    7740
ccattgacga cgtgaccctg gagacctctc agatcttcga gtttccggat gtgtcgaaaa    7800
gaatatccag aatggtttct ggggctgtgc ctcacttcca gaggcttccc gatatccgtc    7860
tgagaccagg agattttgaa tctctaagcg gtagagaaaa gtctcaccat atcggatcag    7920
ctcaggggct cttatactca atcttagtgg caattcacga ctcaggatac aatgatggaa    7980
ccatcttccc tgtcaacata tacgacaagg tttcccctag agactatttg agagggctcg    8040
caaggggagt attgatagga tcctcgattt gcttcttgac aagaatgaca aatatcaata    8100
ttaatagacc tcttgaattg atctcagggg taatctcata tattctcctg aggctagata    8160
accatccctc cttgtacata atgctcagag aaccgtctct tagaggagag atattttcta    8220
tccctcagaa aatccccgcc gcttatccaa ccactatgaa agaaggcaac agatcaatct    8280
tgtgttatct ccaacatgtg ctacgctatg agcgagagat aatcacggcg tctccagaga    8340
atgactggct atggatcttt tcagactta gaagtgccaa aatgacgtac ctaaccctca    8400
ttacttacca gtctcatctt ctactccaga gggttgagag aaacctatct aagagtatga    8460
gagataacct gcgacaattg agttccttga tgaggcaggt gctggcgggg cacggagaag    8520
ataccttaga gtcagacgac aacattcaac gactgctaaa agactcttta cgaaggacaa    8580
gatgggtgga tcaagaggtg cgccatgcag ctagaaccat gactggagat tacagcccca    8640
acaagaaggt gtcccgtaag gtaggatgtt cagaatgggt ctgctctgct caacaggttg    8700
cagtctctac ctcagcaaac ccggcccctg tctcggagct tgacataagg gccctctcta    8760
agaggttcca gaacccttg atctcgggct tgagagtggt tcagtgggca accggtgctc    8820
attataagct taagcctatt ctagatgatc tcaatgtttt cccatctctc tgccttgtag    8880
ttggggacgg gtcaggggg atatcaaggc agtcctcaa catgtttcca gatgccaagc    8940
ttgtgttcaa cagtctctta gaggtgaatg acctgatggc ttccggaaca catccactgc    9000
```

-continued

```
ctccttcagc aatcatgagg ggaggaaatg atatcgtctc cagagtgata gattttgact    9060
caatctggga aaaccgtcc gacttgagaa acttggcaac ctggaaatac ttccagtcag     9120
tccaaaagca ggtcaacatg tcctatgacc tcattatttg cgatgcagaa gttactgaca    9180
ttgcatctat caaccggata accctgttaa tgtccgattt tgcattgtct atagatggac    9240
cactctattt ggtcttcaaa acttatggga ctatgctagt aaatccaaac tacaaggcta    9300
ttcaacacct gtcaagagcg ttcccctcgg tcacagggtt tatcacccaa gtaacttcgt    9360 cttttcatc tgagctctac ctccgattct ccaaacgagg aagttttc agagatgctg       9420 agtacttgac ctcttccacc cttcgagaaa tgagccttgt gttattcaat tgtagcagcc    9480
ccaagagtga gatgcagaga gctcgttcct tgaactatca ggatcttgtg agaggatttc    9540
ctgaagaaat catatcaaat ccttacaatg agatgatcat aactctgatt gacagtgatg    9600
tagaatcttt tctagtccac aagatggttg atgatcttga gttacagagg ggaactctgt    9660
ctaaagtggc tatcattata gccatcatga tagtttctc caacagagtc ttcaacgttt     9720 ccaaaccct aactgacccc ttgttctatc caccgtctga tcccaaaatc ctgaggcact     9780
tcaacatatg ttgcagtact atgatgtatc tatctactgc tttaggtgac gtccctagct    9840
tcgcaagact tcacgacctg tataacagac ctataactta ttacttcaga aagcaattca    9900
ttcgagggaa cgtttatcta tcttggagtt ggtccaacga cacctcagtg ttcaaaaggg    9960
tagcctgtaa ttctagcctg agtctgtcat ctcactggat caggttgatt tacaagatag    10020
tgaagactac cagactcgtt ggcagcatca aggatctatc cagagaagtg gaaagacacc    10080
ttcataggta caacaggtgg atcaccctag aggatatcag atctagatca tccctactag    10140
actacagttg cctgtgatcc ggatactcct ggaagcctgc ccatgctaag actcttgtgt    10200
gatgtatctt gaaaaaaaca agatcctaaa tctgaaccct tggttgtttg attgtttttc    10260 tcattttgt tgtttatttg ttaagcgt                                        10288
```

```
<210> SEQ ID NO 13
<211> LENGTH: 13150
<212> TYPE: DNA
<213> ORGANISM: artificial sequence
<220> FEATURE:
<223> OTHER INFORMATION: Recombinant ERA-2g3 rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2496)..(3101)
<220> FEATURE:
<221> NAME/KEY: misc_feature
<222> LOCATION: (3317)..(4888)
<220> FEATURE:
<221> NAME/KEY: misc_feature
<222> LOCATION: (4988)..(6559)
<220> FEATURE:
<221> NAME/KEY: misc_feature
<222> LOCATION: (6636)..(13016)

<400> SEQUENCE: 13
acgcttaaca accagatcaa agaaaaaaca gacattgtca attgcaaagc aaaaatgtaa      60 caccctaca atggatgccg acaagattgt attcaaagtc aataatcagg tggtctcttt     120
gaagcctgag attatcgtgg atcaacatga gtacaagtac cctgccatca agatttgaa     180 aaagccctgt ataaccctag gaaaggctcc cgatttaaat aaagcataca gtcagttttt    240
```

```
gtcaggcatg agcgccgcca aacttgatcc tgacgatgta tgttcctatt tggcagcggc    300
aatgcagttt tttgagggga catgtccgga agactggacc agctatggaa tcgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttttg agacagcccc    600
ttttgttaaa atcgtggaac accatactct aatgacaact cacaaaatgt gtgctaattg    660
gagtactata ccaaacttca gattttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctaggggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact acttctcagg    1260
tgaaaccaga agtccggagg ctgtttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taagaagttg aataacaaaa    1440
tgccggaaat ctacggattg tgtatatcca tcatgaaaaa aactaacacc cctcctttcg    1500
aaccatccca aacatgagca agatctttgt caatcctagt gctattagag ccggtctggc    1560
cgatcttgag atggctgaag aaactgttga tctgatcaat agaaatatcg aagacaatca    1620
ggctcatctc caaggggaac ccatagaagt ggacaatctc cctgaggata tggggcgact    1680
tcacctggat gatggaaaat cgcccaaccc tggtgagatg gccaaggtgg gagaaggcaa    1740
gtatcgagag gactttcaga tggatgaagg agaggatcct agcttcctgt tccagtcata    1800
cctggaaaat gttggagtcc aaatagtcag acaaatgagg tcaggagaga gatttctcaa    1860
gatatggtca cagaccgtag aagagattat atcctatgtc gcggtcaact ttcccaaccc    1920
tccaggaaag tcttcagagg ataaatcaac ccagactact ggccgagagc tcaagaagga    1980
gacaacaccc actccttctc agagagaaag ccaatcatcg aaagccagga tggcggctca    2040
aattgcttct ggccctccag cccttgaatg gtcggccacc aatgaagagg atgatctatc    2100
agtggaggct gagatcgctc accagattgc agaaagtttc tccaaaaaat ataagtttcc    2160
ctctcgatcc tcagggatac tcttgtataa ttttgagcaa ttgaaaatga accttgatga    2220
tatagttaaa gaggcaaaaa atgtaccagg tgtgacccgt ttagcccatg acgggtccaa    2280
actccccta agatgtgtac tgggatgggt cgctttggcc aactctaaga aattccagtt    2340
gttagtcgaa tccgacaagc tgagtaaaat catgcaagat gacttgaatc gctatacatc    2400
ttgctaaccg aacctctcca ctcagtccct ctagacaata aagtccgaga tgtcctaaag    2460
tcaacatgaa aaaacaggc aacaccactg ataaaatgaa ctttctacgt aagatagtga    2520
aaaattgcag ggacgaggac actcaaaaac cctctcccgt gtcagcccct ctggatgacg    2580
```

```
atgacttgtg gcttccaccc cctgaatacg tcccgctgaa agaacttaca agcaagaaga    2640
acatgaggaa cttttgtatc aacggagggg ttaaagtgtg tagcccgaat ggttactcgt    2700
tcaggatcct gcggcacatt ctgaaatcat tcgacgagat atattctggg aatcatagga    2760
tgatcgggtt agtcaaagta gttattggac tggctttgtc aggatctcca gtccctgagg    2820
gcatgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag gcagaatct    3000 ggtgtatcaa catgaacccg agagcatgtc aactatggtc tgacatgtct cttcagacac    3060
aaaggtccga agaggacaaa gattcctctc tgcttctaga ataatcagat tatatcccgc    3120
aaatttatca cttgtttacc tctggaggag agaacatatg gctcaactc caaccttgg    3180 gagcaatata acaaaaaaca tgttatggtg ccattaaacc gctgcatttc atcaaagtca    3240
agttgattac ctttacattt tgatcctctt ggatgtgaaa aaaactatta acatccctca    3300
aaagactcaa ggaaagatgg ttcctcaggc tctcctgttt gtaccccttc tggttttcc    3360 attgtgtttt gggaaattcc ctatttacac gataccagac aagcttggtc cctggagccc    3420
gattgacata catcacctca gctgcccaaa caatttggta gtggaggacg aaggatgcac    3480
caacctgtca gggttctcct acatggaact taaagtggga tacatcttag ccataaaaat    3540
gaacgggttc acttgcacag gcgttgtgac ggaggctgaa acctacacta acttcgttgg    3600
ttatgtcaca accacgttca aaagaaagca tttccgccca acaccagatg catgtagagc    3660
cgcgtacaac tggaagatgg ccggtgaccc cagatatgaa gagtctctac acaatccgta    3720
ccctgactac cactggcttc gaactgtaaa aaccaccaag gagtctctcg ttatcatatc    3780
tccaagtgtg gcagatttgg acccatatga cagatccctt cactcgaggg tcttccctag    3840
cgggaagtgc tcaggagtag cggtgtcttc tacctactgc tccactaacc acgattacac    3900
catttggatg cccgagaatc cgagactagg gatgtcttgt gacattttta ccaatagtag    3960
agggaagaga gcatccaaag ggagtgagac ttgcggcttt gtagatgaaa gaggcctata    4020 taagtctttta aaaggagcat gcaaactcaa gttatgtgga gttctaggac ttagacttat    4080
ggatggaaca tgggtcgcga tgcaaacatc aaatgaaacc aaatggtgcc ctcccgatca    4140
gttggtgaac ctgcacgact ttcgctcaga cgaaattgag caccttgttg tagaggagtt    4200
ggtcaggaag agagaggagt gtctggatgc actagagtcc atcatgacaa ccaagtcagt    4260
gagtttcaga cgtctcagtc atttaagaaa acttgtccct gggtttggaa aagcatatac    4320
catattcaac aagaccttga tggaagccga tgctcactac aagtcagtcg agacttggaa    4380
tgagatcctc ccttcaaaag ggtgtttaag agttgggggg aggtgtcatc ctcatgtgaa    4440
cggggtgttt ttcaatggta taatattagg acctgacggc aatgtcttaa tcccagagat    4500
gcaatcatcc ctcctccagc aacatatgga gttgttggaa tcctcggtta tccccttgt    4560 gcacccctg gcagacccgt ctaccgtttt caaggacggt gacgaggctg aggattttgt    4620
tgaagttcac cttcccgatg tgcacaatca ggtctcagga gttgacttgg gtctcccgaa    4680
ctgggggaag tatgtattac tgagtgcagg ggccctgact gccttgatgt tgataatttt    4740
cctgatgaca tgttgtagaa gagtcaatcg atcagaacct acgcaacaca atctcagagg    4800 gacaggagg gaggtgtcag tcactcccca aagcgggaag atcatatctt catgggaatc    4860
acacaagagt gggggtgaga ccagactgtg aggactggcc gtcctttcaa ctatccaagt    4920
cctgaagatc acctccccctt gggggggttca tcatgaaaaa aactaacacc cctcctttcg    4980
```

```
ctgcaggatg gttcctcagg ctctcctgtt tgtaccccett ctggttttte cattgtgttt    5040
tgggaaattc cctatttaca cgataccaga caagcttggt ccctggagcc cgattgacat    5100
acatcacctc agctgcccaa acaatttggt agtggaggac gaaggatgca ccaacctgtc    5160
agggttctcc tacatggaac ttaaagttgg atacatctta gccataaaaa tgaacgggtt    5220
cacttgcaca ggcgttgtga cggaggctga aacctacact aacttcgttg gttatgtcac    5280
aaccacgttc aaaagaaagc atttccgccc aacaccagat gcatgtagag ccgcgtacaa    5340
ctggaagatg gccggtgacc ccagatatga agagtctcta cacaatccgt accctgacta    5400
ccactggctt cgaactgtaa aaaccaccaa ggagtctctc gttatcatat ctccaagtgt    5460
ggcagatttg gacccatatg acagatccct tcactcgagg gtcttcccta gcgggaagtg    5520
ctcaggagta gcggtgtctt ctacctactg ctccactaac cacgattaca ccatttggat    5580
gcccgagaat ccgagactag ggatgtcttg tgacatttt accaatagta gagggaagag    5640
agcatccaaa gggagtgaga cttgcggctt tgtagatgaa agaggcctat ataagtcttt    5700
aaaaggagca tgcaaactca agttatgtgg agttctagga cttagactta tggatggaac    5760
atgggtcgcg atgcaaacat caaatgaaac caaatggtgc cctcccgatc agttggtgaa    5820
cctgcacgac tttcgctcag acgaaattga gcaccttgtt gtagaggagt tggtcaggaa    5880
gagagaggag tgtctggatg cactagagtc catcatgaca accaagtcag tgagtttcag    5940
acgtctcagt catttaagaa aacttgtccc tgggtttgga aaagcatata ccatattcaa    6000
caagaccttg atggaagccg atgctcacta caagtcagtc gagacttgga atgagatcct    6060
cccttcaaaa gggtgtttaa gagttggggg gaggtgtcat cctcatgtga acggggtgtt    6120
tttcaatggt ataatattag acctgacgg caatgtctta atcccagaga tgcaatcatc    6180
cctcctccag caacatatgg agttgttgga atcctcggtt atccccttg tgcaccccct    6240
ggcagacccg tctaccgttt tcaaggacgg tgacagggct gaggattttg ttgaagttca    6300
ccttcccgat gtgcacaatc aggtctcagg agttgacttg ggtctcccga actgggggaa    6360
gtatgtatta ctgagtgcag gggccctgac tgccttgatg ttgataattt tcctgatgac    6420
atgttgtaga agagtcaatc gatcagaacc tacgcaacac aatctcagag ggacagggag    6480
ggaggtgtca gtcactcccc aaagcgggaa gatcatatct tcatgggaat cacacaagag    6540
tgggggtgag accagactgt gaggtaccgt cgagaaaaaa acattagatc agaagaacaa    6600
ctggcaacac ttctcaacct gagacctact tcaagatgct cgatcctgga gaggtctatg    6660
atgaccctat tgacccaatc gagttagagg atgaacccag aggaaccccc actgtcccca    6720
acatcttgag gaactctgac tacaatctca actctccttt gatagaagat cctgctagac    6780
taatgttaga atggttaaaa acagggaata gaccttatcg gatgactcta acagacaatt    6840
gctccaggtc tttcagagtt ttgaaagatt atttcaagaa ggtagatttg ggttctctca    6900
aggtgggcgg aatggctgca cagtcaatga tttctctctg gttatatggt gcccactctg    6960
aatccaacag gagccggaga tgtataacag acttggccca tttctattcc aagtcgtccc    7020
ccatagagaa gctgttgaat ctcacgctag gaaatagagg gctgagaatc cccccagagg    7080
gagtgttaag ttgccttgag agggttgatt atgataatgc atttggaagg tatcttgcca    7140
acacgtattc ctcttacttg ttcttccatg taatcacctt atacatgaac gccctagact    7200
gggatgaaga aaagaccatc ctagcattat ggaaagattt aacctcagtg acatcgggaa    7260
aggacttggt aaagttcaaa gaccaaatat ggggactgct gatcgtgaca aaggactttg    7320
```

```
tttactccca aagttccaat tgtcttttgg acagaaacta cacacttatg ctaaaagatc    7380
ttttcttgtc tcgcttcaac tccttaatgg tcttgctctc tcccccagag ccccgatact    7440
cagatgactt gatatctcaa ctatgccagc tgtacattgc tggggatcaa gtcttgtcta    7500
tgtgtggaaa ctccggctat gaagtcatca aaatattgga gccatatgtc gtgaatagtt    7560
tagtccagag agcagaaaag tttaggcctc tcattcattc cttgggagac tttcctgtat    7620
ttataaaaga caaggtaagt caacttgaag agacgttcgg tccctgtgca agaaggttct    7680
ttagggctct ggatcaattc gacaacatac atgacttggt ttttgtgtat ggctgttaca    7740
ggcattgggg gcacccatat atagattatc gaaagggtct gtcaaaacta tatgatcagg    7800
ttcacattaa aaaagtgata gataagtcct accaggagtg cttagcaagc gacctagcca    7860
ggaggatcct tagatggggt tttgataagt actccaagtg gtatctggat tcaagattcc    7920
tagcccgaga ccaccccttg actccttata tcaaaaccca acatggccca cccaaacata    7980
ttgtagactt ggtgggggat acatggcaca agctcccgat cacgcagatc tttgagattc    8040
ctgaatcaat ggatccgtca gaaatattgg atgacaaatc acattctttc accagaacga    8100
gactagcttc ttggctgtca gaaaaccgag ggggacctgt tcctagcgaa aaagttatta    8160
tcacggccct gtctaagccg cctgtcaatc cccgagagtt tctgaggtct atagacctcg    8220
gaggattgcc agatgaagac ttgataattg gcctcaagcc aaaggaacgg gaattgaaga    8280
ttgaaggtcg attctttgct ctaatgtcat ggaatctaag attgtatttt gtcatcactg    8340
aaaaactctt ggccaactac atcttgccac tttttgacgc gctgactatg acagacaacc    8400
tgaacaaggt gtttaaaaag ctgatcgaca gggtcaccgg gcaagggctt ttggactatt    8460
caagggtcac atatgcattt cacctggact atgaaaagtg gaacaaccat caaagattag    8520
agtcaacaga ggatgtattt tctgtcctag atcaagtgtt tggattgaag agagtgtttt    8580
ctagaacaca cgagtttttt caaaaggcct ggatctatta ttcagacaga tcagacctca    8640
tcgggttacg ggaggatcaa atatactgct tagatgcgtc caacggccca acctgttgga    8700
atggccagga tggcgggcta gaaggcttac ggcagaaggg ctggagtcta gtcagcttat    8760
tgatgataga tagagaatct caaatcagga acacaagaac caaaatacta gctcaaggag    8820
acaaccaggt tttatgtccg acatatatgt tgtcgccagg gctatctcaa gaggggctcc    8880
tctatgaatt ggagagaata tcaaggaatg cactttcgat atacagagcc gtcgaggaag    8940
gggcatctaa gctagggctg atcatcaaga aagaagagac catgtgtagt tatgacttcc    9000
tcatctatgg aaaaaccccct tgtttagag gtaacatatt ggtgcctgag tccaaaagat    9060
gggccagagt ctcttgcgtc tctaatgacc aaatagtcaa cctcgccaat ataatgtcga    9120
cagtgtccac caatgcgcta acagtggcac aacactctca atctttgatc aaaccgatga    9180 gggatttttct gctcatgtca gtacaggcag tctttcacta cctgctattt agcccaatct    9240
taaagggaag agtttacaag attctgagcg ctgaagggga tagctttctc ctagccatgt    9300
caaggataat ctatctagat ccttctttgg gaggggtatc tggaatgtcc ctcggaagat    9360
tccatatacg acagttctca gaccctgtct ctgaagggtt atccttctgg agagagatct    9420
ggttaagctc ccacgagtcc tggattcacg cgttgtgtca agaggctgga aacccagatc    9480
ttggagagag aacactcgag agcttcactc gccttctaga agatcctacc accttaaata    9540
tcagaggagg ggccagtcct accattctac tcaaggatgc aatcagaaag gctttatatg    9600
acgaggtgga caaggtggag aattcagagt ttcgagaggc aatcctgttg tccaagaccc    9660
atagagataa ttttatactc ttcttaacat ctgttgagcc tctgtttcct cgatttctca    9720
```

```
gtgagctatt cagttcgtct tttttgggaa tccccgagtc aatcattgga ttgatacaaa    9780
actcccgaac gataagaagg cagtttagaa agagtctctc aaaaacttta gaagaatcct    9840
tctacaactc agagatccac gggattagtc ggatgaccca gacacctcag agggttgggg    9900
gggtgtggcc ttgctcttca gagagggcag atctacttag ggagatctct tggggaagaa    9960
aagtggtagg cacgacagtt cctcacccett ctgagatgtt ggggttactt cccaagtcct   10020
ctatttcttg cacttgtgga gcaacaggag gaggcaatcc tagagtttct gtatcagtac   10080
tcccgtcctt tgatcagtca ttttttttcac gaggcccccct aaaggggtac ttgggctcgt   10140
ccacctctat gtcgacccag ctattccatg catgggaaaa agtcactaat gttcatgtgg   10200
tgaagagagc tctatcgtta aaagaatcta taaactggtt cattactaga gattccaact   10260
tggctcaagc tctaattagg aacattatgt ctctgacagg ccctgatttc cctctagagg   10320
aggcccctgt cttcaaaagg acggggtcag ccttgcatag gttcaagtct gccagataca   10380
gcgaaggagg gtattcttct gtctgcccga acctcctctc tcatatttct gttagtacag   10440
acaccatgtc tgatttgacc caagacggga agaactacga tttcatgttc agccattga   10500 tgctttatgc acagacatgg acatcagagc tggtacagag agacacaagg ctaagagact   10560
ctacgtttca ttggcacctc cgatgcaaca ggtgtgtgag acccattgac gacgtgaccc   10620
tggagacctc tcagatcttc gagtttccgg atgtgtcgaa aagaatatcc agaatggttt   10680
ctggggctgt gcctcacttc cagaggcttc ccgatatccg tctgagacca ggagattttg   10740
aatctctaag cggtagagaa aagtctcacc atatcggatc agctcagggg ctcttatact   10800
caatcttagt ggcaattcac gactcaggat acaatgatgg aaccatcttc cctgtcaaca   10860
tatacgacaa ggtttcccct agagactatt tgagagggct cgcaagggga gtattgatag   10920
gatcctcgat ttgcttcttg acaagaatga caaatatcaa tattaataga cctcttgaat   10980
tgatctcagg ggtaatctca tatattctcc tgaggctaga taaccatccc tccttgtaca   11040
taatgctcag agaaccgtct cttagaggag agatattttc tatccctcag aaaatccccg   11100
ccgcttatcc aaccactatg aaagaaggca acagatcaat cttgtgttat ctccaacatg   11160
tgctacgcta tgagcgagag ataatcacgg cgtctccaga gaatgactgg ctatggatct   11220
tttcagactt tagaagtgcc aaaatgacgt acctaaccct cattacttac cagtctcatc   11280
ttctactcca gagggttgag agaaacctat ctaagagtat gagagataac ctgcgacaat   11340
tgagttcctt tgatgaggcag gtgctgggcg ggcacggaga agatacctta gagtcagacg   11400
acaacattca acgactgcta aaagactctt tacgaaggac aagatgggtg gatcaagagg   11460
tgcgccatgc agctagaacc atgactggag attacagccc caacaagaag gtgtcccgta   11520
aggtaggatg ttcagaatgg gtctgctctg ctcaacaggt tgcagtctct acctcagcaa   11580
acccggcccc tgtctcggag cttgacataa gggccctctc taagaggttc cagaaccctt   11640
tgatctcggg cttgagagtg gttcagtggg caaccggtgc tcattataag cttaagccta   11700
ttctagatga tctcaatgtt ttcccatctc tctgccttgt agttggggac gggtcagggg   11760
ggatatcaag ggcagtcctc aacatgtttc cagatgccaa gcttgtgttc aacagtctct   11820
tagaggtgaa tgacctgatg gcttccggaa cacatccact gcctccttca gcaatcatga   11880
ggggaggaaa tgatatcgtc tccagagtga tagattttga ctcaatctgg gaaaaaccgt   11940
ccgacttgag aaacttggca acctggaaat acttccagtc agtccaaaag caggtcaaca   12000
tgtcctatga cctcattatt tgcgatgcag aagttactga cattgcatct atcaaccgga   12060
```

```
taaccctgtt aatgtccgat tttgcattgt ctatagatgg accactctat ttggtcttca   12120
aaacttatgg gactatgcta gtaaatccaa actacaaggc tattcaacac ctgtcaagag   12180
cgttcccctc ggtcacaggg tttatcaccc aagtaacttc gtcttttca tctgagctct     12240 acctccgatt ctccaaacga gggaagtttt tcagagatgc tgagtacttg acctcttcca   12300
cccttcgaga aatgagcctt gtgttattca attgtagcag ccccaagagt gagatgcaga   12360
gagctcgttc cttgaactat caggatcttg tgagaggatt tcctgaagaa atcatatcaa   12420
atccttacaa tgagatgatc ataactctga ttgacagtga gtagaatct tttctagtcc     12480 acaagatggt tgatgatctt gagttacaga ggggaactct gtctaaagtg ctatcatta    12540 tagccatcat gatagttttc tccaacagag tcttcaacgt ttccaaaccc ctaactgacc   12600
ccttgttcta tccaccgtct gatcccaaaa tcctgaggca cttcaacata tgttgcagta   12660
ctatgatgta tctatctact gctttaggtg acgtccctag cttcgcaaga cttcacgacc   12720
tgtataacag acctataact tattacttca gaaagcaatt cattcgaggg aacgtttatc   12780
tatcttggag ttggtccaac gacacctcag tgttcaaaag ggtagcctgt aattctagcc   12840
tgagtctgtc atctcactgg atcaggttga tttacaagat agtgaagact accagactcg   12900
ttggcagcat caaggatcta tccagagaag tggaaagaca ccttcatagg tacaacaggt   12960
ggatcaccct agaggatatc agatctagat catccctact agactacagt tgcctgtgat   13020
ccggatactc ctggaagcct gcccatgcta agactcttgt gtgatgtatc ttgaaaaaaa   13080
caagatccta aatctgaacc tttggttgtt tgattgtttt tctcattttt gttgtttatt    13140
tgttaagcgt                                                            13150

<210> SEQ ID NO 14
<211> LENGTH: 11976
<212> TYPE: DNA
<213> ORGANISM: artificial sequence
<220> FEATURE:
<223> OTHER INFORMATION: Recombinant ERA-pt rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2542)..(3147)
<220> FEATURE:
<221> NAME/KEY: misc_feature
<222> LOCATION: (3363)..(4934)
<220> FEATURE:
<221> NAME/KEY: misc_feature
<222> LOCATION: (5462)..(11842)

<400> SEQUENCE: 14
acgcttaaca accagatcaa agaaaaaaca gacattgtca attgcaaagc aaaaatgtaa     60 caccectaca atggatgccg acaagattgt attcaaagtc aataatcagg tggtctcttt   120
gaagcctgag attatcgtgg atcaacatga gtacaagtac cctgccatca agatttgaa    180 aaagccctgt ataaccctag gaaaggctcc cgatttaaat aaagcataca agtcagtttt   240
gtcaggcatg agcgccgcca aacttgatcc tgacgatgta tgttcctatt ggcagcggc    300 aatgcagttt tttgagggga catgtccgga agactggacc agctatggaa tcgtgattgc   360
acgaaaagga gataagatca ccccaggttc tctggtggag ataaaacgta ctgatgtaga   420
agggaattgg gctctgacag gaggcatgga actgacaaga gaccccactg tccctgagca   480
```

```
tgcgtcctta gtcggtcttc tcttgagtct gtataggttg agcaaaatat ccgggcaaaa    540
cactggtaac tataagacaa acattgcaga caggatagag cagattttg agacagcccc     600 ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga agaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca acatgagca agatctttgt caatcctagt gctattagag ccggtctggc    1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg agaaggcaa    1740 gtatcgagag actttcaga tggatgaagg agaggatcct agcttcctgt tccagtcata    1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagttttcc   2160 ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaaactaac acccctcctt tcgctgcagt ttggtaccgt cgagaaaaaa   2520
acaggcaaca ccactgataa aatgaacttt ctacgtaaga tagtgaaaaa ttgcagggac   2580
gaggacactc aaaaaccctc tcccgtgtca gcccctctgg atgacgatga cttgtggctt   2640 ccacccctg aatacgtccc gctgaaagaa cttacaagca agaagaacat gaggaacttt    2700
tgtatcaacg gaggggttaa agtgtgtagc ccgaatggtt actcgttcag gatcctgcgg   2760
cacattctga aatcattcga cgagatatat tctgggaatc ataggatgat cgggttagtc   2820
aaagtagtta ttggactggc tttgtcagga tctccagtcc ctgagggcat gaactgggta   2880
```

```
tacaaattga ggagaacctt tatcttccag tgggctgatt ccaggggccc tcttgaaggg    2940
gaggagttgg aatactctca ggagatcact tgggatgatg atactgagtt cgtcggattg    3000
caaataagag tgattgcaaa acagtgtcat atccagggca gaatctgtg tatcaacatg      3060 aacccgagag catgtcaact atggtctgac atgtctcttc agacacaaag gtccgaagag    3120
gacaaagatt cctctctgct tctagaataa tcagattata tcccgcaaat ttatcacttg    3180
tttacctctg gaggagagaa catatgggct caactccaac ccttgggagc aatataacaa    3240
aaaacatgtt atggtgccat taaaccgctg catttcatca aagtcaagtt gattaccttt    3300
acattttgat cctcttggat gtgaaaaaaa ctattaacat ccctcaaaag actcaaggaa    3360
agatggttcc tcaggctctc ctgtttgtac cccttctggt ttttccattg tgttttggga    3420
aattccctat ttacacgata ccagacaagc ttggtccctg gagcccgatt gacatacatc    3480
acctcagctg cccaaacaat ttggtagtgg aggacgaagg atgcaccaac ctgtcagggt    3540
tctcctacat ggaacttaaa gttggataca tcttagccat aaaaatgaac gggttcactt    3600
gcacaggcgt tgtgacggag gctgaaacct cactaacttc gttggttat gtcacaacca     3660 cgttcaaaag aaagcatttc cgcccaacac cagatgcatg tagagccgcg tacaactgga    3720
agatggccgg tgaccccaga tatgaagagt ctctacacaa tccgtaccct gactaccact    3780
ggcttcgaac tgtaaaaacc accaaggagt ctctcgttat catatctcca agtgtggcag    3840
atttggaccc atatgacaga tcccttcact cgagggtctt ccctagcggg aagtgctcag    3900
gagtagcggt gtcttctacc tactgctcca ctaaccacga ttacaccatt tggatgcccg    3960
agaatccgag actagggatg tcttgtgaca ttttttaccaa tagtagaggg aagagagcat    4020 ccaaaggag tgagacttgc ggctttgtag atgaaagagg cctatataag tctttaaaag    4080
gagcatgcaa actcaagtta tgtggagttc taggacttag acttatggat ggaacatggg    4140
tcgcgatgca aacatcaaat gaaaccaaat ggtgccctcc cgatcagttg gtgaacctgc    4200
acgactttcg ctcagacgaa attgagcacc ttgttgtaga ggagttggtc aggaagagag    4260
aggagtgtct ggatgcacta gagtccatca tgacaaccaa gtcagtgagt ttcagacgtc    4320
tcagtcattt aagaaaactt gtccctgggt ttggaaaagc atataccata ttcaacaaga    4380
ccttgatgga agccgatgct cactacaagt cagtcgagac ttggaatgag atcctcccctt   4440 caaaagggtg tttaagagtt ggggggaggt gtcatcctca tgtgaacggg gtgttttca    4500 atggtataat attaggacct gacggcaatg tcttaatccc agagatgcaa tcatccctcc    4560
tccagcaaca tatggagttg ttggaatcct cggttatccc ccttgtgcac cccctggcag    4620
acccgtctac cgttttcaag gacggtacg aggctgagga ttttgttgaa gttcaccttc     4680
ccgatgtgca caatcaggtc tcaggagttg acttgggtct cccgaactgg gggaagtatg    4740
tattactgag tgcaggggcc ctgactgcct tgatgttgat aattttcctg atgacatgtt    4800
gtagaagagt caatcgatca gaacctacgc aacacaatct cagagggaca gggagggagg    4860
tgtcagtcac tccccaaagc gggaagatca tatcttcatg ggaatcacac aagagtgggg    4920
gtgagaccag actgtgagga ctggccgtcc tttcaactat ccaagtcctg aagatcacct    4980
ccccttgggg ggttctttt gaaaaaaacc tgggttcaat agtcctcctt gaactccatg     5040
caactgggta gattcaagag tcatgagatt ttcattaatc ctctcagttg atcaagcaag    5100
atcatgtaga ttctcataat aggggagatc ttctagcagt ttcagtgact aacggtacttt   5160 tcattctcca ggaactgaca ccaacagttg tagacaaacc acgggtgtc tcgggtgact     5220
```

```
ctgtgcttgg gcacagacaa aggtcatggt gtgttccatg atagcggact caggatgagt    5280
taattgagag aggcagtctt cctcccgtga aggacataag cagtagctca caatcatctc    5340
gcgtctcagc aaagtgtgca taattataaa gtgctgggtc atctaagctt ttcagtcgag    5400
aaaaaaacat tagatcagaa gaacaactgg caacacttct caacctgaga cctacttcaa    5460
gatgctcgat cctggagagg tctatgatga ccctattgac ccaatcgagt tagaggatga    5520
acccagagga acccccactg tccccaacat cttgaggaac tctgactaca atctcaactc    5580
tcctttgata aagatcctg ctagactaat gttagaatgg ttaaaaacag ggaatagacc    5640
ttatcggatg actctaacag acaattgctc caggtctttc agagttttga agattattt    5700 caagaaggta gatttgggtt ctctcaaggt gggcggaatg gctgcacagt caatgatttc    5760
tctctggtta tatggtgccc actctgaatc caacaggagc cggagatgta aacagactt    5820 ggcccatttc tattccaagt cgtcccccat agagaagctg ttgaatctca cgctaggaaa    5880
tagagggctg agaatccccc cagagggagt gttaagttgc cttgagaggg ttgattatga    5940
taatgcattt ggaaggtatc ttgccaacac gtattcctct tacttgttct tccatgtaat    6000
caccttatac atgaacgccc tagactggga tgaagaaaag accatcctag cattatggaa    6060
agatttaacc tcagtggaca tcgggaagga cttggtaaag ttcaaagacc aaatatgggg    6120
actgctgatc gtgacaaagg actttgttta ctcccaaagt tccaattgtc ttttgacag    6180 aaactacaca cttatgctaa aagatctttt cttgtctcgc ttcaactcct taatggtctt    6240
gctctctccc ccagagcccc gatactcaga tgacttgata tctcaactat gccagctgta    6300
cattgctggg gatcaagtct tgtctatgtg tggaaactcc ggctatgaag tcatcaaaat    6360
attggagcca tatgtcgtga atagtttagt ccagagagca gaaaagttta ggcctctcat    6420
tcattccttg ggagactttc ctgtatttat aaaagacaag gtaagtcaac ttgaagagac    6480
gttcggtccc tgtgcaagaa ggttctttag ggctctggat caattcgaca acatacatga    6540
cttggttttt gtgtatggct gttacaggca ttgggggcac ccatatatag attatcgaaa    6600
gggtctgtca aaactatatg atcaggttca cattaaaaaa gtgatagata agtcctacca    6660
ggagtgctta gcaagcgacc tagccaggag gatccttaga tgggggtttttg ataagtactc    6720 caagtggtat ctggattcaa gattcctagc ccgagaccac cccttgactc cttatatcaa    6780
aacccaaaca tggccaccca acatattgt agacttggtg ggggatacat ggcacaagct    6840
cccgatcacg cagatctttg agattcctga atcaatggat ccgtcagaaa tattggatga    6900
caaatcacat tctttcacca gaacgagact agcttcttgg ctgtcagaaa accgaggggg    6960
acctgttcct agcgaaaaag ttattatcac ggccctgtct aagccgcctg tcaatccccg    7020
agagtttctg aggtctatag acctcggagg attgccagat gaagacttga taattggcct    7080
caagccaaag gaacgggaat tgaagattga aggtcgattc tttgctctaa tgtcatggaa    7140
tctaagattg tattttgtca tcactgaaaa actcttggcc aactacatct tgccactttt    7200
tgacgcgctg actatgacag acaacctgaa caaggtgttt aaaagctga tcgacagggt    7260 caccgggcaa gggcttttgg actattcaag ggtcacatat gcatttcacc tggactatga    7320
aaagtggaac aaccatcaaa gattagagtc aacagaggat gtatttttctg tcctagatca    7380 agtgtttgga ttgaagagag tgttttctag aacacacgag ttttttcaaa aggcctggat    7440
ctattattca gacagatcag acctcatcgg gttacgggag gatcaaatat actgcttaga    7500
tgcgtccaac ggcccaacct gttggaatgg ccaggatggc gggctagaag gcttacggca    7560
gaagggctgg agtctagtca gcttattgat gatagataga gaatctcaaa tcaggaacac    7620
```

```
aagaaccaaa atactagctc aaggagacaa ccaggttttta tgtccgacat atatgttgtc    7680
gccagggcta tctcaagagg ggctcctcta tgaattggag agaatatcaa ggaatgcact    7740
ttcgatatac agagccgtcg aggaaggggc atctaagcta gggctgatca tcaagaaaga    7800
agagaccatg tgtagttatg acttcctcat ctatggaaaa acccctttgt ttagaggtaa    7860
catattggtg cctgagtcca aaagatgggc cagagtctct tgcgtctcta atgaccaaat    7920
agtcaacctc gccaatataa tgtcgacagt gtccaccaat gcgctaacag tggcacaaca    7980
ctctcaatct ttgatcaaac cgatgaggga ttttctgctc atgtcagtac aggcagtctt    8040
tcactacctg ctatttagcc caatcttaaa gggaagagtt tacaagattc tgagcgctga    8100
aggggatagc tttctcctag ccatgtcaag gataatctat ctagatcctt ctttgggagg    8160
ggtatctgga atgtccctcg aagattccaa tatacgacag ttctcagacc ctgtctctga    8220
agggttatcc ttctggagag agatctggtt aagctcccac gagtcctgga ttcacgcgtt    8280
gtgtcaagag gctggaaacc cagatcttgg agagagaaca ctcgagagct tcactcgcct    8340
tctagaagat cctaccacct taaatatcag gaggggggcc agtcctacca ttctactcaa    8400
ggatgcaatc agaaaggctt tatatgacga ggtggacaag gtggagaatt cagagtttcg    8460
agaggcaatc ctgttgtcca agacccatag agataatttt atactcttct taacatctgt    8520
tgagcctctg tttcctcgat ttctcagtga gctattcagt tcgtcttttt tgggaatccc    8580
cgagtcaatc attggattga tacaaaactc ccgaacgata agaaggcagt ttagaaagag    8640
tctctcaaaa actttagaag aatccttcta caactcagag atccacggga ttagtcggat    8700
gacccagaca cctcagaggg ttggggggggt gtggccttgc tcttcagaga gggcagatct    8760
acttagggag atctcttggg gaagaaaagt ggtaggcacg acagttcctc acccttctga    8820
gatgttgggg ttacttccca agtcctctat ttcttgcact tgtggagcaa caggaggagg    8880
caatcctaga gtttctgtat cagtactccc gtcctttgat cagtcatttt tttcacgagg    8940
ccccctaaag gggtacttgg gctcgtccac ctctatgtcg acccagctat tccatgcatg    9000
ggaaaaagtc actaatgttc atgtggtgaa gagagctcta tcgttaaaag aatctataaa    9060
ctggttcatt actagagatt ccaacttggc tcaagctcta attaggaaca ttatgtctct    9120
gacaggccct gatttccctc tagaggaggc ccctgtcttc aaaaggacgg ggtcagcctt    9180
gcataggttc aagtctgcca gatacagcga aggagggtat tcttctgtct gcccgaacct    9240
cctctctcat atttctgtta gtacagacac catgtctgat ttgacccaag acgggaagaa    9300
ctacgatttc atgttccagc cattgatgct ttatgcacag acatggacat cagagctggt    9360
acagagagac acaaggctaa gagactctac gtttcattgg cacctccgat gcaacaggtg    9420
tgtgagaccc attgacgacg tgaccctgga gacctctcag atcttcgagt ttccggatgt    9480
gtcgaaaaga atatccagaa tggtttctgg ggctgtgcct cacttccaga ggcttcccga    9540
tatccgtctg agaccaggag attttgaatc tctaagcggt agagaaaagt ctcaccatat    9600
cggatcagct caggggctct tatactcaat cttagtggca attcacgact caggatacaa    9660
tgatggaacc atcttccctg tcaacatata cgacaaggtt tccctagag actatttgag    9720 agggctcgca aggggagtat tgataggatc ctcgatttgc ttcttgacaa gaatgacaaa    9780
tatcaatatt aatagacctc ttgaattgat ctcagggtta atctcatata ttctcctgag    9840
gctagataac catccctcct tgtacataat gctcagagaa ccgtctcttta gaggagagat    9900 attttctatc cctcagaaaa tccccgccgc ttatccaacc actatgaaag aaggcaacag    9960
```

| | | |
|---|---|---|
| atcaatcttg tgttatctcc aacatgtgct acgctatgag cgagagataa tcacggcgtc | 10020 |
| tccagagaat gactggctat ggatcttttc agactttaga agtgccaaaa tgacgtacct | 10080 |
| aaccctcatt acttaccagt ctcatcttct actccagagg gttgagagaa acctatctaa | 10140 |
| gagtatgaga gataacctgc gacaattgag ttccttgatg aggcaggtgc tgggcgggca | 10200 |
| cggagaagat accttagagt cagacgacaa cattcaacga ctgctaaaag actctttacg | 10260 |
| aaggacaaga tgggtggatc aagaggtgcg ccatgcagct agaaccatga ctggagatta | 10320 |
| cagccccaac aagaaggtgt cccgtaaggt aggatgttca gaatgggtct gctctgctca | 10380 |
| acaggttgca gtctctacct cagcaaaccc ggccctgtc tcggagcttg acataagggc | 10440 |
| cctctctaag aggttccaga accctttgat ctcgggcttg agagtggttc agtgggcaac | 10500 |
| cggtgctcat tataagctta agcctattct agatgatctc aatgttttcc catctctctg | 10560 |
| ccttgtagtt ggggacgggt caggggggat atcaagggca gtcctcaaca tgtttccaga | 10620 |
| tgccaagctt gtgttcaaca gtctcttaga ggtgaatgac ctgatggctt ccggaacaca | 10680 |
| tccactgcct ccttcagcaa tcatgagggg aggaaatgat atcgtctcca gagtgataga | 10740 |
| ttttgactca atctgggaaa aaccgtccga cttgagaaac ttggcaacct ggaaatactt | 10800 |
| ccagtcagtc caaaagcagg tcaacatgtc ctatgacctc attatttgcg atgcagaagt | 10860 |
| tactgacatt gcatctatca accggataac cctgttaatg tccgattttg cattgtctat | 10920 |
| agatggacca ctctatttgg tcttcaaaac ttatgggact atgctagtaa atccaaacta | 10980 |
| caaggctatt caacacctgt caagagcgtt ccctcggtc acagggttta tcacccaagt | 11040 |
| aacttcgtct ttttcatctg agctctacct ccgattctcc aaacgaggga gttttttcag | 11100 |
| agatgctgag tacttgacct cttccaccct tcgagaaatg agccttgtgt tattcaattg | 11160 |
| tagcagcccc aagagtgaga tgcagagagc tcgttccttg aactatcagg atcttgtgag | 11220 |
| aggatttcct gaagaaatca tatcaaatcc ttacaatgag atgatcataa ctctgattga | 11280 |
| cagtgatgta gaatcttttc tagtccacaa gatggttgat gatcttgagt tacagagggg | 11340 |
| aactctgtct aaagtggcta tcattatagc catcatgata gttttctcca acagagtctt | 11400 |
| caacgttccc aaaccctaa ctgacccctt gttctatcca ccgtctgatc ccaaaatcct | 11460 |
| gaggcacttc aacatatgtt gcagtactat gatgtatcta tctactgctt taggtgacgt | 11520 |
| ccctagcttc gcaagacttc acgacctgta taacagacct ataacttatt acttcagaaa | 11580 |
| gcaattcatt cgagggaacg tttatctatc ttggagttgg tccaacgaca cctcagtgtt | 11640 |
| caaaagggta gcctgtaatt ctagcctgag tctgtcatct cactggatca ggttgattta | 11700 |
| caagatagtg aagactacca gactcgttgg cagcatcaag gatctatcca gagaagtgga | 11760 |
| aagacacctt cataggtaca acaggtggat caccctagag gatatcagat ctagatcatc | 11820 |
| cctactagac tacagttgcc tgtgatccgg atactcctgg aagcctgccc atgctaagac | 11880 |
| tcttgtgtga tgtatcttga aaaaacaag atcctaaatc tgaacctttg gttgtttgat | 11940 |
| tgttttctc attttgttg tttatttgtt aagcgt | 11976 |

```
<210> SEQ ID NO 15
<211> LENGTH: 12662
<212> TYPE: DNA
<213> ORGANISM: artificial sequence
<220> FEATURE:
<223> OTHER INFORMATION: Recombinant ERA-pt-GFP rabies virus genome
<220> FEATURE:
<221> NAME/KEY: misc_feature
<222> LOCATION: (71)..(1420)
<220

```
<221> NAME/KEY: misc_feature
<222> LOCATION: (1514)..(2404)
<220> FEATURE:
<221> NAME/KEY: misc_feature
<222> LOCATION: (2505)..(3185)
<220> FEATURE:
<221> NAME/KEY: misc_feature
<222> LOCATION: (3228)..(3833)
<220> FEATURE:
<221> NAME/KEY: misc_feature
<222> LOCATION: (4049)..(5620)
<220> FEATURE:
<221> NAME/KEY: misc_feature
<222> LOCATION: (6148)..(12528)

<400> SEQUENCE: 15
acgcttaaca accagatcaa agaaaaaaca gacattgtca attgcaaagc aaaaatgtaa      60
caccccctaca atggatgccg acaagattgt attcaaagtc aataatcagg tggtctcttt     120
gaagcctgag attatcgtgg atcaacatga gtacaagtac cctgccatca agatttgaa      180
aaagccctgt ataaccctag aaaggctcc cgatttaaat aaagcataca agtcagtttt      240
gtcaggcatg agcgccgcca aacttgatcc tgacgatgta tgttcctatt tggcagcggc     300
aatgcagttt tttgagggga catgtccgga agactggacc agctatggaa tcgtgattgc     360
acgaaaagga gataagatca ccccaggttc tctggtggag ataaaacgta ctgatgtaga     420
agggaattgg gctctgacag gaggcatgga actgacaaga gaccccactg tccctgagca     480
tgcgtcctta gtcggtcttc tcttgagtct gtataggttg agcaaaatat ccgggcaaaa     540
cactggtaac tataagacaa acattgcaga caggatagag cagattttg agacagcccc     600
ttttgttaaa atcgtggaac accatactct aatgacaact cacaaaatgt gtgctaattg     660
gagtactata ccaaacttca gattttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga agaatgtttg agccagggca     900
ggagacagct gttcctcact cttatttcat ccacttccgt tcactaggct tgagtgggaa     960
atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctaggggct atctgggaga ggaattcttc gggaagggga catttgaaag    1140
aagattcttc agagatgaga agaacttca gaaatacgag gcggctgaac tgacaaagac    1200
tgacgtagca ctggcagatg atggaactgt caactctgac gacgaggact acttctcagg    1260
tgaaaccaga agtccggagg ctgttttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taagaagttg aataacaaaa    1440
tgccggaaat ctacggattg tgtatatcca tcatgaaaaa aactaacacc cctcctttcg    1500
aaccatccca aacatgagca agatctttgt caatcctagt gctattagag ccggtctggc    1560
cgatcttgag atggctgaag aaactgttga tctgatcaat agaaatatcg aagacaatca    1620
ggctcatctc caaggggaac ccatagaagt ggacaatctc cctgaggata tgggggcgact    1680
tcacctggat gatggaaaat cgcccaaccc tggtgagatg gccaaggtgg agaaggcaa    1740
gtatcgagag gactttcaga tggatgaagg agaggatcct agcttcctgt tccagtcata    1800
cctggaaaat gttggagtcc aaatagtcag acaaatgagg tcaggagaga gatttctcaa    1860
```

```
gatatggtca cagaccgtag aagagattat atcctatgtc gcggtcaact ttcccaaccc    1920
tccaggaaag tcttcagagg ataaatcaac ccagactact ggccgagagc tcaagaagga    1980
gacaacaccc actccttctc agagagaaag ccaatcatcg aaagccagga tggcggctca    2040
aattgcttct ggccctccag cccttgaatg gtcggccacc aatgaagagg atgatctatc    2100
agtggaggct gagatcgctc accagattgc agaaagtttc tccaaaaaat ataagtttcc    2160
ctctcgatcc tcagggatac tcttgtataa ttttgagcaa ttgaaaatga accttgatga    2220
tatagttaaa gaggcaaaaa atgtaccagg tgtgacccgt ttagcccatg acgggtccaa    2280
actccccta agatgtgtac tgggatgggt cgctttggcc aactctaaga aattccagtt    2340
gttagtcgaa tccgacaagc tgagtaaaat catgcaagat gacttgaatc gctatacatc    2400
ttgctaaccg aacctctcca ctcagtccct ctagacaata aagtccgaga tgtcctaaag    2460
tcaacatgaa aaaaactaac accctcctt tcgctgcagc caccatgggc gtgatcaagc    2520
ccgacatgaa gatcaagctg cggatggagg gcgccgtgaa cggccacaaa ttcgtgatcg    2580
agggcgacgg gaaaggcaag ccctttgagg gtaagcagac tatggacctg accgtgatcg    2640
agggcgcccc cctgcccttc gcttatgaca ttctcaccac cgtgttcgac tacggtaacc    2700
gtgtcttcgc caagtacccc aaggacatcc ctgactactt caagcagacc ttccccgagg    2760
gctactcgtg ggagcgaagc atgacatacg aggaccaggg aatctgtatc gctacaaacg    2820
acatcaccat gatgaagggt gtggacgact gcttcgtgta caaaatccgc ttcgacgggg    2880
tcaacttccc tgctaatggc ccggtgatgc agcgcaagac cctaaagtgg gagcccagta    2940
ccgagaagat gtacgtgcgg gacggcgtac tgaagggcga tgttaatatg gcactgctct    3000
tggagggagg cggccactac cgctgcgact caagaccac ctacaaagcc aagaaggtgg    3060
tgcagcttcc cgactaccac ttcgtggacc accgcatcga gatcgtgagc cacgacaagg    3120
actacaacaa agtcaagctg tacgagcacg ccgaagccca cagcggacta ccccgccagg    3180
ccggctaagg taccgtcgag aaaaaaacag gcaacaccac tgataaaatg aactttctac    3240
gtaagatagt gaaaaattgc agggacgagg acactcaaaa accctctccc gtgtcagccc    3300
ctctggatga cgatgacttg tggcttccac cccctgaata cgtcccgctg aaagaactta    3360
caagcaagaa gaacatgagg aacttttgta tcaacggagg ggttaaagtg tgtagcccga    3420
atggttactc gttcaggatc ctgcggcaca ttctgaaatc attcgacgag atatattctg    3480
ggaatcatag gatgatcggg ttagtcaaag tagttattgg actggctttg tcaggatctc    3540
cagtccctga gggcatgaac tgggtataca aattgaggag aacctttatc ttccagtggg    3600
ctgattccag gggccctctt gaaggggagg agttggaata ctctcaggag atcacttggg    3660
atgatgatac tgagttcgtc ggattgcaaa taagagtgat tgcaaaacag tgtcatatcc    3720
agggcagaat ctggtgtatc aacatgaacc cgagagcatg tcaactatgg tctgacatgt    3780
ctcttcagac acaaaggtcc gaagaggaca agattcctc tctgcttcta gaataatcag    3840
attatatccc gcaaatttat cacttgttta cctctggagg agagaacata tgggctcaac    3900
tccaaccctt gggagcaata taacaaaaaa catgttatgg tgccattaaa ccgctgcatt    3960
tcatcaaagt caagttgatt acctttacat tttgatcctc ttggatgtga aaaaaactat    4020
taacatccct caaaagactc aaggaaagat ggttcctcag gctctcctgt ttgtaccct    4080
tctggttttt ccattgtgtt ttgggaaatt ccctatttac acgataccag acaagcttgg    4140
tccctggagc ccgattgaca tacatcacct cagctgccca aacaatttgg tagtggagga    4200
cgaaggatgc accaacctgt cagggttctc ctacatggaa cttaaagttg gatacatctt    4260
```

```
agccataaaa atgaacgggt tcacttgcac aggcgttgtg acggaggctg aaacctacac   4320
taacttcgtt ggttatgtca caaccacgtt caaaagaaag catttccgcc caacaccaga   4380
tgcatgtaga gccgcgtaca actggaagat ggccggtgac cccagatatg aagagtctct   4440
acacaatccg taccctgact accactggct tcgaactgta aaaaccacca aggagtctct   4500
cgttatcata tctccaagtg tggcagattt ggacccatat gacagatccc ttcactcgag   4560
ggtcttccct agcgggaagt gctcaggagt agcggtgtct tctacctact gctccactaa   4620
ccacgattac accatttgga tgcccgagaa tccgagacta gggatgtctt gtgacatttt   4680
taccaatagt agagggaaga gagcatccaa agggagtgag acttgcggct tgtagatga   4740 aagaggccta tataagtctt taaaaggagc atgcaaactc aagttatgtg agttctagg   4800 acttagactt atggatggaa catgggtcgc gatgcaaaca tcaaatgaaa ccaaatggtg   4860
ccctcccgat cagttggtga acctgcacga ctttcgctca gacgaaattg agcaccttgt   4920
tgtagaggag ttggtcagga agagagagga gtgtctggat gcactagagt ccatcatgac   4980
aaccaagtca gtgagtttca gacgtctcag tcatttaaga aaacttgtcc ctggggtttgg   5040 aaaagcatat accatattca acaagacctt gatggaagcc gatgctcact acaagtcagt   5100
cgagacttgg aatgagatcc tcccttcaaa agggtgttta agagttgggg ggaggtgtca   5160
tcctcatgtg aacggggtgt ttttcaatgg tataatatta ggacctgacg gcaatgtctt   5220
aatcccagag atgcaatcat ccctcctcca gcaacatatg gagttgttgg aatcctcggt   5280
tatccccctt gtgcaccccc tggcagaccc gtctaccgtt ttcaaggacg gtgacgaggc   5340
tgaggatttt gttgaagttc accttcccga tgtgcacaat caggtctcag gagttgactt   5400
gggtctcccg aactggggga agtatgtatt actgagtgca ggggccctga ctgccttgat   5460
gttgataatt ttcctgatga catgttgtag aagagtcaat cgatcagaac ctacgcaaca   5520
caatctcaga gggacaggga gggaggtgtc agtcactccc caaagcggga agatcatatc   5580
ttcatgggaa tcacacaaga gtgggggtga gaccagactg tgaggactgg ccgtcctttc   5640
aactatccaa gtcctgaaga tcacctcccc ttggggggtt cttttttgaaa aaacctggg   5700 ttcaatagtc ctccttgaac tccatgcaac tgggtagatt caagagtcat gagattttca   5760
ttaatcctct cagttgatca agcaagatca tgtagattct cataataggg gagatcttct   5820
agcagtttca gtgactaacg gtactttcat tctccaggaa ctgacaccaa cagttgtaga   5880
caaaccacgg ggtgtctcgg gtgactctgt gcttgggcac agacaaaggt catggtgtgt   5940
tccatgatag cggactcagg atgagttaat tgagagaggc agtcttcctc ccgtgaagga   6000
cataagcagt agctcacaat catctcgcgt ctcagcaaag tgtgcataat tataaagtgc   6060
tgggtcatct aagcttttca gtcgagaaaa aaacattaga tcagaagaac aactggcaac   6120
acttctcaac ctgagaccta cttcaagatg ctcgatcctg gagaggtcta tgatgaccct   6180
attgacccaa tcgagttaga ggatgaaccc agaggaaccc ccactgtccc caacatcttg   6240
aggaactctg actacaatct caactctcct ttgatagaag atcctgctag actaatgtta   6300
gaatggttaa aaacagggaa tagaccttat cggatgactc taacagacaa ttgctccagg   6360
tctttcagag ttttgaaaga ttatttcaag aaggtagatt tgggttctct caaggtgggc   6420
ggaatggctg cacagtcaat gatttctctc tggttatatg gtgcccactc tgaatccaac   6480
aggagccgga gatgtataac agacttggcc catttctatt ccaagtcgtc ccccatagag   6540
aagctgttga atctcacgct aggaaataga gggctgagaa tcccccagaa gggagtgtta   6600
```

```
agttgccttg agagggttga ttatgataat gcatttggaa ggtatcttgc caacacgtat   6660
tcctcttact tgttcttcca tgtaatcacc ttatacatga acgccctaga ctgggatgaa   6720
gaaaagacca tcctagcatt atggaaagat ttaacctcag tggacatcgg aaggacttg    6780 gtaaagttca aagaccaaat atgggggactg ctgatcgtga caaggacttt gtttactcc   6840 caaagttcca attgtctttt tgacagaaac tacacactta tgctaaaaga tcttttcttg   6900
tctcgcttca actccttaat ggtcttgctc tctccccag agccccgata ctcagatgac    6960
ttgatatctc aactatgcca gctgtacatt gctggggatc aagtcttgtc tatgtgtgga   7020
aactccggct atgaagtcat caaaatattg gagccatatg tcgtgaatag tttagtccag   7080
agagcagaaa agtttaggcc tctcattcat tccttgggag actttcctgt atttataaaa   7140
gacaaggtaa gtcaacttga agagacgttc ggtccctgtg caagaaggtt ctttagggct   7200
ctggatcaat tcgacaacat acatgacttg gttttgtgt atggctgtta caggcattgg    7260
gggcacccat atatagatta tcgaaagggt ctgtcaaaac tatatgatca ggttcacatt   7320
aaaaaagtga tagataagtc ctaccaggag tgcttagcaa gcgacctagc caggaggatc   7380
cttagatggg gttttgataa gtactccaag tggtatctgg attcaagatt cctagcccga   7440
gaccacccct tgactcctta tatcaaaacc caaacatggc cacccaaaca tattgtagac   7500
ttggtggggg atacatggca caagctcccg atcacgcaga tctttgagat tcctgaatca   7560
atggatccgt cagaaatatt ggatgacaaa tcacattctt tcaccagaac gagactagct   7620
tcttggctgt cagaaaaccg aggggggacct gttcctagcg aaaagttat tatcacggcc    7680 ctgtctaagc cgcctgtcaa tccccgagag tttctgaggt ctatagacct cggaggattg   7740
ccagatgaag acttgataat tggcctcaag ccaaaggaac gggaattgaa gattgaaggt   7800
cgattctttg ctctaatgtc atggaatcta agattgtatt ttgtcatcac tgaaaaactc   7860
ttggccaact acatcttgcc actttttgac gcgctgacta tgacagacaa cctgaacaag   7920
gtgtttaaaa agctgatcga cagggtcacc gggcaagggc ttttggacta ttcaagggtc   7980
acatatgcat ttcacctgga ctatgaaaag tggaacaacc atcaaagatt agagtcaaca   8040
gaggatgtat tttctgtcct agatcaagtg tttggattga agagagtgtt ttctagaaca   8100
cacgagtttt ttcaaaaggc ctggatctat tattcagaca gatcagacct catcgggtta   8160
cgggaggatc aaatatactg cttagatgcg tccaacggcc caacctgttg gaatggccag   8220 gatgcgggc tagaaggctt acggcagaag ggctggagtc tagtcagctt attgatgata    8280
gatagagaat ctcaaatcag gaacacaaga accaaaatac tagctcaagg agacaaccag   8340
gttttatgtc cgacatatat gttgtcgcca gggctatctc aagagggct cctctatgaa    8400 ttggagagaa tatcaaggaa tgcactttcg atatacagag ccgtcgagga agggcatct    8460 aagctagggc tgatcatcaa gaagaagag accatgtgta gttatgactt cctcatctat   8520 ggaaaaccc ctttgtttag aggtaacata ttggtgcctg agtccaaaag atgggccaga    8580
gtctcttgcg tctctaatga ccaaatagtc aacctcgcca atataatgtc gacagtgtcc   8640
accaatgcgc taacagtggc acaacactct caatctttga tcaaaccgat gagggatttt   8700
ctgctcatgt cagtacaggc agtctttcac tacctgctat ttagcccaat cttaaaggga   8760
agagtttaca agattctgag cgctgaaggg gatagctttc tcctagccat gtcaaggata   8820
atctatctag atccttcttt gggaggggta tctggaatgt ccctcggaag attccatata   8880
cgacagttct cagaccctgt ctctgaaggg ttatccttct ggagagagat ctggttaagc   8940
tcccacgagt cctggattca cgcgttgtgt caagaggctg gaaacccaga tcttggagag   9000
```

```
agaacactcg agagcttcac tcgccttcta gaagatccta ccaccttaaa tatcagagga   9060
ggggccagtc ctaccattct actcaaggat gcaatcagaa aggctttata tgacgaggtg   9120
gacaaggtgg agaattcaga gtttcgagag gcaatcctgt tgtccaagac ccatagagat   9180
aattttatac tcttcttaac atctgttgag cctctgtttc ctcgatttct cagtgagcta   9240
ttcagttcgt ctttttttggg aatccccgag tcaatcattg gattgataca aaactcccga   9300
acgataagaa ggcagtttag aaagagtctc tcaaaaactt tagaagaatc cttctacaac   9360
tcagagatcc acgggattag tcggatgacc cagacacctc agagggttgg ggggtgtgg    9420 ccttgctctt cagagagggc agatctactt agggagatct cttggggaag aaaagtggta   9480
ggcacgacag ttcctcaccc ttctgagatg ttggggttac ttcccaagtc ctctatttct   9540
tgcacttgtg gagcaacagg aggaggcaat cctagagttt ctgtatcagt actcccgtcc   9600
tttgatcagt cattttttc acgaggcccc ctaaagggt acttgggctc gtccacctct     9660
atgtcgaccc agctattcca tgcatgggaa aaagtcacta atgttcatgt ggtgaagaga   9720
gctctatcgt taaagaatc tataaactgg ttcattacta gagattccaa cttggctcaa    9780
gctctaatta ggaacattat gtctctgaca ggccctgatt tccctctaga ggaggcccct   9840
gtcttcaaaa ggacggggtc agccttgcat aggttcaagt ctgccagata cagcgaagga   9900
gggtattctt ctgtctgccc gaacctcctc tctcatattt ctgttagtac agacaccatg   9960
tctgatttga cccaagacgg gaagaactac gatttcatgt tccagccatt gatgctttat  10020
gcacagacat ggacatcaga gctggtacag agagacacaa ggctaagaga ctctacgttt  10080
cattggcacc tccgatgcaa caggtgtgtg agacccattg acgacgtgac cctggagacc  10140
tctcagatct tcgagtttcc ggatgtgtcg aaaagaatat ccagaatggt ttctgggct   10200 gtgcctcact tccagaggct tcccgatatc cgtctgagac caggagattt tgaatctcta  10260
agcggtagag aaaagtctca ccatatcgga tcagctcagg ggctcttata ctcaatctta  10320
gtggcaattc acgactcagg atacaatgat ggaaccatct tccctgtcaa catatacgac  10380
aaggtttccc ctagagacta tttgagaggg ctcgcaaggg gagtattgat aggatcctcg  10440
atttgcttct tgacaagaat gacaaatatc aatattaata gacctcttga attgatctca  10500
ggggtaatct catatattct cctgaggcta gataaccatc cctccttgta cataatgctc  10560
agagaaccgt ctcttagagg agagatattt tctatccctc agaaaatccc cgccgcttat  10620
ccaaccacta tgaaagaagg caacagatca atcttgtgtt atctccaaca tgtgctacgc  10680
tatgagcgag agataatcac ggcgtctcca gagaatgact ggctatggat cttttcagac  10740
tttagaagtg ccaaaatgac gtacctaacc ctcattactt accagtctca tcttctactc  10800
cagagggttg agagaaacct atctaagagt atgagagata acctgcgaca attgagttcc  10860
ttgatgaggc aggtgctggg cgggcacgga gaagatacct tagagtcaga cgacaacatt  10920
caacgactgc taaaagactc tttacgaagg acaagatggg tggatcaaga ggtgcgccat  10980
gcagctagaa ccatgactgg agattacagc cccaacaaga aggtgtcccg taaggtagga  11040
tgttcagaat gggtctgctc tgctcaacag gttgcagtct ctacctcagc aaacccggcc  11100
cctgtctcgg agcttgacat aagggccctc tctaagaggt tccagaaccc tttgatctcg  11160
ggcttgagag tggttcagtg ggcaaccggt gctcattata gcttaagcc tattctagat   11220 gatctcaatg ttttcccatc tctctgcctt gtagttgggg acgggtcagg ggggatatca  11280
agggcagtcc tcaacatgtt tccagatgcc aagcttgtgt tcaacagtct cttagaggtg  11340
```

-continued

```
aatgacctga tggcttccgg aacacatcca ctgcctcctt cagcaatcat gagggagga      11400
aatgatatcg tctccagagt gatagatttt gactcaatct gggaaaaacc gtccgacttg      11460
agaaacttgg caacctggaa atacttccag tcagtccaaa agcaggtcaa catgtcctat      11520
gacctcatta tttgcgatgc agaagttact gacattgcat ctatcaaccg gataaccctg      11580
ttaatgtccg attttgcatt gtctatagat ggaccactct atttggtctt caaaacttat      11640
gggactatgc tagtaaatcc aaactacaag gctattcaac acctgtcaag agcgttcccc      11700
tcggtcacag ggtttatcac ccaagtaact tcgtcttttt catctgagct ctacctccga      11760
ttctccaaac gagggaagtt tttcagagat gctgagtact tgacctcttc cacccttcga      11820
gaaatgagcc ttgtgttatt caattgtagc agccccaaga gtgagatgca gagagctcgt      11880
tccttgaact atcaggatct tgtgagagga tttcctgaag aaatcatatc aaatccttac      11940
aatgagatga tcataactct gattgacagt gatgtagaat cttttctagt ccacaagatg      12000
gttgatgatc ttgagttaca gaggggaact ctgtctaaag tggctatcat tatagccatc      12060
atgatagttt tctccaacag agtcttcaac gtttccaaac ccctaactga ccccttgttc      12120
tatccaccgt ctgatcccaa aatcctgagg cacttcaaca tatgttgcag tactatgatg      12180
tatctatcta ctgctttagg tgacgtccct agcttcgcaa gacttcacga cctgtataac      12240
agacctataa cttattactt cagaaagcaa ttcattcgag ggaacgttta tctatcttgg      12300
agttggtcca acgacacctc agtgttcaaa agggtagcct gtaattctag cctgagtctg      12360
tcatctcact ggatcaggtt gatttacaag atagtgaaga ctaccagact cgttggcagc      12420
atcaaggatc tatccagaga agtggaaaga caccttcata ggtacaacag gtggatcacc      12480
ctagaggata tcagatctag atcatcccta ctagactaca gttgcctgtg atccggatac      12540
tcctggaagc ctgcccatgc taagactctt gtgtgatgta tcttgaaaaa aacaagatcc      12600
taaatctgaa cctttggttg tttgattgtt tttctcattt ttgttgttta tttgttaagc      12660
gt                                                                     12662
```

<210> SEQ ID NO 16
<211> LENGTH: 11914
<212> TYPE: DNA
<213> ORGANISM: artificial sequence
<220> FEATURE:
<223> OTHER INFORMATION: Recombinant ERAgm rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2505)..(4076)
<220> FEATURE:
<221> NAME/KEY: misc_feature
<222> LOCATION: (4122)..(4727)
<220> FEATURE:
<221> NAME/KEY: misc_feature
<222> LOCATION: (5400)..(11780)

<400> SEQUENCE: 16

```
acgcttaaca accagatcaa agaaaaaaca gacattgtca attgcaaagc aaaaatgtaa       60
caccccctaca atggatgccg acaagattgt attcaaagtc aataatcagg tggtctcttt     120
gaagcctgag attatcgtgg atcaacatga gtacaagtac cctgccatca agatttgaa      180
aaagccctgt ataaccctag gaaaggctcc cgatttaaat aaagcataca agtcagtttt     240
```

```
gtcaggcatg agcgccgcca aacttgatcc tgacgatgta tgttcctatt tggcagcggc    300
aatgcagttt tttgagggga catgtccgga agactggacc agctatggaa tcgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttg agacagcccc     600
tttgttaaa atcgtggaac accatactct aatgacaact cacaaaatgt gtgctaattg     660
gagtactata ccaaacttca gattttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga agaatgtttg agccagggca    900
ggagacagct gttcctcact cttatttcat ccacttccgt tcactaggct tgagtgggaa     960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga agaacttca agaatacgag gcggctgaac tgacaaagac   1200
tgacgtagca ctggcagatg atggaactgt caactctgac gacgaggact acttctcagg   1260
tgaaaccaga agtccggagg ctgtttatac tcgaatcatg atgaatggag tcgactaaa    1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg agaaggcaa    1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata aagtccgaga tgtcctaaag   2460
tcaacatgaa aaaactaac accccctctt tcgctgcagc caccatggtt cctcaggctc   2520
tcctgttgt acccccttctg gtttttccat tgtgttttgg gaaattccct atttacacga   2580
taccagacaa gcttggtccc tggagcccga ttgacataca tcacctcagc tgcccaaaca   2640
```

```
atttggtagt ggaggacgaa ggatgcacca acctgtcagg gttctcctac atggaactta    2700
aagttggata catcttagcc ataaaaatga acgggttcac ttgcacaggc gttgtgacgg    2760
aggctgaaac ctacactaac ttcgttggtt atgtcacaac cacgttcaaa agaaagcatt    2820
tccgcccaac accagatgca tgtagagccg cgtacaactg aagatggcc ggtgacccca    2880 gatatgaaga gtctctacac aatccgtacc ctgactacca ctggcttcga actgtaaaaa    2940
ccaccaagga gtctctcgtt atcatatctc caagtgtggc agatttggac ccatatgaca    3000
gatcccttca ctcgagggtc ttccctagcg ggaagtgctc aggagtagcg gtgtcttcta    3060
cctactgctc cactaaccac gattacacca tttggatgcc cgagaatccg agactaggga    3120
tgtcttgtga cattttacc aatagtagag ggaagagagc atccaaaggg agtgagactt    3180
gcggctttgt agatgaaaga ggcctatata agtctttaaa aggagcatgc aaactcaagt    3240
tatgtggagt tctaggactt agacttatgg atggaacatg ggtcgcgatg caaacatcaa    3300
atgaaaccaa atggtgccct cccgatcagt tggtgaacct gcacgacttt cgctcagacg    3360
aaattgagca ccttgttgta gaggagttgg tcaggaagag agaggagtgt ctggatgcac    3420
tagagtccat catgacaacc aagtcagtga gtttcagacg tctcagtcat ttaagaaaac    3480
ttgtccctgg gtttggaaaa gcatatacca tattcaacaa gaccttgatg gaagccgatg    3540
ctcactacaa gtcagtcaga acttggaatg agatcctccc ttcaaaaggg tgtttaagag    3600 ttgggggggag tgtcatcct catgtgaacg gggtgttttt caatggtata atattaggac    3660
ctgacggcaa tgtcttaatc ccagagatgc aatcatccct cctccagcaa catatggagt    3720
tgttggaatc ctcggttatc ccccttgtgc acccctggc agaccgtct accgttttca    3780 aggacgtga cgaggctgag gattttgttg aagttcacct tcccgatgtg cacaatcagg    3840
tctcaggagt tgacttgggt ctcccgaact gggggaagta tgtattactg agtgcagggg    3900
ccctgactgc cttgatgttg ataattttcc tgatgacatg ttgtagaaga gtcaatcgat    3960
cagaacctac gcaacacaat ctcagaggga cagggaggga ggtgtcagtc actccccaaa    4020 gcggaagat catatcttca tgggaatcac acaagagtgg gggtgagacc agactgtgat    4080
ttggtaccgt cgagaaaaaa acaggcaaca ccactgataa aatgaacttt ctacgtaaga    4140
tagtgaaaaa ttgcagggac gaggacactc aaaaaccctc tcccgtgtca gcccctctgg    4200
atgacgatga cttgtggctt ccaccccctg aatacgtccc gctgaaagaa cttacaagca    4260
agaagaacat gaggaacttt tgtatcaacg gaggggttaa agtgtgtagc ccgaatggtt    4320
actcgttcag gatcctgcgg cacattctga atcattcga cgagatatat tctgggaatc    4380
ataggatgat cgggttagtc aaagtagtta ttggactggc tttgtcagga tctccagtcc    4440
ctgagggcat gaactgggta tacaaattga ggagaacctt tatcttccag tgggctgatt    4500
ccaggggccc tcttgaaggg gaggagttgg aatactctca ggagatcact tgggatgatg    4560
atactgagtt cgtcggattg caaataagag tgattgcaaa acagtgtcat atccagggca    4620
gaatctggtg tatcaacatg aacccgagag catgtcaact atggtctgac atgtctcttc    4680
agacacaaag gtccgaagag gacaaagatt cctctctgct tctagaataa tcagattata    4740
tcccgcaaat ttatcacttg tttacctctg gaggagagaa catatgggct caactccaac    4800
ccttgggagc aatataacaa aaaacatgtt atggtgccat taaccgctg catttcatca    4860 aagtcaagtt gattacccttt acattttgat cctcttggat gtgaaaaaa ctaacacccc    4920 tctgcagttt ggtaccttga aaaaaccctg ggttcaatag tcctccttga actccatgca    4980
```

```
actgggtaga ttcaagagtc atgagatttt cattaatcct ctcagttgat caagcaagat    5040
catgtagatt ctcataatag gggagatctt ctagcagttt cagtgactaa cggtactttc    5100
attctccagg aactgacacc aacagttgta gacaaaccac ggggtgtctc gggtgactct    5160
gtgcttgggc acagacaaag gtcatggtgt gttccatgat agcggactca ggatgagtta    5220
attgagagag gcagtcttcc tcccgtgaag gacataagca gtagctcaca atcatctcgc    5280
gtctcagcaa agtgtgcata attataaagt gctgggtcat ctaagctttt cagtcgagaa    5340
aaaaacatta gatcagaaga acaactggca acacttctca acctgagacc tacttcaaga    5400
tgctcgatcc tggagaggtc tatgatgacc ctattgaccc aatcgagtta gaggatgaac    5460
ccagaggaac ccccactgtc cccaacatct tgaggaactc tgactacaat ctcaactctc    5520
ctttgataga agatcctgct agactaatgt tagaatggtt aaaaacaggg aatagacctt    5580
atcggatgac tctaacagac aattgctcca ggtctttcag agttttgaaa gattatttca    5640
agaaggtaga tttgggttct ctcaaggtgg gcggaatggc tgcacagtca atgatttctc    5700
tctggttata tggtgcccac tctgaatcca acaggagccg gagatgtata acagacttgg    5760
cccatttcta ttccaagtcg tcccccatag agaagctgtt gaatctcacg ctaggaaata    5820
gagggctgag aatcccccca gagggagtgt taagttgcct tgagagggtt gattatgata    5880
atgcatttgg aagtatctt gccaacacgt attcctctta cttgttcttc catgtaatca    5940
ccttatacat gaacgcccta gactgggatg aagaaaagac catcctagca ttatggaaag    6000
atttaacctc agtggacatc gggaaggact tggtaaagtt caaagaccaa atatggggac    6060
tgctgatcgt gacaaaggac tttgtttact cccaaagttc caattgtctt tttgacagaa    6120
actacacact tatgctaaaa gatcttttct tgtctcgctt caactcctta atggtcttgc    6180
tctctccccc agagccccga tactcagatg acttgatatc tcaactatgc cagctgtaca    6240
ttgctgggga tcaagtcttg tctatgtgtg gaaactccgg ctatgaagtc atcaaaatat    6300
tggagccata tgtcgtgaat agtttagtcc agagagcaga aaagtttagg cctctcattc    6360
attccttggg agactttcct gtatttataa aagacaaggt aagtcaactt gaagagacgt    6420
tcggtccctg tgcaagaagg ttctttaggg ctctggatca attcgacaac atacatgact    6480
tggttttgt gtatggctgt tacaggcatt gggggcaccc atatatagat tatcgaaagg    6540
gtctgtcaaa actatatgat caggttcaca ttaaaaaagt gatagataag tcctaccagg    6600
agtgcttagc aagcgaccta gccaggagga tccttagatg gggttttgat aagtactcca    6660
agtggtatct ggattcaaga ttcctagccc gagaccaccc cttgactcct tatatcaaaa    6720
cccaaacatg gccacccaaa catattgtag acttggtggg ggatacatgg cacaagctcc    6780
cgatcacgca gatctttgag attcctgaat caatggatcc gtcagaaata ttggatgaca    6840
aatcacattc tttccaccaga acgagactag cttcttggct gtcagaaaac cgagggggac    6900
ctgttcctag cgaaaaagtt attatcacgg ccctgtctaa gccgcctgtc aatccccgag    6960
agtttctgag gtctatagac ctcggaggat tgccagatga agacttgata attggcctca    7020
agccaaagga acgggaattg aagattgaag gtcgattctt tgctctaatg tcatggaatc    7080
taagattgta ttttgtcatc actgaaaaac tcttggccaa ctacatcttg ccactttttg    7140
acgcgctgac tatgacagac aacctgaaca aggtgtttaa aaagctgatc gacagggtca    7200
ccggggcaagg gcttttggac tattcaaggg tcacatatgc atttcacctg gactatgaaa    7260
agtggaacaa ccatcaaaga ttagagtcaa cagaggatgt attttctgtc ctagatcaag    7320
tgtttggatt gaagagagtg ttttctagaa cacacgagtt ttttcaaaag gcctggatct    7380
```

```
attattcaga cagatcagac ctcatcgggt tacgggagga tcaaatatac tgcttagatg   7440
cgtccaacgg cccaacctgt tggaatggcc aggatggcgg gctagaaggc ttacggcaga   7500
agggctggag tctagtcagc ttattgatga tagatagaga atctcaaatc aggaacacaa   7560
gaaccaaaat actagctcaa ggagacaacc aggttttatg tccgacatat atgttgtcgc   7620
cagggctatc tcaagagggg ctcctctatg aattggagag aatatcaagg aatgcacttt   7680
cgatatacag agccgtcgag gaaggggcat ctaagctagg gctgatcatc aagaaagaag   7740
agaccatgtg tagttatgac ttcctcatct atggaaaaac ccctttgttt agaggtaaca   7800
tattggtgcc tgagtccaaa agatgggcca gagtctcttg cgtctctaat gaccaaatag   7860
tcaacctcgc caatataatg tcgacagtgt ccaccaatgc gctaacagtg gcacaacact   7920
ctcaatcttt gatcaaaccg atgagggatt ttctgctcat gtcagtacag gcagtctttc   7980
actacctgct atttagccca atcttaaagg gaagagttta caagattctg agcgctgaag   8040
gggatagctt tctcctagcc atgtcaagga taatctatct agatccttct ttgggagggg   8100
tatctggaat gtccctcgga agattccata tacgacagtt ctcagaccct gtctctgaag   8160
ggttatcctt ctggagagag atctggttaa gctcccacga gtcctggatt cacgcgttgt   8220
gtcaagaggc tggaaaccca gatcttggag agagaacact cgagagcttc actcgccttc   8280
tagaagatcc taccacctta aatatcagag gaggggccag tcctaccatt ctactcaagg   8340
atgcaatcag aaaggcttta tatgacgagg tggacaaggt ggagaattca gagtttcgag   8400
aggcaatcct gttgtccaag acccatagag ataattttat actcttctta acatctgttg   8460
agcctctgtt tcctcgattt ctcagtgagc tattcagttc gtctttttg ggaatccccg   8520 agtcaatcat tggattgata caaaactccc gaacgataag aaggcagttt agaaagagtc   8580
tctcaaaaac tttagaagaa tccttctaca actcagagat ccacgggatt agtcggatga   8640
cccagacacc tcagagggtt ggggggggtgt ggccttgctc ttcagagagg gcagatctac   8700
ttagggagat ctcttgggga agaaaagtgg taggcacgac agttcctcac ccttctgaga   8760
tgttggggtt acttcccaag tcctctattt cttgcacttg tggagcaaca ggaggaggca   8820
atcctagagt ttctgtatca gtactcccgt cctttgatca gtcattttt tcacgaggcc   8880 ccctaaaggg gtacttgggc tcgtccacct ctatgtcgac ccagctattc catgcatggg   8940
aaaaagtcac taatgttcat gtggtgaaga gagctctatc gttaaaagaa tctataaact   9000
ggttcattac tagagattcc aacttggctc aagctctaat taggaacatt atgtctctga   9060
caggccctga tttccctcta gaggaggccc ctgtcttcaa aaggacgggg tcagccttgc   9120
ataggttcaa gtctgccaga tacagcgaag gagggtattc ttctgtctgc ccgaacctcc   9180
tctctcatat ttctgttagt acagacacca tgtctgattt gacccaagac gggaagaact   9240
acgatttcat gttccagcca ttgatgcttt atgcacagac atggacatca gagctggtac   9300
agagagacac aaggctaaga gactctacgt ttcattggca cctccgatgc aacaggtgtg   9360
tgagacccat tgacgacgtg accctggaga cctctcagat cttcgagttt ccggatgtgt   9420
cgaaaagaat atccagaatg gtttctgggg ctgtgcctca cttccagagg cttcccgata   9480
tccgtctgag accaggagat tttgaatctc taagcggtag agaaaagtct caccatatcg   9540
gatcagctca ggggctctta tactcaatct tagtggcaat tcacgactca ggatacaatg   9600
atggaaccat cttccctgtc aacatatacg acaaggtttc ccctagagac tatttgagag   9660
ggctcgcaag gggagtattg ataggatcct cgatttgctt cttgacaaga atgacaaata   9720
```

-continued

```
tcaatattaa tagacctctt gaattgatct caggggtaat ctcatatatt ctcctgaggc    9780
tagataacca tccctccttg tacataatgc tcagagaacc gtctcttaga ggagagatat    9840
tttctatccc tcagaaaatc cccgccgctt atccaaccac tatgaaagaa ggcaacagat    9900
caatcttgtg ttatctccaa catgtgctac gctatgagcg agagataatc acggcgtctc    9960
cagagaatga ctggctatgg atcttttcag actttagaag tgccaaaatg acgtacctaa   10020
ccctcattac ttaccagtct catcttctac tccagagggt tgagagaaac ctatctaaga   10080
gtatgagaga taacctgcga caattgagtt ccttgatgag gcaggtgctg ggcgggcacg   10140
gagaagatac cttagagtca gacgacaaca ttcaacgact gctaaaagac tctttacgaa   10200
ggacaagatg ggtggatcaa gaggtgcgcc atgcagctag aaccatgact ggagattaca   10260
gccccaacaa gaaggtgtcc cgtaaggtag gatgttcaga atgggtctgc tctgctcaac   10320
aggttgcagt ctctacctca gcaaacccgg ccctgtctc ggagcttgac ataagggccc    10380
tctctaagag gttccagaac cctttgatct cgggcttgag agtggttcag tgggcaaccg   10440
gtgctcatta taagcttaag cctattctag atgatctcaa tgttttccca tctctctgcc   10500
ttgtagttgg ggacgggtca gggggatat caagggcagt cctcaacatg tttccagatg    10560
ccaagcttgt gttcaacagt ctcttagagg tgaatgacct gatggcttcc ggaacacatc   10620
cactgcctcc ttcagcaatc atgagggag gaaatgatat cgtctccaga gtgatagatt    10680
ttgactcaat ctgggaaaaa ccgtccgact tgagaaactt ggcaacctgg aaatacttcc   10740
agtcagtcca aaagcaggtc aacatgtcct atgacctcat tatttgcgat gcagaagtta   10800
ctgacattgc atctatcaac cggataaccc tgttaatgtc cgattttgca ttgtctatag   10860
atggaccact ctatttggtc ttcaaaactt atgggactat gctagtaaat ccaaactaca   10920
aggctattca acacctgtca agagcgttcc cctcggtcac agggtttatc acccaagtaa   10980
cttcgtcttt ttcatctgag ctctacctcc gattctccaa acgagggaag tttttcagag   11040
atgctgagta cttgacctct tccacccttc gagaaatgag ccttgtgtta ttcaattgta   11100
gcagccccaa gagtgagatg cagagagctc gttccttgaa ctatcaggat cttgtgagag   11160
gatttcctga agaaatcata tcaaatcctt acaatgagat gatcataact ctgattgaca   11220
gtgatgtaga atcttttcta gtccacaaga tggttgatga tcttgagtta cagagggggaa   11280
ctctgtctaa agtggctatc attatagcca tcatgatagt tttctccaac agagtcttca   11340
acgtttccaa accectaact gacccettgt tctatccacc gtctgatccc aaaatcctga   11400
ggcacttcaa catatgttgc agtactatga tgtatctatc tactgcttta ggtgacgtcc   11460
ctagcttcgc aagacttcac gacctgtata acagacctat aacttattac ttcagaaagc   11520
aattcattcg agggaacgtt tatctatctt ggagttggtc caacgacacc tcagtgttca   11580
aaagggtagc ctgtaattct agcctgagtc tgtcatctca ctggatcagg ttgatttaca   11640
agatagtgaa gactaccaga ctcgttggca gcatcaagga tctatccaga gaagtggaaa   11700
gacaccttca taggtacaac aggtggatca ccctagagga tatcagatct agatcatccc   11760
tactagacta cagttgcctg tgatccggat actcctggaa gcctgcccat gctaagactc   11820
ttgtgtgatg tatcttgaaa aaacaagat cctaaatctg aacctttggt tgtttgattg    11880
tttttctcat ttttgttgtt tatttgttaa gcgt                               11914
```

<210> SEQ ID NO 17
<211> LENGTH: 11914
<212> TYPE: DNA
<213> ORGANISM: artificial seuqence -continued
<220> FEATURE:
<223> OTHER INFORMATION: Recombinant ERAg3m rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2505)..(4076)
<220> FEATURE:
<221> NAME/KEY: misc_feature
<222> LOCATION: (4122)..(4727)
<220> FEATURE:
<221> NAME/KEY: misc_feature
<222> LOCATION: (5400)..(11780)

<400> SEQUENCE: 17
acgcttaaca accagatcaa agaaaaaaca gacattgtca attgcaaagc aaaaatgtaa 60 caccoctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300
aatgcagttt tttgagggga catgtccgga agactggacc agctatggaa tcgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540
cactggtaac tataagacaa acattgcaga caggatagag cagatttttg agacagcccc 600
ttttgttaaa atcgtggaac accatactct aatgacaact cacaaaatgt gtgctaattg 660
gagtactata ccaaacttca gatttttggc cggaacctat gacatgtttt tctcccggat 720
tgagcatcta tattcagcaa tcagagtggg cacagttgtc actgcttatg aagactgttc 780
aggactggta tcatttactg ggttcataaa acaaatcaat ctcaccgcta gagaggcaat 840
actatatttc ttccacaaga actttgagga agagataaga agaatgtttg agccagggca 900
ggagacagct gttcctcact cttatttcat ccacttccgt tcactaggct tgagtgggaa 960
atctccttat tcatcaaatg ctgttggtca cgtgttcaat ctcattcact ttgtaggatg 1020
ctatatgggt caagtcagat ccctaaatgc aacggttatt gctgcatgtg ctcctcatga 1080
aatgtctgtt ctagggggct atctgggaga ggaattcttc gggaaaggga catttgaaag 1140
aagattcttc agagatgaga aagaacttca agaatacgag gcggctgaac tgacaaagac 1200
tgacgtagca ctggcagatg atggaactgt caactctgac gacgaggact acttctcagg 1260
tgaaaccaga agtccggagg ctgtttatac tcgaatcatg atgaatggag gtcgactaaa 1320
gagatctcac atacggagat atgtctcagt cagttccaat catcaagccc gtccaaactc 1380
attcgccgag tttctaaaca agacatattc gagtgactca taagaagttg aataacaaaa 1440
tgccggaaat ctacggattg tgtatatcca tcatgaaaaa aactaacacc cctcctttcg 1500
aaccatccca aacatgagca agatctttgt caatcctagt gctattagag ccggtctggc 1560
cgatcttgag atggctgaag aaactgttga tctgatcaat agaaatatcg aagacaatca 1620
ggctcatctc caaggggaac ccatagaagt ggacaatctc cctgaggata tggggcgact 1680
tcacctggat gatggaaaat cgcccaaccc tggtgagatg gccaaggtgg gagaaggcaa 1740
gtatcgagag gactttcaga tggatgaagg agaggatcct agcttcctgt tccagtcata 1800

```
cctggaaaat gttggagtcc aaatagtcag acaaatgagg tcaggagaga gatttctcaa    1860
gatatggtca cagaccgtag aagagattat atcctatgtc gcggtcaact ttcccaaccc    1920
tccaggaaag tcttcagagg ataaatcaac ccagactact ggccgagagc tcaagaagga    1980
gacaacaccc actccttctc agagagaaag ccaatcatcg aaagccagga tggcggctca    2040
aattgcttct ggccctccag cccttgaatg gtcggccacc aatgaagagg atgatctatc    2100
agtggaggct gagatcgctc accagattgc agaaagtttc tccaaaaaat ataagtttcc    2160
ctctcgatcc tcagggatac tcttgtataa ttttgagcaa ttgaaaatga accttgatga    2220
tatagttaaa gaggcaaaaa atgtaccagg tgtgacccgt ttagcccatg acgggtccaa    2280 actccccta agatgtgtac tgggatgggt cgctttggcc aactctaaga aattccagtt    2340
gttagtcgaa tccgacaagc tgagtaaaat catgcaagat gacttgaatc gctatacatc    2400
ttgctaaccg aacctctcca ctcagtccct ctagacaata aagtccgaga tgtcctaaag    2460
tcaacatgaa aaaactaac accctcctt tcgctgcagc caccatggtt cctcaggctc     2520
tcctgtttgt acccttctg gttttccat tgtgtttgg gaaattccct atttacacga       2580
taccagacaa gcttggtccc tggagtccga ttgacataca tcacctcagc tgcccaaaca    2640
atttggtagt ggaggacgaa ggatgcacca acctgtcagg gttctcctac atggaactta    2700
aagttggata catcttagcc ataaaagtga acgggttcac ttgcacaggc gttgtgacgg    2760
aggctgaaac ctacactaac ttcgttggtt atgtcacaac cacgttcaaa agaaagcatt    2820
tccgcccaac accagatgca tgtagagccg cgtacaactg gaagatggcc ggtgacccca    2880
gatatgaaga gtctctacac aatccgtacc ctgactaccg ctggcttcga actgtaaaaa    2940
ccaccaagga gtctctcgtt atcatatctc caagtgtggc agatttggac ccatatgaca    3000
gatcccttca ctcgagggtc ttccctagcg ggaagtgctc aggagtagcg gtgtcttcta    3060
cctactgctc cactaaccac gattacacca tttggatgcc cgagaatccg agactaggga    3120
tgtcttgtga cattttacc aatagtagag ggaagagagc atccaaaggg agtgagactt     3180
gcggctttgt agatgaaaga ggcctatata agtctttaaa aggagcatgc aaactcaagt    3240
tatgtggagt tctaggactt agacttatgg atggaacatg ggtctcgatg caaacatcaa    3300
atgaaaccaa atggtgccct cccgataagt tggtgaacct gcacgacttt cgctcagacg    3360
aaattgagca ccttgttgta gaggagttgg tcaggaagag agaggagtgt ctggatgcac    3420
tagagtccat catgacaacc aagtcagtga gtttcagacg tctcagtcat ttaagaaaac    3480
ttgtccctgg gtttggaaaa gcatatacca tattcaacaa gaccttgatg gaagccgatg    3540
ctcactacaa gtcagtcgag acttggaatg agatcctccc ttcaaaaggg tgtttaagag    3600 ttgggggag gtgtcatcct catgtgaacg gggtgttttt caatggtata atattaggac    3660
ctgacggcaa tgtcttaatc ccagagatgc aatcatccct cctccagcaa catatggagt    3720
tgttggaatc ctcggttatc cccttgtgc acccctggc agaccgtct accgttttca       3780 aggacggtga cgaggctgag gattttgttg aagttcacct tcccgatgtg cacaatcagg    3840
tctcaggagt tgacttgggt ctcccgaact gggggaagta tgtattactg agtgcagggg    3900
ccctgactgc cttgatgttg ataatttcc tgatgacatg ttgtagaaga gtcaatcgat     3960
cagaacctac gcaacacaat ctcagaggga cagggaggga ggtgtcagtc actccccaaa    4020
gcgggaagat catatcttca tgggaatcac acaagagtgg gggtgagacc agactgtaat    4080
ttggtaccgt cgagaaaaaa acaggcaaca ccactgataa aatgaacttt ctacgtaaga    4140
```

```
tagtgaaaaa ttgcagggac gaggacactc aaaaaccctc tcccgtgtca gcccctctgg    4200
atgacgatga cttgtggctt ccaccccctg aatacgtccc gctgaaagaa cttacaagca    4260
agaagaacat gaggaacttt tgtatcaacg gaggggttaa agtgtgtagc ccgaatggtt    4320
actcgttcag gatcctgcgg cacattctga aatcattcga cgagatatat tctgggaatc    4380
ataggatgat cgggttagtc aaagtagtta ttggactggc tttgtcagga tctccagtcc    4440
ctgagggcat gaactgggta tacaaattga ggagaacctt tatcttccag tgggctgatt    4500 ccagggccc tcttgaaggg gaggagttgg aatactctca ggagatcact tgggatgatg    4560
atactgagtt cgtcggattg caaataagag tgattgcaaa acagtgtcat atccagggca    4620
gaatctggtg tatcaacatg aacccgagag catgtcaact atggtctgac atgtctcttc    4680
agacacaaag gtccgaagag gacaaagatt cctctctgct tctagaataa tcagattata    4740
tcccgcaaat ttatcacttg tttacctctg gaggagagaa catatgggct caactccaac    4800
ccttgggagc aatataacaa aaacatgtt atggtgccat taaaccgctg catttcatca    4860
aagtcaagtt gattaccttt acattttgat cctcttggat gtgaaaaaaa ctaacacccc    4920
tctgcagttt ggtaccttga aaaaaacctg ggttcaatag tcctccttga actccatgca    4980
actgggtaga ttcaagagtc atgagatttt cattaatcct ctcagttgat caagcaagat    5040
catgtagatt ctcataatag gggagatctt ctagcagttt cagtgactaa cggtactttc    5100
attctccagg aactgacacc aacagttgta gacaaaccac ggggtgtctc gggtgactct    5160
gtgcttgggc acagacaaag gtcatggtgt gttccatgat agcggactca ggatgagtta    5220
attgagagag gcagtcttcc tcccgtgaag gacataagca gtagctcaca atcatctcgc    5280
gtctcagcaa agtgtgcata attataaagt gctgggtcat ctaagctttt cagtcgagaa    5340
aaaaacatta gatcagaaga acaactggca acacttctca acctgagacc tacttcaaga    5400
tgctcgatcc tggagaggtc tatgatgacc ctattgaccc aatcgagtta gaggatgaac    5460
ccagaggaac ccccactgtc cccaacatct tgaggaactc tgactacaat ctcaactctc    5520
ctttgataga agatcctgct agactaatgt tagaatggtt aaaaacaggg aatagacctt    5580
atcggatgac tctaacagac aattgctcca ggtctttcag agttttgaaa gattatttca    5640
agaaggtaga tttgggttct ctcaaggtgg gcggaatggc tgcacagtca atgatttctc    5700
tctggttata tggtgcccac tctgaatcca acaggagccg gagatgtata acagacttgg    5760
cccatttcta ttccaagtcg tcccccatag agaagctgtt gaatctcacg ctaggaaata    5820
gagggctgag aatcccccca gagggagtgt taagttgcct tgagagggtt gattatgata    5880
atgcatttgg aagtatcttg ccaacacgt attcctctta cttgttcttc catgtaatca    5940
ccttatacat gaacgcccta gactgggatg aagaaaagac catcctagca ttatggaaag    6000
atttaacctc agtggacatc gggaaggact tggtaaagtt caaagaccaa atatggggac    6060
tgctgatcgt gacaaaggac tttgtttact cccaaagttc caattgtctt tttgacagaa    6120
actacacact tatgctaaaa gatcttttct tgtctcgctt caactcctta atggtcttgc    6180
tctctccccc agagccccga tactcagatg acttgatatc tcaactatgc cagctgtaca    6240
ttgctgggga tcaagtcttg tctatgtgtg gaaactccgg ctatgaagtc atcaaaatat    6300
tggagccata tgtcgtgaat agtttagtcc agagagcaga aaagtttagg cctctcattc    6360
attccttggg agactttcct gtatttataa aagacaaggt aagtcaactt gaagagacgt    6420
tcggtccctg tgcaagaagg ttcttttaggg ctctggatca attcgacaac atacatgact    6480 tggttttttgt gtatggctgt tacaggcatt gggggcaccc atatatagat tatcgaaagg    6540
```

```
gtctgtcaaa actatatgat caggttcaca ttaaaaaagt gatagataag tcctaccagg    6600
agtgcttagc aagcgaccta gccaggagga tccttagatg gggttttgat aagtactcca    6660
agtggtatct ggattcaaga ttcctagccc gagaccaccc cttgactcct tatatcaaaa    6720
cccaaacatg gccacccaaa catattgtag acttggtggg ggatacatgg cacaagctcc    6780
cgatcacgca gatctttgag attcctgaat caatggatcc gtcagaaata ttggatgaca    6840
aatcacattc tttcaccaga acgagactag cttcttggct gtcagaaaac cgagggggac    6900
ctgttcctag cgaaaaagtt attatcacgg ccctgtctaa gccgcctgtc aatccccgag    6960
agtttctgag gtctatagac ctcggaggat tgccagatga agacttgata attggcctca    7020
agccaaagga acgggaattg aagattgaag gtcgattctt tgctctaatg tcatggaatc    7080
taagattgta ttttgtcatc actgaaaaac tcttggccaa ctacatcttg ccacttttttg   7140 acgcgctgac tatgacagac aacctgaaca aggtgtttaa aaagctgatc gacagggtca    7200
ccgggcaagg gcttttggac tattcaaggg tcacatatgc atttcacctg gactatgaaa    7260
agtggaacaa ccatcaaaga ttagagtcaa cagaggatgt attttctgtc ctagatcaag    7320
tgtttggatt gaagagagtg ttttctagaa cacacgagtt ttttcaaaag gcctggatct    7380
attattcaga cagatcagac ctcatcgggt tacgggagga tcaaatatac tgcttagatg    7440
cgtccaacgg cccaacctgt tggaatggcc aggatggcgg gctagaaggc ttacggcaga    7500
agggctggag tctagtcagc ttattgatga tagatagaga atctcaaatc aggaacacaa    7560
gaaccaaaat actagctcaa ggagacaacc aggttttatg tccgacatat atgttgtcgc    7620
cagggctatc tcaagagggg ctcctctatg aattggagag aatatcaagg aatgcacttt    7680
cgatatacag agccgtcgag gaaggggcat ctaagctagg gctgatcatc aagaaagaag    7740
agaccatgtg tagttatgac ttcctcatct atggaaaaac ccctttgttt agaggtaaca    7800
tattggtgcc tgagtccaaa agatgggcca gagtctcttg cgtctctaat gaccaaaatag   7860 tcaacctcgc caatataatg tcgacagtgt ccaccaatgc gctaacagtg gcacaacact    7920
ctcaatcttt gatcaaaccg atgagggatt ttctgctcat gtcagtacag gcagtctttc    7980
actacctgct atttagccca atcttaaagg gaagagttta caagattctg agcgctgaag    8040
gggatagctt tctcctagcc atgtcaagga taatctatct agatccttct ttgggagggg    8100
tatctggaat gtccctcgga agattccata tacgacagtt ctcagaccct gtctctgaag    8160
ggttatcctt ctggagagag atctggttaa gctcccacga gtcctggatt cacgcgttgt    8220
gtcaagaggc tggaaaccca gatcttggag agagaacact cgagagcttc actcgccttc    8280
tagaagatcc taccaccttaa aatatacgag gaggggccag tcctaccatt ctactcaagg    8340
atgcaatcag aaaggcttta tatgacgagg tggacaaggt ggagaattca gagtttcgag    8400
aggcaatcct gttgtccaag acccatagag ataattttat actcttctta acatctgttg    8460
agcctctgtt tcctcgattt ctcagtgagc tattcagttc gtctttttg ggaatccccg     8520 agtcaatcat tggattgata caaaactccc gaacgataag aaggcagttt agaaagagtc    8580
tctcaaaaac tttagaagaa tccttctaca actcagagat ccacgggatt agtcggatga    8640
cccagacacc tcagagggtt gggggggtgt ggccttgctc ttcagagagg gcagatctac    8700
ttagggagat ctcttgggga agaaaagtgg taggcacgac agttcctcac ccttctgaga    8760
tgttggggtt acttcccaag tcctctattt cttgcacttg tggagcaaca ggaggaggca    8820
atcctagagt ttctgtatca gtactcccgt cctttgatca gtcatttttt tcacgaggcc    8880
```

```
ccctaaaggg gtacttgggc tcgtccacct ctatgtcgac ccagctattc catgcatggg    8940
aaaaagtcac taatgttcat gtggtgaaga gagctctatc gttaaaagaa tctataaact    9000
ggttcattac tagagattcc aacttggctc aagctctaat taggaacatt atgtctctga    9060
caggccctga tttccctcta gaggaggccc ctgtcttcaa aaggacgggg tcagccttgc    9120
ataggttcaa gtctgccaga tacagcgaag gagggtattc ttctgtctgc ccgaacctcc    9180
tctctcatat ttctgttagt acagacacca tgtctgattt gacccaagac gggaagaact    9240
acgatttcat gttccagcca ttgatgcttt atgcacagac atggacatca gagctggtac    9300
agagagacac aaggctaaga gactctacgt ttcattggca cctccgatgc aacaggtgtg    9360
tgagacccat tgacgacgtg accctggaga cctctcagat cttcgagttt ccggatgtgt    9420 cgaaagaat atccagaatg gtttctgggg ctgtgcctca cttccagagg cttcccgata    9480
tccgtctgag accaggagat tttgaatctc taagcggtag agaaaagtct caccatatcg    9540
gatcagctca ggggctctta tactcaatct tagtggcaat tcacgactca ggatacaatg    9600
atggaaccat cttccctgtc aacatatacg acaaggtttc ccctagagac tatttgagag    9660
ggctcgcaag gggagtattg ataggatcct cgatttgctt cttgacaaga atgacaaata    9720
tcaatattaa tagacctctt gaattgatct cagggtaat ctcatatatt ctcctgaggc    9780
tagataacca tccctccttg tacataatgc tcagagaacc gtctcttaga ggagagatat    9840
tttctatccc tcagaaaatc cccgccgctt atccaaccac tatgaaagaa ggcaacagat    9900
caatcttgtg ttatctccaa catgtgctac gctatgagcg agataatc acggcgtctc      9960 cagagaatga ctggctatgg atcttttcag actttagaag tgccaaaatg acgtacctaa   10020
ccctcattac ttaccagtct catcttctac tccagagggt tgagagaaac ctatctaaga   10080
gtatgagaga taacctgcga caattgagtt ccttgatgag gcaggtgctg ggcgggcacg   10140
gagaagatac cttagagtca gacgacaaca ttcaacgact gctaaaagac tctttacgaa   10200
ggacaagatg ggtggatcaa gaggtgcgcc atgcagctag aaccatgact ggagattaca   10260
gccccaacaa gaaggtgtcc cgtaaggtag gatgttcaga atgggtctgc tctgctcaac   10320
aggttgcagt ctctacctca gcaaacccgg cccctgtctc ggagcttgac ataagggccc   10380
tctctaagag gttccagaac cctttgatct cgggcttgag agtggttcag tgggcaaccg   10440
gtgctcatta taagcttaag cctattctag atgatctcaa tgttttccca tctctctgcc   10500
ttgtagttgg ggacgggtca ggggggatat caagggcagt cctcaacatg tttccagatg   10560
ccaagcttgt gttcaacagt ctcttagagg tgaatgacct gatggcttcc ggaacacatc   10620
cactgcctcc ttcagcaatc atgagggag gaaatgatat cgtctccaga gtgatagatt   10680
ttgactcaat ctgggaaaaa ccgtccgact tgagaaactt ggcaacctgg aaatacttcc   10740
agtcagtcca aaagcaggtc aacatgtcct atgacctcat tatttgcgat gcagaagtta   10800
ctgacattgc atctatcaac cggataaccc tgttaatgtc cgattttgca ttgtctatag   10860 atgaccact ctatttggtc ttcaaaactt atgggactat gctagtaaat ccaaactaca   10920
aggctattca acacctgtca agagcgttcc cctcggtcac agggtttatc acccaagtaa   10980
cttcgtcttt ttcatctgag ctctacctcc gattctccaa acgagggaag ttttcagag    11040 atgctgagta cttgacctct tccacccttg gagaaatgag ccttgtgtta ttcaattgta   11100
gcagccccaa gagtgagatg cagagagctc gttccttgaa ctatcaggat cttgtgagag   11160
gatttcctga gaaaatcata tcaaatcctt acaatgagat gatcataact ctgattgaca   11220
gtgatgtaga atcttttcta gtccacaaga tggttgatga tcttgagtta cagaggggaa   11280
```

```
ctctgtctaa agtggctatc attatagcca tcatgatagt tttctccaac agagtcttca    11340
acgtttccaa accccctaact gaccccttgt tctatccacc gtctgatccc aaaatcctga   11400
ggcacttcaa catatgttgc agtactatga tgtatctatc tactgcttta ggtgacgtcc    11460
ctagcttcgc aagacttcac gacctgtata acagacctat aacttattac ttcagaaagc   11520
aattcattcg agggaacgtt tatctatctt ggagttggtc caacgacacc tcagtgttca    11580
aaagggtagc ctgtaattct agcctgagtc tgtcatctca ctggatcagg ttgatttaca   11640
agatagtgaa gactaccaga ctcgttggca gcatcaagga tctatccaga gaagtggaaa   11700
gacaccttca taggtacaac aggtggatca ccctagagga tatcagatct agatcatccc   11760
tactagacta cagttgcctg tgatccggat actcctggaa gcctgcccat gctaagactc    11820
ttgtgtgatg tatcttgaaa aaacaagat cctaaatctg aacctttggt tgtttgattg     11880 ttttctcat ttttgttgtt tatttgttaa gcgt                                 11914
```

<210> SEQ ID NO 18
<211> LENGTH: 13556
<212> TYPE: DNA
<213> ORGANISM: artificial sequence
<220> FEATURE:
<223> OTHER INFORMATION: Recombinant ERAgmg rabies virus genome
<220> FEATURE:
<221> NAME/KEY: misc_feature
<222> LOCATION: (71)..(1420)
<220> FEATURE:
<221> NAME/KEY: misc_feature
<222> LOCATION: (1514)..(2404)
<220> FEATURE:
<221> NAME/KEY: misc_feature
<222> LOCATION: (2505)..(4076)
<220> FEATURE:
<221> NAME/KEY: misc_feature
<222> LOCATION: (4122)..(4727)
<220> FEATURE:
<221> NAME/KEY: misc_feature
<222> LOCATION: (4943)..(6514)
<220> FEATURE:
<221> NAME/KEY: misc_feature
<222> LOCATION: (7042)..(13422)

<400> SEQUENCE: 18
acgcttaaca accagatcaa agaaaaaaca gacattgtca attgcaaagc aaaaatgtaa 60
cacccctaca atggatgccg acaagattgt attcaaagtc aataatcagg tggtctcttt 120
gaagcctgag attatcgtgg atcaacatga gtacaagtac cctgccatca aagatttgaa 180
aaagccctgt ataaccctag gaaaggctcc cgatttaaat aaagcataca agtcagtttt 240
gtcaggcatg agcgccgcca aacttgatcc tgacgatgta tgttcctatt tggcagcggc 300
aatgcagttt tttgagggga catgtccgga agactggacc agctatggaa tcgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540
cactggtaac tataagacaa acattgcaga caggatagag cagatttttg agacagcccc 600
ttttgttaaa atcgtggaac accatactct aatgacaact cacaaaatgt gtgctaattg 660
gagtactata ccaaacttca gatttttggc cggaacctat gacatgtttt tctcccggat 720
tgagcatcta tattcagcaa tcagagtggg cacagttgtc actgcttatg aagactgttc 780
aggactggta tcatttactg ggttcataaa acaaatcaat ctcaccgcta gagaggcaat 840

```
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctaggggct atctgggaga ggaattcttc gggaaaggga catttgaaag    1140
aagattcttc agagatgaga aagaacttca agaatacgag gcggctgaac tgacaaagac   1200
tgacgtagca ctggcagatg atggaactgt caactctgac gacgaggact acttctcagg   1260
tgaaaccaga agtccggagg ctgttttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca acatgagca agatctttgt caatcctagt gctattagag ccggtctggc    1560
cgatcttgag atggctgaag aaactgttga tctgatcaat agaaatatcg aagacaatca   1620
ggctcatctc caaggggaac ccatagaagt ggacaatctc cctgaggata tggggcgact   1680
tcacctggat gatggaaaat cgcccaaccc tggtgagatg gccaaggtgg agaaggcaa    1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggccacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctcca ctcagtccct ctagacaata agtccgaga tgtcctaaag    2460
tcaacatgaa aaaactaac accctcctt tcgctgcagc caccatggtt cctcaggctc    2520
tcctgtttgt accccttctg gttttttcat tgtgttttgg gaaattccct atttacacga   2580
taccagacaa gcttggtccc tggagcccga ttgacataca tcacctcagc tgcccaaaca   2640
atttggtagt ggaggacgaa ggatgcacca acctgtcagg gttctcctac atggaactta   2700
aagttggata catcttagcc ataaaaatga cgggttcac ttgcacaggc gttgtgacgg    2760
aggctgaaac ctacactaac ttcgttggtt atgtcacaac cacgttcaaa agaaagcatt   2820
tccgcccaac accagatgca tgtagagccg cgtacaactg aagatggcc ggtgaccca     2880
gatatgaaga gtctctacac aatccgtacc ctgactacca ctggcttcga actgtaaaaa   2940
ccaccaagga gtctctcgtt atcatatctc caagtgtggc agatttggac ccatatgaca   3000
gatcccttca ctcgagggtc ttccctagcg ggaagtgctc aggagtagcg gtgtcttcta   3060
cctactgctc cactaaccac gattacacca tttggatgcc cgagaatccg agactaggga   3120
tgtcttgtga catttttacc aatagtagag ggaagagagc atccaaaggg agtgagactt   3180
gcggctttgt agatgaaaga ggcctatata agtctttaaa aggagcatgc aaactcaagt   3240
```

```
tatgtggagt tctaggactt agacttatgg atggaacatg ggtcgcgatg caaacatcaa    3300
atgaaaccaa atggtgccct cccgatcagt tggtgaacct gcacgacttt cgctcagacg    3360
aaattgagca ccttgttgta gaggagttgg tcaggaagag agaggagtgt ctggatgcac    3420
tagagtccat catgacaacc aagtcagtga gtttcagacg tctcagtcat ttaagaaaac    3480
ttgtccctgg gtttggaaaa gcatataccatattcaacaa gaccttgatg gaagccgatg    3540
ctcactacaa gtcagtcaga acttggaatg agatcctccc ttcaaaaggg tgtttaagag    3600 ttgggggggag tgtcatcct catgtgaacg gggtgttttt caatggtata atattaggac    3660
ctgacggcaa tgtcttaatc ccagagatgc aatcatccct cctccagcaa catatggagt    3720
tgttggaatc ctcggttatc ccccttgtgc accccctggc agacccgtct accgttttca    3780
aggacggtga cgaggctgag gattttgttg aagttcacct tcccgatgtg cacaatcagg    3840
tctcaggagt tgacttgggt ctcccgaact gggggaagta tgtattactg agtgcagggg    3900
ccctgactgc cttgatgttg ataattttcc tgatgacatg ttgtagaaga gtcaatcgat    3960
cagaacctac gcaacacaat ctcagaggga caggagggga ggtgtcagtc actccccaaa    4020
gcgggaagat catatcttca tgggaatcac acaagagtgg gggtgagacc agactgtgat    4080
ttggtaccgt cgagaaaaaa acaggcaaca ccactgataa aatgaacttt ctacgtaaga    4140
tagtgaaaaa ttgcagggac gaggacactc aaaaaccctc tcccgtgtca gcccctctgg    4200
atgacgatga cttgtggctt ccacccccctg aatacgtccc gctgaaagaa cttacaagca    4260
agaagaacat gaggaacttt tgtatcaacg gaggggttaa agtgtgtagc ccgaatggtt    4320
actcgttcag gatcctgcgg cacattctga aatcattcga cgagatatat tctgggaatc    4380
ataggatgat cgggttagtc aaagtagtta ttggactggc tttgtcagga tctccagtcc    4440
ctgagggcat gaactgggta tacaaattga ggagaacctt tatcttccag tgggctgatt    4500
ccaggggccc tcttgaaggg gaggagttgg aatactctca ggagatcact tgggatgatg    4560
atactgagtt cgtcggattg caaataagag tgattgcaaa acagtgtcat atccagggca    4620
gaatctggtg tatcaacatg aacccgagag catgtcaact atggtctgac atgtctcttc    4680
agacacaaag gtccgaagag gacaaagatt cctctctgct tctagaataa tcagattata    4740
tcccgcaaat ttatcacttg tttacctctg gaggagagaa catatgggct caactccaac    4800
ccttgggagc aatataacaa aaaacatgtt atggtgccat taaaccgctg catttcatca    4860
aagtcaagtt gattacctttacattttgat cctcttggat gtgaaaaaaa ctattaacat    4920
ccctcaaaag actcaaggaa agatggttcc tcaggctctc ctgtttgtac cccttctggt    4980
ttttccattg tgttttggga aattcccctat ttacacgata ccagacaagc ttggtccctg    5040
gagcccgatt gacatacatc acctcagctg cccaaacaat ttggtagtgg aggacgaagg    5100
atgcaccaac ctgtcagggt tctcctacat ggaacttaaa gttggataca tcttagccat    5160
aaaaatgaac gggttcactt gcacaggcgt tgtgacggag gctgaaacct acactaactt    5220
cgttggttat gtcacaacca cgttcaaaag aaagcatttc cgcccaacac cagatgcatg    5280
tagagccgcg tacaactgga agatggccgg tgaccccaga tatgaagagt ctctacacaa    5340
tccgtaccct gactaccact ggcttcgaac tgtaaaaacc accaaggagt ctctcgttat    5400
catatctcca agtgtggcag atttggaccc atatgacaga tcccttcact cgagggtctt    5460
ccctagcggg aagtgctcag gagtagcggt gtcttctacc tactgctcca ctaaccacga    5520
ttacaccatt tggatgcccg agaatccgag actagggatg tcttgtgaca tttttaccaa    5580
```

```
tagtagaggg aagagagcat ccaaagggag tgagacttgc ggctttgtag atgaaagagg   5640
cctatataag tctttaaaag gagcatgcaa actcaagtta tgtggagttc taggacttag   5700
acttatggat ggaacatggg tcgcgatgca aacatcaaat gaaaccaaat ggtgccctcc   5760
cgatcagttg gtgaacctgc acgactttcg ctcagacgaa attgagcacc ttgttgtaga   5820
ggagttggtc aggaagagag aggagtgtct ggatgcacta gagtccatca tgacaaccaa   5880
gtcagtgagt ttcagacgtc tcagtcattt aagaaaactt gtccctgggt ttggaaaagc   5940
atataccata ttcaacaaga ccttgatgga agccgatgct cactacaagt cagtcagaac   6000
ttggaatgag atcctcccct tcaaaagggtg tttaagagtt ggggggaggt gtcatcctca   6060
tgtgaacggg gtgttttca atggtataat attaggacct gacggcaatg tcttaatccc   6120
agagatgcaa tcatccctcc tccagcaaca tatgagttg ttggaatcct cggttatccc   6180
ccttgtgcac cccctggcag acccgtctac cgttttcaag gacggtgacg aggctgagga   6240
ttttgttgaa gttcaccttc ccgatgtgca caatcaggtc tcaggagttg acttgggtct   6300
cccgaactgg gggaagtatg tattactgag tgcaggggcc ctgactgcct tgatgttgat   6360 aatttttcctg atgacatgtt gtagaagagt caatcgatca gaacctacgc aacacaatct   6420
cagagggaca gggagggagg tgtcagtcac tccccaaagc gggaagatca tatcttcatg   6480
ggaatcacac aagagtgggg gtgagaccag actgtgagga ctggccgtcc tttcaactat   6540
ccaagtcctg aagatcacct cccccttgggg ggttcttttt gaaaaaaacc tgggttcaat   6600
agtcctcctt gaactccatg caactgggta gattcaagag tcatgagatt ttcattaatc   6660
ctctcagttg atcaagcaag atcatgtaga ttctcataat aggggagatc ttctagcagt   6720
ttcagtgact aacggtactt tcattctcca ggaactgaca ccaacagttg tagacaaacc   6780
acggggtgtc tcgggtgact ctgtgcttgg gcacagacaa aggtcatggt gtgttccatg   6840
atagcggact caggatgagt taattgagag aggcagtctt cctcccgtga aggacataag   6900
cagtagctca caatcatctc gcgtctcagc aaagtgtgca taattataaa gtgctgggtc   6960
atctaagctt ttcagtcgag aaaaaaacat tagatcagaa gaacaactgg caacacttct   7020
caacctgaga cctacttcaa gatgctcgat cctggagagg tctatgatga ccctattgac   7080
ccaatcgagt tagaggatga acccagagga acccccactg tccccaacat cttgaggaac   7140
tctgactaca atctcaactc tcctttgata gaagatcctg ctagactaat gttagaatgg   7200
ttaaaaacag ggaatagacc ttatcggatg actctaacag acaattgctc caggtctttc   7260
agagttttga aagattattt caagaaggta gatttgggtt ctctcaaggt gggcggaatg   7320
gctgcacagt caatgatttc tctctggtta tatggtgccc actctgaatc caacaggagc   7380
cggagatgta taacagactt ggcccatttc tattccaagt cgtcccccat agagaagctg   7440
ttgaatctca cgctaggaaa tagagggctg agaatccccc cagagggagt gttaagttgc   7500
cttgagaggg ttgattatga taatgcattt ggaaggtatc ttgccaacac gtattcctct   7560
tacttgttct tccatgtaat caccttatac atgaacgccc tagactggga tgaagaaaag   7620
accatcctag cattatggaa agatttaacc tcagtggaca tcgggaagga cttggtaaag   7680
ttcaaagacc aaatatgggg actgctgatc gtgacaaagg actttgttta ctcccaaagt   7740
tccaattgtc tttttgacag aaactacaca cttatgctaa aagatctttt cttgtctcgc   7800
ttcaactcct taatggtctt gctctctccc ccagagcccc gatactcaga tgacttgata   7860
tctcaactat gccagctgta cattgctggg gatcaagtct tgtctatgtg tggaaactcc   7920
ggctatgaag tcatcaaaat attggagcca tatgtcgtga atagtttagt ccagagagca   7980
```

```
gaaaagttta ggcctctcat tcattccttg ggagactttc ctgtatttat aaaagacaag    8040
gtaagtcaac ttgaagagac gttcggtccc tgtgcaagaa ggttctttag ggctctggat    8100
caattcgaca acatacatga cttggttttt gtgtatggct gttacaggca ttggggcac    8160 ccatatatag attatcgaaa gggtctgtca aaactatatg atcaggttca cattaaaaaa    8220
gtgatagata agtcctacca ggagtgctta gcaagcgacc tagccaggag gatccttaga    8280
tggggttttg ataagtactc caagtggtat ctggattcaa gattcctagc ccgagaccac    8340
cccttgactc cttatatcaa aacccaaaca tggccaccca acatattgt agacttggtg     8400 ggggatacat ggcacaagct cccgatcacg cagatctttg agattcctga atcaatggat    8460
ccgtcagaaa tattggatga caaatcacat tctttcacca gaacgagact agcttcttgg    8520
ctgtcagaaa accgagggg acctgttcct agcgaaaaag ttattatcac ggccctgtct     8580
aagccgcctg tcaatcccg agagtttctg aggtctatag acctcggagg attgccagat    8640
gaagacttga taattggcct caagccaaag gaacgggaat tgaagattga aggtcgattc    8700
tttgctctaa tgtcatggaa tctaagattg tatttttgtca tcactgaaaa actcttggcc   8760
aactacatct tgccactttt tgacgcgctg actatgacag acaacctgaa caaggtgttt    8820
aaaaagctga tcgacagggt caccgggcaa gggcttttgg actattcaag ggtcacatat    8880
gcatttcacc tggactatga aaagtggaac aaccatcaaa gattagagtc aacagaggat    8940
gtattttctg tcctagatca agtgtttgga ttgaagagag tgttttctag aacacacgag    9000 tttttttcaaa aggcctggat ctattattca gacagatcag acctcatcgg gttacgggag    9060
gatcaaatat actgcttaga tgcgtccaac ggcccaacct gttggaatgg ccaggatggc    9120
gggctagaag gcttacggca aagggctgg agtctagtca gcttattgat gatagataga    9180
gaatctcaaa tcaggaacac aagaaccaaa atactagctc aaggagacaa ccaggtttta    9240
tgtccgacat atatgttgtc gccagggcta tctcaagagg ggctcctcta tgaattggag    9300
agaatatcaa ggaatgcact ttcgatatac agagccgtcg aggaaggggc atctaagcta    9360
gggctgatca tcaagaaaga agagaccatg tgtagttatg acttcctcat ctatggaaaa    9420 accccttttgt ttagaggtaa catattggtg cctgagtcca aaagatgggc cagagtctct   9480
tgcgtctcta atgaccaaat agtcaacctc gccaatataa tgtcgacagt gtccaccaat    9540
gcgctaacag tggcacaaca ctctcaatct ttgatcaaac cgatgaggga ttttctgctc    9600
atgtcagtac aggcagtctt tcactacctg ctatttagcc caatcttaaa gggaagagtt    9660
tacaagattc tgagcgctga aggggatagc tttctcctag ccatgtcaag gataatctat    9720
ctagatcctt ctttgggagg ggtatctgga atgtccctcg gaagattcca tatacgacag    9780
ttctcagacc ctgtctctga agggttatcc ttctggagag atctggtt aagctcccac      9840 gagtcctgga ttcacgcgtt gtgtcaagag gctggaaacc cagatcttgg agagagaaca    9900
ctcgagagct tcactcgcct tctagaagat cctaccacct aaatatcag aggaggggcc     9960 agtcctacca ttctactcaa ggatgcaatc agaaaggctt tatatgacga ggtggacaag    10020
gtggagaatt cagagtttcg agaggcaatc ctgttgtcca agacccatag agataatttt    10080
atactcttct taacatctgt tgagcctctg tttcctcgat ttctcagtga gctattcagt    10140
tcgtcttttt tgggaatccc cgagtcaatc attggattga tacaaaactc ccgaacgata    10200
agaaggcagt ttagaaagag tctctcaaaa actttagaag aatccttcta caactcagag    10260
atccacggga ttagtcggat gacccagaca cctcagaggg ttgggggggt gtggcctttgc   10320
```

```
tcttcagaga gggcagatct acttagggag atctcttggg gaagaaaagt ggtaggcacg   10380
acagttcctc acccttctga gatgttgggg ttacttccca agtcctctat ttcttgcact   10440
tgtggagcaa caggaggagg caatcctaga gtttctgtat cagtactccc gtcctttgat   10500
cagtcatttt tttcacgagg cccctaaag gggtacttgg gctcgtccac ctctatgtcg   10560
acccagctat tccatgcatg ggaaaagtc actaatgttc atgtggtgaa gagagctcta   10620
tcgttaaaag aatctataaa ctggttcatt actagagatt ccaacttggc tcaagctcta   10680
attaggaaca ttatgtctct gacaggccct gatttccctc tagaggaggc ccctgtcttc   10740
aaaaggacgg ggtcagcctt gcataggttc aagtctgcca gatacagcga aggagggtat   10800
tcttctgtct gcccgaacct cctctctcat atttctgtta gtacagacac catgtctgat   10860
ttgacccaag acgggaagaa ctacgatttc atgttccagc cattgatgct ttatgcacag   10920
acatggacat cagagctggt acagagagac acaaggctaa gagactctac gtttcattgg   10980
cacctccgat gcaacaggtg tgtgagaccc attgacgacg tgaccctgga gacctctcag   11040
atcttcgagt ttccggatgt gtcgaaaaga atatccagaa tggtttctgg ggctgtgcct   11100
cacttccaga ggcttcccga tatccgtctg agaccaggag attttgaatc tctaagcggt   11160
agagaaaagt ctcaccatat cggatcagct caggggctct tatactcaat cttagtggca   11220
attcacgact caggatacaa tgatggaacc atcttccctg tcaacatata cgacaaggtt   11280
tcccctagag actatttgag agggctcgca aggggagtat tgataggatc ctcgatttgc   11340
ttcttgacaa gaatgacaaa tatcaatatt aatagacctc ttgaattgat ctcagggta   11400 atctcatata ttctcctgag gctagataac catccctcct tgtacataat gctcagagaa   11460
ccgtctctta gaggagagat attttctatc cctcagaaaa tccccgccgc ttatccaacc   11520
actatgaaag aaggcaacag atcaatcttg tgttatctcc aacatgtgct acgctatgag   11580
cgagagataa tcacggcgtc tccagagaat gactggctat ggatcttttc agactttaga   11640
agtgccaaaa tgacgtacct aaccctcatt acttaccagt ctcatcttct actccagagg   11700
gttgagagaa acctatctaa gagtatgaga gataacctgc gacaattgag ttccttgatg   11760
aggcaggtgc tgggcgggca cggagaagat acctagagt cagacgacaa cattcaacga   11820
ctgctaaaag actctttacg aaggacaaga tgggtggatc aagaggtgcg ccatgcagct   11880
agaaccatga ctggagatta cagccccaac aagaaggtgt cccgtaaggt aggatgttca   11940
gaatgggtct gctctgctca acaggttgca gtctctacct cagcaaaccc ggccctgtc   12000 tcggagcttg acataagggc cctctctaag aggttccaga acccctttgat ctcgggcttg   12060 agagtggttc agtgggcaac cggtgctcat tataagctta agcctattct agatgatctc   12120
aatgttttcc catctctctg ccttgtagtt ggggacgggt caggggggat atcaagggca   12180
gtcctcaaca tgtttccaga tgccaagctt gtgttcaaca gtctcttaga ggtgaatgac   12240
ctgatggctt ccggaacaca tccactgcct ccttcagcaa tcatgagggg aggaaatgat   12300
atcgtctcca gagtgataga ttttgactca atctgggaaa aaccgtccga cttgagaaac   12360
ttggcaacct ggaaatactt ccagtcagtc caaaagcagg tcaacatgtc ctatgacctc   12420
attatttgcg atgcagaagt tactgacatt gcatctatca accggataac cctgttaatg   12480
tccgattttg cattgtctat agatggacca ctctatttgg tcttcaaaac ttatgggact   12540
atgctagtaa atccaaacta caaggctatt caacacctgt caagagcgtt ccctcggtc   12600 acagggttta tcacccaagt aacttcgtct ttttcatctg agctctacct ccgattctcc   12660
aaacgaggga agttttttcag agatgctgag tacttgacct cttccaccct tcgagaaatg   12720
```

-continued

```
agccttgtgt tattcaattg tagcagcccc aagagtgaga tgcagagagc tcgttccttg    12780
aactatcagg atcttgtgag aggatttcct gaagaaatca tatcaaatcc ttacaatgag    12840
atgatcataa ctctgattga cagtgatgta gaatcttttc tagtccacaa gatggttgat    12900
gatcttgagt tacagagggg aactctgtct aaagtggcta tcattatagc catcatgata    12960
gttttctcca acagagtctt caacgtttcc aaaccoctaa ctgacccctt gttctatcca    13020
ccgtctgatc ccaaaatcct gaggcacttc aacatatgtt gcagtactat gatgtatcta    13080
tctactgctt taggtgacgt ccctagcttc gcaagacttc acgacctgta taacagacct    13140
ataacttatt acttcagaaa gcaattcatt cgagggaacg tttatctatc ttggagttgg    13200
tccaacgaca cctcagtgtt caaaagggta gcctgtaatt ctagcctgag tctgtcatct    13260
cactggatca ggttgattta caagatagtg aagactacca gactcgttgg cagcatcaag    13320
gatctatcca gagaagtgga aagacacctt cataggtaca acaggtggat caccctagag    13380
gatatcagat ctagatcatc cctactagac tacagttgcc tgtgatccgg atactcctgg    13440
aagcctgccc atgctaagac tcttgtgtga tgtatcttga aaaaaacaag atcctaaatc    13500
tgaacctttg gttgtttgat tgttttctc attttgttg tttatttgtt aagcgt          13556
```

```
<210> SEQ ID NO 19
<211> LENGTH: 10
<212> TYPE: DNA
<213> ORGANISM: artificial sequence
<220> FEATURE:
<223> OTHER INFORMATION: hammerhead terminus

<400> SEQUENCE: 19
tgttaagcgt                                                                10

<210> SEQ ID NO 20
<211> LENGTH: 27
<212> TYPE: DNA
<213> ORGANISM: artificial sequence
<220> FEATURE:
<223> OTHER INFORMATION: synthetic oligonucleotide encoding SV40 nuclear
      localization signal

<400> SEQUENCE: 20
atgccaaaaa agaagagaaa ggtagaa                                             27

<210> SEQ ID NO 21
<211> LENGTH: 10
<212> TYPE: DNA
<213> ORGANISM: artificial sequence
<220> FEATURE:
<223> OTHER INFORMATION: Artificial Kozak sequence

<400> SEQUENCE: 21
accaccatgg                                                                10

<210> SEQ ID NO 22
<211> LENGTH: 10
<212> TYPE: DNA
<213> ORGANISM: artificial sequence
<220> FEATURE:
<223> OTHER INFORMATION: Artificial Kozak sequence

<400> SEQUENCE: 22
accaccatga                                                                10
```

<210> SEQ ID NO 23
<211> LENGTH: 10
<212> TYPE: DNA
<213> ORGANISM: artificial sequence
<220> FEATURE:
<223> OTHER INFORMATION: Artificial Kozak sequence

<400> SEQUENCE: 23
accaccatgc                                                                10

<210> SEQ ID NO 24
<211> LENGTH: 11
<212> TYPE: DNA
<213> ORGANISM: artificial sequence
<220> FEATURE:
<223> OTHER INFORMATION: oligonucleotide primer Le5

<400> SEQUENCE: 24
acgcttaaca a                                                              11

<210> SEQ ID NO 25
<211> LENGTH: 24
<212> TYPE: DNA
<213> ORGANISM: artificial sequence
<220> FEATURE:
<223> OTHER INFORMATION: oligonucleotide primer Blp5

<400> SEQUENCE: 25
gtcgcttgct aagcactcct ggta                                                24

<210> SEQ ID NO 26
<211> LENGTH: 11
<212> TYPE: DNA
<213> ORGANISM: artificial sequence
<220> FEATURE:
<223> OTHER INFORMATION: oligonucleotide primer Le3

<400> SEQUENCE: 26
tgcgaattgt t                                                              11

<210> SEQ ID NO 27
<211> LENGTH: 24
<212> TYPE: DNA
<213> ORGANISM: artificial sequence
<220> FEATURE:
<223> OTHER INFORMATION: oligonucleotide primer Blp5

<400> SEQUENCE: 27
ccaggagtgc ttagcaagcg acct                                                24

<210> SEQ ID NO 28
<211> LENGTH: 32
<212> TYPE: DNA
<213> ORGANISM: artificial sequence
<220> FEATURE:
<223> OTHER INFORMATION: oligonucleotide primer Le5-Kpn

<400> SEQUENCE: 28
ccgggtacca cgcttaacaa ccagatcaaa ga                                       32

<210> SEQ ID NO 29
<211> LENGTH: 31
<212> TYPE: DNA
<213> ORGANISM: artificial sequence
<220> FEATURE:
<223> OTHER INFORMATION: oligonucleotide primer Le3-Blp -continued

```
<400> SEQUENCE: 29
taggtcgctt gctaagcact cctggtagga c                                    31

<210> SEQ ID NO 30
<211> LENGTH: 31
<212> TYPE: DNA
<213> ORGANISM: artificial sequence
<220> FEATURE:
<223> OTHER INFORMATION: oligonucleotide primer Tr5-Blp

<400> SEQUENCE: 30
gtcctaccag gagtgcttag caagcgacct a                                    31

<210> SEQ ID NO 31
<211> LENGTH: 34
<212> TYPE: DNA
<213> ORGANISM: artificial sequence
<220> FEATURE:
<223> OTHER INFORMATION: oligonucleotide primer Tr3-Pst

<400> SEQUENCE: 31
aaaactgcag acgcttaaca aataaacaac aaaa                                 34

<210> SEQ ID NO 32
<211> LENGTH: 79
<212> TYPE: DNA
<213> ORGANISM: artificial sequence
<220> FEATURE:
<223> OTHER INFORMATION: oligonucleotide primer HH1

<400> SEQUENCE: 32
caaggctagc tgttaagcgt ctgatgagtc cgtgaggacg aaactatagg aaaggaattc     60
ctatagtcgg taccacgct                                                  79

<210> SEQ ID NO 33
<211> LENGTH: 79
<212> TYPE: DNA
<213> ORGANISM: artificial sequence
<220> FEATURE:
<223> OTHER INFORMATION: oligonucleotide primer HH2

<400> SEQUENCE: 33
agcgtggtac cgactatagg aattcctttc ctatagtttc gtcctcacgg actcatcaga     60
cgcttaacag ctagccttg                                                  79

<210> SEQ ID NO 34
<211> LENGTH: 108
<212> TYPE: DNA
<213> ORGANISM: artificial sequence
<220> FEATURE:
<223> OTHER INFORMATION: oligonucleotide primer HDV3

<400> SEQUENCE: 34
gacctgcagg ggtcggcatg gcatctccac ctcctcgcgg tccgacctgg gcatccgaag     60
gaggacgcac gtccactcgg atggctaagg gagggcgcgg ccgcactc                 108

<210> SEQ ID NO 35
<211> LENGTH: 108
<212> TYPE: DNA
<213> ORGANISM: artificial sequence
<220> FEATURE:
<223> OTHER INFORMATION: oligonucleotide primer HDV 4

<400> SEQUENCE: 35
```

```
gagtgcggcc gcgccctccc ttagccatcc gagtggacgt gcgtcctcct tcggatgccc    60
aggtcggacc gcgaggaggt ggagatgcca tgccgacccc tgcaggtc                108
```

<210> SEQ ID NO 36
<211> LENGTH: 25
<212> TYPE: DNA
<213> ORGANISM: artificial sequence
<220> FEATURE:
<223> OTHER INFORMATION: oligonucleotide primer 5N

<400> SEQUENCE: 36

```
accaccatgg atgccgacaa gattg                                          25
```

<210> SEQ ID NO 37
<211> LENGTH: 33
<212> TYPE: DNA
<213> ORGANISM: artificial sequence
<220> FEATURE:
<223> OTHER INFORMATION: oligonucleotide primer 3N

<400> SEQUENCE: 37

```
ggcccatggt tatgagtcac tcgaatatgt ctt                                 33
```

<210> SEQ ID NO 38
<211> LENGTH: 33
<212> TYPE: DNA
<213> ORGANISM: artificial sequence
<220> FEATURE:
<223> OTHER INFORMATION: oligonucleotide primer 5P

<400> SEQUENCE: 38

```
ttggtaccac catgagcaag atctttgtca atc                                 33
```

<210> SEQ ID NO 39
<211> LENGTH: 34
<212> TYPE: DNA
<213> ORGANISM: artificial sequence
<220> FEATURE:
<223> OTHER INFORMATION: oligonucleotide primer 3P

<400> SEQUENCE: 39

```
ggagaggaat tcttagcaag atgtatagcg attc                                34
```

<210> SEQ ID NO 40
<211> LENGTH: 32
<212> TYPE: DNA
<213> ORGANISM: artificial sequence
<220> FEATURE:
<223> OTHER INFORMATION: oligonucleotide primer 5G

<400> SEQUENCE: 40

```
ttggtaccac catggttcct caggctctcc tg                                  32
```

<210> SEQ ID NO 41
<211> LENGTH: 33
<212> TYPE: DNA
<213> ORGANISM: artificial sequence
<220> FEATURE:
<223> OTHER INFORMATION: oligonucleotide primer 3G

<400> SEQUENCE: 41

```
aaaactgcag tcacagtctg gtctcacccc cac                                 33
```

<210> SEQ ID NO 42

```
<211> LENGTH: 36
<212> TYPE: DNA
<213> ORGANISM: artificial sequence
<220> FEATURE:
<223> OTHER INFORMATION: oligonucleotide primer 5L

<400> SEQUENCE: 42
accgctagca ccaccatgct cgatcctgga gaggtc                              36

<210> SEQ ID NO 43
<211> LENGTH: 34
<212> TYPE: DNA
<213> ORGANISM: artificial sequence
<220> FEATURE:
<223> OTHER INFORMATION: oligonucleotide primer 3L

<400> SEQUENCE: 43
aaaactgcag tcacaggcaa ctgtagtcta gtag                                34

<210> SEQ ID NO 44
<211> LENGTH: 38
<212> TYPE: DNA
<213> ORGANISM: artificial sequence
<220> FEATURE:
<223> OTHER INFORMATION: oligonucleotide primer 5T7

<400> SEQUENCE: 44
tcgctagcac caccatgaac acgattaaca tcgctaag                            38

<210> SEQ ID NO 45
<211> LENGTH: 33
<212> TYPE: DNA
<213> ORGANISM: artificial sequence
<220> FEATURE:
<223> OTHER INFORMATION: oligonucleotide primer 3T7

<400> SEQUENCE: 45
gatgaattct tacgcgaacg cgaagtccga ctc                                 33

<210> SEQ ID NO 46
<211> LENGTH: 63
<212> TYPE: DNA
<213> ORGANISM: artificial sequence
<220> FEATURE:
<223> OTHER INFORMATION: oligonucleotide primer 5T7NLS

<400> SEQUENCE: 46
tcgctagcca ccatgccaaa aagaagaga aggtagaaa acacgattaa catcgctaag      60
aac                                                                 63

<210> SEQ ID NO 47
<211> LENGTH: 31
<212> TYPE: DNA
<213> ORGANISM: artificial sequence
<220> FEATURE:
<223> OTHER INFORMATION: oligonucleotide primer GFP5

<400> SEQUENCE: 47
aaaactgcag gccaccatgg gcgtgatcaa g                                   31

<210> SEQ ID NO 48
<211> LENGTH: 31
<212> TYPE: DNA
<213> ORGANISM: artificial sequence
<220> FEATURE:
<223> OTHER INFORMATION: oligonucleotide primer GFP3
```

```
<400> SEQUENCE: 48
ccgctcggta cctattagcc ggcctggcgg g                              31

<210> SEQ ID NO 49
<211> LENGTH: 25
<212> TYPE: DNA
<213> ORGANISM: artificial sequence
<220> FEATURE:
<223> OTHER INFORMATION: oligonucleotide primer EF5G5

<400> SEQUENCE: 49
caccatggtt cctcaggctc tcctg                                     25

<210> SEQ ID NO 50
<211> LENGTH: 23
<212> TYPE: DNA
<213> ORGANISM: artificial sequence
<220> FEATURE:
<223> OTHER INFORMATION: oligonucleotide primer EF5G3

<400> SEQUENCE: 50
tcacagtctg gtctcacccc cac                                       23

<210> SEQ ID NO 51
<211> LENGTH: 46
<212> TYPE: DNA
<213> ORGANISM: artificial sequence
<220> FEATURE:
<223> OTHER INFORMATION: oligonucleotide primer 5delpsi

<400> SEQUENCE: 51
ccctctgcag tttggtaccg tcgagaaaaa aacattagat cagaag              46

<210> SEQ ID NO 52
<211> LENGTH: 24
<212> TYPE: DNA
<213> ORGANISM: artificial sequence
<220> FEATURE:
<223> OTHER INFORMATION: oligonucleotide primer SnaB5

<400> SEQUENCE: 52
atgaactttc tacgtaagat agtg                                      24

<210> SEQ ID NO 53
<211> LENGTH: 46
<212> TYPE: DNA
<213> ORGANISM: artificial sequence
<220> FEATURE:
<223> OTHER INFORMATION: oligonucleotide primer 3delpsi

<400> SEQUENCE: 53
caaactgcag aggggtgtta gttttttca aaagaaccc cccaag                46

<210> SEQ ID NO 54
<211> LENGTH: 44
<212> TYPE: DNA
<213> ORGANISM: artificial sequence
<220> FEATURE:
<223> OTHER INFORMATION: oligonucleotide primer 3deltag

<400> SEQUENCE: 54
caaactgcag aggggtgtta gttttttca catccaagag gatc                 44

<210> SEQ ID NO 55
```

-continued

```
<211> LENGTH: 42
<212> TYPE: DNA
<213> ORGANISM: artificial sequence
<220> FEATURE:
<223> OTHER INFORMATION: oligonucleotide primer 5deltag

<400> SEQUENCE: 55
cctctgcagt ttggtacctt gaaaaaaacc tgggttcaat ag                               42

<210> SEQ ID NO 56
<211> LENGTH: 35
<212> TYPE: DNA
<213> ORGANISM: artificial sequence
<220> FEATURE:
<223> OTHER INFORMATION: oligonucleotide primer M5G

<400> SEQUENCE: 56
ctcactacaa gtcagtcgag acttggaatg agatc                                      35

<210> SEQ ID NO 57
<211> LENGTH: 35
<212> TYPE: DNA
<213> ORGANISM: artificial sequence
<220> FEATURE:
<223> OTHER INFORMATION: oligonucleotide primer M3G

<400> SEQUENCE: 57
gactgacttt gagtgagcat cggcttccat caagg                                      35

<210> SEQ ID NO 58
<211> LENGTH: 524
<212> TYPE: PRT
<213> ORGANISM: artificial sequence
<220> FEATURE:
<223> OTHER INFORMATION: Mutated G protein Aa333

<400> SEQUENCE: 58
```

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Pro
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Glu
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520

<210> SEQ ID NO 59
<211> LENGTH: 60
<212> TYPE: DNA
<213> ORGANISM: artificial sequence
<220> FEATURE:
<223> OTHER INFORMATION: oligonucleotide primer 3psicis

<400> SEQUENCE: 59
ccaaactgca gcgaaaggag gggtgttagt tttttcatg atgaaccccc caaggggagg      60

<210> SEQ ID NO 60
<211> LENGTH: 39

```
<212> TYPE: DNA
<213> ORGANISM: artificial sequence
<220> FEATURE:
<223> OTHER INFORMATION: oligonucleotide primer cis55

<400> SEQUENCE: 60
gactcactat agggagaccc aagctggcta gctgttaag                                39

<210> SEQ ID NO 61
<211> LENGTH: 60
<212> TYPE: DNA
<213> ORGANISM: artificial sequence
<220> FEATURE:
<223> OTHER INFORMATION: oligonucleotide primer cis53

<400> SEQUENCE: 61
ccaaactgca gcgaaaggag gggtgttagt tttttcatg ttgactttag gacatctcgg          60

<210> SEQ ID NO 62
<211> LENGTH: 61
<212> TYPE: DNA
<213> ORGANISM: artificial sequence
<220> FEATURE:
<223> OTHER INFORMATION: oligonucleotide primer cis35

<400> SEQUENCE: 62
cctttcgctg cagtttggta ccgtcgagaa aaaacaggc aacaccactg ataaaatgaa          60
c                                                                         61

<210> SEQ ID NO 63
<211> LENGTH: 30
<212> TYPE: DNA
<213> ORGANISM: artificial sequence
<220> FEATURE:
<223> OTHER INFORMATION: cis33

<400> SEQUENCE: 63
cctccccttc aagagggccc ctggaatcag                                          30

<210> SEQ ID NO 64
<211> LENGTH: 46
<212> TYPE: DNA
<213> ORGANISM: artificial sequence
<220> FEATURE:
<223> OTHER INFORMATION: oligonucleotide primer TU1

<400> SEQUENCE: 64
ctaacacccc tcctttcgct gcagtttggt accgtcgaga aaaaaa                        46

<210> SEQ ID NO 65
<211> LENGTH: 53
<212> TYPE: DNA
<213> ORGANISM: artificial sequence
<220> FEATURE:
<223> OTHER INFORMATION: TU2

<400> SEQUENCE: 65 ttttttgat tgtggggagg aaagcgacgt caaaccatgg cagctctttt ttt                 53
```

RABIES VIRUS VECTOR SYSTEMS AND COMPOSITIONS AND METHODS THEREOF

REFERENCE TO RELATED APPLICATION(S)

This application is the U.S. National Stage of International Application No. PCT/US2006/040134, filed Oct. 13, 2006, which was published in English under PCT Article 21(2), and which claims the benefit of U.S. Provisional Application No. 60/727,038, filed Oct. 14, 2005. Both applications are incorporated herein by reference in their entirety.

STATEMENT OF GOVERNMENT SUPPORT

This invention was made by the Centers for Disease Control and Prevention, an agency of the United States Government. Therefore, the United States Government has certain rights in this invention.

FIELD

This disclosure relates to the field of virology. More specifically, this disclosure relates to compositions and methods that are useful for the production of immunogenic compositions for protecting mammals from infection by rabies virus.

BACKGROUND OF THE DISCLOSURE

Rabies remains one of the most dreadful infectious diseases affecting human and animals, despite significant scientific advances in its prevention and control. Rabies presents as a distinct problem in different parts of the world. In the Americas, reservoirs of rabies exist in many wild animal species, including raccoons, skunks, foxes, and bats (Rupprecht et al., *Emerg. Infect. Dis.* 1(4):107-114, 1995). Outbreaks of rabies infections in these terrestrial mammals are found in broad geographic areas across the United States. For example, raccoon rabies affects an area of more than 1 million square kilometers from Florida to Maine. Although wildlife rabies still exists in developed countries, progress has been made in control and elimination of wildlife rabies using oral immunization of wild animals.

Nonetheless, rabies remains a major threat to public health and persists to cause between 50,000 and 60,000 human deaths each year (World Health Organization, April 2003). Humans get infected with the rabies virus mostly through bites from rabid domestic and wildlife animals. In developing countries, dogs are responsible for about 94% of human rabies deaths. Dog rabies is still epizootic in most countries of Africa, Asia and South America and in these countries dogs are responsible for most human deaths from the disease. Controlling rabies virus infection in domestic and wildlife animals, therefore, not only reduces the mortality in these animals but also reduces the risks of human exposure.

The rabies virus is transmitted through broken skin by the bite or scratch of an infected animal. Exposure to rabies virus results in its penetration of peripheral, unmyelineated nerve endings, followed by spreading through retrograde axonal transport, replication occurring exclusively in the neurons, and finally arrival in the central nervous system (CNS). Infection of the CNS causes cellular dysfunction and death (Rupprecht & Dietzschold, *Lab Invest.* 57:603, 1987). Since rabies virus spreads directly from cell to cell, it largely evades immune recognition (Clark & Prabhakar, Rabies, In: Olson et al., eds., *Comparative Pathology of Viral Disease,* 2:165, Boca Raton, Fla., CRC Press, 1985).

The rabies virus (RV) is a rhabdovirus—a nonsegmented RNA virus with negative sense polarity. Within the Rhabdoviridae family, rabies virus is the prototype of the Lyssavirus genus. RV is composed of two major structural components: a nucleocapsid or ribonucleoprotein (RNP), and an envelope in the form of a bilayer membrane surrounding the RNP core. The infectious component of all rhabdoviruses is the RNP core, which consists of the negative strand RNA genome encapsidated by nucleoprotein (N) in combination with RNA-dependent RNA-polymerase (L) and phosphoprotein (P). The membrane surrounding the RNP contains two proteins: the trans-membrane glycoprotein (G) and the matrix (M) protein, located at the inner site of the membrane. Thus, the viral genome codes for these five proteins: the three proteins in the RNP (N, L and P), the matrix protein (M), and the glycoprotein (G).

The molecular determinants of pathogenicity of various rabies virus strains have not been fully elucidated. RV pathogenicity was attributed to multigenic events (Yamada et al., *Microbiol. Immunol.* 50:25-32, 2006). For example, some positions in the RV genome if mutated, affect viral transcription or replication, reducing virulence. Mutations at serine residue 389 of the phosphorylation site in the N gene (Wu et al., *J. Virol.* 76:4153-4161, 2002) or GDN core sequence of the highly conserved C motif in the L gene (Schnell and Conzelmann, *Virol.* 214:522-530, 1995) dramatically reduced RV transcription and replication.

The G protein, also referred to as spike protein, is involved in cell attachment and membrane fusion of RV. The amino acid region at position 330 to 340 (referred to as antigenic site III) of the G protein has been identified as important for virulence of certain strains of RV. Several studies support the concept that the pathogenicity of fixed RV strains is determined by the presence of arginine or lysine at amino acid residue 333 of the glycoprotein (Dietzschold et al., *Proc. Natl. Acad. Sci. USA* 80: 70-74, 1983; Tuffereau et al., *Virol.* 172: 206-212, 1989).

This phenomenon seems to apply at least to fixed rabies viruses such as CVS, ERA, PV, SAD-B19 and HEP-Flury strains (Anilionis et al, *Nature* 294:275-278, 1981; Morimoto et al., *Virol.* 173:465-477, 1989). For example, rabies vaccine viruses possessing an amino acid differing from Arg at position 333 of the glycoprotein are described, for instance, in WO 00/32755 (describing RV mutants in which all three nucleotides in the G protein $Arg_{333}$ codon are altered compared to the parent virus, such that the Arg at position 333 is substituted with another amino acid); European Patent 350398 (describing an avirulent RV mutant SAG1 derived from the Bern SAD strain of RV, in which the Arg at position 333 of the glycoprotein has been substituted to Ser); and European patent application 583998 (describing an attenuated RV mutant, SAG2, in which the Arg at position 333 in the G protein has been substituted by Glu).

Other strains, such as the RC-HL strain, possess an arginine residue at position 333 of the G, but does not cause lethal infection in adult mice (Ito et al., *Microl. Immunol.* 38:479-482, 1994; Ito et al., *J. Virol.* 75:9121-9128, 2001). As such, the entire G may contribute to the virulence of RV, although the determinants or regions have not previously been identified. The G gene encodes the only protein that induces viral neutralizing antibody. At least three states of RV glycoprotein are known: the native state (N) being responsible for receptor binding; an active hydrophobic state (A) necessary in the initial step in membrane fusion process (Gaudin, *J. Cell Biol.* 150:601-612, 2000), and a fusion inactive conformation (I). Correct folding and maturation of the G play important roles for immune recognition. The three potential glycosylated positions in ERA G extracellular domain occur at $Asn^{37}$, $Asn^{247}$ and $Asn^{319}$ residues (Wojczyk et al., *Glycobiology*. 8: 121-130, 1998), respectively. Nonglycosylation of G not only affects conformation, but also inhibits presentation of the protein at the cell surface. Thus, elucidating the molecular determinants underlying pathogenicity of rabies virus presents a complex problem.

SUMMARY OF THE DISCLOSURE

The complete sequence of the virus strain corresponding to the fixed vaccine of Evelyn-Rokitnicki-Abelseth (ERA) for rabies virus is disclosed herein, along with methods for sequencing this and other strains of lyssavirus.

A reverse genetics system for rabies virus is also described, in particular using the rabies virus strain ERA as an exemplar. Use of a T7 RNA polymerase, containing an eight amino acid nuclear localization signal (NLS) at the N terminal end facilitated virus recovery. Besides the parental ERA virus strain, several other derivative viruses are described, including ERA—(deletion of the psi-region), ERAgreen1 (green fluorescent protein gene inserted in psi region), ERAgreen2 (green fluorescent protein gene inserted at the phosphoprotein and matrix protein intergenic region), ERA2g (containing an extra copy of the glycoprotein in the psi-region), ERAg3 (with a mutation at amino acid 333 in glycoprotein), ERA2g3 (with an extra copy of altered glycoprotein at amino acid 333 in psi-region), ERA-G (from which the glycoprotein has been deleted) ERAgm (M and G genes switched in the genome), and ERAgmg (two copies of G in the rearranged ERAgm construct). The extra transcription unit was incorporated into ERA virus genome for efficient expression of Open Reading Frames (ORFs). By optimizing propagation conditions, which are described herein, rescued viruses reach titers in excess of $10^9$ ffu/ml in either bioreactors or stationary tissue flasks.

Also disclosed is a modified cell line that constitutively expresses the ERA glycoprotein. The cell line, designated BSR-G, is useful for the production of recombinant, including attenuated and/or replication deficient, rabies virus.

The foregoing and other objects, features, and advantages of the invention will become more apparent from the following detailed description.

BRIEF DESCRIPTION OF THE FIGURES

FIG. 1A. Schematic illustration of the ERA transcription plasmid. Positions of the hammerhead ribozymes and antigenomic ERA genome are indicated graphically. Relative positions of the N, P, M G and L proteins are shown in a 5' to 3' direction.

FIG. 1B. Schematic diagram of the construction of the full-length ERA rabies virus genomic cDNA plasmid pTMF. RT-PCR products F1, F2 fragments, and restriction enzyme recognition sites (Nhe1, Kpn1, Blp1, Pst1 and Not1) (not drawn to scale). The bar on the left indicates a RdRz-hammerhead ribozyme and the right bar indicates the HDVRz-hepatitis delta virus ribozyme. The symbol ♦ indicates that Kpn1 or Pst1 sites were deleted, and ⇓ vertical arrow indicates that Nhe1 or Not1 sites were left intact.

FIG. 3. Schematic diagram of the ten derivative ERA virus genomes. The size of each gene is not drawn to scale. Symbol "*" denotes mutations of G at the Aa333 residue and ψ is the Psi-region.

FIG. 9A. Survival following infection with Alabama Bat Rabies virus. Hamsters were inoculated with live Alabama Bat Rabies Virus, then treated post-exposure with either ERAg3 virus or with rabies immune globulin and commercially available inactivated RV vaccine. Survival was assessed over a more than three month period.

FIG. 9B. Survival following infection with That Street Dog Rabies virus. Hamsters were inoculated with live Alabama Bat Rabies Virus, then treated post-exposure with either ERAg3 virus or with rabies immune globulin and commercially available inactivated RV vaccine. Survival was assessed over a more than three month period.

FIG. 9C. Survival following infection with Texas Coyote Dog Rabies virus. Hamsters were inoculated with live Alabama Bat Rabies Virus, then treated post-exposure with either ERAg3 virus or with rabies immune globulin and commercially available inactivated RV vaccine. Survival was assessed over a more than three month period.

SEQUENCE LISTING

Figure 2:
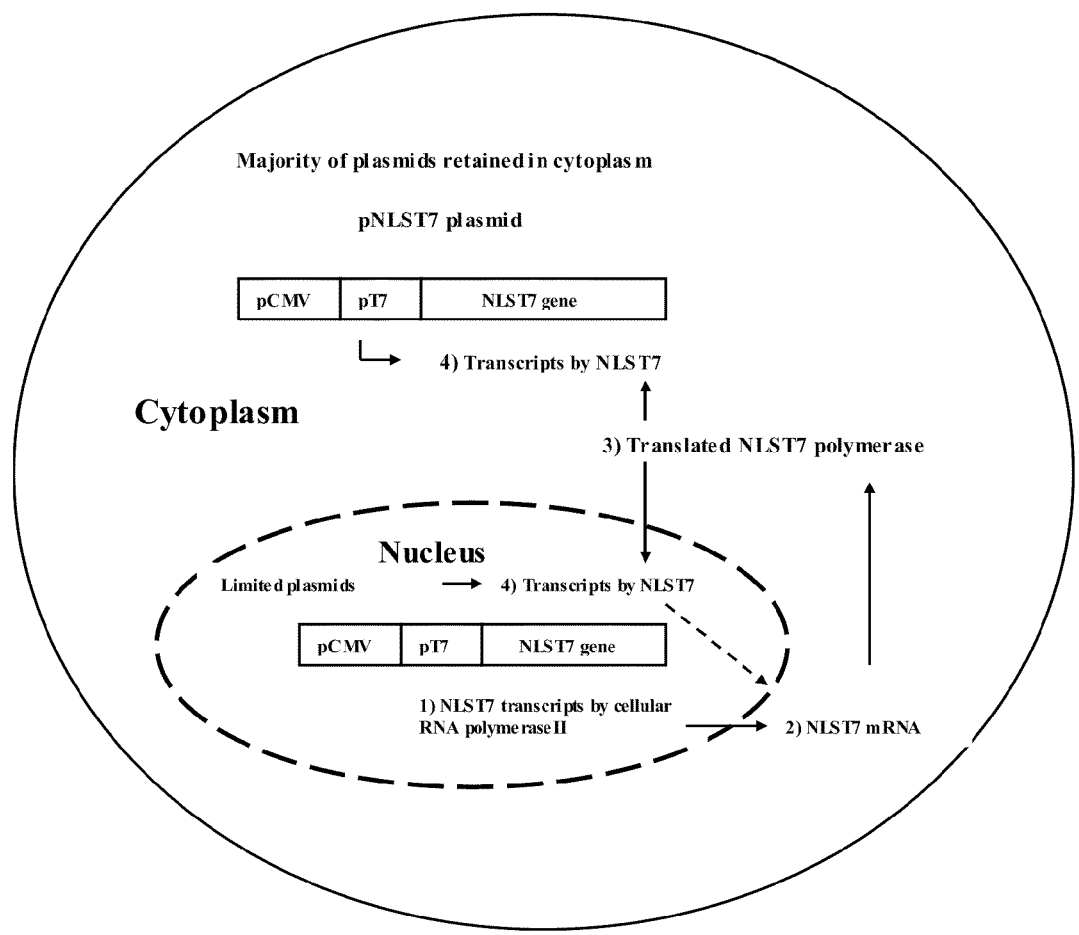
FIG. 2. Schematic illustration of the proposed mechanism of NLST7 RNA polymerase autogene action by pNLST7 plasmids. The DNA-transfection reagent complex is taken into cells by endocytosis. The majority of the DNA released from lysosomes and endosomes is retained in the cell cytoplasm. A limited amount of plasmids are transferred to the nucleus: 1) through a CMV immediate early promoter, the NLST7 gene is transcribed by cellular RNA polymeraseII; 2) mature NLST7 mRNA is transported from the nucleus to the cytoplasm for NLST7 RNA polymerase synthesis; 3) Newly synthesized NLST7 RNA polymerase is trans-located to the nucleus, while a trace amount of NLST7 remains in the cytoplasm; 4) NLST7 RNA polymerase initiates transcription through a pT7 promoter. By posttranscriptional modifications, additional NLST7 mRNA is produced for protein synthesis, thus increasing virus recovery efficiency.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand unless the context makes it clear that only one strand is intended. As appropriate, it will be understood that a sequence presented as DNA can be converted to RNA by replacing thiamine residues with uracils.

SEQ ID NO: 1. ERA CDC wild type virus, 11,931 nucleotides
  1-58 nucleotides, Leader region
  71-1420 nucleotides, N gene
  1514-2404 nucleotides, P gene
  2496-3101 nucleotides, M gene
  3317-4888 nucleotides, G gene
  4964-5362 nucleotides, Psi-region
  5417-11797 nucleotides, L gene
  11862-11931 nucleotides, Trailer region SEQ ID NO: 2. ERACDC: 71 to 1420: 450 aa, N protein.
SEQ ID NO: 3. ERACDC: 1514 to 2404: 297 aa, P protein.
SEQ ID NO: 4. ERACDC: 2496 to 3101: 202 aa, M protein.
SEQ ID NO: 5. ERACDC: 3317 to 4888: 524 aa, G protein.
SEQ ID NO: 6. ERACDC: 5417 to 11797: 2127 aa, L protein.
SEQ ID NO: 7. Recombinant ERA (rERA) recovered by reverse genetics system is 11,930 nucleotides. The specific poly ($A_8$) tract between G gene and psi-region in wild type ERA strain was mutated to a poly ($A_7$) tract in recombinant ERA reverse genetics system as a sequence marker. In light of this, rERA is one nucleotide shorter than wild type ERA. All the other sequence information is exactly the same.

SEQ ID NO: 8. ERAg3 strain (11,930 nucleotides), amino acid in the G protein (333 Aa) has been altered; the corresponding nucleic acids are at positions 4370 to 4372.

SEQ ID NO: 9. ERA-(11,577 nucleotides), without the psi (pseudo-gene) region; an extra transcription unit has been introduced at nucleotide positions 4950 to 5008.

SEQ ID NO: 10. ERA-2G (13,150 nucleotides), this strain has two copies of the G gene; the second copy is inserted at positions 4988 to 6559.

SEQ ID NO: 11. ERAgreen (12,266 nucleotides), this strain contains the coding sequence for GFP at positions 4993 to 5673; it appears green under UV light after infection of cells or tissue.

SEQ ID NO: 12. ERA-G (10,288 nucleotides), this strain has no G gene.

SEQ ID NO: 13. ERA-2g3 (13,150 nucleotides); this strain has two copies of the G gene (the second of which is at positions 4988 to 6559), both of which are substituted at amino acid 333 (corresponding to nucleotide positions 4370-4372 and 6041-6043 in the shown sequence).

SEQ ID NO: 14. ERA-pt (11,976 nucleotides, with an extra transcription unit after the P gene, at positions 2469 to 2521).

SEQ ID NO: 15. ERA-pt-GFP (12,662 nucleotides, with GFP gene inserted after P gene at 2505 to 3185).

SEQ ID NO: 16. ERAgm (11,914 nucleotides) positions of G and M genes are switched with G at positions 2505-4076 and M at positions 4122-4727, respectively.

SEQ ID NO: 17. ERAg3m (11,914 nucleotides) positions of G and M genes are switched with G at positions 2505-4076 and M at positions 4122-4727, respectively. The G gene is mutated at amino acid position 333.

SEQ ID NO: 18. ERAgmg (13,556 nucleotides), this strain has two copies of the G gene at positions 2505-4076 and 4943-6514, flanking the M gene at positions 4122-4727.

SEQ ID NO: 19. First ten nucleotides of hammerhead ribozyme corresponding to 5' end of rabies virus ERA genome.

SEQ ID NO: 20. Nucleotide sequence encoding the SV40 T antigen nuclear localization signal (NLS).

SEQ ID NOs: 21-23. Artificial Kozak sequences.

SEQ ID NOs: 24-57. Synthetic oligonucleotides.

SEQ ID NO: 58. Amino acid sequence of G protein mutated at amino acid position 333 (from Arg to Glu).

SEQ ID NOs: 59-65. Synthetic oligonucleotides.

DETAILED DESCRIPTION

I. Introduction

Viral zoonoses are difficult to prevent. One major paradigm is the control of wildlife rabies by oral vaccination. All current licensed oral rabies vaccines are based on one common source. The fixed rabies virus (RV) of Evelyn-Rokitnicki-Abelseth (ERA) was derived from the Street-Alabama-Dufferin (SAD) strain, first isolated from a rabid dog in Alabama (USA) in 1935. The ERA strain was derived after multiple passages of SAD RV in mouse brains, baby hamster kidney (BHK) cells, and chicken embryos. Repeated cloning of ERA in BHK cells resulted eventually in a B-19 clone, which was named SAD-B19 for vaccine studies. The first RV strain recovered by reverse genetics was SAD-B19. Although SAD-B19 and ERA RV derived from the same source, different outcomes have been observed in various animal oral vaccine studies. For example, ERA did not induce obvious neutralizing antibodies in either skunks or raccoons per os, while SAD-B19 did. To elucidate potential differences between these two RV strains, a reverse genetics system for the ERA RV strain is required.

Reverse genetics presents a feasible way to modify RNA viruses in defined ways. A system for reverse genetics of an initial strain of rabies virus was successfully established in 1994 (Schnell et al., *The EMBO J.* 13, 4195-4203, 1994). In the intervening decade, improvements to the system have been made, resulting in increased efficiency of virus recovery. This increased efficiency has facilitated the elucidation of virus pathogenicity, protein-protein, and protein-RNA interactions.

Within the rabies virus genome, it has been proposed that some regions contain important signals, such as viral distal promoters region, nucleoprotein encapsidation, RNA dependent RNA polymerase L transcription initiation site, polyadenylation and termination sites. These signals are important for ensuring efficient recovery of virus and for designing an extra transcription unit for accepting an exogenous Open Reading Frame (ORF) into the rabies virus genome.

This disclosure provides an efficient reverse genetics system, and describes its use to produce variants of the ERA strain virus. Modifications described herein have resulted in strains that are suitable candidates for accepting ORF expression and vaccine development.

The reverse genetics system is composed of a set of plasmids. A first plasmid includes an ERA viral cRNA. In order to create authentic viral anti-genomic ends in transcribed viral cDNA, ERA genomic cDNA is flanked by a hammerhead ribozyme at the 3' end and a hepatitis delta virus ribozyme at the 5' end. The antigenomic cassette is fused to the bacteria phage T7 transcription initiation signal, which is optionally also under the control of cytomegalovirus (CMV) immediate-early promoter.

The system also includes a plurality of helper plasmids that encode proteins involved in viral encapsidation. For example, the system typically includes helper plasmids that encode the viral nucleoprotein (N), phosphoprotein (P), RNA dependent polymerase (L), and optionally the viral glycoprotein (G). The system also includes a plasmid that encodes the phage T7 RNA polymerase (T7), which can be modified by the addition of a nuclear localization signal (NLS) to increase expression of the T7 polymerase in the nucleus of transfected cells. The T7 RNA polymerase expression plasmid is constructed as an "autogene," which transcribes the whole length of viral anti-genomic cRNA for nucleoprotein encapsidation after transfection into cells.

The reverse genetics system is useful in the design and production of immunogenic compositions for the treatment (pre and/or post exposure) of rabies virus, and for producing rabies virus ERA vectors for expressing exogenous Open Reading Frames (ORFs). For example, an extra transcription unit can be designed, tested and incorporated into the ERA genome at either the Psi-region and/or at phosphoprotein (P)-matrix (M) protein intergenic region. Essentially any ORF of interest can be expressed in the context to the ERA vector, including ORFs encoding antigens of viruses and other pathogens, such as antigens of other lyssaviruses, as well as for expressing other proteins of therapeutic interest.

Thus, the methods and compositions disclosed herein are useful for the design and production of rabies virus immunogenic compositions, including compositions suitable as vaccines for the pre and/or post exposure treatment of rabies virus.

II. Abbreviations

| | |
|---|---|
| ADE | antibody-dependant enhancement |
| Ag-ELISA | antigen-capture ELISA |
| DNA | deoxyribosenucleic acid |
| ERA | Rabies virus strain Evelyn-Rokitnicki-Abelseth |
| ELISA | enzyme-linked immunoabsorbent assay |
| G | glycoprotein |
| i.c. | intracerebral |
| IFA | indirect immuno-fluorescence assay |
| i.m. | intramuscular |
| L | RNA-dependent RNA-polymerase |
| M | matrix protein |
| mAb | monoclonal antibody |
| N | nucleoprotein |
| ORF | open reading frame |
| P | phosphoprotein |
| PCR | polymerase chain reaction |
| RACE | 5' rapid amplification of cDNA ends |
| RNA | ribosenucleic acid |
| RNP | ribonucleoprotein |
| RT-PCR | reverse transcription-polymerase chain reaction |
| RV | rabies virus |
| trans 1 | extra transcription unit 1 |
| trans 2 | extra transcription unit 2 |

III. Terms

Unless otherwise explained, all technical and scientific terms used herein have the same meaning as commonly understood by one of ordinary skill in the art to which this invention belongs. Similarly, unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

In order to facilitate review of the various embodiments of the invention, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts and the MF59 microemulsion are the only vaccine adjuvants approved for human use.

Amplification: Amplification of a nucleic acid molecule (e.g., a DNA or RNA molecule) refers to use of a laboratory technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by such techniques as electrophoresis, restriction endonuclease cleavage patterns, oligonucleotide hybridization or ligation, and/or nucleic acid sequencing.

Other examples of amplification methods include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320,308; gap filling ligase chain reaction amplification, as disclosed in U.S. Pat. No. 5,427,930; and NASBA™ RNA transcription-free amplification, as disclosed in U.S. Pat. No. 6,025,134. An amplification method can be modified, including for example by additional steps or coupling the amplification with another protocol.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and compositions of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller ($K_d$) indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope.

In one example, antibody binding affinity is measured by end-point titration in an Ag-ELISA assay. Antibody binding affinity is substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a virus antigen.

Attentuated: In the context of a live virus, such as a rabies virus, the virus is attenuated if its ability to infect a cell or subject and/or its ability to produce disease is reduced (for example, eliminated). Typically, an attenuated virus retains at least some capacity to elicit an immune response following administration to an immunocompetent subject. In some cases, an attenuated virus is capable of eliciting a protective immune response without causing any signs or symptoms of infection.

Binding or Stable Binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including functional or physical binding assays. Binding can be detected functionally by determining whether binding has an observable effect upon a biosynthetic process such as expression of a gene, DNA replication, transcription, translation, and the like.

Physical methods of detecting the binding of complementary strands of DNA or RNA are well known in the art, and include such methods as DNase I or chemical footprinting, gel shift and affinity cleavage assays, Northern blotting, Southern blotting, dot blotting, and light absorption detection procedures. For example, a method which is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Electrophoresis: Electrophoresis refers to the migration of charged solutes or particles in a liquid medium under the influence of an electric field. Electrophoretic separations are widely used for analysis of macromolecules. Of particular importance is the identification of proteins and nucleic acid sequences. Such separations can be based on differences in size and/or charge. Nucleotide sequences have a uniform charge and are therefore separated based on differences in size. Electrophoresis can be performed in an unsupported liquid medium (for example, capillary electrophoresis), but more commonly the liquid medium travels through a solid supporting medium. The most widely used supporting media are gels, for example, polyacrylamide and agarose gels.

Sieving gels (for example, agarose) impede the flow of molecules. The pore size of the gel determines the size of a molecule that can flow freely through the gel. The amount of time to travel through the gel increases as the size of the molecule increases. As a result, small molecules travel through the gel more quickly than large molecules and thus progress further from the sample application area than larger molecules, in a given time period. Such gels are used for size-based separations of nucleotide sequences.

Fragments of linear DNA migrate through agarose gels with a mobility that is inversely proportional to the $\log_{10}$ of their molecular weight. By using gels with different concentrations of agarose, different sizes of DNA fragments can be resolved. Higher concentrations of agarose facilitate separation of small DNAs, while low agarose concentrations allow resolution of larger DNAs.

Epitope: An antigenic determinant. These are particular chemical groups, such as contiguous or non-contiguous peptide sequences, on a molecule that are antigenic, that is, that elicit a specific immune response. An antibody binds a particular antigenic epitope based on the three dimensional structure of the antibody and the matching (or cognate) three dimensional structure of the epitope.

A "substituted epitope" comprises at least one structural substitution in the epitope, such as a substitution of one amino acid for another Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Immune stimulatory composition: A term used herein to mean a composition useful for stimulating or eliciting a specific immune response (or immunogenic response) in a vertebrate. The immune stimulatory composition can be a protein antigen or a plasmid vector used to express a protein antigen. In some embodiments, the immunogenic response is protective or provides protective immunity, in that it enables the vertebrate animal to better resist infection with or disease progression from the organism against which the immune stimulatory composition is directed.

Without wishing to be bound by a specific theory, it is believed that an immunogenic response induced by an immune stimulatory composition may arise from the generation of an antibody specific to one or more of the epitopes provided in the immune stimulatory composition. Alternatively, the response may comprise a T-helper or cytotoxic cell-based response to one or more of the epitopes provided in the immune stimulatory composition. All three of these responses may originate from naïve or memory cells. One specific example of a type of immune stimulatory composition is a vaccine.

In some embodiments, an "effective amount" or "immune-stimulatory amount" of an immune stimulatory composition is an amount which, when administered to a subject, is sufficient to engender a detectable immune response. Such a response may comprise, for instance, generation of an antibody specific to one or more of the epitopes provided in the immune stimulatory composition. Alternatively, the response may comprise a T-helper or CTL-based response to one or more of the epitopes provided in the immune stimulatory composition. All three of these responses may originate from naïve or memory cells. In other embodiments, a "protective effective amount" of an immune stimulatory composition is an amount which, when administered to a subject, is sufficient to confer protective immunity upon the subject.

Inhibiting or treating a disease: Inhibiting the full development of a disease or condition, for example, in a subject who is at risk for a disease. A specific example of diseases is rabies. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Oligonucleotide: A nucleic acid molecule generally comprising a length of 300 bases or fewer. The term often refers to single-stranded deoxyribonucleotides, but it can refer as well to single- or double-stranded ribonucleotides, RNA:DNA hybrids and double-stranded DNAs, among others. The term "oligonucleotide" also includes oligonucleosides (that is, an oligonucleotide minus the phosphate) and any other organic base polymer.

In some examples, oligonucleotides are about 10 to about 90 bases in length, for example, 12, 13, 14, 15, 16, 17, 18, 19 or 20 bases in length. Other oligonucleotides are about 25, about 30, about 35, about 40, about 45, about 50, about 55, about 60 bases, about 65 bases, about 70 bases, about 75 bases or about 80 bases in length. Oligonucleotides may be single-stranded, for example, for use as probes or primers, or may be double-stranded, for example, for use in the construction of a mutant gene. Oligonucleotides can be either sense or anti-sense oligonucleotides. An oligonucleotide can be modified as discussed above in reference to nucleic acid molecules. Oligonucleotides can be obtained from existing nucleic acid sources (for example, genomic or cDNA), but can also be synthetic (for example, produced by laboratory or in vitro oligonucleotide synthesis).

Open Reading Frame (ORF): A series of nucleotide triplets (codons) coding for amino acids without any internal termination codons. These sequences are usually translatable into a peptide/polypeptide/protein/polyprotein.

It is recognized in the art that the following codons (shown for RNA) can be used interchangeably to code for each specific amino acid or termination: Alanine (Ala or A) GCU, GCG, GCA, or GCG; Arginine (Arg or R) CGU, CGC, CGA, CGG, AGA, or AGG; Asparagine (Asn or N) AAU or AAC; Aspartic Acid (Asp or D) GAU or GAC; Cysteine (Cys or C) UGU or UGC; Glutamic Acid (Glu or E) GAA or GAG; Glutamine (Gln or Q) CAA or CAG; Glycine (Gly or G) GGU, GGC, GGA, or GGG; Histidine (H is or H) CAU or CAC; Isoleucine (Ile or I) AUU, AUC, or AUA; Leucine (Leu or L) UUA, UUG, CUU, CUC, CUA, or CUG; Lysine (Lys or K) AAA or AAG; Methionine (Met or M) AUG; Phenylalanine (Phe or F) UUU or UUC; Proline (Pro or P) CCU, CCC, CCA, or CCG; Serine (Ser or S) UCU, UCC, UCA, UCG, AGU, or AGC; Termination codon UAA (ochre) or UAG (amber) or UGA (opal); Threonine (Thr or T) ACU, ACC, ACA, or ACG; Tyrosine (Tyr or Y) UAU or UAC; Tryptophan (Trp or W) UGG; and Valine (Val or V) GUU, GUC, GUA, or GUG. The corresponding codons for DNA have T substituted for U in each instance.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence is the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Paratope: That portion of an antibody that is responsible for its binding to an antigenic determinant (epitope) on an antigen.

Pharmaceutically Acceptable Carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues joined together through amide bonds. When the amino acids are alpha-amino acids, either the L-optical isomer or the D-optical isomer can be used, the L-isomers being preferred for many biological uses. The terms "polypeptide" or "protein" as used herein are intended to encompass any amino acid molecule and include modified amino acid molecules. The term "polypeptide" is specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan, and tyrosine are classified as both polar and aromatic amino acids. Additional amino acids that are classified in each of the above groups are known to those of ordinary skill in the art.

Substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Probes and primers: A probe comprises an isolated nucleic acid molecule attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989 and Ausubel et al. *Short Protocols in Molecular Biology*, $4^{th}$ ed., John Wiley & Sons, Inc., 1999.

Primers are short nucleic acid molecules, for instance DNA oligonucleotides 6 nucleotides or more in length, for example that hybridize to contiguous complementary nucleotides or a sequence to be amplified. Longer DNA oligonucleotides may be about 10, 12, 15, 20, 25, 30, or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989; Ausubel et al. *Short Protocols in Molecular Biology*, 4th ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

Protein: A biological molecule, particularly a polypeptide, expressed by a gene and comprised of amino acids.

Purified: The term "purified" does not require absolute purity; rather, it is intended as a relative term. Thus, for example, a purified protein preparation is one in which the subject protein is more pure than in its natural environment within a cell. Generally, a protein preparation is purified such that the protein represents at least 50% of the total protein content of the preparation.

Recombinant nucleic acid: A nucleic acid molecule that is not naturally occurring or has a sequence that is made by an artificial combination of two otherwise separated segments of sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of a natural nucleic acid molecule.

Regulatory sequences or elements: These terms refer generally to a class of DNA sequences that influence or control expression of genes. Included in the term are promoters, enhancers, locus control regions (LCRs), insulators/boundary elements, silencers, matrix attachment regions (MARs, also referred to as scaffold attachment regions), repressor, transcriptional terminators, origins of replication, centromeres, and meiotic recombination hotspots. Promoters are sequences of DNA near the 5'-end of a gene that act as a binding site for DNA-dependent RNA polymerase, and from which transcription is initiated. Enhancers are control elements that elevate the level of transcription from a promoter, usually independently of the enhancer's orientation or distance from the promoter. LCRs confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also know as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. MARs are sequences within DNA that bind to the nuclear scaffold; they can affect transcription, possibly by separating chromosomes into regulatory domains. It is believed that MARs mediate higher-order, looped structures within chromosomes. Transcriptional terminators are regions within the gene vicinity where RNA polymerase is released from the template. Origins of replication are regions of the genome that, during DNA synthesis or replication phases of cell division, begin the replication process of DNA. Meiotic recombination hotspots are regions of the genome that recombine more frequently than average during meiosis.

Replicon: Any genetic element (e.g., plasmid, chromosome, virus) that functions as an autonomous, self-replicating unit of DNA replication in vivo.

Sample: A portion, piece, or segment that is representative of a whole. This term encompasses any material, including for instance samples obtained from an animal, a plant, or the environment.

An "environmental sample" includes a sample obtained from inanimate objects or reservoirs within an indoor or outdoor environment. Environmental samples include, but are not limited to: soil, water, dust, and air samples; bulk samples, including building materials, furniture, and landfill contents; and other reservoir samples, such as animal refuse, harvested grains, and foodstuffs.

A "biological sample" is a sample obtained from a plant or animal subject. As used herein, biological samples include all samples useful for detection of viral infection in subjects, including, but not limited to: cells, tissues, and bodily fluids, such as blood; derivatives and fractions of blood (such as serum); extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; BAL; saliva; cervical swabs; vaginal swabs; and oropharyngeal wash.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls. Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996).

ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzy mol.*, 266:131-41, 1996; Altschul et al., *Nucleic Acids Res.*, 25:3389-402, 1997; and Zhang and Madden, *Genome Res.*, 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specific binding agent: An agent that binds substantially only to a defined target. Thus a protein-specific binding agent binds substantially only the defined protein, or to a specific region within the protein. As used herein, protein-specific binding agents include antibodies and other agents that bind substantially to a specified polypeptide. The antibodies may be monoclonal or polyclonal antibodies that are specific for the polypeptide, as well as immunologically effective portions ("fragments") thereof.

The determination that a particular agent binds substantially only to a specific polypeptide may readily be made by using or adapting routine procedures. Examples of suitable in vitro assays which make use of the Western blotting procedure include IFA and Ag-ELISA, and are described in many standard texts, including Harlow and Lane, *Using Antibodies: A Laboratory Manual*, CSHL, New York, 1999.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art.

Virus: Microscopic infectious organism that reproduces inside living cells. A virus typically consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Overview of Several Embodiments

Provided herein in a first embodiment is a recombinant rabies virus genome comprising the nucleic acid as set forth in SEQ ID NO: 1 (full length ERA sequence). Also provided are isolated rabies virus proteins encoded by that genome, including specific proteins comprising an amino acid sequence as set forth in SEQ ID NO: 2 (N protein); SEQ ID NO: 3 (P protein); SEQ ID NO: 4 (M protein); SEQ ID NO: 5 (G protein); or SEQ ID NO: 6 (L protein); and isolated nucleic acid molecules that encode such proteins. By way of example, such isolated nucleic acid molecules comprise a nucleotide sequence as set forth in: nucleotides 71-1423 of SEQ ID NO: 1 (N protein); nucleotides 1511-2407 of SEQ ID NO: 1 (P protein); nucleotides 2491-3104 of SEQ ID NO: 1 (M protein); nucleotides 3318-4892 of SEQ ID NO: 1 (G protein); or nucleotides 5418-11,801 of SEQ ID NO: 1 (L protein).

Also provided is a recombinant virus genome with the nucleic acid sequence as set forth in SEQ ID NO: 7, which differs from SEQ ID NO: 1 by virtue of a deletion of one adenosine residue in the polyA tract between the G gene and the psi-region. SEQ ID NO: 7 also encodes the proteins shown as SEQ ID NOs: 2-6.

Also provided are genomes of derivatives of the ERA strain of virus, as shown in SEQ ID NOs: 8-18. In certain embodiments, the genomes are present in a vector, such as a plasmid.

Yet another described embodiment is a system for sequencing full length rabies virus genome using a method as described herein. Viral vector systems for expression of heterologous proteins are also described.

Another embodiment provides compositions that comprise one or more nucleic acid molecules, or one or more proteins, provided herein. Optionally, such compositions contain a pharmaceutically acceptable carrier, an adjuvant, or a combination of two or more thereof.

Also provided is a method of eliciting an immune response against an antigenic epitope in a subject, comprising introducing into the subject a composition comprising a nucleotide, peptide, or polypeptide described herein, thereby eliciting an immune response in the subject.

Another aspect of the disclosure relates to a vector system for producing recombinant rabies virus. The vector system includes a first vector (transcription vector) containing a full-length rabies virus antigenomic DNA (or a derivative thereof) and a set of helper vectors containing nucleic acids that encode at least one rabies virus strain ERA protein. Expression of the vectors in a transfected host cell results in production of a live recombinant rabies virus. In certain embodiments, the antigenomic DNA is of the ERA strain (for example, SEQ ID NO: 1 or SEQ ID NO: 7) or a derivative thereof, such as one of SEQ ID NOs: 8-18. In certain embodiments, the vectors are plasmids.

To facilitate recovery of full length viral RNA, the transcription vector can include, in a 5' to 3' direction: a hammerhead ribozyme; a rabies virus antigenomic cDNA; and a hepatitis delta virus ribozyme. Nucleotides of the hammerhead ribozyme are selected to be complementary to the antisense genomic sequence of the rabies virus. Transcription of the antigenomic cDNA is under the transcription regulatory control of at least one of the CMV promoter and the phage T7 RNA polymerase promoter, and commonly under the control of both of these promoters.

The helper vectors typically include a vector comprising a polynucleotide sequence that encodes a rabies virus N protein; a vector comprising a polynucleotide sequence that encodes a rabies virus P protein; a vector comprising a polynucleotide sequence that encodes a rabies virus M protein; a vector comprising a polynucleotide sequence that encodes a rabies virus L protein; and a vector comprising a polynucleotide sequence that encodes a phage T7 RNA polymerase. In an embodiment, the T7 RNA polymerase comprises a nuclear localization signal (NLS). Optionally, the vector system also includes a vector comprising a polynucleotide sequence that encodes a rabies virus G protein.

Transcription of one or more of the polynucleotide sequences that encode the rabies virus P, M, L or G protein or the T7 polymerase is under the transcription regulatory control of both the CMV promoter and the T7 promoter. In contrast, transcription of the polynucleotide sequence that encodes the rabies virus N protein is under the transcription regulatory control of the T7 promoter, and transcription is cap-independent.

Yet more embodiments are live rabies vaccines, each comprising a recombinant rabies virus genome as provided herein. Examples of such recombinant rabies genomes comprise the sequence shown as ERA G333 (SEQ ID NO: 13); the sequence shown as ERA 2G (SEQ ID NO: 8); and the sequence shown herein as ERA 2G333 (SEQ ID NO: 10). Optionally, the rabies vaccine is attenuated.

Also provided is a method of producing a live rabies virus (for example, for use in an immunogenic composition, such as a vaccine) by introducing the vector system into a host cell. After transfection of vector system into a suitable host cell, live and optionally attenuated virus is recovered. Production and administration of a live rabies vaccine produced by such methods is also contemplated herein.

Also disclosed is a method of vaccinating a subject against rabies, which method comprises administering an effective amount of the live rabies vaccine according to the provided description to a subject, such that cells of the subject are infected with the rabies vaccine, wherein an anti-rabies immune response is produced in the subject. In one embodiment, the subject is a human. In another embodiment, the subject is a non-human animal. For instance, the non-human animal in some instances is a cat, dog, rat, mouse, bat, fox, raccoon, squirrel, opossum, coyote, or wolf.

In certain embodiments, the rabies vaccine is administered enterally. For instance, the enteral administration in some cases comprises oral administration. Oral administration includes administration through food-baits designed to vaccinate wild animal populations, for instance.

Pharmaceutical compositions that include the described live rabies vaccines (for instance, an attenuated live rabies vaccine) and a pharmaceutically acceptable carrier or excipient are also provided.

V. Method of Sequencing Entire Lyssavirus Genome

To facilitate sequencing of the full length ERA genome, a method for sequencing a full length negative strand RNA virus was developed. This method is applicable to the sequencing of a lyssavirus, such as a rabies virus, as well as other negative strand RNA viruses. Rabies virus is a single negative stranded RNA virus with a genome around 12 kb, with the range between 11,918 (Australian bat lyssavirus) and 11,940 (Mokola virus) bases. The available rabies viral nucleic acid sequences in GENBANK mainly focus on the sequences that encode proteins—nucleocapsid protein (N), glycoprotein (G), phosphoprotein (P) and matrix protein (M) genes, which are close to the 3' end of the genome. Prior phylogenetic analysis is mostly based on N and G genes. But, for remotely related rabies viral strains, RNA dependent RNA polymerase (L) gene is the most suitable candidate for phylogenetic analysis. Unfortunately, few L gene sequences are available in public gene databases. In addition, it has been proposed that both leader and trailer regions at rabies viral termini play very important roles for (regulation of) viral transcription and replication. These could be the conserved regions for nucleoprotein encapsidation or the binding sites for L/P proteins, for instance. Also the inter-genic regions among leader-N, N-P, P-M, M-G, pseudo-gene region and G-L serve as the signals for initiation of viral transcription. Thus, not only coding regions, but also non-coding regions within the viral genome, could be applied to phylogenetic analysis or evolution research. These sequences can all more readily be analyzed using the whole-genome sequencing methods provided herein.

The method includes a single step reverse transcription and a two step cloning into a suitable vector. This method produces a readily sequenced genome in the vector, without the need to perform error-prone repeated RT-PCR reactions. Exploiting the inverted repeat found at the ends of the rabies genome (and the genomes of other lyssaviruses), universal primers have been designed and are described herein for use in the rapid full-genome sequencing procedures described herein.

The leader and trailer regions in rabies virus contain signals for viral transcription and replication. Based on analysis the genome sequence available from GenBank, the terminal 11 nucleotides are strictly conserved in rabies viruses or rabies-related viruses, including Mokola virus. The rationale for the sequencing methods provided herein is based on the terminal 11 complementary nucleotides. Because these two 11 nucleotide sequences are complementary, they could are not used in the follow-up PCR reactions. It will be understood that other viruses with inverted repeats can similarly be amplified using primers corresponding to the sequences of those repeats. The 11 antigenome sense nucleotides were designed as reverse transcription primers for the purified ERA genome, whose integrity was verified by size comparison and Northern blots. The whole genome cDNA was also confirmed by Northern blot with N, P, M, G, L gene probes and 11 nucleotides as an oligonucleotide probe, which only bound genomic RNA, not viral mRNA.

It is reasonably feasible to reverse transcribe rabies viral whole genome in one reaction, using carefully designed conserved terminal sequence-corresponding primes, provided the quality of the viral genome preparation is high.

The sequence of the ERA is closely related to that of SAD, which is one of its derivatives. This is not surprising, because ERA was sent from CDC in the 1970s to Switzerland, where researchers adapted it to grow in cells, before sending it to Germany, where it was further derived, and the derivative fully sequenced in ~1990. Until now, rabies and rabies-related viruses have been classified into seven different types: classic rabies virus type1 (ERA is included), type2 (Lagos bat), type3 (Mokola), type4 (Duvenhage), type5 (European bat lyssavirus [EBL] I, type6 (EBL II) and type7 (Australian bat virus) according to serum cross protection and genetic studies. Sequence analysis plays an important role in phylogenetics, evolution research, gene function predictive studies and other related areas, including locating viral transcription and replication regulatory regions, and hence bioinformatics towards potential therapeutic drugs.

With the development of techniques in reverse transcriptional polymerase chain reaction (RT-PCR), which are known to those of ordinary skill in the art, now it is relatively easy to reverse transcribe as much as 12 kb or more of RNA to cDNA in one reaction. Under optimized conditions, PCR can amplify targets of more than 30 kb in one reaction.

With the provision herein of methods for generating full-length virus genome sequences, in particularly rabies genome sequences, it now becomes practical to analyze differ strains of virus. Effective design of attenuated virus, for instance for use in immunization or production of immune stimulatory compositions and vaccines, is also enabled using the resultant full length genomes.

There is no "general" rabies virus genome, but these genomes are related. The similarities range from 60% to 100% in different types. Some regions, such as the L gene, seem more conserved, whereas others, such as the psi region, which does not code for a polypeptide, are more variable. Not only will rabies and rabies related viruses drift, but also any RNA viruses will change over time. How the viruses adapt and emerge, is an open question. For this reason, whole genome sequence analysis is important for evolutionary, pathogenicity and gene function studies.

This system described herein is the first for rabies virus as concerns whole genome sequencing. It is believed to be suitable for other RNA viruses, particularly in the lyssavirus genus. At present, for rabies virus phylogenetic studies, scientists only make use of the N, P, or G genes, which are most abundant in the infected cells or tissues. It is known that for remote strain comparison, the L gene comprising more than half of the genome may be an ideal candidate site, which should be used. Unfortunately, such evolutionary comparisons are not possible due to the very limited data available, let alone the whole genome sequence. Also for viral transcription and replication studies, it is supposed that the leader and trailer regions located at the 3' and 5' extremities of the genome play important roles. The inter-genic regions are also the signals for viral trans and cis studies. All these data are quite limited, because they are not included in the mRNA. Only the whole genome sequence can provide the necessary information at this level. Whole genome sequencing is useful not only for vaccine development, it is also applicable for basic virus transcription and replication studies. It is also applicable for development siRNA and gene therapy as well.

VI. ERA Genome Sequence

Using the method described herein, the unique sequence of the ERA rabies virus genome has been generated. This sequence is shown in SEQ ID NO: 1. The five proteins of the ERA rabies virus (SEQ ID NOs: 2-6) are encoded at the following positions of the genome: N, 71-1423; P, 1511-2407; M, 2491-3104; G, 3318-4892; and L, 5418-11801. The homology between ERA and SAD-B19 are: N 99.56%, P 98.65%, M 96.53%, G 99.05% and L 99.20%, respectively. One specific difference between ERA and SAD-B 19 is the intergenic region between G and the pseudo-gene, with the SAD-B19 G transcription stop/polyadenylation signal destroyed.

The ERA rabies virus whole genome sequence is the prerequisite for vaccine development and pathogenicity studies using reverse genetics VII. Optimized System for Production of Virus Examples 6 and 7 provide an optimized set of conditions for ERA virus production, in which titers reach as high as $10^{10}$ ffu per ml. In bioreactors, the recovered virus can grow to ~$10^9$ to $10^{10}$ ffu/ml. Such high levels of production are of paramount importance for oral vaccine development, so sufficient vaccine material can be produced in a reasonable amount of time with reasonable resource allocation.

The provided growth conditions can stably produce such high virus titer for both parental and recombinant ERA strains. These production data are very important for potential rabies oral vaccine development.

VIII. BSR-G Cell Line for Production of -G Virus

Although strains of RV with deletions of the G protein have been previously rescued from BHK cells, this was not possible with ERA strain virus lacking the G protein. After inoculation of mice intracerebrally or intramuscularly with ERA-G, no mice died or showed any rabies symptoms.

The ERA-G (without glycoprotein) can only grow in cells with the supplementation of the glycoprotein. Otherwise, the mutated virus cannot spread. To help ERA-G grow, a BSR-G cell line was established, which constitutively expressed ERA glycoprotein. Production of this cell line is described in the Examples below. This cell line is useful for recovery of RV strains such as ERA-G that are refractory to recovery in the absence of G, as well as for optimizing recovery of other strains.

IX. Reverse Genetics System for Engineering Rabies Virus Vaccines and Expression of Heterologous Proteins RNA cannot readily be manipulated directly by molecular biological methods. Traditional RNA virus vaccines are from naturally attenuated isolates, which are difficult to control and provide unpredictable results. Reverse genetics technology makes it possible to manipulate RNA viruses as DNA, which can be mutated, deleted or reconstructed according to deliberate designs. Every gene function can be studied carefully, independently, and in concert, which benefits vaccine development. Reverse genetics involves reverse transcription of the RNA viral genome into cDNA, and cloning into a vector, such as a plasmid. After transfection of host cells, the vector is transcribed into RNA, to be encapsidated by structural proteins, which can also be supplied by plasmids. The encapsidated RNA forms a ribonucleoprotein complex, which results in virions that can be recovered.

Although three systems for rabies virus (RV) reverse genetics have been published (Schnell et al, *The EMBO J.* 13, 4195-4203, 1994; Inoue et al., *J. Virol. Method.* 107, 229-236, 2003; Ito et al., *Microbiol. Immunol.* 47, 613-617, 2003), these systems are not readily adaptable to other strains. At present, no rabies virus strain has been recovered with the aid of helper plasmids from a different strain, even when the strains are closely related. Thus, for any specific virus strain mutation or vaccine development, a specifically tailored system must be developed.

The ERA strain is a good candidate for rabies oral vaccine development, but its residual pathogenicity is obvious. During the 1970s, the ERA RV underwent extensive vaccine development (Black and Lawson, *Can. J. Comp. Med.* 44:169-176, 1980; Charlton, and Casey, *Can. J. Vet. Res.* 20:168-172, 1978; Lawson, and Crawley, *Can. J. Vet. Res.* 36: 339-344, 1972). Both ERA and SAD-B19 are derived from SAD. In primary oral vaccine trials, SAD-B19 was effective in both raccoons and skunks, while ERA was not. Additionally, ERA kills two-week old mice administrated intra cerebrally (i.c.), as demonstrated in animal tests. These observations raise questions of the relationship between these two RV strains and the potential effects of subtle alterations. From full viral genome sequence comparison, ERA and SAD-B19 share extremely high nucleotide identity and amino acid homologies. To clarify the genetic basis of immunogenicity and pathogenicity of these highly related strains of rabies virus, an efficient reverse genetics system was developed for ERA, which differs from reverse genetics systems previously reported for rabies virus.

The rabies reverse genetics system disclosed herein is useful for a variety of purposes, including: (1) to attenuate ERA virus in a defined manner for vaccine development; (2) to produce ERA virus vectors for expressing heterologous ORFs (e.g., in the context of therapeutic compositions, such as vaccines and gene therapy); (3) to define the genetic basis of ERA RV pathogenesis; and (4) to determine the biological effects of genetic differences between the ERA and SAD viruses.

The reverse genetics system has some or all of the following characteristics, illustrated schematically in FIG. 1A using the exemplary ERA strain antigenomic cDNA.

This system is based a full length transcription plasmid plus a plurality of helper plasmids (e.g., five helper plasmids). The helper plasmids encode the N, P, L proteins, and optionally the G protein, as well as the T7 polymerase. Although the G protein is not necessary for virus rescue, it improves virus recovery efficiency or virus budding when included in transfection.

Transcription involves both cellular RNA dependent RNA polymerase II, which is available in mammalian cells, and T7 RNA polymerase, which is supplied by pNLST7 plasmids. The dual polymerases result in virus recovery efficiency is both high and stable.

In the transcription plasmid, hammerhead and hepatitis delta virus ribozymes flank a rabies virus (e.g., ERA strain) antigenomic cDNA, enabling the production of authentic 5' and 3' ends of antigenomic vRNA by transcription. The first ten nucleotides of the hammerhead sequence are designed to be complementary to the first ten nucleotides of the antisense genomic sequence. For example, the first ten nucleotides of the hammerhead sequence for the ERA antigenomic cDNA are: TGTTAAGCGT (SEQ ID NO: 19).

Two modified T7 RNA polymerase constructs have been established, which support virus recovery more efficiently than the wild type T7 RNA polymerase applied previously. One T7 RNA polymerase has been mutated from the first ATG to AT. The second T7 RNA polymerase has an eight amino acid nuclear localization signal (NLS) derived from the SV40 virus large T antigen fused after the first ATG from the parental T7: ATG CCAAAAAAGAAGAGAAAGGTAGAA (SEQ ID NO: 20). The NLS is underlined. Addition of the NLS results in the T7 RNA polymerase being present predominantly in the nucleus. Following transfection mechanism of the NLS modified plasmid, the DNA/transfection reagent complex binds to surface of the cell. Through endocytosis, the complex is taken into the endosome/lysosome, and the DNA is released into the cytosol. In the absence of the NLS, the majority of the transfected plasmids are retained in the cytosol and only a small percentage of the released DNA reaches the nucleus, where it is transcribed into RNA. After protein synthesis, the NLST7 RNA polymerase is transported back to the cell nucleus, and the helper plasmids (with T7/CMV promoters) in the nucleus will be transcribed by both NLST7 and cellular polymerase II. Thus, more mRNAs of the helper plasmids and cRNA of the full-length pTMF or its derivatives were synthesized and resulted in high efficiency of virus recovery.

After the initial expression of NLST7 by CMV promoter, NLST7 polymerase binds to pT7 for transcription of NLST7 gene. Through modification of the transcripts in the nucleus, more NLST7 mRNA is synthesized, resulting in more expression of NLST7 polymerase. The pT7 of the NLST7 polymerase as well as of the full length antigenomic transcription unit is under the control of the NLST7 polymerase, which acts as an "autogene." The autogene mechanism of NLST7 RNA polymerase is illustrated in FIG. 2. After expression of T7 RNA polymerase in the nucleus, the transfected T7 constructs continue to transcribe full length RNA template for N protein encapsidation and/or L protein binding, enhancing virus recovery efficiency.

The T7 polymerase, and all other plasmids, except the N protein encoding plasmid pTN, are placed under control of both CMV and T7 transcriptional regulatory elements. The N protein encoding nucleic acid is under the control of a T7 promoter and is translated in cap-independent manner based on an IRES (Internal Ribosome Entry Site). Cellular RNA polymeraseII alone can help the recovery of RV if all the plasmids were cloned under the control of the CMV promoter (19). In the ERA reverse genetics system disclosed herein, only pTN is under the control of the T7 promoter and was translated in a cap-independent manner. All other constructs are under control of both CMV and the T7 transcriptional regulatory elements. Typically, in RV, N synthesis is abundant and the ratio among N, P and L is approximately 50:25:1. To mimic the wild type viral transcription and assembly in RV reverse genetics, N expression should be the highest. With the aid of NLST7 polymerase and IRES translation mode, N protein was expressed efficiently after plasmid transfection. This reduces competition for transcription with house keeping genes in host cells, because the T7 transcription initiation signal does not exist in mammalian cells, and results in increased efficiency of T7 transcription.

To enhance production of viral proteins, the helper plasmids can be constructed to incorporate a Kozak sequence that has been optimized for the translation efficiency for each protein encoding sequence. Exemplary optimized Kozak sequences are shown in Table 2.

TABLE 2

Optimized Kozak sequences.

| constructs | promoters | Kozak context | SEQ ID NO: | Special characters |
|---|---|---|---|---|
| pTMF | CMV/T7 | n/a | n/a | HamRZ/HdvRZ at ends |
| pTN | T7/IRES | ACCACCATGG | SEQ ID NO: 21 | n/a |
| pMP | CMV/T7 | ACCACCATGA | SEQ ID NO: 22 | n/a |
| pMG | CMV/T7 | ACCACCATGG | SEQ ID NO: 21 | n/a |
| pML | CMV/T7 | ACCACCATGC | SEQ ID NO: 23 | n/a |
| pNLST7 | CMV/T7 | ACCACCATGA | SEQ ID NO: 22 | 8 amino acids NLS |

CMV/T7 symbolizes the CMV promoter ahead of a pT7 promoter. The HdRz indicates a hammerhead ribozyme and HDVRz is the hepatitis delta virus ribozyme. The pTMF is the full-length transcription plasmid, and the pTN, pMP, pMG, pML and pNLST7 are helper plasmids.

After five days posttransfection in the ERA reverse genetics system, the rescued virus reliably and repeatably grew to 10⁷ ffu/ml without further amplification.

X. Derivative Viruses

The complete mechanism of Rabies virus pathogenicity has not been fully characterized, making rational vaccine design problematic. For example, the RV glycoprotein appears to play a role both in pathogenicity and immunogenicity of rabies virus. Mutations (such as at position 333 of the glycoprotein) result in virus that does not cause lethal infection in adult mice (Ito et al., *Microl. Immunol.* 38, 479-482, 1994; Ito et al., *J. Virol.* 75, 9121-9128, 2001). However, overexpression of RV glycoprotein has been shown to lead to the enhancement of apoptosis and antiviral immune response (Faber et al., *J. Virol.* 76, 3374-3381, 2002). Thus ERA strain virus with a modified (for example, deleted, amino acid substituted) G protein could be a particular strain for vaccine development.

Recombinant rabies viruses with favorable properties can be designed using the reverse genetics system disclosed herein. Exemplary recombinant viruses disclosed herein include, in addition to the parental ERA strain, ERA without Psi-region (ERA–), ERAgreen1 (green fluorescent gene inserted in the Psi-region), ERAgreen2 (green fluorescent gene cloned at P-M intergenic region), ERA2g (containing an extra copy of G in Psi-region), ERAg3 (G mutated at 333 amino acid), ERA2g3 (containing an extra copy of mutated G in Psi-region), ERAgm (M and G genes switched in the genome), and ERAgmg (two copies of G in the rearranged ERAgm construct). These exemplary strains are illustrated schematically in FIG. 3.

Modified strains having deleted and/or mutated glycoproteins are particularly suited for use as immunogenic compositions for pre and post exposure treatment of rabies virus because such viruses are incapable of spreading between cells and causing disease. Additionally, modified viruses such as ERA2g3, which overexpresses the G protein due to a duplication of sequences encoding a mutated glycoprotein is predicted enhance apoptosis and elicit an increased anti-viral immune response.

For example, after intracerebral and intramuscular inoculation of mice with a deletion of G (ERA-G), no adverse events were observed. Moreover, the ERA-G protected mice from lethal challenge by a street RV strain. Thus, ERA-G appears to be a safer strain that ERA for vaccine development. Additionally, mutation of arginine at amino acid position 333 of the ERA G to glutamic acid (from nucleotides AGA to GAG, as in the ERAg3 and ERA2g3 strains) results in an attenuated virus. Attenuation was confirmed via animal inoculation tests. Because overexpression of RV G results in the enhancement of apoptosis and antiviral immune responses, attenuated viruses such as ERA2g3 that possess multiple copies of G are particularly favorable as vaccine candidates.

The system for rabies vaccine development described herein is not limited to modifications of the G gene, but is similarly applicable to each of the viral proteins. To facilitate a systematic approach to modifying the various protein components, detailed mapping of pathogenicity can be solved by reverse genetics based on the sequence data presented herein.

The reverse genetics system described herein also enables a rabies virus vector system for foreign (heterologous) gene expression. The described, non-limiting embodiment is based on the ERA virus. An extra transcription unit is shown herein to be functional in two different locations after incorporation into the ERA RV genome. In one embodiment, an extra transcription unit is incorporated in the position of the psi region (trans 1). In an alternative embodiment, an extra transcription unit is inserted into the RV P-M intergenic region.

In single stranded negative RNA viruses, the 3'-distal sequences of the genome serve mainly as a transcription promoter, while the 5'-terminal sequences of the genome serve as a replication promoter (Conzelmann and Schnell, *J. Virol.* 68:713-719, 1994; Finke et al., *J. Virol.* 71:7281-7288, 1997). Thus, trans2 occupies a position that results in stronger transcription for driving ORFs expression than trans1. Thus, the vectors disclosed herein can be used to modulate expression of a heterologous ORF to a desired level, simply by selecting the position into which the ORF is inserted in the vector. For example, when high levels of expression of a protein is desired, the trans 2 is typically an ideal position for the insertion of the heterologous ORF. Similarly, if more moderate levels of expression are desired, the heterologous ORF can be inserted into trans 1. Optimal expression levels for each ORF and for particular applications can be determined by one of skill in the art without undue experimentation.

Thus, the viral vectors provided herein are excellent construct for foreign gene insertion and expression, as is demonstrated herein with respect to expression of the green fluorescent protein gene. Although the utility and efficacy of the disclosed vectors is demonstrated with respect to GFP, it should be noted that the vectors are equally suitable for expressing any gene or ORF of interest.

As noted, the rabies-based heterologous expression system provided herein can be used to express any foreign (heterologous) protein(s). It is particularly contemplated, by way of example, that such heterologous genes are from another pathogenic organism, such as other pathogenic viruses, for instance SARS virus, Nipah virus, etc. In addition, the disclosed vectors can be used for delivery of other therapeutic genes, including for example, that encode proteins of therapeutic value or functional RNA molecules, such as siRNAs.

XI. Pharmaceutical and Immune Stimulatory Compositions and Uses Thereof

Pharmaceutical compositions including attenuated or fixed rescued viruses, virus nucleic acid sequences or virus polypeptides comprising at least one virus epitope are also encompassed by the present disclosure. These pharmaceutical compositions include a therapeutically effective amount of one or more active compounds, such as an attenuated or fixed virus, a virus polypeptides comprising at least one virus epitope, or one or more nucleic acid molecules encoding these polypeptides, in conjunction with a pharmaceutically acceptable carrier. It is contemplated that in certain embodiments, virus nucleic acid sequences or virus polypeptides comprising multiple virus epitopes will be useful in preparing the pharmaceutical compositions of the disclosure.

Disclosed herein are substances suitable for use as immune stimulatory compositions for the inhibition or treatment (either pre-exposure or post-exposure) of a virus infection, for example, a rabies virus infection.

In one embodiment, an immune stimulatory composition contains an attenuated or fixed rescued (recombinant) virus. In another embodiment, the composition contains an isolated or recombinant virus polypeptide including at least one virus epitope (such as a rabies virus G protein). In a further embodiment, the immune stimulatory composition contains a nucleic acid vector that includes at least one virus nucleic acid molecule described herein, or that includes a nucleic acid sequence encoding at least one virus epitope. In a specific, non-limiting example, a nucleic acid sequence encoding at least one virus epitope is expressed in a transcriptional unit, such as those described in published PCT Application Nos. PCT/US99/12298 and PCT/US02/10764 (both of which are incorporated herein in their entirety).

The immune stimulatory viruses, virus polypeptides, constructs or vectors encoding such polypeptides, are combined with a pharmaceutically acceptable carrier or vehicle for administration as an immune stimulatory composition to human or animal subjects.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immune stimulatory compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to about 1.0 ml. Those of ordinary skill in the art will know appropriate volumes for different routes of administration.

A relatively recent development in the field of immune stimulatory compounds (for example, vaccines) is the direct injection of nucleic acid molecules encoding peptide antigens (broadly described in Janeway & Travers, *Immunobiology: The Immune System In Health and Disease*, page 13.25, Garland Publishing, Inc., New York, 1997; and McDonnell & Askari, *N. Engl. J. Med.* 334:42-45, 1996). Vectors that include nucleic acid molecules described herein, or that include a nucleic acid sequence encoding a virus polypeptide comprising at least one virus epitope may be utilized in such DNA vaccination methods.

Thus, the term "immune stimulatory composition" as used herein also includes nucleic acid vaccines in which a nucleic acid molecule encoding a virus polypeptide comprising at least one virus epitope is administered to a subject in a pharmaceutical composition. For genetic immunization, suitable delivery methods known to those skilled in the art include direct injection of plasmid DNA into muscles (Wolff et al, *Hum. Mol. Genet.* 1:363, 1992), delivery of DNA complexed with specific protein carriers (Wu et al., *J. Biol. Chem.* 264:16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992; Eisenbraun et al., *DNA Cell Biol.* 12:791, 1993), and in vivo infection using cloned retroviral vectors (Seeger et al., *Proc. Natl. Acad. Sci.* 81:5849, 1984). Similarly, nucleic acid vaccine preparations can be administered via viral carrier.

The amount of immunostimulatory compound in each dose of an immune stimulatory composition is selected as an amount that induces an immunostimulatory or immunoprotective response without significant, adverse side effects. Such amount will vary depending upon which specific immunogen is employed and how it is presented. Initial injections may range from about 1 μg to about 1 mg, with some embodiments having a range of about 10 μg to about 800 μg, and still other embodiments a range of from about 25 μg to about 500 μg. Following an initial administration of the immune stimulatory composition, subjects may receive one or several booster administrations, adequately spaced. Booster administrations may range from about 1 μg to about 1 mg, with other embodiments having a range of about 10 μg to about 750 μg, and still others a range of about 50 µg to about 500 µg. Periodic boosters at intervals of 1-5 years, for instance three years, may be desirable to maintain the desired levels of protective immunity.

It is also contemplated that the provided immunostimulatory molecules and compositions can be administered to a subject indirectly, by first stimulating a cell in vitro, which stimulated cell is thereafter administered to the subject to elicit an immune response. Additionally, the pharmaceutical or immune stimulatory compositions or methods of treatment may be administered in combination with other therapeutic treatments.

The preparation of food-baits containing immune stimulatory compositions is also within the ordinary skill of those in the art. For example, the preparation of food-baits containing live RV vaccines is disclosed in Wandeler et al. (*Rev. Infect. Dis.* 10 (suppl. 4):649-653, 1988), Aubert et al. (pp. 219-243, in *Lyssaviruses* (Rupprecht et al., eds.), Springer-Verlag, New York, 1994), and Fu et al. (pp. 607-617, in New Generation Vaccines ($2^{nd}$ Edit.) (Levine et al., eds.), Marcel Dekker, Inc., New York, 1997), the entire disclosures of each of which are incorporated by reference herein.

XII. Kits

Also provided herein are kits useful in the detection and/or diagnosis of virus infection, for instance infection with a rabies virus or other lyssavirus. An example of an assay kit provided herein is a recombinant virus polypeptide (or fragment thereof) as an antigen and an enzyme-conjugated anti-human antibody as a second antibody. Examples of such kits also can include one or more enzymatic substrates. Such kits can be used to test if a sample from a subject contains antibodies against a virus-specific protein. In such a kit, an appropriate amount of a virus polypeptide (or fragment thereof) is provided in one or more containers, or held on a substrate. A virus polypeptide can be provided in an aqueous solution or as a freeze-dried or lyophilized powder, for instance. The container(s) in which the virus polypeptide(s) are supplied can be any conventional container that is capable of holding the supplied form, for instance, microfuge tubes, ampoules, or bottles.

The amount of each polypeptide supplied in the kit can be any appropriate amount, and can depend on the market to which the product is directed. For instance, if the kit is adapted for research or clinical use, the amount of each polypeptide provided would likely be an amount sufficient for several assays. General guidelines for determining appropriate amounts can be found, for example, in Ausubel et al. (eds.), *Short Protocols in Molecular Biology*, John Wiley and Sons, New York, N.Y., 1999 and Harlow and Lane, *Using Antibodies: A Laboratory Manual*, CSHL, New York, 1999.

The following examples are provided to illustrate certain particular features and/or embodiments. These examples should not be construed to limit the invention to the particular features or embodiments described.

EXAMPLES

Example 1

Sequencing of ERA RV

This example provides a description of a method for sequencing the full length genome of a rhabdovirus, particularly in this case a rabies virus.

Rabies virus strain ERA was obtained from the CDC archive and was propagated in baby hamster kidney (BHK-21) cells. Virus was harvested after four days infection at 37° C., in a 5% $CO_2$ incubator and was purified. Briefly, the cell supernatant was collected and centrifuged at 2,000 rpm for 15 minutes to remove the cell debris. The clear supernatant was subjected to further centrifugation at 18,000 rpm for 1 hour. The pellet was resuspended in PBS and subjected to rabies genomic RNA extraction.

Total RNA from ERA-infected BHK-21 cells was extracted with Trizol reagent (GIBCO Invitrogen) according to the protocol recommended by the manufacturer. ERA genomic RNA was purified from the concentrated ERA virus supernatant with a high pure viral RNA kit from Roche.

Integrity of the purified ERA genomic RNA was verified by gel electrophoresis and Northern blot by N, P, G, and M hybridization probes. Briefly, 5 µg of genomic RNA was loaded in a denatured RNA gel and transferred to a nylon membrane for hybridization. The probe was labeled using the Dig DNA labeling kit from Roche, according to manufacturer's instructions.

The 11 conserved nucleotides from the rabies virus 5' antigenome were designed as a primer for reverse transcription. The RT reaction was carried out with a first-strand cDNA synthesis kit from Invitrogen. The complete cDNA from the ERA genome was confirmed by Northern blot using N, P, M, and G probe hybridization, as well as the 11 conserved nucleotides as oligonucleotide probes labeled by Digoxin.

Two sets of primers were chosen for PCR reactions, which amplify the whole ERA genome in two contiguous fragments. One set of primers is composed of the 11 nucleotides at 5' antigenome end, Le5: ACGCTTAACAA (SEQ ID NO: 24) and BLp3: GTCGCTTGCTAAGCACTCCTGGTA (SEQ ID NO: 25). Another set contains the 11 complementary nucleotides at the 5' genome end, Le3: TGCGAATTGTT (SEQ ID NO: 26) and BLp5 CCAG GAGTGCTTAG-CAAGCGACCT (SEQ ID NO: 27). The Blp3 and Blp5 primers are located in a relatively conserved region in the rabies virus genome.

PCR fragments were purified and cloned into the TOPO vector purchased from Invitrogen. Sequencing was conducted in an ABI 310 sequencer and the sequence was assembled by BioEdit software or SeqMerge software from Accelrys in the GCG environment.

The complete aligned sequence of the ERA genome is provided in SEQ ID NO: 1. The positions of individual protein encoding sequences are provided in Table 3, with reference to SEQ ID NO: 1. The amino acid sequences of the N, P, M, G and L proteins are provided in SEQ ID NOs: 2 through 6, respectively.

TABLE 3

Positions of protein encoding sequences of rabies virus ERA strain

| Gene/genome | NT | Positions in rERA sequence |
|---|---|---|
| ERA | 11930 | 1-11930 |
| N | 1412 | 71-1423 |
| P | 962 | 1511-2407 |
| M | 789 | 2491-3104 |
| G | 1647 | 3318-4892 |
| Psi-region | 398 | |
| L | 6445 | 5418-11801 |
| Leader | 58 | |
| Trailer | 70 | |

This method can be used for both rabies and rabies-related viruses. Rabies and rabies-related viruses have at least seven putative species types. The provided sequence method can be used also for other negative stranded RNA viruses. This is because almost all the negative-stranded RNA virus genomes have approximately 12 conserved nucleotides at both distal ends, which similarly can serve as primers for RT-PCR. The primers will of course be different for different viral species, and the sequence of specific primers can be determined by one of ordinary skill based on the teachings herein.

Example 2

Construction of Plasmids for a Reverse Genetics System for Rabies Virus

This example describes the design and development of a Reverse Genetics System for Rabies Virus. Rabies virus strain ERA was obtained from the ATCC and was prepared as described (Wu et al., *J. Virol.* 76, 4153-4161, 2002). To obtain virus genome full-length virus cDNA, BSR cells (a clone of baby hamster kidney, BHK, cells) were infected with ERA strain virus and grown in Dulbecco's minimal essential medium supplemented with 10% of fetal bovine serum. Supernatants were recovered and subjected to centrifugation at 22,000 g for 1 hour. The virus pellets were collected for viral genomic RNA purification by use of a RNA virus extraction kit purchased from Qiagen (Valencia, Calif.) according to the manufacturer's instructions. The integrity of viral genomic RNA was confirmed by gel electrophoresis. Viral genomic cDNA was transcribed with the first-strand cDNA synthesis kit from Invitrogen (Carlsbad, Calif.). The reverse transcription (RT) reaction mixture was applied to amplification by the polymerase chain reaction (PCR) for the synthesis of full-length viral genomic cDNA, N, P, G and L genes, respectively. For assembling the full-length virus genomic cDNA, a pTMF plasmid was constructed in four sequential steps as illustrated schematically in FIG. 1B. Superscript III reverse transcriptase and proof reading platinum pfx polymerase (Invitrogen, Carlsbad, Calif.) were applied for cDNA transcript synthesis and consecutive PCR amplifications. For reverse transcription reactions, 1 μg of purified genomic RNA was used in the RT reaction mix and incubated at 50° C. for 80 min, followed by heating at 85° C. for 5 minutes to inactivate Superscript III. After the RT reaction, 1 unit of RNaseH was added to digest template RNA in the cDNA-RNA hybrids.

To generate full-length virus genomic cDNA, two overlapping fragments were amplified by RT-PCR as follows: Fragment1 (F1) was RT-PCR amplified with primers: Le5-Kpn (CCG<u>GGTACC</u>ACGCTTAAC AACCAGATCAAAGA; SEQ ID NO: 28, Kpn1 recognition site underlined) and Le3-Blp (TAGGTCGCTT<u>GCTAAGC</u>ACTCCTGGTAGGAC; SEQ ID NO: 29, Blp1 recognition site underlined). Fragment 2 (F2) was RT-PCR amplified with primers: Tr5-Blp (GTCCTACCAGGAGT<u>GCTTAGC</u>AAGCGACCTA; SEQ ID NO: 30, Blp1 recognition site underlined) and Tr3-Pst (AAAA<u>CTGCAG</u>ACGCTTAACAAATAAACAACAAAA; SEQ ID NO: 31, Pst1 recognition site underlined). After successful synthesis of the above two fragments, F1 digested by Kpn1 and Blp1 restriction enzymes was subjected to gel purification and cloned to pBluescriptIISK(+) phagemid (Stratagene, La Jolla, Calif.) to form the pSKF1 plasmid. The gel purified F2 fragment, cut by Blp1 and Pst1 was consecutively cloned to the pSKF1 plasmid to form the full-length viral antigenomic cDNA. Hammerhead ribozyme (oligo1, CAAG <u>GCTAGC</u>TGTTAAGCGTCTGATGAGTCCGTGAGGAC GAAACTATAGGAAAGGAAT TCCTATAGTC GG<u>TACC</u>ACGCT; SEQ ID NO: 32, Nhe1 and Kpn1 recognition sites underlined; Oligo2, AGCGT GG<u>TACC</u>GACTATAGGAATTCCTTTCCTATAGTTTCGT CCTCACGGACTCATCAGA CG<u>CTTAACA</u> <u>GCTAGC</u>CTTG; SEQ ID NO: 33, Kpn1 and Nhe1 recognition sites underlined) was synthesized containing a Nhe1 recognition site at the 5' end and a Kpn1 site at the 3' end. This was fused ahead of the 5' end of the F1 fragment. A hepatitis delta virus ribozyme (oligo3, GAC <u>CTGCAG</u>GGGTCGGCATGGCATCTCCACCTCCTCGCG GTCCGACCTGGGCATCCGAA GGAGGACGCACGTC-CACTCGGATGGCTAAGGGAGGGC G<u>CGGCCGC</u>ACTC; SEQ ID NO: 34, Pst1 and Not1 recognition sites underlined; Oligo4, GAGT <u>GCGGCCGC</u>GCCCTCCCTTAGCCATCCGAGTGGACG TGCGTCCTCCTTCGGATGCC CAGGTCGGACCGC-GAGGAGGTGGAGATGCCATGCCGACCC <u>CTGCAG</u>GTC; SEQ ID NO: 35, Not1 and Pst1 recognition sites underlined)(Symons, *Annu. Rev. Biochem.* 61: 641-671, 1992) was synthesized, having a Pst1 site at its 5' end and a Not1 site at its 3' end, and was fused to the 3' end of the F2 fragment. The connective Kpn1 recognition site, between the hammerhead ribozyme and the F1 fragment, and the Pst1 site between the F2 fragment and the hepatitis delta virus ribozyme, were deleted by site-directed mutagenesis. The full-length viral antigenomic cDNA was sandwiched by the hammerhead and hepatitis delta virus ribozymes. This was removed and cloned to the pBluescriptIISK(+) phagemid to make a pSKF construct. The full viral antigenomic cDNA with two ribozymes was fused downstream of the T7 transcription initiation site under control of the CMV immediate-early promoter in pcDNA3.1/Neo (+) plasmid (Invitrogen, Carlsbad, Calif.). This last step finished the construction of the pTMF plasmid.

The wild type ERA viral genome includes a polyA tract of eight residues (polyA$_8$) in the intergenic region between the G and Psi regions. To distinguish the rescued ERA (rERA) virus from the parental strain, a stretch of seven A (polyA$_7$) was introduced to the pTMF construct by deletion of one A instead of the original polyA$_8$. After rERA virus was recovered, RT-PCR was performed and subsequent sequence data confirmed the existence of the introduced poly A$_7$ sequence marker.

pTN plasmid: The N gene was amplified by RT-PCR with primers (5N: ACCA<u>CCATGG</u>ATGCCGACAAGATTG; SEQ ID NO: 36, Nco1 recognition site and start codon underlined; and 3N: GGC<u>CCATGG</u>TTATGAGTCACTCGAATATGTCTT; SEQ ID NO: 37, Nco1 recognition site and stop codon underlined) and cloned to the pCITE-2a(+) (Cap-Independent Translation Enhancer) plasmid (Novagen, Madison Wis.).

pMP plasmid: the P gene was amplified by RT-PCR with primers (5P: TT<u>GGTACC</u>ACC<u>ATG</u>AGCAAGATCTTTGTCAATC; SEQ ID NO: 38, Kpn1 recognition site and start codon underlined; and 3P: GGAGAG<u>GAATTC</u>TTAGCAAGATGTATAGCGATTC; SEQ ID NO: 39, EcoR1 recognition site and stop codon underlined) and cloned to the pcDNA3.1/Neo (+) plasmid.

pMG plasmid: the G gene was amplified by RT-PCR with primers (5G: TT<u>GGTACC</u>ACC<u>ATG</u>GTTCCTCAGGCTCTCCTG; SEQ ID NO: 40, Kpn1 recognition site and start codon underlined; and 3G: AAAA<u>CTGCAG</u>TCACAGTCTGGTCTCACCCCCAC; SEQ ID NO: 41, Pst1 recognition site and stop codon underlined) and cloned to the pcDNA3.1/Neo (+) plasmid.

pML plasmid: the L gene was amplified by RT-PCR with primers (5L: ACC<u>GCTAGC</u>ACCACC<u>ATG</u>CTCGATCCTGGAGAGGTC; SEQ ID NO: 42, Nhe1 recognition site and start codon underlined; and 3L: AAAA<u>CTGCAG</u>TCACAGGCAACTGTAGTCTAGTAG; SEQ ID NO: 43, Pst1 recognition site and stop codon underlined) and cloned to the pcDNA3.1/Neo (+) plasmid.

pT7 plasmid: genomic DNA from bacteria BL-21 (Novagene, Madison, Wis.) was extracted with the Dneasy Tissue Kit (Qiagen, Valencia, Calif.) according to the manufacturer's instructions. The T7 RNA polymerase gene was amplified from the purified genomic DNA by PCR with primers (5T7: TCGCTAGCACCACC ATGAACACGATTAACATCGCTAAG; SEQ ID NO: 44, Nhe1 recognition site and start codon underline; and 3T7: GATGAATTCTTACGCGAACGCGAAGTCCGACTC; SEQ ID NO: 45, EcoR1 recognition site and stop codon underlined) and cloned to the pcDNA3.1/Neo (+) plasmid.

pNLST7 plasmid: an eight amino acid nuclear location signal (NLS), derived from SV40 large T antigen, was added to the N terminus of the T7 RNA polymerase by PCR amplification, using the pT7 plasmid as the template, with primers (5T7NLS: TCGCTAGCCACCATG CCAAAAAAGAAGAGAAAGGTAGAAAACACGATTAA CATCGCTA AGAAC; SEQ ID NO: 46, NLS underlined and 3T7 primer). The amplified fragment was designated NLST7, and was cloned to pcDNA3.1/Neo (+) to form the pNLST7 construct.

pGFP plasmid: Monster Green Fluorescent Protein (GFP) plasmid phMGFP was purchased from Promega (Madison, Wis.). The GFP gene was amplified by PCR with primers (GFP5: AAAACTGCAGGCCACC ATGGGCGTGATCAAG; SEQ ID NO: 47, Pst1 recognition site and start codon underlined; and GFP3: CCGCTC GGTACCTATTAGCCGGCCTGGCGGG; SEQ ID NO: 48, Kpn1 recognition site and stop codon underlined) and cloned to the pcDNA3.1/Neo (+) plasmid.

All plasmid constructs were sequenced at least three times to confirm the absence of unexpected mutations or deletions after cloning, site-directed mutagenesis, or gene deletion. Additionally, presence of a marker sequence consisting of a polyA tract having seven adenosine residues rather than the eight residues observed in the wild type ERA genome between the glycoprotein and Psi region was confirmed.

Example 3

T7 RNA Polymerase Expression in BSR Cells

This example demonstrates that addition of a nuclear localization signal to the phage T7 RNA polymerase directs expression of the polymerase in the nucleus of transfected cells. Transfection of BSR cells was performed as described by Wu, et al. (*J. Virol.* 76, 4153-4161, 2002). Briefly, BSR cells near 80% confluence in a six-well-plate were transfected with 0.5 μg of pT7 or pNLST7 plasmid per well, respectively. At 48 hours after transfection, cells were fixed with 80% chilled acetone for 1 h and dried at room temperature. Mouse monoclonal antibody against the T7 RNA polymerase and goat anti mouse IgG-FITC conjugate were successively added, and were washed in the two-step indirect fluorescent staining procedure. Results were recorded after UV microscopy. The T7 RNA polymerase expressed from pT7 without a nuclear localization signal was observed primarily in the cytosol, whereas NLST7 polymerase including a nuclear localization signal was present predominantly in the nucleus of cells. These results indicated that addition of an NLS effectively targeted the T7 RNA polymerase to the nucleus of transfected cells.

Example 4

Establishment of Constitutively Expressed ERA Glycoprotein BSR Cell Line

This example describes the design and production of a BHK cell line that constitutively expresses the ERA glycoprotein. A BHK cell line that expresses the ERA glycoprotein was constructed using the Flp-In™ system (Invitrogen, Carlsbad, Calif.). Briefly, Flp-In™-BHK cells (containing a single integrated Flp recombination target site) were grown to approximately 20% confluence in one six-well-plate and maintained in common DMEM medium, supplemented with 100 μg/ml of Zeocin, before transfection. The ERA G gene was amplified by PCR using pMG plasmid as template with primers EF5G5 (CACCATGGTTCCTCAGGCTCTCCTG; SEQ ID NO: 49) and EF5G3 (TCACAGTCTGGTCTCAC-CCCCAC; SEQ ID NO: 50), and cloned to a pEF5/FRT/V5-D-TOPO vector (Invitrogen, Carlsbad, Calif.) to create the pEFG construct. The pOG44 plasmid expressing Flp recombinase together with pEFG at the ratio of 10:1 was co-transfected to the Flp-In™-BHK cells. After transfection, the cells were kept in DMEM without Zeocin, but with hygromycin B at 400 μg/ml. After 48 hours, the cells were split so that no more than 20% confluency occurred the next day. The cells were grown in hygromycin B selective medium at 37° C. for approximately one week. The target ERA G expression was detected by indirect fluorescent staining with human anti-G monoclonal antibody and goat anti-human IgG-FITC conjugate. The cell line constitutively expressing the G was designated as BHK-G, and was used for the growth of ERA-G virus.

Example 5

Defined Modification of Rabies Virus Evelyn-Rokitnicki-Abelseth (ERA) Strain

In addition to the parental ERA virus strain described above, derivative virus strains were developed using the reverse genetics system disclosed herein. Several exemplary modified viruses were produced, namely ERA-(deletion of the whole psi-region), ERAgreen1 (green florescent protein gene inserted in ERA viral genome psi region), ERAgreen2 (green florescent protein gene inserted in phosphoprotein and matrix protein intergenic region), ERA2g (containing an extra copy of glycoprotein in the psi-region), ERAg3 (with a mutation at amino acid 333 in glycoprotein), ERA2g3 (with an extra copy of mutated glycoprotein at Aa333 in psi-region), ERA-G (with glycoprotein deleted) ERAgm (M and G genes switched in the genome), and ERAgmg (two copies of G in the rearranged ERAgm construct) These derivatives are illustrated schematically in FIG. 3. By optimizing the growth conditions as described, all of the rescued viruses can be obtained at virus titers of $10^9$ to 1010 ffu/ml in both tissue culture flasks and bioreactors.

Gene Deletion and Site-Directed Mutagenesis in the Reverse Genetics System

Deletion of the Psi Region of the Rabies Virus ERA Genome

The complete Psi-region of the rabies virus ERA genome was deleted as follows: 3'Δψ fragment was amplified using pTMF as template by PCR with primers (5Δψ: CCCTCTGCAGTTTGGTACCGTCGAGAAAAAAACATTAGATCAGAAG; SEQ ID NO: 51, Pst1 and Kpn1 recognition sites underlined; and Le3-Blp primer) and was cloned to pCR-BluntII-TOPO vector (Invitrogen, Carlsbad, Calif.) for the construction of pPΔ5ψ plasmid. The 5'Δψ fragment was amplified using the same template by PCR with primers (SnaB5: ATGAACTTTCTACGTAAGATAGTG; SEQ ID NO: 52, SnaB1 recognition site underlined; and 3Δψ: CAAACTGCAGAGGGGTGTTAGTTTTTTTCAAAAAGAACCCCCCAAG; SEQ ID NO: 53, Pst1 recognition site underlined) was successively cloned to the above pPΔ5ψ plasmid to finish the construction of the pPΔψ plasmid. The fragment recovered by SnaB1 and Pst1 restriction enzyme digestion from the pPΔψ plasmid substituted the counterpart in the pSKF construct to make the pSKFΔψ plasmid. The whole DNA fragment containing the ERA genomic cDNA, digested by Nhe1 and Not1 from pSKFΔψ plasmid, was re-cloned to the pcDNA3.1/Neo (+) plasmid to finalize the construction of pTMFΔψ. For verification of the rescued strain lacking Psi, designated Era-, primers covering the Psi-region were applied in RT-PCR with total RNA from ERA-infected BSR cells. A 400 bp fragment corresponding to the Psi region was amplified only from rERA virus, but not from ERA. Sequence data verified the complete deletion of the Psi-region.

Deletion of the Glycoprotein Gene in the Rabies Virus ERA Genome:

The 5'gΔψ fragment was amplified using pSKF as template by PCR with primers (SnaB5 primer, and 3Δg: CAAACTGCAGAGGGGTGTTAGTTTTTTTCACATCCAAGAGGATC; SEQ ID NO: 54). After digestion by SnaB1 and Pst1 restriction enzymes, this recovered fragment was cloned to replace its counterpart in the pSKFΔψ construct. The 3'gΔψ fragment was amplified using the same template by PCR with primers (5Δg: CCTCTGCAGTTTGGTACCTTGAAAAAAACCTGGGTTCAATAG; SEQ ID NO: 55, and Le3-Blp primer), and was consecutively cloned to the modified pSKFΔψ, to replace its counterpart. The final fragment, recovered by SnaB1 and Blp1 restriction enzymes cut from this pSKFΔψ without the G gene, was re-cloned to pcDNA3.1/Neo (+) plasmid to form the pTMFΔg construct for virus recovery.

Glycoprotein Gene Site-Directed Mutagenesis:

Site directed mutagenesis to introduce a three nucleotide change from AGA to GAG at amino acid position 333 of the glycoprotein was performed as previously described (Wu et al., *J. Virol.* 76: 4153-4161, 2002). The primers in the mutagenesis reaction were M5G primer: CTCACTACAAGTCAGTCGAGACTTGGAATGAGATC (SEQ ID NO: 56, the three mutated nucleotides in bold) and M3G primer: GACTGACTTTGAGTGAGCATCGGCTTCCATCAAGG (SEQ ID NO: 57). For the recovered strain (ERAg3), three nucleotide changes from AGA to GAG at amino acid position 333 (aa333) were confirmed by sequencing after RT-PCR with primers 5G and 3G. After confirmation by DNA sequencing, the mutated G was cloned back to the pTMF plasmid to make the pTMFg3 construct for virus recovery. The glycoprotein encoded by this mutated G gene is represented by SEQ ID NO: 58.

Incorporation of an Exogenous Orf into ERA Rabies Virus Genome

To express exogenous ORFs in RV, an extra transcription unit with Pst1 and Kpn1 recognition sites were created and incorporated at the Psi or P-M gene intergenic regions, respectively. In brief, for creation of an extra transcription unit at the Psi-region, the same steps were followed, except for the 5Δψ fragment amplification step, the 3Δψ primer was changed to 3Δψcis: CCAAACTGCAGCGAAAG-GAGGGGTGTTAGTTTTTTTCATGAT-GAACCCCCCAAGGGGAGG (SEQ ID NO: 59). The final construct without the Psi-region, but with an extra transcription unit, was designated as pMTFΔψcis. The GFP, ERA G, or mutated G at amino acid residues 333 were cloned to this transcriptional unit to form pMTFgfp1, pMTF2g, pMTFg3, pMTF2g3 constructs, respectively, for virus rescue.

To incorporate an extra transcription unit to the P-M intergenic region, the cisp5 fragment was amplified using pMTF as template with primers cis55: GACTCACTATAGGGAGACCCAAGCTGGCTAGCTGTTAAG (SEQ ID NO: 60), cis53: CCAAACTGCAGCGAAAGGAGGGGTGTTAGTTTTTTTCATGTTGACTTTAGGACATCTCGG (SEQ ID NO: 61), and was cloned in substitution of its counterpart in the pMTF plasmid. The cisp3 fragment was amplified and cloned in a similar way with primers cis35: CCTTTCGCTGCAGTTTGGTACCGTCGAGAAAAAAACAGGCAACACCACTGATAAAATGAAC (SEQ ID NO: 62) and cis33: CCTCCCCTTCAAGAGGGCCCCTGGAATCAG (SEQ ID NO: 63). After assembling the cisp5 and cisp3 fragments together, the final construct was designated as pMTFcisp, for accepting ORFs. The recombinant construct containing the GFP gene was named pTMFgfp2 for virus recovery.

To produce an ERA derivative, designated ERAgm, in which the glycoprotein encoding sequence was reversed in order with the matrix protein encoding sequence, the glycoprotein gene was deleted as described above. The G gene (amplified as disclosed above) was then inserted between P and M genes, yielding a rabies virus genome in the order of N-P-G-M-L. Similarly, the same strategy was applied to produce the ERAg3m derivative, in which the glycoprotein has a triple nucleotide mutation at 333 amino acid residue (from AGA to GAG) by substituting the G gene produced by site directed mutagenesis as described above. To produce the ERAgmg construct, an extra copy of glycoprotein gene was inserted between P and M genes, and made the rabies virus genome in the order of N-P-G-M-G-L.

An extra transcription unit was modified and incorporated into two different regions of the ERA genome, namely psi-region and P-M intergenic region. When heterologous ORFs are incorporated into these transcription units, designated trans 1 and trans 2, respectively, efficient production of the encoded product results.

Sequence of the transcription unit is:

```
CTAACACCCCTCCTTTCGCTGCAGTTTGGTACCGTCGAGAAAAAAA (SEQ ID NO: 64, Pst1 and Kpn1 were underlined).
```

Example 6

Recovery of Parental and Derivative Viruses

This example describes the recovery of parental ERA virus and exemplary derivatives using the reverse genetics system disclosed herein. BSR cells were transfected at near 80% confluence in six-well-plates with viral full length transcription plasmid pTMF (pTMFΔψ, pTMFg3, pTMF2g, pTMF2g3, pTMFgfp1, pTMFgfp2, pTMFΔg, pTMFgm, or pTMFgmg, respectively) at 3 g/well, together with five helper plasmids: pTN (1 μg/well), pMP (0.5 μg/well), pML (0.5

μg/well), pMG (0.5 μg/well) and pNLST7 (1 μg/well) by TransIT-LT1 reagent (Mirus, Madison, Wis.) following the protocol recommended by the manufacturer. Four days after transfection, 1 ml of fresh BSR cell suspension (about 5×10$^5$ cells) was added to each well. Cells were incubated at 37° C., 5% $CO_2$ for 3 days. Cell supernatants were collected for virus titration.

To titrate the recovered virus, monolayers of BSR cells in LAB-TEK eight-well-plates (Naperville, Ill.) were infected with serial 10-fold dilutions of virus supernatant and incubated at 37° C., 0.5% $CO_2$ for 48 h. Cells were fixed in 80% chilled acetone at room temperature for 1 h and stained with FITC-labeled anti-rabies virus N monoclonal antibody at 37° C. for 30 minutes. After three rinses of the plates with PBS, stained foci were counted using direct fluorescent microscopy. Details for direct RV fluorescent assay (DFA) can be found on the world wide web at cdc.gov/ncidod/dvrd/rabies/professional/publications/DFA-diagnosis/DFA_protocol.htm.

All of the viruses except ERA-G were recovered at high titer from cultured BSR cells as indicated in Table 3. Surprisingly, rearrangement and switching of the G gene with the M gene did not hinder recovery of recombinant derivative ERA virus. Rearrangement of the G gene in the RV genomes was previously not believed feasible due to cell death from overexpression of G protein (Faber et al., *J. Virol* 76:3374-3381, 2002). However, these results demonstrate that rearrangement is possible in the ERA strain. Accordingly, it is likely that RV gene shuffling is possible not only for the G gene, but also for other genes as well.

Figure 4A:
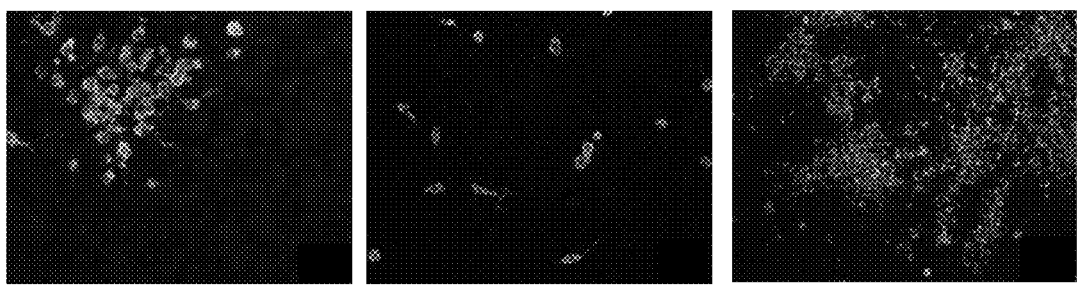
FIG. 4A. Analysis of recovered ERA-G virus in transfected cells, spread and growth in a BHK-G cell line. In A, the ERA-G viral foci were restrained even after seven-day post transfection with plasmids for virus recovery. In B, rescued ERA-G virus did not spread after passage in normal BSR cells. Only individual cells were stained by DFA. In C, the ERA-G virus grew well in the constitutive BHK-G cell line.
Figure 4B:
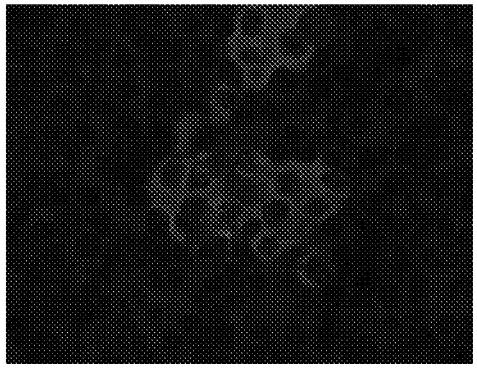
FIG. 4B. Analysis of G expression in a BHK-G cell line. By indirect fluorescent staining, the ERA rabies virus G was expressed in the cytoplasm in a stable cell line BHK-G.
Figure 4C:
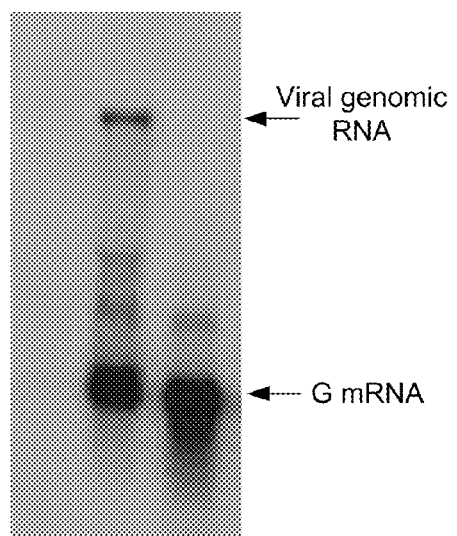
FIG. 4C. Analysis of G mRNA in ERA-G virus-infected cells by Northern blot with a G probe. Lane 2 shows that the G gene mRNA was detected in ERA-G virus infected BHK-G cells, while virus genomic RNA was not. Lane 1 was the control of total RNA from ERA—rabies virus-infected BHK-G cells, in which both G mRNA and viral genomic RNA were detected.

The ERA-G (without G) virus was recovered after plasmid transfection following the same procedure as for the other viral constructs rescue, but virus foci were very limited and restrained in local areas after the first round of transfection. The rescued virus was not capable of spreading further to the nearby healthy BSR cells (FIG. 4A) even after one week of incubation at 37° C., 5% $CO_2$. Infection of normal BSR cells with the above transfection supernatants presented single cell staining in the DFA test, which suggested the recovered virus was incapable of spread. To amplify the ERA-G virus, a BHK cell line constitutively expressing ERA G was established as described in Example 4 (designated BHK-G). By indirect fluorescent assay screening, a pool of BHK cells expressing G were selected and maintained for amplification of ERA-G virus (FIG. 4B). With the aid of the BHK-G cell line, ERA-G virus grew to 10$^7$ ffu/ml. Total RNA from ERA-G virus-infected BHK-G cells was extracted for Northern blot analysis (FIG. 4C) with a G gene probe. The G gene was absent in the viral genomic RNA, however G mRNA was detected, which came from infected supportive BHK-G cells. In purified ERA-G viral genomic RNA, no hybridization signal was detected by G probe, indicating the deletion of the G gene in the ERA genome.

Example 7

Growth of Rescued ERA Virus and its Derivatives to High Titer in a Bioreactor

Figure 5:
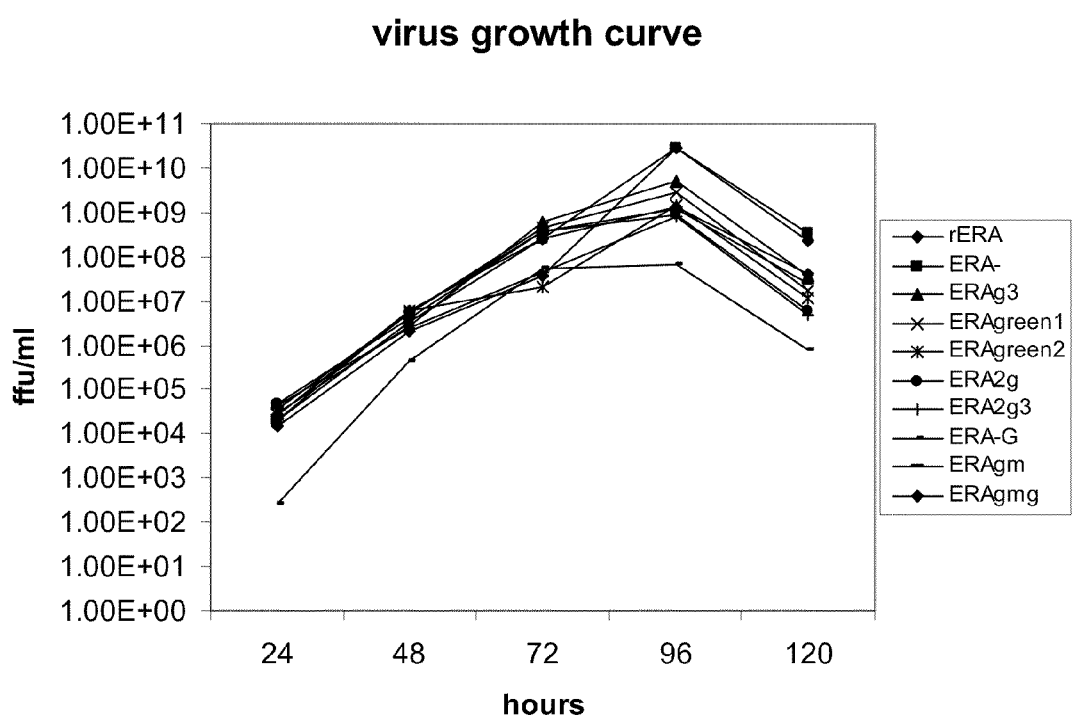
FIG. 5. Single-step virus growth curve All recovered rabies virus ERA strains grew to $10^9$ or $10^{10}$ ffu/ml, but the ERA-G only reached $10^7$ ffu/ml.

In oral vaccine development, high virus titer is typically required to elicit reliable immunity after administration. This example demonstrates that the ERA virus and derivatives can be grown to high titer in a bioreactor at volumes applicable to commercial scale-up. All 10 rescued ERA viruses were amplified in a bioreactor, CELLine AD1000 (IBS Integra Bioscience, Chur, Switherland) to titers ranging from 10$^7$ to 10$^{10}$ ffu/ml. In brief, BSR cells were transfected with the exemplary antigenome transcription vectors and helper vectors, as described above. Cells were inoculated at a multiplicity of infection of 1 virion per cell, at a concentration of 10$^6$ cells/ml in one tenth the bioreactor vessel volume. Transfected cells were grown at 37° C., 5% $CO_2$ in DMEM supplemented with 10% fetal bovine serum. The supernatant was harvested every three to five days for between two and three harvests. The deficient ERA-G grew less well compared with other viruses, with only 10$^8$ ffu/ml for the ERA-G (TABLE 3. and FIG. 5).

TABLE 3

Full-length plasmid constructs and corresponding rescued viruses

| Plasmid constructs | Rescued viruses | Titers ffu/ml from cultured cells | Titers ffu/ml in bioreactors |
| --- | --- | --- | --- |
| pTMF | rERA | 5 × 10$^7$ | 3 × 10$^{10}$ |
| pTMFΔΨ | ERA- | 6.3 × 10$^7$ | 3.2 × 10$^{10}$ |
| pTMFg3 | ERAg3 | 3 × 10$^6$ | 1.8 × 10$^9$ |
| pTMFgfp1 | ERAgreen1 | 3.5 × 10$^6$ | 5.6 × 10$^9$ |
| pTMFgfp2 | ERAgreen2 | 2 × 10$^7$ | 6.2 × 10$^9$ |
| pTMF2g | ERA2g | 1.6 × 10$^6$ | 3.9 × 10$^9$ |
| pTMF2g3 | ERA2g3 | 8 × 10$^7$ | 4.6 × 10$^9$ |
| pTMFΔg | ERA-G | 1.2 × 10$^2$ | 1.5 × 10$^7$ |
| pTMFgm | ERAgm | 5.31 × 10$^6$ | 1.9 × 10$^9$ |
| pTMFgmg | ERAgmg | 3.1 × 10$^6$ | 1.2 × 10$^9$ |

Example 8

Expression of Exogenous Proteins from Extra Transcriptional Units in Rabies Virus This example demonstrates the expression of recombinant proteins from a heterologous ORF inserted into a rabies virus vector. In this example, the ERA virus vector is used as a prototype rabies virus vector. To construct ERA virus as a vector for accepting ORFs, a conservative RV transcriptional unit between the N and P genes was modified and introduced into the ERA genome at two different locations: 1) at the psi region (trans 1), and 2) at the P-M intergenic region (trans 2). The transcriptional unit was designed to possess two unique restriction enzyme recognition sites to facilitate introduction of heterologous polynucleotide sequences:

(TTTTTTTGATTGTGGGGAGGAAAGC<u>GACGTC</u>AAA<u>CCATGG</u>CAGCTCTTT

TTTT: SEQ ID NO: 65, Pst1 and Kpn1 sites underlined).

Figure 6:
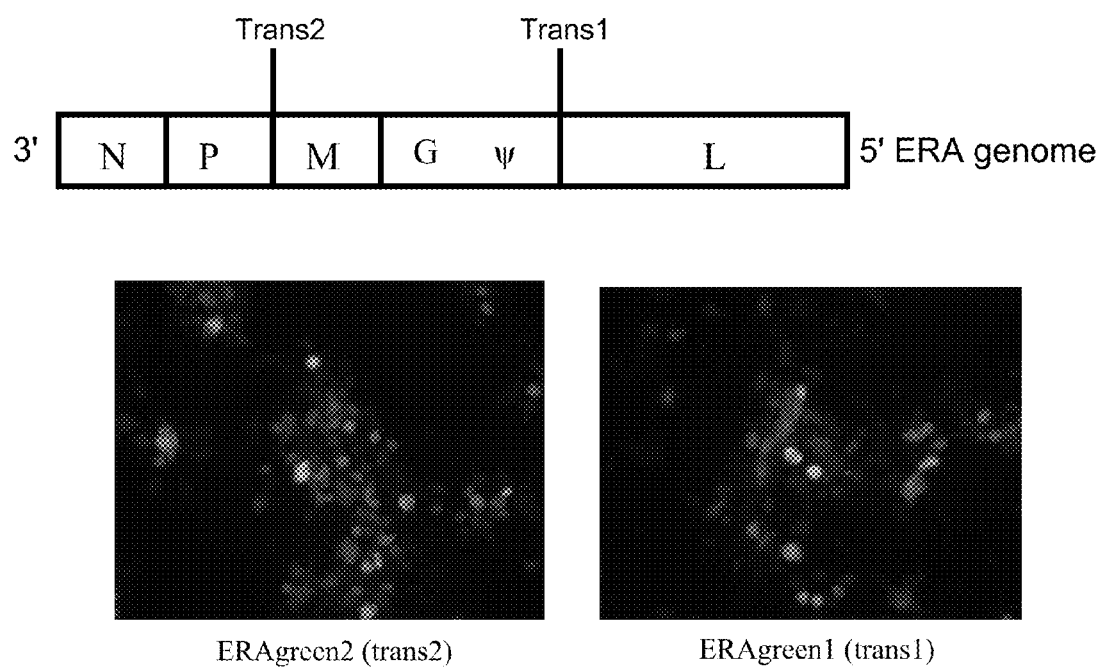
FIG. 6. Green foci in ERAgreen1/ERAgreen2 rabies virus-infected BSR cells Trans1 is the transcriptional unit incorporated at the Psi and L intergenic regions. Trans2 is the transcriptional unit at the P and M intergenic region. Both ERAgreen2 and ERAgreen1 expressed the GFP protein stably in virus-infected BSR cells, while the occurrence of the green foci of ERAgreen2 was 48 hours earlier after virus infection than in ERAgreen1.

In a first example, the GFP gene was cloned into this unit for virus recovery, since GFP expression could be observed directly under a UV microscope when the transfected BSR cells were still incubating. Expression of the GFP protein was directly visible by fluorescent microscopy with an excitation filter of 470±20 nm. The ERAgreen2 (GFP gene inserted after P gene in RV genome-trans 2)-infected cells showed clear green foci after three days of plasmid transfection, while ERAgreen1 (GFP gene inserted after G gene in the "traditional" Ψ region-trans 1) did not present obvious green foci until five days post-transfection (FIG. 6). The introduced transcriptional unit was functional in the RV genome at both locations, although expression and accumulation was apparent more rapidly when GFP was expressed from trans 2. Thus, these results also indicate that the level of expression from a heterologous ORF can be modulated by selecting the transcription unit into which the ORF is cloned.

Figure 7:
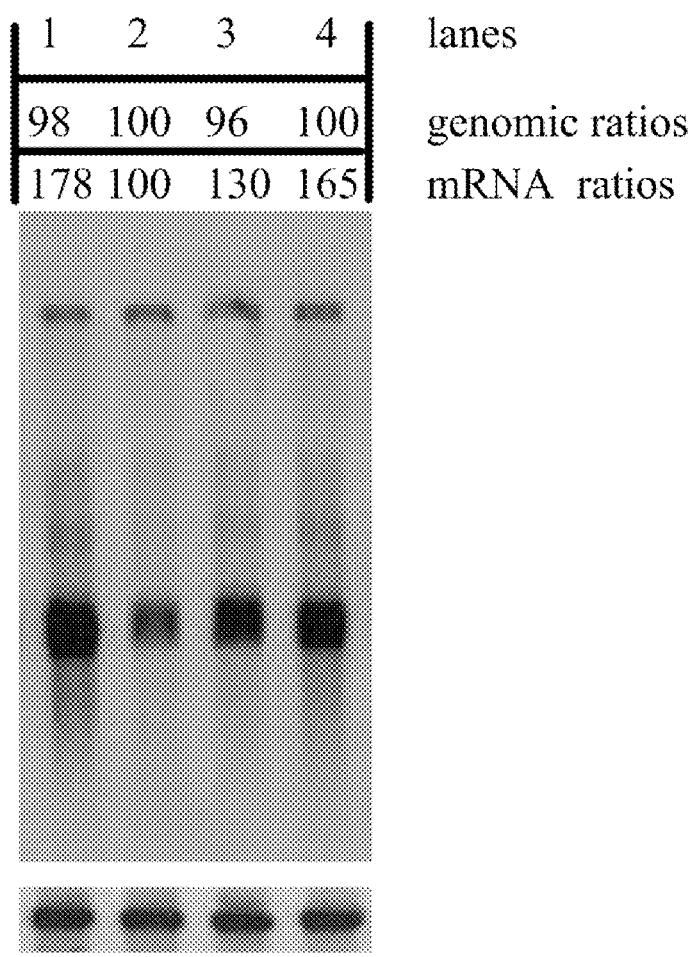
FIG. 7. Analysis of G mRNA expression in double G, and G, M rearranged ERA rabies viruses. In the Northern blot with a G probe, the measurement by density photometry of G mRNA in ERA2g (lane 1), ERAgm (lane 3) and ERA2g3 (lane 4) represented enhanced mRNA levels, compared with ERA-virus-infected cells (lane 2). The ratios were calculated by the use of ERA-virus as 100%.

In other examples, 1) an additional copy of ERA G; or 2) an additional copy of ERA G with an amino acid substitution at position 333, was incorporated into the ERA viral genome. The successfully rescued viruses were named ERA2g and ERA2g3, respectively. Since quantitation of viral G expression was not practical, the relative increase in expression levels of G in ERA2g and ERA2g3-infected cells was confirmed by Northern-blot with a G probe. In brief, the ERA G gene probe was labeled using the Dig DNA Labeling Kit (Roche, Indianapolis, Ind.) and imaged with Dig Nucleic Acid Detection Kit (Roche, Indianapolis, Ind.) and was measured by density spectrophotometry (FIG. 7). The tandem linked G genes in the recovered viruses were also confirmed by RT-PCR with 5G and 3G primers. A predominant band indicating a single G copy was observed at 1.5 kb. In addition, a second weaker band was observed at approximately 3.0 kb indicative of the two Gs in a tandem arrangement.

These results demonstrate that introduction of transcription units into the ERA genome can be used to express diverse heterologous proteins from introduced ORFs. Furthermore, expression of the protein encoded by the heterologous ORF is modulated by the position into which the ORF is inserted. Thus, ERA virus is a widely adaptable vector for the expression of recombinant proteins.

Example 9

In Vivo Immune Response to Engineered Viruses

This example demonstrates the in vivo effects of inoculation with the engineered ERA virus and exemplary derivatives. All animal care and experimental procedures were performed in compliance with the CDC Institutional Animal Care and Use Guidelines. Eighty three-week old mice were divided into 8 groups of 10 each for intramuscular (i.m) administration of recovered viruses (106 ffu of virus per mouse). Ten healthy mice were held as uninfected mock controls. For the ERA and ERAg3 constructs, additional intracerebral (i.c) injections of the same dose of viruses were applied to another group of ten three-week old mice. In two-day old suckling mice, only the ERAg3 and ERA-G viruses were inoculated intracerebrally, with the same dose. Animals were checked daily for illness. Ill animals were euthanized by $CO_2$ intoxication and brains were removed for rabies virus diagnosis. Ten days after infection, blood was collected by the retro orbital route and sera obtained for neutralizing antibody assays, following the standard rapid fluorescent focus inhibition test (RFFIT) (Smith et al, Bulletin of the World Health Organization. 48: 535-541, 1973). One month after infection, surviving animals were challenged with a lethal dose of street rabies virus (dog/coyote salivary gland homogenate) (Orciari et al., *Vaccine*. 19:4511-4518, 2001).

Mouse monoclonal antibody (Mab 523-11) against rabies virus G was maintained at CDC (Hamir et al., *Vet Rec.* 136, 295-296, 1995) and FITC-conjugated anti-N monoclonal antibody was purchased from Centocor (Horsham, Pa.). T7 RNA polymerase monoclonal antibody was from Novagen (Madison, Wis.). Goat anti-mouse IgG-FITC conjugate was purchased from Sigma-Aldrich (St. Louis, Mo.). Anti-rabies virus G monoclonal antibody (Mab 1-909) was maintained at CDC and goat anti-human IgG-FITC conjugate was purchased from Sigma-Aldrich (St. Louis, Mo.).

Figure 8A:
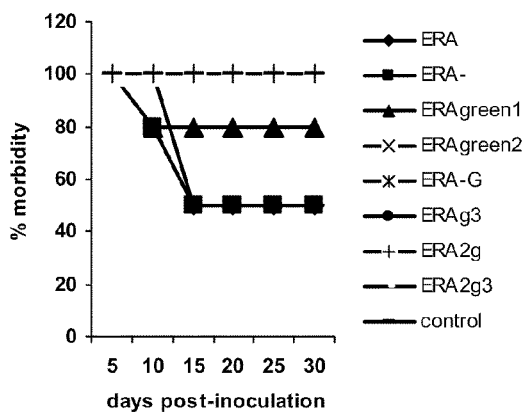
FIG. 8A. Morbidity induced by in vivo inoculation with recombinant ERA and derivatives. Three-week old mice were inoculated intramuscularly with the eight recovered viruses. At 10 days post inoculation, in ERA, ERA- and ERAgreen1 groups, 50%, 50% and 20% of mice showed compatible clinical signs of rabies, but no mortality, respectively. No adverse signs were observed in the other groups.
Figure 8B:
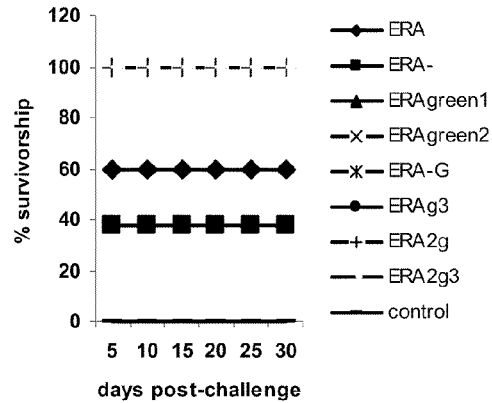
FIG. 8B. Post challenge survival in mice inoculated with recombinant ERA and derivtives. Mice surviving from the tests shown in FIG. 8A were challenged intramuscularly with a Texas dog/coyote rabies virus. At 5 days post challenge, in the ERA and ERA-groups, 40 and 62% of mice showed signs of rabies and were euthanized, respectively. In all other groups, no signs of rabies were observed.
Figure 8C:
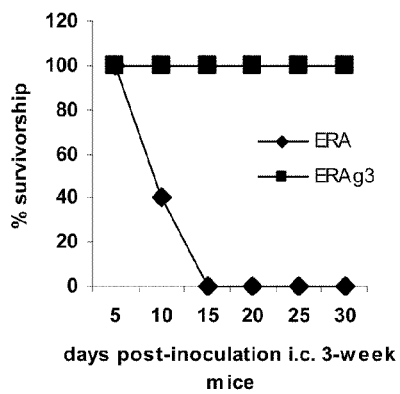
FIG. 8C. Survival following i.c. inoculation with recombinant ERA and ERAg3 viruses. Three-week old mice were inoculated intracerebrally with ERA and ERAg3 virus strains, respectively. All mice succumbed 15 days postinoculation in the ERA group, while in the ERAg3 group, all mice survived with no clinical signs.
Figure 8D:
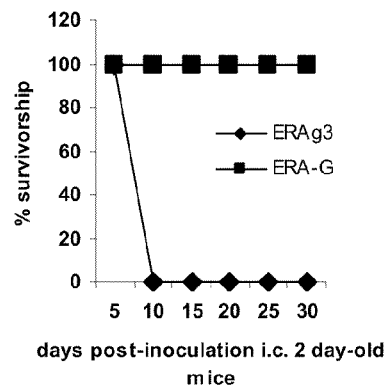
FIG. 8D. Survival following i.c. inoculation of suckling mice. Two-day old suckling mice were inoculated intracerebrally with ERAg3 and ERA-G virus constructs, respectively. All mice succumbed in the ERAg3 group, while no mice died in the ERA-G group.
Figure 8E:
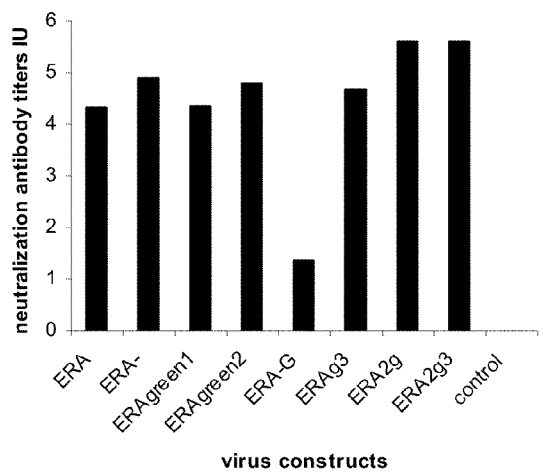
FIG. 8E. Neutralizing antibody titer in mice inoculated with recombinant ERA and derivative viruses. Mouse neutralization antibody titers were determined by the RFFIT, ranging from 1.36 to 5.61 IU per ml among the virus-inoculated groups.

Among the three-week old mice inoculated intramuscularly by the eight different virus constructs, 50% of mice inoculated with ERA (rERA) or ERA-, and 20% of mice inoculated with ERAgreen1 showed mild neurological signs at 10 days after inoculation. No other groups showed any sign suggestive of rabies virus infection (FIG. 8A). Sera were collected for neutralizing antibody titration before challenge. The ERA2g (5.60 IU) and ERA2g3 (5.61 IU) elicited higher titers than the single-copy G virus constructs (FIG. 8E). Mice surviving one month after inoculation were subjected to challenge with a lethal dog/coyote street virus (0.05 ml, maintained at CDC for standard animal challenge tests). In the ERA and ERA-groups, 40 to 62% of the mice showed mild rabies signs, respectively, and were euthanized. All other groups survived without any signs of rabies (FIG. 8B). In the i.c groups, three-week old mice survived after ERAg3 inoculation, but succumbed after ERA injection (FIG. 8C). The ERA-G construct did not kill 2-day old suckling mouse, however ERAg3 was virulent enough to kill all infected suckling mice (FIG. 8D). Exemplary antibody titers are shown in Table 4.

TABLE 4

Production of rabies specific antibodies

| Group | Average Titer |
| --- | --- |
| ERA | 433 |
| G333 | 468 |
| 2G | 560 |
| 2G333 | 561 |
| -PSI | 490 |
| GFP | 437 |
| G green | 833 |
| G minus | 136 |
| Controls | <1/5 |

These data demonstrate that all of the ERA based viruses were capable of eliciting an immune response following inoculation. As expected, the parental ERA virus was virulent, resulting in substantial morbidity and mortality in infected animals. In contrast, the various exemplary derivatives elicited a protective immune response when mice were inoculated prior to challenge.

In addition to the pre-exposure assessment described above, the ability of the ERA virus derivatives to elicit a protective immune response following infection with virulent rabies virus was determined. In brief, groups of hamsters were infected with one of three different strains of rabies virus (n=9 per group), and either given the recombinant vaccine (ERA-g333), or rabies immune globulin plus inactivated commercial rabies vaccines. Approximately 80-100% of control animals succumb, whereas approximately 60-100% of vaccinated animals survive as shown in FIGS. 9A-C. These results demonstrate that post-exposure administration of the derivative rabies virus confers substantial protection against different strains of rabies virus.

In view of the many possible embodiments to which the principles of the disclosed invention may be applied, it will be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A vector system comprising:
   a first vector comprising a full-length rabies virus antigenomic DNA, wherein the full-length antigenomic DNA comprises the nucleic acid sequence of SEQ ID NO: 16; and,
   a plurality of helper vectors comprising nucleic acids that encode at least one rabies virus strain ERA protein,
   wherein expression of the plurality of vectors in a transfected host cell results in production of a recombinant rabies virus.

2. The vector system of claim 1, wherein the first vector comprises in a 5' to 3' direction: a hammerhead ribozyme; a rabies virus antigenomic DNA; and a hepatitis delta virus ribozyme, wherein a plurality of nucleotides of the hammerhead ribozyme are complementary to the antisense genomic sequence of the rabies virus.

3. The vector system of claim 2, wherein transcription of the antigenomic DNA is under the transcription regulatory control of at least one of the CMV promoter and the phage T7 RNA polymerase promoter.

4. The vector system of claim 1, wherein the plurality of helper vectors comprises:
   a vector comprising a polynucleotide sequence that encodes a rabies virus N protein;
   a vector comprising a polynucleotide sequence that encodes a rabies virus P protein;
   a vector comprising a polynucleotide sequence that encodes a rabies virus M protein;
   a vector comprising a polynucleotide sequence that encodes a rabies virus L protein; and
   a vector comprising a polynucleotide sequence that encodes a phage T7 RNA polymerase.

5. The vector system of claim 4, further comprising a vector comprising a polynucleotide sequence that encodes a rabies virus G protein.

6. The vector system of claim 4, wherein transcription of one or more of the polynucleotide sequences that encode the rabies virus P, M, L or G protein or the T7 polymerase are under the transcription regulatory control of both the CMV promoter and the T7 promoter.

7. A recombinant virus genome comprising the nucleic acid sequence as set forth in SEQ ID NO: 16.

8. The recombinant virus genome of claim 7, further comprising a vector.

9. A recombinant virus comprising a genome as set forth in claim 7.

10. A live rabies virus vaccine comprising at least one recombinant rabies virus genome, wherein the at least one recombinant rabies virus genome comprises the sequence shown in SEQ ID NO: 16.

11. A method of producing a live rabies virus vaccine, comprising introducing the vector system of claim 4 into a host cell, and recovering live recombinant rabies virus.

12. A method of vaccinating a subject against rabies, comprising administering an effective amount of the live rabies virus vaccine produced according to the method of claim 11 to a subject, such that cells of the subject are infected with the rabies virus vaccine, wherein an anti-rabies immune response is produced in the subject.

13. The method of claim 12, wherein the subject is a human.

14. The method of claim 12, wherein the subject is a non-human animal.

15. The method of claim 12, wherein the administration comprises oral administration.

16. The method of claim 15, wherein the oral administration comprises administration through food-baits designed to vaccinate wild animal populations.

17. A pharmaceutical composition comprising the live rabies vaccine of claim 10 and a pharmaceutically acceptable carrier or excipient.

18. A method of eliciting an immune response against rabies in a subject, comprising administering an effective amount of the recombinant rabies virus of claim 9 to a subject, such that cells of the subject are infected with the rabies virus, wherein an anti-rabies immune response is produced in the subject.

19. A method of producing a recombinant rabies virus, comprising introducing the vector system of claim 4 into a host cell, and recovering recombinant rabies virus.

* * * * *

UNITED STATES PATENT AND TRADEMARK OFFICE
CERTIFICATE OF CORRECTION

PATENT NO. : 7,863,041 B2
APPLICATION NO. : 12/090083
DATED : January 4, 2011
INVENTOR(S) : Rupprecht et al.

It is certified that error appears in the above-identified patent and that said Letters Patent is hereby corrected as shown below:

On the Cover:

Item (56) Other Publications, following Anilionis *et al.*, "rabis" should read --rabies--

In the Specification:

Column 1, line 31, "human" should read --humans--

Column 2, line 55, "does not cause" should read --do not cause--

Column 3, line 6, "underyling" should read --underlying--

Column 3, line 29, "deleted) ERAgm" should read --deleted), ERA gm--

Column 3, line 50, "P, M G" should read --P, M, G--

Column 3, line 56, "RdRz" should read --HdRz--

Column 4, line 31, "curve All" should read --curve. All--

Column 4, line 35, "cells Trans1" should read --cells. Trans1--

Column 4, line 58, "derivtives" should read --derivatives--

Column 4, line 61, "ERA-groups" should read --ERA- groups--

Column 5, line 19, "That Street Dog" should read --Thai Street Dog--

Column 8, line 4, "dependant" should read --dependent--

Column 8, line 6, "deoxyribosenucleic" should read --deoxyribonucleic--

Column 8, line 18, "ribosenucleic" should read --ribonucleic--

Column 10, line 40, "Attentuated" should read --Attenuated--

Column 11, line 56, "another" should read --another.--

Column 12, line 1, "between to distinct" should read --between two distinct--

Column 13, line 25, "example of diseases" should read --example of a disease--

Column 14, line 46, "H is" should read --His--

Signed and Sealed this
Ninth Day of August, 2011

David J. Kappos
*Director of the United States Patent and Trademark Office*

CERTIFICATE OF CORRECTION (continued)

Column 14, line 62, "sequence is the promoter" should read --sequence if the promoter--

Column 17, lines 26-27, "a target nucleotide sequences" should read --a target nucleotide sequence--

Column 16, line 66, "nucleic-acid" should read --nucleic acid--

Column 17, lines 26-27, "a target nucleotide sequences" should read --a target nucleotide sequence--

Column 18, line 2, "know as" should read --known as--

Column 20, line 23, "host cells' normal" should read --host cell's normal--

Column 22, line 67, "could are not used" should read --could be used--

Column 23, line 13, "primes" should read --primers--

Column 23, line 24, "[EBL] I" should read --[EBL] I)--

Column 23, line 39, "differ" should read --different--

Column 24, line 7, "development siRNA" should read --development of siRNA--

Column 24, line 23, "genetics" should read --genetics.--

Column 25, lines 22-23, "intra cerebrally" should read --intracerebrally--

Column 25, line 45, "based a" should read --based on a--

Column 25, line 55, "efficiency is" should read --efficiency that is--

Column 26, lines 58-59, "house keeping" should read --housekeeping--

Column 27, Table 2, under Special characters, "HamRZ/HdvRZ" should read --HdRz/HDVRz--

Column 27, lines 59-60, "predicted enhance" should read --predicted to enhance--

Column 27, line 66, "that ERA" should read --than ERA--

Column 29, line 20, "a virus polypeptides" should read --a virus polypeptide--

Column 35, line 11, "codon underline" should read --codon underlined--

Column 36, line 47, "florescent" should read --fluorescent--

Column 36, line 49, "florescent" should read --fluorescent--

Column 36, line 54, "deleted) ERAgm" should read --deleted), ERAgm--

Column 36, line 56, "construct) These" should read --construct). These--

Column 36, line 59, "1010" should read --$10^{10}$--

Column 37, line 9, "C̲T̲A̲C̲G̲T̲A̲" should read --C̲TACGTA--

Column 37, line 13, "was successively cloned" should read --and was successively cloned--

CERTIFICATE OF CORRECTION (continued)
U.S. Pat. No. 7,863,041 B2

Column 37, lines 49-50,

"CTCACTACAAGTCAGTCGAGACTTGGAATGAGATC" should read

--CTCACTACAAGTCAGTCGAGACTTGGAATGAGATC--

Column 38, line 2, "5Δψ" should read --5' Δψ--

Column 38, line 65, "pTMFAg" should read --pTMFΔg--

Column 38, line 66, "at 3 g/well" should read --at 3μg/well--

Column 39, line 21, "Table 3" should read --Table 4--

Column 39, line 66, "Switherland" should read --Switzerland--

Column 40, line 9, "TABLE 3" should read --TABLE 4--

Column 40, line 12, "TABLE 3" should read --TABLE 4--

Column 40, line 25, "1.2 × 109" should read --1.2 × $10^9$--

Column 41, line 35, "(i.m)" should read --(i.m.)--

Column 41, line 36, "106 ffu" should read --$10^6$ ffu--

Column 41, line 39, "(i.c)" should read --(i.c.)--

Column 42, line 8, "ERA-groups" should read --ERA- groups--

Column 42, line 14, "suckling mouse" should read --suckling mice--

Column 42, line 17, "Table 4" should read --Table 5--

Column 42, line 19, "TABLE 4" should read --TABLE 5--